United States Patent
Cooper et al.

(10) Patent No.: US 8,426,443 B2
(45) Date of Patent: Apr. 23, 2013

(54) COMPOUNDS WHICH HAVE ACTIVITY AT $M_1$ RECEPTOR AND THEIR USES IN MEDICINE

(75) Inventors: David Gwyn Cooper, Harlow (GB); Ian Thomson Forbes, Harlow (GB); Vincenzo Garzya, Harlow (GB); Dale James Johnson, Harlow (GB); Graeme Irvine Stevenson, Harlow (GB); Paul Adrian Wyman, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/592,785

(22) Filed: Aug. 23, 2012

(65) Prior Publication Data

US 2012/0316196 A1 Dec. 13, 2012

Related U.S. Application Data

(62) Division of application No. 12/678,347, filed as application No. PCT/EP2008/062400 on Sep. 18, 2008, now Pat. No. 8,278,328.

(51) Int. Cl.
*A61K 31/445* (2006.01)
*A61K 31/425* (2006.01)
*A61K 31/42* (2006.01)

(52) U.S. Cl.
USPC ............................ 514/321; 514/367; 514/376

(58) Field of Classification Search .................. 514/321, 514/364, 376; 546/196; 548/188, 228
See application file for complete search history.

(56) References Cited

U.S. PATENT DOCUMENTS 3,161,645 A 12/1964 Adriaan et al.
2006/0199799 A1 9/2006 Kelly et al.

FOREIGN PATENT DOCUMENTS

EP 0068261 A1 1/1983
WO WO2008/119721 10/2008

OTHER PUBLICATIONS

Felder CC, Porter AC, Skillman TL, Zhang L, Bymaster FP, Nathanson NM, Hamilton SE, Gomeza J, Wess J, McKinzie DL. Elucidating the role of muscarinic receptors in psychosis. Life Sci. Apr. 27, 2001;68(22-23):2605-13.*
Jassen, et al. "Benzimidazolinon . . ." CA 84:135657 (1976).
Poulain, R., et al: "From hit to lead." Journal of Medicinal Chemistry, vol. 44 No. 21, Oct. 2001, pp. 3378-3390.
Rossi, A., et al: "Benzimidazol-Derivate and verwandte Heterocyclen V. Die Kondensation von o-Phenylendiamine mit aliphatischen und alicyclischen beta-Ketoestern" Helvetica Chimica Acta, vol. 43, No. 5, Aug. 1, 1960, pp. 1298-1313.

* cited by examiner

*Primary Examiner* — Paul Zarek
(74) *Attorney, Agent, or Firm* — Linda E. Hall; John L. Lemanowicz

(57) ABSTRACT

Compounds of formula (I) or a salt thereof are provided:

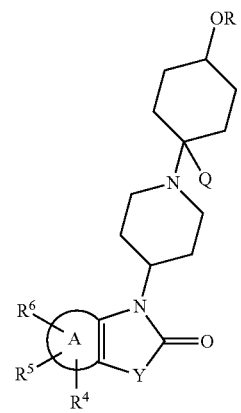

wherein $R^4$, $R^5$, $R^6$, Q, A, Y and R are as defined in the description. Uses of the compounds as medicaments and in the manufacture of medicaments for treating psychotic disorders, cognitive impairments and Alzheimer's Disease are disclosed. The invention further discloses pharmaceutical compositions comprising the compounds.

8 Claims, No Drawings

COMPOUNDS WHICH HAVE ACTIVITY AT $M_1$ RECEPTOR AND THEIR USES IN MEDICINE

CROSS REFERENCE TO PRIOR APPLICATIONS

This application is a Divisional of application Ser. No. 12/678,347 filed Mar. 16, 2010 now U.S. Pat. No. 8,276,328 which is a 371 National Phase Entry of Application No. PCT/EP2008/062400 filed 18 Sep. 2008, which claims the priority of GB 0718419.5, filed 20 Sep. 2007 and GB0814903.1 filed 14 Aug. 2008.

This invention relates to novel compounds, pharmaceutical compositions containing them and their use in therapy, in particular as antipsychotic agents, as agents for the treatment of cognitive impairment associated with schizophrenia, and as agents for treatment of Alzheimer's Disease.

Muscarinic acetylcholine receptors are members of the G protein-coupled receptor superfamily which mediate the actions of the neurotransmitter acetylcholine in both the central and peripheral nervous system. Five muscarinic receptor subtypes have been cloned, $M_1$ to $M_5$. The muscarinic $M_1$ receptor is predominantly expressed in the cerebral cortex and hippocampus, although it is also expressed in the periphery e.g. exocrine glands.

Muscarinic receptors in the central nervous system, especially $M_1$, play a critical role in mediating higher cognitive processing. Diseases associated with cognitive impairments, such as Alzheimer's Disease, are accompanied by loss of cholinergic neurons in the basal forebrain. Furthermore, in animal models, blockade or lesion of central cholinergic pathways results in profound cognitive deficits.

Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to side effects resulting from stimulation of peripheral muscarinic receptors including disturbed gastrointestinal motility and nausea.

The dopamine hypothesis of schizophrenia suggests that excess dopaminergic stimulation is responsible for the positive symptoms of the disease, hence the utility of dopamine receptor antagonists to reduce psychotic symptoms. However, conventional dopamine receptor antagonists can cause extrapyramidal side effects (EPS) in patients, including tremor and tardive dyskinesias.

$M_1$ receptor agonists have been sought for the symptomatic treatment of cognitive decline. More recently, a number of groups have shown that muscarinic receptor agonists display an atypical antipsychotic-like profile in a range of pre-clinical paradigms. The muscarinic agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine-induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile.

Xanomeline has also been shown to reduce psychotic symptoms such as suspiciousness, hallucinations and delusions in Alzheimer's patients and has subsequently been assessed in a small phase II trial in schizophrenic patients where it showed a trend to improvement in PANSS and separation from placebo in a cognitive readout. However, the relatively non-selective nature of the compound gives rise to dose-limiting peripheral cholinergic side effects.

Over-production of β amyloid is a critical pathogenic event in Alzheimer's Disease (AD) and data have been published showing that $M_1$ receptor agonists modulate the processing of β-APP, the precursor of β amyloid, to increase the production of sAPPa (non-amyloidogenic). Subsequent studies have demonstrated that this event is accompanied by a decreased secretion of β amyloid (for review see Current Opinion in Investigational Drugs, 2002, 3 (11), 1633-1636). In addition, it has recently been reported that an $M_1$ receptor agonist can affect APP processing toward the non-amyloidogenic pathway, in vivo (Neuron, 2006, 49, 671-682). Thus $M_1$ selective agonists have potential for a preventative/disease modifying role in AD therapy.

Certain $M_1$ receptor agonists are known, for example in PCT/EP2007/052640. We have now found a novel group of compounds which are $M_1$ receptor agonists.

In a first aspect therefore, the invention provides a compound of formula (I) or a salt thereof:

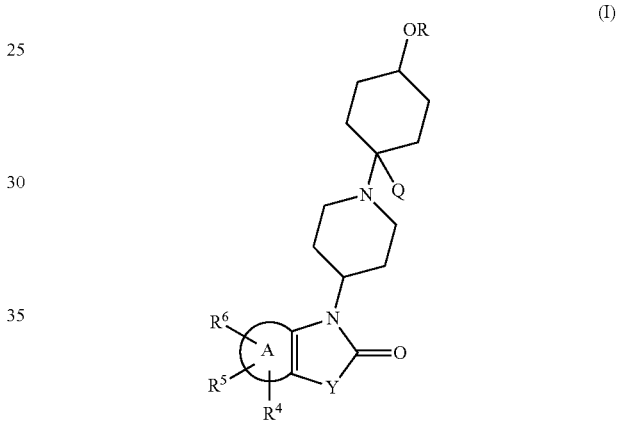

(I)

wherein:

$R^4$, $R^5$ and $R^6$ are independently selected from hydrogen, halogen, $C_{1-6}$alkyl, $C_{1-6}$alkyl substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-6}$alkyl)C$_{1-6}$alkyl, —C$_{1-6}$alkoxyC$_{1-6}$alkyl, and —C(O)NR$_a$R$_b$;

$R_a$ and $R_b$ are each independently H or $C_{1-6}$ alkyl, or together with the nitrogen atom to which they are attached form a five or six membered ring;

ring A represents a benzene ring, or a 6-membered aromatic heterocylic ring containing one or two nitrogen atoms;

R is selected from $C_{1-6}$alkyl, $C_{3-6}$cycloalkyl, $C_{3-6}$cycloalkylC$_{1-4}$alkyl, $C_{1-6}$alkyloxyC$_{1-6}$alkyl, $C_{3-6}$cycloalkyloxyC$_{1-6}$alkyl and $C_{3-6}$cycloalkylC$_{1-4}$alkyloxyC$_{1-6}$alkyl, wherein any alkyl or cycloalkyl group is optionally substituted by one or more fluorine atoms;

Q is selected from hydrogen and $C_{1-6}$alkyl; and

Y is selected from O, S, $CH_2$ optionally substituted with one or two fluorine atoms or optionally substituted with one or two methyl groups, $CH_2CH_2$, $OCH_2$, and $CH_2O$.

As used herein, the term "alkyl" refers to a straight or branched hydrocarbon chain containing the specified number of carbon atoms. For example, "$C_{1-6}$alkyl" means a straight or branched alkyl containing at least 1, and at most 6, carbon atoms. Examples of "$C_{1-6}$alkyl" include, but are not limited to, methyl, ethyl, n-propyl, n-butyl, n-pentyl, n-hexyl, isobutyl, isopropyl, t-butyl and 1,1-dimethylpropyl "$C_{1-4}$alkyl" means a straight or branched alkyl containing at least 1, and at most 4, carbon atoms. Examples of "$C_{1-4}$alkyl" include, but are not limited to, methyl, ethyl, n-propyl, n-butyl, isobutyl, isopropyl, and t-butyl.

As used herein, the term "alkoxy" refers to the group "O-alkyl" where "alkyl" is as hereinbefore defined. For example, "$C_{1-6}$alkoxy" means a straight or branched alkoxy group containing at least 1, and at most 6, carbon atoms. Examples of "$C_{1-6}$alkoxy" as used herein include, but are not limited to, methoxy, ethoxy, propoxy, prop-2-oxy, butoxy, but-2-oxy, 1-methylethyl-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, "$C_{3-6}$cycloalkyl" means a non-aromatic carbocyclic ring containing at least three, and at most six, ring carbon atoms. Examples of "$C_{3-6}$cycloalkyl" as used herein include, but are not limited to, cyclopropyl, cyclobutyl, cyclopentyl and cyclohexyl.

As used herein, the term "halogen" (or the abbreviated form "halo") refers to the elements fluorine (which may be abbreviated to "fluoro" or "F"), chlorine (which may be abbreviated to "chloro" or "Cl"), bromine (which may be abbreviated to "bromo" or "Br") and iodine (which may be abbreviated to "iodo" or "I"). Examples of halogens are fluorine, chlorine and bromine.

As used herein, the term "$C_{1-6}$alkylsulfonyl" refers to a group $SO_2$—$C_{1-6}$alkyl, wherein $C_{1-6}$alkyl is as hereinbefore defined. Examples of "$C_{1-6}$alkylsulfonyl" as used herein include, but are not limited to, methylsulphonyl, ethylsulphonyl, propylsulphonyl, butylsulphonyl, pentylsulphonyl and hexylsulphonyl.

As used herein, the term "$C_{1-6}$alkanoyl" refers to a group —C(O)$C_{1-6}$alkyl wherein $C_{1-6}$alkyl is as hereinbefore defined. Examples of "$C_{1-6}$alkanoyl" as use herein include, but are not limited to, methanoyl, ethanoyl, propanoyl, butanoyl, pentanoyl and hexanoyl.

As used herein, the term "$C_{1-6}$alkoxy$C_{1-6}$alkyl" refers to a group $C_{1-6}$alkyl-O—$C_{1-6}$alkyl wherein $C_{1-6}$alkyl is as hereinbefore defined. Examples of "$C_{1-6}$alkoxy$C_{1-6}$alkyl" as used herein include, but are not limited to, methoxymethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, and ethoxyhexyl.

As used herein, the term "$C_{3-6}$cycloalkyl$C_{1-4}$alkyl" refers to a group $C_{3-6}$cycloalkly-$C_{1-4}$alkyl wherein $C_{3-6}$cycloalkyl and $C_{1-4}$alkyl are as hereinbefore defined. Examples of "$C_{3-6}$cycloalkyl$C_{1-4}$alkyl" as used herein include, but are not limited to, cyclopropylmethyl, cyclobutylmethyl, cyclopentylmethyl, cyclohexylmethyl, cyclopropylethyl, cyclobutylethyl, cyclopentylethyl, and cyclohexylethyl.

As used herein, the term "$C_{3-6}$cycloalkyloxy$C_{1-6}$alkyl" refers to a group $C_{3-6}$cycloalkyl-O—$C_{1-6}$alkyl wherein $C_{3-6}$cycloalkyl and $C_{1-6}$alkyl are as hereinbefore defined. Examples of "$C_{3-6}$cycloalkyloxy$C_{1-6}$alkyl" as used herein include, but are not limited to cyclopropyloxymethyl, cyclobutyloxymethyl, cyclopentyloxymethyl, cyclohexyloxymethyl, cyclopropyloxyethyl, cyclobutyloxyethyl, cyclopentyloxyethyl, and cyclohexyloxyethyl.

As used herein, the term "$C_{3-6}$cycloalkyl$C_{1-6}$alkyloxy$C_{1-6}$alkyl" refers to a group $C_{3-6}$cycloalkyl-$C_{1-4}$alkyl-O—$C_{1-6}$alkyl wherein $C_{3-6}$cycloalkyl, $C_{1-4}$alkyl and $C_{1-6}$alkyl are as hereinbefore defined. Examples of "$C_{3-6}$cycloalkyl$C_{1-4}$alkyloxy$C_{1-6}$alkyl" as used herein include, but are not limited to, cyclopropylmethyloxymethyl, cyclobutylmethyloxymethyl, cyclopentylmethyloxymethyl, cyclohexylmethyloxymethyl, cyclopropylethyloxymethyl, cyclobutylethyloxymethyl, cyclopentylethyloxymethyl, and cyclohexylethyloxymethyl.

As used herein, the term "substituted" refers to substitution with the named substituent or substituents, multiple degrees of substitution being allowed unless otherwise stated. For example, there may be 1, 2 or 3 substituents on a given substituted group. For example, if $R^6$ is a $C_{1-6}$alkyl group, it may be substituted by 1, 2, 3 or 4 fluoro groups; and if $R^6$ is a $C_{1-6}$alkoxy group, it may be substituted by 1, 2, 3 or 4 fluoro groups.

In one embodiment, there is provided a compound of formula (I) or a salt thereof, wherein:

$R^4$, $R^5$ and $R^6$ are independently selected from hydrogen, halogen, $C_{1-6}$alkyl, $C_{1-6}$alkyl substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-5}$alkyl)C$_{1-5}$alkyl, —C$_{1-4}$alkoxyC$_{1-4}$alkyl, and —C(O)NR$_a$R$_b$;

$R_a$ and $R_b$ are each independently H or $C_{1-6}$ alkyl, or together with the nitrogen atom to which they are attached form a five or six membered ring;

d ring A represents a benzene ring, or a 6-membered aromatic heterocylic ring containing one or two nitrogen atoms;

R is selected from $C_{3-6}$cycloalkyl$C_{1-4}$alkyl, $C_{3-6}$cycloalkyloxy$C_{1-6}$alkyl and $C_{3-6}$cycloalkyl$C_{1-4}$alkyloxy$C_{1-6}$alkyl, wherein any alkyl or cycloalkyl group is optionally substituted by one or more fluorine atoms;

Q is selected from hydrogen and $C_{1-6}$alkyl; and

Y is selected from O, S, $CH_2CH_2$, $OCH_2$, and $CH_2O$.

In one embodiment there is provided a compound of formula (I) or a salt thereof wherein:

$R^4$, $R^5$ and $R^6$ are independently selected from hydrogen, halogen, $C_{1-6}$alkyl, substituted with one or more fluorine atoms, cyano, $C_{1-6}$alkylsulfonyl, $C_{1-6}$alkylsulfonyl substituted with one or more fluorine atoms, $C_{3-6}$cycloalkyl, $C_{1-6}$alkoxy, $C_{1-6}$alkoxy substituted with one or more fluorine atoms, $C_{1-6}$alkanoyl, —C(=NOC$_{1-5}$alkyl)C$_{1-5}$alkyl, —C$_{1-4}$alkoxyC$_{1-4}$alkyl, and —C(O)NR$_a$R$_b$;

$R_a$ and $R_b$ are each independently H or $C_{1-6}$ alkyl, or together with the nitrogen atom to which they are attached form a five or six membered ring;

ring A represents a benzene ring, or a 6-membered aromatic heterocylic ring containing one or two nitrogen atoms;

R is selected from $C_{1-6}$alkyl and $C_{3-6}$cycloalkyl, wherein any alkyl or cycloalkyl group is optionally substituted by one or more fluorine atoms;

Q is selected from hydrogen and $C_{1-6}$alkyl; and

Y is $CH_2$ optionally substituted with one or two fluorine atoms or optionally substituted with one or two methyl groups.

In one embodiment $R^4$, $R^5$ and $R^6$ are independently selected from hydrogen, halogen, $C_{1-6}$alkyl optionally substituted with one or more fluorine atoms, cyano, $C_{1-6}$alkylsulfonyl, $CF_3SO_2$, $C_{1-6}$alkoxy optionally substituted with one or more fluorine atoms, and $C_{1-4}$alkoxy$C_{1-4}$alkyl. In a further embodiment $R^4$, $R^5$ and $R^6$ are independently selected from hydrogen, halogen, $C_{1-4}$alkyl optionally substituted with one or more fluorine atoms, cyano, $C_{1-4}$alkylsulfonyl, and $C_{1-4}$alkoxy optionally substituted with one or more fluorine atoms. In a further embodiment $R^4$, $R^5$ and $R^6$ are independently selected from hydrogen, halogen, $C_{1-2}$alkyl optionally substituted with one or more fluorine atoms, cyano, $C_{1-2}$alkylsulfonyl, and $C_{1-2}$alkoxy optionally substituted with one or more fluorine atoms. In a further embodiment $R^4$, $R^5$ and $R^6$ are independently selected from hydrogen, fluorine, methyl, trifluoromethyl, cyano, methylsulfonyl, ethylsulfonyl, methoxy, difluoromethoxy, trifluoromethoxy, and methoxymethyl.

In one embodiment $R^4$ is selected from hydrogen, halogen, $C_{1-6}$alkyl (optionally substituted with one or more fluorine atoms), cyano, $C_{1-6}$alkylsulfonyl (optionally substituted with one or more fluorine atoms), $C_{1-6}$alkoxy (optionally substituted with one or more fluorine atoms), and $C_{1-4}$alkoxy$C_{1-4}$alkyl.

In one embodiment $R^4$ is selected from hydrogen, halogen, $C_{1-4}$alkyl optionally substituted with one or more fluorine atoms, cyano, $C_{1-4}$alkylsulfonyl, and $C_{1-4}$alkoxy optionally substituted with one or more fluorine atoms.

In one embodiment $R^4$ is selected from hydrogen, halogen, $C_{1-2}$alkyl optionally substituted with one or more fluorine atoms, cyano, $C_{1-2}$alkylsulfonyl, and $C_{1-2}$alkoxy optionally substituted with one or more fluorine atoms.

In one embodiment $R^4$ is selected from hydrogen, fluorine, methyl, trifluoromethyl, cyano, methylsulfonyl, ethylsulfonyl, methoxy, difluoromethoxy, trifluoromethoxy, and methoxymethyl.

In one embodiment $R^4$ is hydrogen or fluorine.

In one embodiment, $R^4$ is hydrogen.

In one embodiment $R^5$ is selected from hydrogen, halogen, $C_{1-6}$alkyl (optionally substituted with one or more fluorine atoms), cyano, $C_{1-6}$alkylsulfonyl (optionally substituted with one or more fluorine atoms), $C_{1-6}$alkoxy (optionally substituted with one or more fluorine atoms), and $C_{1-4}$alkoxy$C_{1-4}$alkyl.

In one embodiment $R^5$ is selected from hydrogen, halogen, $C_{1-4}$alkyl (optionally substituted with one or more fluorine atoms), cyano, $C_{1-4}$alkylsulfonyl, and $C_{1-4}$alkoxy (optionally substituted with one or more fluorine atoms).

In one embodiment $R^5$ is selected from hydrogen, halogen, $C_{1-2}$alkyl (optionally substituted with one or more fluorine atoms), cyano, $C_{1-2}$alkylsulfonyl, and $C_{1-2}$alkoxy (optionally substituted with one or more fluorine atoms).

In one embodiment $R^5$ is selected from hydrogen, fluorine, methyl, trifluoromethyl, cyano, methylsulfonyl, ethylsulfonyl, methoxy, difluoromethoxy, trifluoromethoxy, and methoxymethyl.

In one embodiment, $R^5$ is selected from hydrogen, fluorine, cyano and methyl.

In one embodiment, $R^5$ is hydrogen.

In one embodiment $R^6$ is selected from hydrogen, halogen, $C_{1-6}$alkyl (optionally substituted with one or more fluorine atoms), cyano, $C_{1-6}$alkylsulfonyl (optionally substituted with one or more fluorine atoms), $C_{1-6}$alkoxy (optionally substituted with one or more fluorine atoms), $C_{1-4}$alkoxy$C_{1-4}$alkyl, $C_{1-6}$alkanoyl, —C(=NO$C_{1-5}$alkyl)$C_{1-5}$alkyl and —C(O)NR$_a$R$_b$.

In one embodiment $R^6$ is selected from hydrogen, halogen, $C_{1-4}$alkyl (optionally substituted with one or more fluorine atoms), cyano, $C_{1-4}$alkylsulfonyl (optionally substituted with one or more fluorine atoms), $C_{1-4}$alkoxy (optionally substituted with one or more fluorine atoms), $C_{1-4}$alkoxy$C_{1-4}$alkyl, $C_{1-4}$alkanoyl, —C(=NO$C_{1-4}$alkyl)$C_{1-4}$alkyl and —C(O)NR$_a$R$_b$.

In one embodiment $R^6$ is selected from hydrogen, halogen, $C_{1-2}$alkyl (optionally substituted with one or more fluorine atoms), cyano, $C_{1-2}$alkylsulfonyl (optionally substituted with one or more fluorine atoms), $C_{1-2}$alkoxy (optionally substituted with one or more fluorine atoms), $C_{1-2}$alkoxy$C_{1-2}$alkyl, $C_{1-2}$alkanoyl, —C(=NO$C_{1-2}$alkyl)$C_{1-2}$alkyl and —C(O)NR$_a$R$_b$.

In one embodiment $R^6$ is selected from hydrogen, fluorine, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl.

In one embodiment $R^6$ is selected from hydrogen, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl.

In one embodiment, $R^6$ is cyano.

In one embodiment ring A represents a benzene ring or a pyridine ring.

In one embodiment ring A represents a benzene ring.

In one embodiment ring A represents a pyridine ring.

In one embodiment, the invention provides a compound of formula (Ia) or a salt thereof:

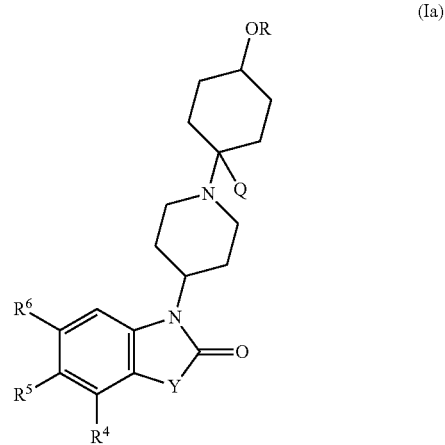

(Ia)

wherein $R^4$, $R^5$, $R^6$, Y, Q and R are as hereinbefore defined for a compound of formula (I). In one embodiment R is selected from $C_{3-6}$cycloalkyl$C_{1-4}$alkyl, $C_{1-6}$alkyloxy$C_{1-6}$alkyl, $C_{3-6}$cycloalkyloxy$C_{1-6}$alkyl and $C_{3-6}$cycloalkyl$C_{1-4}$alkyloxy$C_{1-6}$alkyl, wherein any alkyl or cycloalkyl group is optionally substituted by one or more fluorine atoms.

In one embodiment R is selected from $C_{1-6}$alkyl and $C_{3-6}$cycloalkyl.

In one embodiment R is selected from $C_{1-6}$alkyl, $C_{3-6}$cycloalkyl$C_{1-4}$alkyl and $C_{1-6}$alkyloxy$C_{1-6}$alkyl.

In one embodiment R is selected from $C_{1-6}$alkyl, $C_{3-6}$cycloalkyl$C_{1-4}$alkyl and $C_{1-6}$alkyloxy$C_{1-6}$alkyl.

In one embodiment R is selected from methyl, ethyl, n-propyl, i-propyl, cyclopropylmethyl and methoxyethyl.

In one embodiment R is selected from $C_{3-6}$cycloalkyl$C_{1-4}$alkyl and $C_{1-6}$alkyloxy$C_{1-6}$alkyl.

In one embodiment R is selected from $C_{3-6}$cycloalkyl$C_{1-4}$alkyl and $C_{1-4}$alkyloxy$C_{1-4}$alkyl.

In one embodiment R is $C_{1-6}$alkyloxy$C_{1-6}$alkyl.

In one embodiment R is selected from cyclopropylmethyl and methoxyethyl.

In one embodiment R is methoxyethyl.

In one embodiment Q is selected from the group consisting of H and $C_{1-4}$alkyl.

In one embodiment, Q is selected from the group consisting of H and $C_{1-2}$alkyl.

In one embodiment, Q is H or methyl.
In one embodiment, Q is methyl.
In one embodiment, Q is H.
In one embodiment Y is selected from O, OCH$_2$, CH$_2$ or CH$_2$CH$_2$ and C(CH$_3$)$_2$.
In one embodiment Y is selected from O, S, OCH$_2$, CH$_2$O and CH$_2$CH$_2$.
In one embodiment Y is selected from CH$_2$ optionally substituted with one or two fluorine atoms or optionally substituted with one or two methyl groups.
In one embodiment, Y is O.
In one embodiment, there is provided a compound of formula (I) or a salt thereof wherein:
R$^4$ is hydrogen or fluorine;
R$^5$ is selected from hydrogen, fluorine, cyano and methyl;
R$^6$ is selected from hydrogen, fluorine, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
A is a benzene ring or a pyridine ring;
R is selected from methyl, ethyl, n-propyl, i-propyl, cyclopropylmethyl and methoxyethyl;
Q is H or methyl; and
Y is selected from O, OCH$_2$, CH$_2$, CH$_2$CH$_2$ and C(CH$_3$)$_2$.

In one embodiment, there is provided a compound of formula (I) or a salt thereof wherein:
R$^4$ is hydrogen or fluorine;
R$^5$ is selected from hydrogen, fluorine, cyano and methyl;
R$^6$ is selected from hydrogen, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
A is a benzene ring or a pyridine ring;
R is selected from methyl, ethyl, n-propyl, i-propyl, cyclopropylmethyl and methoxyethyl;
Q is H or methyl; and
Y is selected from O, OCH$_2$, CH$_2$, CH$_2$CH$_2$ and C(CH$_3$)$_2$.

In one embodiment, the compound of formula (I) is a compound of formula (Ia) wherein:
R$^4$ is hydrogen or fluorine;
R$^5$ is selected from hydrogen, fluorine, cyano and methyl;
R$^6$ is selected from hydrogen, fluorine, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
R is selected from methyl, ethyl, n-propyl, i-propyl, cyclopropylmethyl and methoxyethyl;
Q is H or methyl; and
Y is selected from O, OCH$_2$, CH$_2$, CH$_2$CH$_2$ and C(CH$_3$)$_2$.

In one embodiment, the compound of formula (I) is a compound of formula (Ia) wherein:
R$^4$ is hydrogen or fluorine;
R$^5$ is selected from hydrogen, fluorine, cyano and methyl;
R$^6$ is selected from hydrogen, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
R is selected from methyl, ethyl, n-propyl, i-propyl, cyclopropylmethyl and methoxyethyl;
Q is H or methyl; and
Y is selected from O, OCH$_2$, CH$_2$, CH$_2$CH$_2$ and C(CH$_3$)$_2$.

In one embodiment, there is provided a compound of formula (I) or a salt thereof wherein:
R$^4$ is hydrogen or fluorine;
R$^5$ is selected from hydrogen, fluorine, cyano and methyl;
R$^6$ is selected from hydrogen, fluorine, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
A is a benzene ring or a pyridine ring;
R is selected from cyclopropylmethyl and methoxyethyl;
Q is H or methyl; and
Y is selected from O, OCH$_2$ and CH$_2$CH$_2$.

In one embodiment, there is provided a compound of formula (I) or a salt thereof wherein:
R$^4$ is hydrogen or fluorine;
R$^5$ is selected from hydrogen, fluorine, cyano and methyl;
R$^6$ is selected from hydrogen, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
A is a benzene ring or a pyridine ring;
R is selected from cyclopropylmethyl and methoxyethyl;
Q is H or methyl; and
Y is selected from O, OCH$_2$ and CH$_2$CH$_2$.

In one embodiment, the compound of formula (I) is a compound of formula (Ia) wherein:
R$^4$ is hydrogen or fluorine;
R$^5$ is selected from hydrogen, fluorine, cyano and methyl;
R$^6$ is selected from hydrogen, fluorine, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
R is selected from cyclopropylmethyl and methoxyethyl;
Q is H or methyl; and
Y is selected from O, OCH$_2$ and CH$_2$CH$_2$.

In one embodiment, the compound of formula (I) is a compound of formula (Ia) wherein:
R$^4$ is hydrogen or fluorine;
R$^5$ is selected from hydrogen, fluorine, cyano and methyl;
R$^6$ is selected from hydrogen, methyl, trifluoromethyl, cyano, methylsulfonyl, ethylsulfonyl, trifluoromethylsulfonyl, methoxy, difluoromethoxy, trifluoromethoxy, —C(O)NH$_2$, —C(O)CH$_3$, —C(=NOCH$_3$)CH$_3$, and methoxymethyl;
R is selected from cyclopropylmethyl and methoxyethyl;
Q is H or methyl; and
Y is selected from O, OCH$_2$ and CH$_2$CH$_2$.

In one embodiment, the compound of formula (I) is a compound of formula (Ia) wherein:
R$^4$ is hydrogen or fluorine;
R$^5$ is selected from hydrogen, fluorine and cyano;
R$^6$ is selected from methyl, trifluoromethyl, cyano, methylsulfonyl, methoxy, —C(O)NH$_2$, —C(O)CH$_3$, —C(=NOCH$_3$)CH$_3$, and methoxymethyl;
R is selected from cyclopropylmethyl and methoxyethyl;
Q is H or methyl; and
Y is O.

In one embodiment, the compound of formula (I) is a compound of formula (Ia) wherein:
R$^4$ is hydrogen, R$^5$ is hydrogen, R$^6$ is cyano, R is methoxyethyl, Q is methyl, and Y is O.

In one embodiment, the invention provides a compound of formula (I') or a salt or solvate thereof:

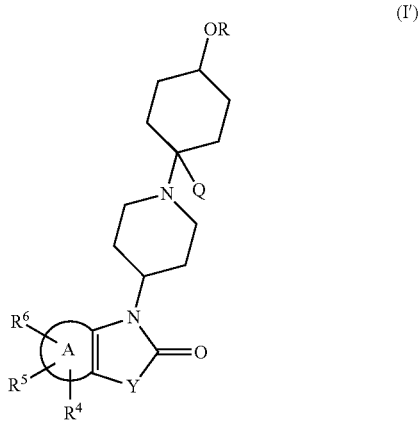

(I')

wherein
- R⁴, R⁵ and R⁶ are independently selected from hydrogen, halogen, $C_{1-6}$alkyl, substituted with one or more fluorine atoms, cyano, $C_{1-6}$alkylsulfonyl, $C_{3-6}$cycloalkyl, $C_{1-6}$alkoxy, and $C_{1-6}$alkoxy substituted with one or more fluorine atoms;
- ring A represents a benzene ring, or a 6-membered aromatic heterocylic ring containing one or two nitrogen atoms;
- R is selected from $C_{1-6}$alkyl, $C_{3-6}$cycloalkyl, $C_{3-6}$cycloalkyl$C_{1-4}$alkyl, $C_{1-6}$alkyloxy$C_{1-6}$alkyl, $C_{3-6}$cycloalkyloxy$C_{1-6}$alkyl and $C_{3-6}$cycloalkyl$C_{1-4}$alkyloxy$C_{1-6}$alkyl, wherein any alkyl or cycloalkyl group is optionally substituted by one or more fluorine atoms;
- Q is selected from hydrogen and $C_{1-6}$alkyl; and
- Y is selected from O, S, $CH_2$ optionally substituted with one or two fluorine atoms, $CH_2CH_2$, $OCH_2$, and $CH_2O$.

It will be appreciated that the present invention covers all combinations of features and embodiments described hereinbefore.

All features and embodiments for formula (I) apply to compounds of formula (I') and (Ia) mutatis mutandis. Hereinafter, all references to compounds of formula (I) include compounds of formula (I') and (Ia).

In one embodiment the salt of the compound of formula (I) is a pharmaceutically acceptable salt. In one embodiment, the invention provides a compound of formula (I), or a pharmaceutically acceptable salt thereof.

In one embodiment, the invention provides a compound of formula (I) as the free base.

It will be appreciated that for use in medicine the salts of formula (I) should be pharmaceutically acceptable. Suitable salts will be apparent to those skilled in the art and include for example mono- or di-basic salts formed with inorganic acids e.g. hydrochloric, hydrobromic, sulfuric, nitric, sulfamic phosphoric, hydroiodic, phosphoric or metaphosphoric acid; and with organic acids, such as tartaric, acetic, trifluoroacetic, citric, malic, lactic, fumaric, benzoic, formic, propionic, glycolic, gluconic, maleic, succinic, (1R)-(−)-10-camphorsulphonic, (1S)-(+)-10-camphorsulphonic, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example naphthalene-1,5-disulphonic, naphthalene-1,3-disulphonic, benzenesulfonic, and p-toluenesulfonic, acids. Other non-pharmaceutically acceptable salts e.g. oxalates, may be used, for example in the isolation of compounds of formula (I) and are included within the scope of this invention. Certain of the compounds of formula (I) may form acid addition salts with less than one (for example, 0.5 equivalent of a dibasic acid) or one or more equivalents of an acid. The present invention includes within its scope all possible stoichiometric and non-stoichiometric forms thereof.

The compounds of the present invention may be in the form of their free base or pharmaceutically acceptable salts thereof, particularly the hydrochloride, formate, trifluoroacetate, methanesulfonate, or 4-methylbenzenesulfonate salts.

In one embodiment, the pharmaceutically acceptable salt is a hydrochloride salt, a trifluoroacetate salt, or a formate salt.

In one embodiment the pharmaceutically acceptable salt is the hydrocholoride salt.

Solvates of the compounds of formula (I) and solvates of the salts of compounds of formula (I) are included within the scope of the present invention. As used herein, the term "solvate" refers to a complex of variable stoichiometry formed by a solute (in this invention, a compound of formula (I) or a salt thereof) and a solvent. Those skilled in the art of organic chemistry will appreciate that many organic compounds can form such complexes with solvents in which they are reacted or from which they are precipitated or crystallised. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Where the solvent used is water such a solvate may then also be referred to as a hydrate.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Possible prodrugs for some compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

The compounds of formula (I) may have the ability to crystallise in more than one form. This is a characteristic known as polymorphism, and it is understood that such polymorphic forms ("polymorphs") are within the scope of formula (I). Polymorphism generally can occur as a response to changes in temperature or pressure or both and can also result from variations in the crystallisation process. Polymorphs can be distinguished by various physical characteristics known in the art such as x-ray diffraction patterns, solubility, and melting point.

Hereinafter, compounds of formula (I) (whether in solvated or unsolvated form) or their pharmaceutically acceptable salts (whether in solvated or unsolvated form) or prodrugs thereof defined in any aspect of the invention (except intermediate compounds in chemical processes) are referred to as "compounds of the invention".

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as $^3$H or $^{14}$C is incorporated, are useful in drug and/or substrate tissue distribution studies. Tritiated, i.e., $^3$H, and carbon-14, i.e., isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

It will be appreciated that compounds of formula (I) can exist in cis or trans isomeric forms (the OR group on the cyclohexane ring in relation to the piperidine substituent).

It will be appreciated that the cis form may be drawn in the following different ways, although both represent the same isomeric form:

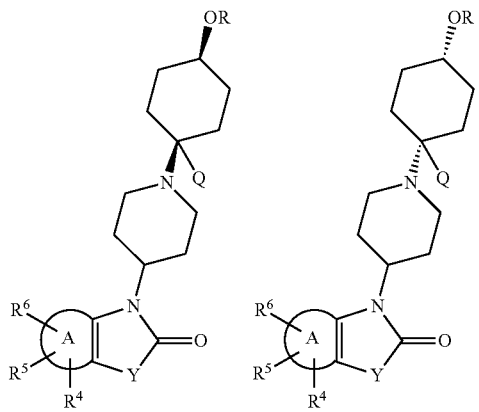

It will be appreciated that the trans form may be drawn in the following different ways, although both represent the same isomeric form:

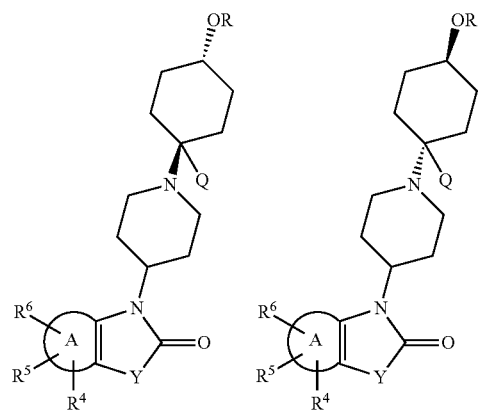

The individual isomers (cis and trans) and mixtures of these are included within the scope of the present invention. The isomers may be separated one from the other by the usual methods or by methods detailed for the example compounds below. Any given isomer may also be obtained by stereospecific synthesis. The invention also extends to any tautomeric forms and mixtures thereof.

In one embodiment, the compounds of formula (I) are trans isomers.

In another embodiment, the compounds of formula (I) are cis isomers.

Mixtures of cis- and trans-compounds, or compounds in which the cis/trans conformation have not been determined, are drawn herein as shown below:

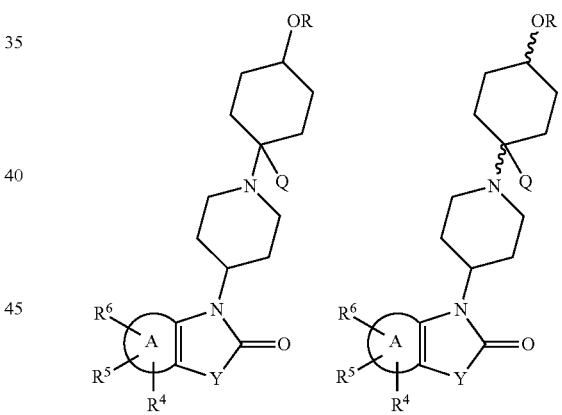

Compounds according to the invention include:—
3-{1-[trans-4-(Ethyloxy)-1-methylcyclohexyl]-4-piperidinyl}-1,3-benzoxazol-2(3H)-one;
3-{1-[trans-1-Methyl-4-(propyloxy)cyclohexyl]-4-piperidinyl}-1,3-benzoxazol-2(3H)-one;
3-{1-[trans-4-(Ethyloxy)-1-methylcyclohexyl]-4-piperidinyl}-2-oxo-2,3-dihydro-1,3-benzoxazole-5-carbonitrile;
3-{1-[trans-4-(Ethyloxy)-1-methylcyclohexyl]-4-piperidinyl}-6-fluoro-5-methyl-1,3-benzoxazol-2(3H)-one;
3-{1-[trans-4-(Ethyloxy)-1-methylcyclohexyl]-4-piperidinyl}-5-(methylsulfonyl)-1,3-benzoxazol-2(3H)-one;
3-{1-[trans-4-(Ethyloxy)-1-methylcyclohexyl]-4-piperidinyl}-5-(ethylsulfonyl)-1,3-benzoxazol-2(3H)-one;
5-Fluoro-3-{1-[trans-1-methyl-4-(propyloxy)cyclohexyl]-4-piperidinyl}-1,3-benzoxazol-2(3H)-one;
3-{1-[trans-4-(Ethyloxy)-1-methylcyclohexyl]-4-piperidinyl}-5-fluoro-1,3-benzoxazol-2(3H)-one;

3-{1-[trans-4-(Ethyloxy)-1-methylcyclohexyl]-4-piperidinyl}-5-(methyloxy)-1,3-benzoxazol-2(3H)-one;
3-{1-[trans-4-(Ethyloxy)cyclohexyl]-4-piperidinyl}-5-methyl-1,3-benzoxazol-2(3H)-one;
4-{1-[trans-4-(Ethyloxy)-1-methylcyclohexyl]-4-piperidinyl}-6-methyl-2H-1,4-benzoxazin-3(4H)-one;
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile;
3-[1-(cis-1-Methyl-4-{[2-(methyloxy)ethyl]oxy}cyclohexyl)-4-piperidnyl]-2-oxo-2,3-dihydro-1,3-benzoxazole-5-carbonitrile;
6-Methyl-1-{1-[trans-1-methyl-4-(propyloxy)cyclohexyl]-4-piperidinyl}-1,3-dihydro-2H-indol-2-one;
3-{1-[trans-4-Ethoxy-1-methylcyclohexyl]-4-piperidinyl}-7-fluoro-5-methyl-1,3-benzoxazol-2(3H)-one;
3-{1-[trans-4-Ethoxy-1-methylcyclohexyl]-4-piperidinyl}-6,7-difluoro-5-methyl-1,3-benzoxazol-2(3H)-one;
5-Methyl-3-{1-[trans-1-methyl-4-(methyloxy)cyclohexyl]-4-piperidinyl}-1,3-benzoxazol-2(3H)-one;
3-{1-[trans-4-(Ethyloxy)-1-methylcyclohexyl]-4-piperidinyl}-5,7-difluoro-1,3-benzoxazol-2(3H)-one;
3-{1-[trans-4-(Ethyloxy)-1-methylcyclohexyl]-4-piperidinyl}-5-[(trifluoromethyl)oxy]-1,3-benzoxazol-2(3H)-one;
3-{1-[trans-4-(Ethyloxy)-1-methylcyclohexyl]-4-piperidinyl}-5,6-difluoro-1,3-benzoxazol-2(3H)-one;
3-{1-[trans-4-(Ethyloxy)-1-methylcyclohexyl]-4-piperidinyl}-5-(trifluoromethyl)-1,3-benzoxazol-2(3H)-one;
6-Methyl-1-{1-[trans-1-methyl-4-(methyloxy)cyclohexyl]-4-piperidinyl}-1,3-dihydro-2H-indol-2-one;
3-{1-[trans-1-Methyl-4-(methyloxy)cyclohexyl]-4-piperidinyl}-2-oxo-2,3-dihydro-1,3-benzoxazole-5-carbonitrile;
1-{1-[trans-4-(Ethyloxy)-1-methylcyclohexyl]-4-piperidinyl}-6-methyl-1,3-dihydro-2H-indol-2-one;
3-{1-[trans-1-Methyl-4-(propyloxy)cyclohexyl]-4-piperidinyl}-5-(methylsulfonyl)-1,3-benzoxazol-2(3H)-one;
1-{1-[trans-4-(Ethyloxy)-1-methylcyclohexyl]-4-piperidinyl}-7-methyl-3,4-dihydro-2(1H)-quinolinone;
and salts thereof.
Further compounds according to the invention include:
3,3,6-Trimethyl-1-{1-[trans-1-methyl-4-(propyloxy)cyclohexyl]-4-piperidinyl}-1,3-dihydro-2H-indol-2-one;
6-Methyl-1-[1-(trans-1-methyl-4-{[2-(methyloxy)ethyl]oxy}cyclohexyl)-4-piperidnyl]-1,3-dihydro-2H-indol-2-one;
3-{1-[trans-1-Methyl-4-(propyloxy)cyclohexyl]-4-piperidinyl}-5-[(trifluoromethyl)sulfonyl]-1,3-benzoxazol-2(3H)-one;
6-Methyl-3-{1-[trans-1-methyl-4-(propyloxy)cyclohexyl]-4-piperidinyl}-5-(methylsulfonyl)-1,3-benzoxazol-2(3H)-one;
6-Methyl-5-(methylsulfonyl)-3-{1-[trans-4-(propyloxy)cyclohexyl]-4-piperidinyl}-1,3-benzoxazol-2(3H)-one;
5-Methyl-3-[1-(trans-1-methyl-4-{[2-(methyloxy)ethyl]oxy}cyclohexyl)-4-piperidinyl]-2-oxo-2,3-dihydro-1,3-benzoxazole-6-carbonitrile;
5-(Difluoromethoxy)-3-{1-[trans-4-(ethyloxy)-1-methylcyclohexyl]-4-piperidinyl}-1,3-benzoxazol-2(3H)-one;
5-Methyl-3-[1-(trans-1-methyl-4-{[2-(methyloxy)ethyl]oxy}cyclohexyl)-4-piperidinyl]-1,3-benzoxazol-2(3H)-one;
3-[1-(trans-1-Methyl-4-{[2-(methyloxy)ethyl]oxy}cyclohexyl)-4-piperidinyl]-5-(methyloxy)-1,3-benzoxazol-2(3H)-one;
3-(1-{trans-4-[(Cyclopropylmethyl)oxy]-1-methylcyclohexyl}-4-piperidinyl)-5-(methylsulfonyl)-1,3-benzoxazol-2(3H)-one;
3-(1-{trans-1-Methyl-4-[(1-methylethyl)oxy]cyclohexyl}-4-piperidinyl)-5-(methylsulfonyl)-1,3-benzoxazol-2(3H)-one;
3-[1-(trans-1-methyl-4-{[2-(methyloxy)ethyl]oxy}cyclohexyl)-4-piperidinyl]-5-(trifluoromethyl)-1,3-benzoxazol-2(3H)-one;
6-Fluoro-5-methyl-3-[1-(trans-1-methyl-4-{[2-(methyloxy)ethyl]-oxy}cyclohexyl)-4-piperidinyl]-1,3-benzoxazol-2(3H)-one;
7-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile;
7-Fluoro-5-methyl-3-[1-(trans-1-methyl-4-{[2-(methyloxy)ethyl]oxy}cyclohexyl)-4-piperidinyl]-1,3-benzoxazol-2(3H)-one;
6-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile;
3-[1-(trans-1-Methyl-4-{[2-(methyloxy)ethyl]oxy}cyclohexyl)-4-piperidinyl]-5-(methylsulfonyl)-1,3-benzoxazol-2(3H)-one;
3-[1-(trans-1-Methyl-4-{[2-(methyloxy)ethyl]oxy}cyclohexyl)-4-piperidinyl]-5-[(methyloxy)methyl]-1,3-benzoxazol-2(3H)-one;
1-[1-(trans-1-Methyl-4-[2-(methoxyethoxy)cyclohexyl]-4-piperidinyl]-6-(methoxymethyl)-1,3-dihydro-2H-indol-2-one;
3-{1-[trans-4-(Ethyloxy)-1-methylcyclohexyl]-4-piperidinyl}-2-oxo-2,3-dihydro-1,3-benzoxazole-5-carboxamide;
3-[1-(trans-1-Methyl-4-{[2-(methyloxy)ethyl]oxy}cyclohexyl)-4-piperidinyl]-2-oxo-2,3-dihydro-1,3-benzoxazole-5-carboxamide;
5-Acetyl-3-[1-(trans-1-methyl-4-{[2-(methyloxy)ethyl]oxy}cyclohexyl)-4-piperidinyl]-1,3-benzoxazol-2(3H)-one;
3-[1-(trans-1-Methyl-4-{[2-(methyloxy)ethyl]oxy}cyclohexyl)-4-piperidinyl]-5-[N-(methyloxy)ethanimidoyl]-1,3-benzoxazol-2(3H)-one;
1-[1-(trans-4-{2-Methoxyethoxy}cyclohexyl)-4-piperidinyl]-2-oxo-2,3-d hydro-1H-indole-6-carbonitrile;
1-[1-(cis-4-{2-Methoxyethoxy}cyclohexyl)-4-piperidinyl]-2-oxo-2,3-dihydro-1H-indole-6-carbonitrile;
3-{1-[trans-4-(Ethyloxy)cyclohexyl]-4-piperidinyl}-5-fluoro-1,3-benzoxazol-2(3H)-one;
and
3-{1-[trans-4-(Ethyloxy)-1-methylcyclohexyl]-4-piperidinyl}-5-methyl[1,3]oxazolo[4,5-b]pyridin-2(3H)-one;
and salts thereof.
In one embodiment, the salt of a compound listed above is a pharmaceutically acceptable salt.
In one embodiment, the pharmaceutically acceptable salt is a hydrochloride salt, a trifluoroacetate salt, a methanesulfonate salt, a 4-methylbenzenesulfonate salt, or a formate salt.
In one embodiment, the pharmaceutically acceptable salt is a hydrochloride salt, a trifluoroacetate salt, or a formate salt.
In one embodiment the pharmaceutically acceptable salt is the hydrochloride salt.
In one embodiment, the compound of the present invention is selected from:—
3-{1-[trans-4-(Ethyloxy)-1-methylcyclohexyl]-4-piperidinyl}-1,3-benz oxazol-2(3H)-one hydrochloride;
3-{1-[trans-1-Methyl-4-(propyloxy)cyclohexyl]-4-piperidinyl}-1,3-benzoxazol-2(3H)-one hydrochloride;

3-{1-[trans-4-(Ethyloxy)-1-methylcyclohexyl]-4-piperidinyl}-2-oxo-2,3-dihydro-1,3-benzoxazole-5-carbonitrile hydrochloride;
3-{1-[trans-4-(Ethyloxy)-1-methylcyclohexyl]-4-piperidinyl}-6-fluoro-5-methyl-1,3-benzoxazol-2(3H)-one hydrochloride;
3-{1-[trans-4-(Ethyloxy)-1-methylcyclohexyl]-4-piperidinyl}-5-(methylsulfonyl)-1,3-benzoxazol-2(3H)-one hydrochloride;
3-{1-[trans-4-(Ethyloxy)-1-methylcyclohexyl]-4-piperidinyl}-5-(ethylsulfonyl)-1,3-benzoxazol-2(3H)-one hydrochloride;
5-Fluoro-3-{1-[trans-1-methyl-4-(propyloxy)cyclohexyl]-4-piperidinyl}-1,3-benzoxazol-2(3H)-one hydrochloride;
3-{1-[trans-4-(Ethyloxy)-1-methylcyclohexyl]-4-piperidinyl}-5-fluoro-1,3-benzoxazol-2(3H)-one hydrochloride;
3-{1-[trans-4-(Ethyloxy)-1-methylcyclohexyl]-4-piperidinyl}-5-(methyloxy)-1,3-benzoxazol-2(3H)-one hydrochloride;
3-{1-[trans-4-(Ethyloxy)cyclohexyl]-4-piperidinyl}-5-methyl-1,3-benzoxazol-2(3H)-one hydrochloride;
4-{1-[trans-4-(Ethyloxy)-1-methylcyclohexyl]-4-piperidinyl}-6-methyl-2H-1,4-benzoxazin-3(4H)-one hydrochloride;
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile hydrochloride;
3-[1-(cis-1-Methyl-4-{[2-(methyloxy)ethyl]oxy}cyclohexyl)-4-piperidinyl]-2-oxo-2,3-dihydro-1,3-benzoxazole-5-carbonitrile hydrochloride;
6-Methyl-1-{1-[trans-1-methyl-4-(propyloxy)cyclohexyl]-4-piperidinyl}-1,3-dihydro-2H-indol-2-one hydrochloride;
3-{1-[trans-4-Ethoxy-1-methylcyclohexyl]-4-piperidinyl}-7-fluoro-5-methyl-1,3-benzoxazol-2(3H)-one hydrochloride;
3-{1-[trans-4-Ethoxy-1-methylcyclohexyl]-4-piperidinyl}-6,7-difluoro-5-methyl-1,3-benzoxazol-2(3H)-one hydrochloride;
5-Methyl-3-{1-[trans-1-methyl-4-(methyloxy)cyclohexyl]-4-piperidinyl}-1,3-benzoxazol-2(3H)-one hydrochloride;
3-{1-[trans-4-(Ethyloxy)-1-methylcyclohexyl]-4-piperidinyl}-5,7-difluoro-1,3-benzoxazol-2(3H)-one hydrochloride;
3-{1-[trans-4-(Ethyloxy)-1-methylcyclohexyl]-4-piperidinyl}-5-[(trifluoromethyl)oxy]-1,3-benzoxazol-2(3H)-one hydrochloride;
3-{1-[trans-4-(Ethyloxy)-1-methylcyclohexyl]-4-piperidinyl}-5,6-difluoro-1,3-benzoxazol-2(3H)-one hydrochloride;
3-{1-[trans-4-(Ethyloxy)-1-methylcyclohexyl]-4-piperidinyl}-5-(trifluoromethyl)-1,3-benzoxazol-2(3H)-one hydrochloride;
6-Methyl-1-{1-[trans-1-methyl-4-(methyloxy)cyclohexyl]-4-piperidinyl}-1,3-dihydro-2H-indol-2-one hydrochloride;
3-{1-[trans-1-Methyl-4-(methyloxy)cyclohexyl]-4-piperidinyl}-2-oxo-2,3-dihydro-1,3-benzoxazole-5-carbonitrile hydrochloride;
1-{1-[trans-4-(Ethyloxy)-1-methylcyclohexyl]-4-piperidinyl}-6-methyl-1,3-dihydro-2H-indol-2-one hydrochloride;
3-{1-[trans-1-Methyl-4-(propyloxy)cyclohexyl]-4-piperidinyl}-5-(methylsulfonyl)-1,3-benzoxazol-2(3H)-one hydrochloride; and
1-{1-[trans-4-(Ethyloxy)-1-methylcyclohexyl]-4-piperidinyl}-7-methyl-3,4-dihydro-2(1H)-quinolinone.

In one embodiment, the compound of the present invention is selected from:—
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile;
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile hydrochloride;
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile 4-methylbenzenesulfonate; and
3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile methanesulfonate.

In one embodiment, the compound of the present invention is selected from:—
3,3,6-Trimethyl-1-{1-[trans-1-methyl-4-(propyloxy)cyclohexyl]-4-piperidinyl}-1,3-dihydro-2H-indol-2-one hydrochloride;
6-Methyl-1-[1-(trans-1-methyl-4-{[2-(methyloxy)ethyl]oxy}cyclohexyl)-4-piperidinyl]-1,3-dihydro-2H-indol-2-one hydrochloride;
3-{1-[trans-1-Methyl-4-(propyloxy)cyclohexyl]-4-piperidinyl}-5-[(trifluoromethyl)sulfonyl]-1,3-benzoxazol-2(3H)-one hydrochloride;
6-Methyl-3-{1-[trans-1-methyl-4-(propyloxy)cyclohexyl]-4-piperidinyl}-5-(methylsulfonyl)-1,3-benzoxazol-2(3H)-one hydrochloride;
6-Methyl-5-(methylsulfonyl)-3-{1-[trans-4-(propyloxy)cyclohexyl]-4-piperidinyl}-1,3-benzoxazol-2(3H)-one hydrochloride;
5-Methyl-3-[1-(trans-1-methyl-4-{[2-(methyloxy)ethyl]oxy}cyclohexyl)-4-piperidinyl]-2-oxo-2,3-dihydro-1,3-benzoxazole-6-carbonitrile hydrochloride;
5-(Difluoromethoxy)-3-{1-[trans-4-(ethyloxy)-1-methylcyclohexyl]-4-piperidinyl}-1,3-benzoxazol-2(3H)-one hydrochloride;
5-Methyl-3-[1-(trans-1-methyl-4-{[2-(methyloxy)ethyl]oxy}cyclohexyl)-4-piperidinyl]-1,3-benzoxazol-2(3H)-one hydrochloride;
3-[1-(trans-1-Methyl-4-{[2-(methyloxy)ethyl]oxy}cyclohexyl)-4-piperidinyl]-5-(methyloxy)-1,3-benzoxazol-2(3H)-one hydrochloride;
3-(1-{trans-4-[(Cyclopropylmethyl)oxy]-1-methylcyclohexyl}-4-piperidinyl)-5-(methylsulfonyl)-1,3-benzoxazol-2(3H)-one hydrochloride;
3-(1-{trans-1-Methyl-4-[(1-methylethyl)oxy]cyclohexyl}-4-piperidinyl)-5-(methylsulfonyl)-1,3-benzoxazol-2(3H)-one hydrochloride;
3-[1-(trans-1-methyl-4-{[2-(methyloxy)ethyl]oxy}cyclohexyl)-4-piperidinyl]-5-(trifluoromethyl)-1,3-benzoxazol-2(3H)-one hydrochloride;
6-Fluoro-5-methyl-3-[1-(trans-1-methyl-4-{[2-(methyloxy)ethyl]-oxy}cyclohexyl)-4-piperidinyl]-1,3-benzoxazol-2(3H)-one hydrochloride;
7-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride;
7-Fluoro-5-methyl-3-[1-(trans-1-methyl-4-{[2-(methyloxy)ethyl]oxy}cyclohexyl)-4-piperidinyl]-1,3-benzoxazol-2(3H)-one hydrochloride;

6-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride;

3-[1-(trans-1-Methyl-4-{[2-(methyloxy)ethyl]oxy}cyclohexyl)-4-piperidinyl]-5-(methylsulfonyl)-1,3-benzoxazol-2(3H)-one hydrochloride;

3-[1-(trans-1-Methyl-4-{[2-(methyloxy)ethyl]oxy}cyclohexyl)-4-piperidinyl]-5-[(methyloxy)methyl]-1,3-benzoxazol-2(3H)-one hydrochloride;

1-[1-(trans-1-Methyl-4-[2-(methoxyethoxy)cyclohexyl]-4-piperidinyl]-6-(methoxymethyl)-1,3-dihydro-2H-indol-2-one;

1-[1-(trans-1-Methyl-4-[2-(methoxyethoxy)cyclohexyl]-4-piperidinyl]-6-(methoxymethyl)-1,3-dihydro-2H-indol-2-one hydrochloride;

3-{1-[trans-4-(Ethyloxy)-1-methylcyclohexyl]-4-piperidinyl}-2-oxo-2,3-dihydro-1,3-benzoxazole-5-carboxamide hydrochloride;

3-[1-(trans-1-Methyl-4-{[2-(methyloxy)ethyl]oxy}cyclohexyl)-4-piperidinyl]-2-oxo-2,3-dihydro-1,3-benzoxazole-5-carboxamide hydrochloride;

5-Acetyl-3-[1-(trans-1-methyl-4-{[2-(methyloxy)ethyl]oxy}cyclohexyl)-4-piperidinyl]-1,3-benzoxazol-2(3H)-one hydrochloride;

3-[1-(trans-1-Methyl-4-{[2-(methyloxy)ethyl]oxy}cyclohexyl)-4-piperidinyl]-5-[N-(methyloxy)ethanimidoyl]-1,3-benzoxazol-2(3H)-one hydrochloride;

1-[1-(trans-4-{2-Methoxyethoxy}cyclohexyl)-4-piperidinyl]-2-oxo-2,3-dihydro-1H-indole-6-carbonitrile;

1-[1-(cis-4-{2-Methoxyethoxy}cyclohexyl)-4-piperidinyl]-2-oxo-2,3-dihydro-1H-indole-6-carbonitrile;

3-{1-[trans-4-(Ethyloxy)cyclohexyl]-4-piperidinyl}-5-fluoro-1,3-benzoxazol-2(3H)-one;

and

3-{1-[trans-4-(Ethyloxy)-1-methylcyclohexyl]-4-piperidinyl}-5-methyl[1,3]oxazolo[4,5-b]pyridin-2(3H)-one hydrochloride.

In one embodiment, the compound of the present invention is selected from 3-[1-(1-methyl-4-{[2-(methyloxy)ethyl]oxy}cyclohexyl)-4-piperidinyl]-2-oxo-2,3-dihydro-1,3-benzoxazole-5-carbonitrile and pharmaceutically acceptable salts thereof.

In one embodiment, the compound of the present invention is selected from 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile and pharmaceutically acceptable salts thereof.

In one embodiment, the compound of the present invention is 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile.

In one embodiment, the compound of the present invention is 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride.

In a further aspect, the invention provides a general process (A1) for preparing compounds of formula (I) in which Q=H, which process comprises:

coupling a compound of formula (II):

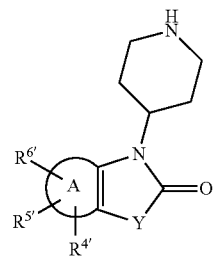

with a compound of formula (III)

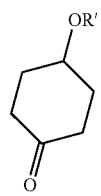

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, and Y is O, S, $CH_2$ optionally substituted with one or two fluorine atoms, $CH_2$ optionally substituted with one or two methyl groups, $CH_2CH_2$, $OCH_2$, or $CH_2O$.

The reaction is carried out under conditions suitable for reductive alkylation. The reductive alkylation reaction is typically carried out using sodium triacetoxyborohydride in dichloroethane, optionally in the presence of triethylamine, and optionally in the presence of titanium tetraisopropoxide. Alternatively sodium cyanoborohydride can be used as the reducing reagent in solvents such as methanol or ethanol, or the reductive alkylation can be effected under catalytic hydrogenation conditions using a palladium catalyst. In a further variation, the compounds (II) and (III) can be condensed under dehydrating conditions e.g. molecular sieves or magnesium sulfate, and the resultant imine or enamine reduced using for example sodium borohydride or by catalytic hydrogenation.

This reaction can generate a mixture of cis and trans isomers which can be separated, for example, by chromatography or crystallisation.

A modification of general process (A1) is required where Q is $C_{1-6}$alkyl. Thus, in general process (A2), a compound of formula (II) can be reacted with a compound of formula (III) in the presence of a source of cyanide, e.g. acetone cyanohydrin, to form the cyano intermediate (IV) which can be reacted with an alkyl Grignard reagent QMgX to form compounds of formula (I) in which Q is $C_{1-6}$alkyl.

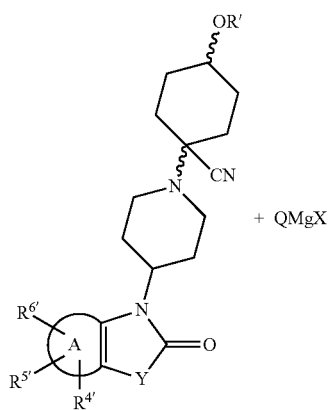

(IV)

+ QMgX wherein R$^{6'}$ is a group R$^6$ as previously defined, or a group convertible to R$^6$, R$^{5'}$ is a group R$^5$ as previously defined, or a group convertible to R$^5$, R$^{4'}$ is a group R$^4$ as previously defined, or a group convertible to R$^4$, ring A is as previously defined, R' is a group R as previously defined, or a group convertible to R, Y is O, S, CH$_2$ optionally substituted with one or two fluorine atoms, CH$_2$ optionally substituted with one or two methyl groups, CH$_2$CH$_2$, OCH$_2$, or CH$_2$O, Q is C$_{1-6}$alkyl, and X is bromo or iodo or chloro.

This reaction can generate a mixture of cis and trans isomers which can be separated, for example, by chromatography or crystallisation.

In a further aspect, the invention provides a general process (B) for preparing compounds of formula (I) in which Y=O or S, which process comprises:
coupling a compound of formula (V)

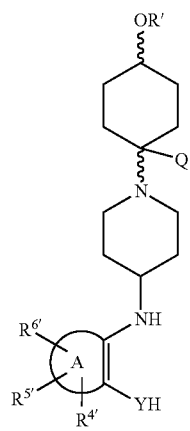

(V)

with a compound of formula (VI)

(VI)

wherein R$^{6'}$ is a group R$^6$ as previously defined, or a group convertible to R$^6$, R$^{5'}$ is a group R$^5$ as previously defined, or a group convertible to R$^5$, R$^{4'}$ is a group R$^4$ as previously defined, or a group convertible to R$^4$, ring A is as previously defined, R' is a group R as previously defined, or a group convertible to R, Y is O or S, Q is as previously defined, and X and X' both represent leaving groups. X and X' can be the same or different and examples are Cl, PhO, EtO, and imidazole. When X and X' are both Cl, i.e. (VI) is phosgene, this reagent can be generated in situ e.g. from diphosgene or triphosgene.

The above reaction can be carried out using standard methodology e.g. reacting the amine (V) with the reagent (VI) in an inert solvent for example dichloromethane or toluene, optionally in the presence of a base such as triethylamine or potassium carbonate, and optionally with heating.

It will be appreciated that compounds of formula (V) can be pure cis or trans isomers, or a mixture of isomers. If necessary, separation of pure cis and trans isomers after the reaction with (VI) can be achieved by chromatography or crystallisation.

In a further aspect, the invention provides a general process (C) for preparing compounds of formula (I) in which Y=CH$_2$, which process comprises hydrolysis, decarboxylation and cyclisation of a compound of formula (VII):

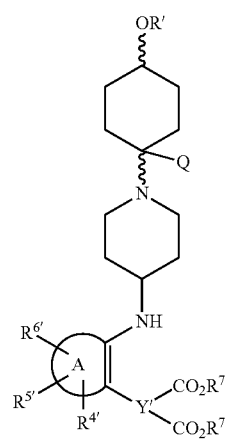

(VII)

wherein R$^{6'}$ is a group R$^6$ as previously defined, or a group convertible to R$^6$, R$^{5'}$ is a group R$^5$ as previously defined, or a group convertible to R$^5$, R$^{4'}$ is a group R$^4$ as previously defined, or a group convertible to R$^4$, ring A is as previously defined, R' is a group R as previously defined, or a group convertible to R, Y' is CH, Q is as previously defined, and R$^7$ represents C$_{1-6}$alkyl, benzyl, or other acid protecting group; using conditions similar to those described in Tet Lett 2001, 42, 6943.

It will be appreciated that compounds of formula (VII) can be pure cis or trans isomers, or a mixture of isomers. If necessary, separation of pure cis and trans isomers after the cyclisation of (VII) can be achieved by chromatography or crystallisation.

In a further aspect, the invention provides a general process (D) for preparing compounds of formula (I) in which Y=CH$_2$CH$_2$, which process comprises:

hydrolysis and cyclisation of a compound of formula (VIII)

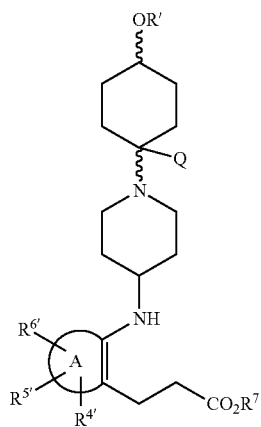

(VIII)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Q is as previously defined, and $R^7$ represents $C_{1-6}$alkyl, benzyl, or other acid protecting group. Hydrolysis of the ester group $CO_2R_7$ can be accomplished using standard conditions, and cyclisation can be effected by activation of the acid group using for example EDC (1-ethyl-3-(dimethylaminopropyl)carbodiimide) and HOBT (1-hydroxybenzotriazole).

It will be appreciated that compounds of formula (VIII) can be pure cis or trans isomers, or a mixture of isomers. If necessary, separation of pure cis and trans isomers after the cyclisation of (VIII) can be achieved by chromatography or crystallisation.

In a further aspect, the invention provides a general process (E) for preparing compounds of formula (I) in which $Y=OCH_2$, which process comprises:

treatment of a compound of formula (IX) with a base, such as KO'Bu in an inert solvent for example THF, optionally with heating

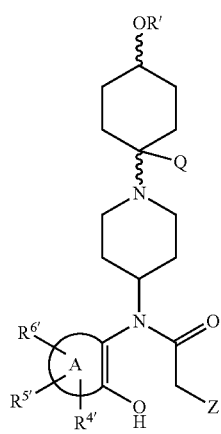

(IX)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Q is as previously defined, and Z is a leaving group such as bromo or chloro.

It will be appreciated that compounds of formula (IX) can be pure cis or trans isomers, or a mixture of isomers. If necessary, separation of pure cis and trans isomers after the cyclisation of (IX) can be achieved by chromatography or crystallisation.

In a further aspect, the invention provides a general process (F) for preparing compounds of formula (I) which process comprises:

treatment of a compound of formula (X)

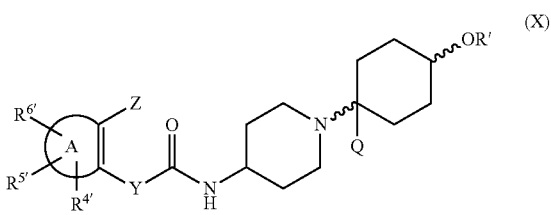

(X)

with a palladium or copper catalyst to effect an intramolecular cyclisation; wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Y is O, S, $CH_2$ optionally substituted with one or two fluorine atoms, $CH_2$ optionally substituted with one or two $CH_3$ groups, $CH_2CH_2$, $OCH_2$, or $CH_2O$, Q is as previously defined, and Z is a leaving group such as bromo, iodo, chloro or triflate.

The cyclisation reaction can be carried out using a variety of palladium or copper reagents as described in the literature (JACS, 2003, 125, 6653; Tet. Lett., 2004, 45, 8535; or JACS, 2002, 124, 7421.)

It will be appreciated that compounds of formula (X) can be pure cis or trans isomers, or a mixture of isomers. If necessary, separation of pure cis and trans isomers after the intramolecular cyclisation can be achieved by chromatography or crystallisation.

In a further aspect, the invention provides a general process (G) for preparing compounds of formula (I) which process comprises:

coupling a compound of formula (XIII):

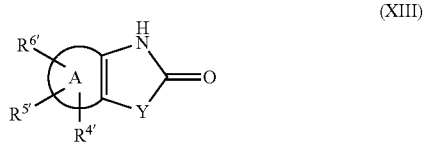

(XIII)

with a compound of formula (XIV)

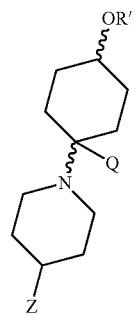

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Y is O, S, $CH_2$ optionally substituted with one or two fluorine atoms, $CH_2$ optionally substituted with one or two $CH_3$ groups, $CH_2CH_2$, $OCH_2$, or $CH_2O$, Q is as previously defined, and Z is hydroxy or a leaving group such as chloro, bromo or iodo, or alkyl/aryl sulfonate.

The alkylation reaction can be carried out under classical alkylation (Z=a leaving group) or Mitsunobu reaction (Z=OH) conditions. Using classical alkylation conditions, the intermediate (XIII) can be deprotonated using a base such as sodium hydride in an inert solvent such as dimethylformamide, and then treated with the alkylating reagent (XIV), optionally with heating. The Mitsunobu reaction with (XIII) and (XIV) Z=OH can be carried out using standard conditions e.g. triphenylphosphine and diethylazodicarboxylate in an inert solvent such as dichloromethane or tetrahydrofuran at room temperature.

It will be appreciated that compounds of formula (XIV) can be pure cis or trans isomers, or a mixture of isomers. If necessary, separation of pure cis and trans isomers after the displacement reaction can be achieved by chromatography or crystallisation.

Conversion of $R^{6'}$, $R^{5'}$ and $R^{4'}$ to $R^6$, $R^5$ and $R^4$ respectively, or interconversions of $R^6$, $R^5$ and $R^4$ may be accomplished as illustrated below for $R^{6'}$ For example, when $R^{6'}$ is a halogen, it can be converted to an alkoxy, trifluoromethyl or methylsulphonyl group by copper catalysed reaction, using an alcohol, methyl fluorosulfonyl(difluoro)acetate or sodium methanesulphinate respectively. It may also be converted to an alkyl group with an organometallic reagent, for example an alkylstannane.

Alternatively, when $R^{6'}$ is a halogen, it can also be converted to a cyano group, for example, by palladium catalysed reaction using zinc cyanide.

As another example, when $R^{6'}$ is hydroxy, it may be converted to alkoxy by reaction with an alkyl halide or sulfonate, or to trifluoromethoxy by conversion to the xanthate followed by oxidation in the presence of fluoride ion.

As a further example, when $R^{6'}$ is methyl, it may be converted to trifluoromethyl by chlorination or bromination followed by displacement of the introduced halogens with fluoride.

Conversion of R' to R or interconversions of R may be accomplished as indicated below.

For example when R' is benzyl, the benzyl group can be removed using standard methodology, e.g. catalytic hydrogenation over palladium on carbon, to provide the alcohol. Alkylation of the resultant alcohol using a strong base e.g. sodium hydride and a $C_{1-6}$ alkylating agent e.g. methyl iodide, ethyl iodide or propyl iodide, will afford the desired product.

As another example, when R is methyl, the methyl group can be removed by treatment with a dealkylating agent such as boron tribromide to afford the alcohol intermediate, which can be alkylated in a similar manner to that described above. Alternatively the alcohol intermediate can be converted to R=trifluoromethyl by conversion to the xanthate followed by oxidation in the presence of fluoride ion.

Conversion of compounds wherein Y=$CH_2$ to compounds wherein Y=$C(Me)_2$ can be achieved by treatment of the Y=$CH_2$ compound with strong base e.g. sodium hydride in an inert solvent e.g. DMF, followed by addition of excess methyl iodide.

Compounds of formula (II) are generally known in the literature or can be prepared by a range of different processes, for example:
(a) reductive amination of the amine (XV) with the ketone (XVI), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, Y' is a group OH or SH or a group convertible to Y', and P represents a nitrogen protecting group (e.g. Boc, acetyl, trifluoroacetyl, ethoxycarbonyl, benzyloxycarbonyl), to give (XVII), followed by deprotection of Y' if necessary, and cyclisation using phosgene or a phosgene equivalent, and deprotection of the piperidine nitrogen using standard literature conditions (Scheme 1).

Scheme 1.

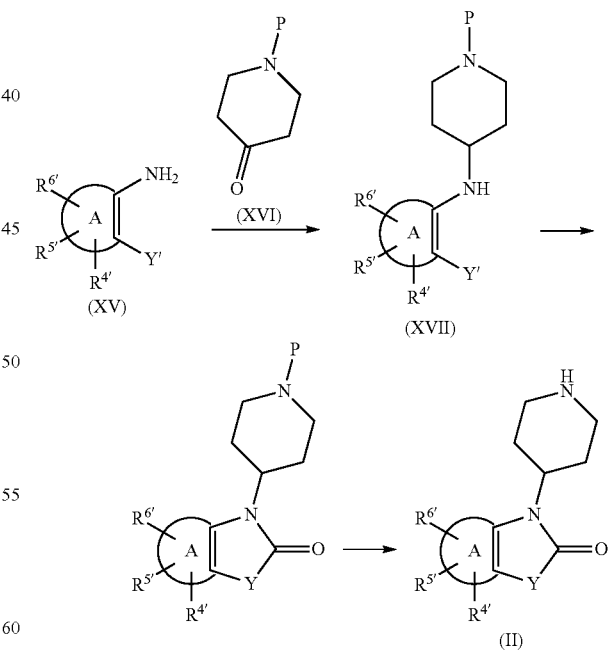

Compounds of formula (XV) are commercially available or can be prepared by standard methodology. The compound (XVI) in which P=Boc is commercially available.
(b) metal catalysed cyclisation of an intermediate (XVIII) followed by deprotection of the piperidine nitrogen, wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, Y is O, S, $CH_2$ optionally substituted with one or two fluorine atoms, $CH_2CH_2$, $OCH_2$, or $CH_2O$, P represents a nitrogen protecting group (e.g. Boc, acetyl, trifluoroacetyl, benzyloxycarbonyl), and Z represents a leaving group such as bromo, iodo, chloro or triflate. Reaction conditions for the metal catalysed cyclisation are summarised in Process F. The carbamate, thiocarbamate or amide intermediate (XVIII) can be prepared using any of the classical methods for formation of this functionality as illustrated in Scheme 2. Compounds of formula (XIX) and (XI) are commercially available or can be prepared by known methodology. The compound (XX) in which P=Boc is commercially available. The compound (LX) can be prepared from N-protected piperidine-4-carboxylic acid, for example by Curtius rearrangement using diphenylphosphoryl azide.

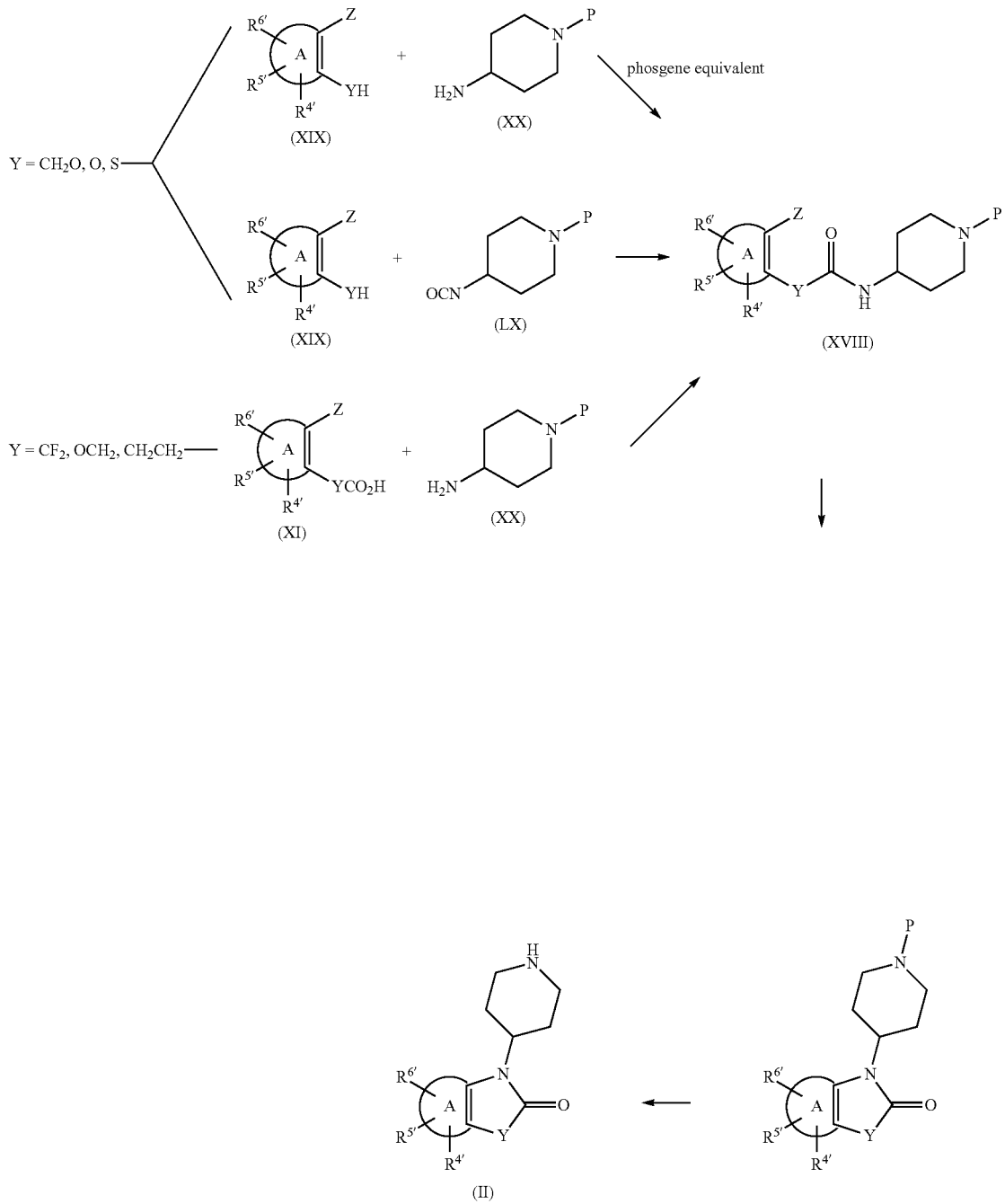

(c) metal catalysed reaction between the amine (XX) and a suitably substituted aromatic compound (XXI) wherein R⁶' is a group R⁶ as previously defined, or a group convertible to R⁶, R⁵' is a group R⁵ as previously defined, or a group convertible to R⁵, R⁴' is a group R⁴ as previously defined, or a group convertible to R⁴, ring A is as previously defined, Y' is OH or SH or a group convertible to Y', P represents a nitrogen protecting group (e.g. Boc, acetyl, trifluoroacetyl, benzyloxycarbonyl), and Z represents a leaving group such as bromo, iodo, chloro or triflate (Scheme 3). This process generates intermediates of formula (XXII) and subsequent reactions are similar to that for Scheme 1. Compounds of formula (XXI) are commercially available or can be prepared by known methodology. The compound (XX) in which P=Boc is commercially available.

Compounds of formula (XIII) are commercially available or can be prepared by known methodology. Compounds of formula (XXIII) are commercially available, or can be prepared using standard literature methodology.

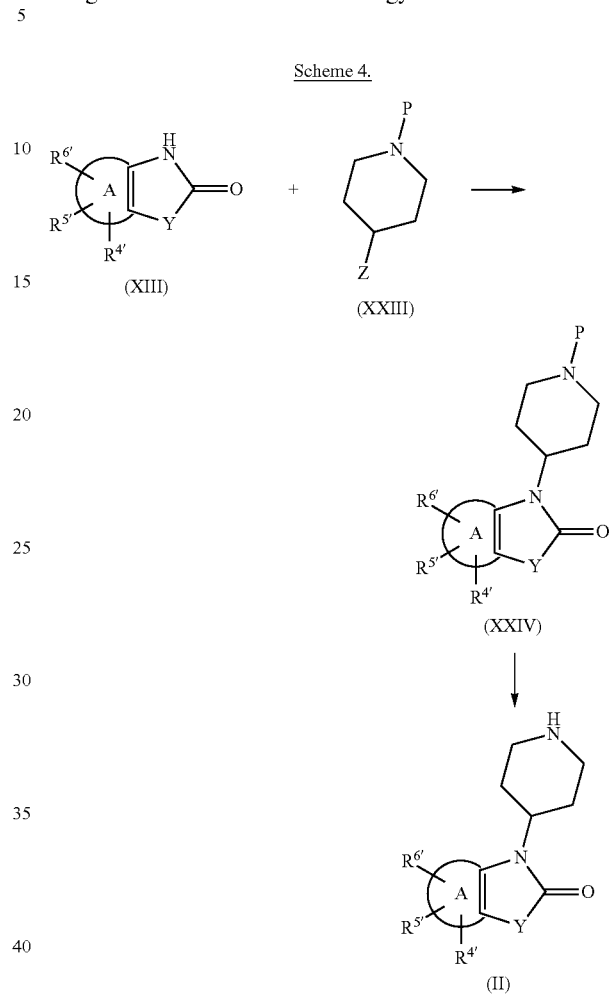

(d) alkylation of the heterocycle (XIII) with the intermediate (XXIII) wherein R⁶' is a group R⁶ as previously defined, or a group convertible to R⁶, R⁵ is a group R⁵ as previously defined, or a group convertible to R⁵, R⁴' is a group R⁴ as previously defined, or a group convertible to R⁴, ring A is as previously defined, Y is O, S or CH₂ optionally substituted with one or two fluorine atoms, P represents a nitrogen protecting group (e.g. Boc, acetyl, trifluoroacetyl, benzyloxycarbonyl), and Z represents a leaving group such as bromo, iodo, chloro, or mesylate, to give the intermediate (XXIV), followed by deprotection of the piperidine nitrogen (Scheme 4).

Compounds of formula (III) can be prepared by standard literature methodology.

Compounds of formula (V) can be prepared by a number of different processes e.g.:

(e) metal catalysed reaction of the amine (XXV) with the ortho substituted aromatic compound (XXI), wherein R⁶' is a group R⁶ as previously defined, or a group convertible to R⁶, R⁵' is a group R⁵ as previously defined, or a group convertible to R⁵, R⁴' is a group R⁴ as previously defined, or a group convertible to R⁴, ring A is as previously defined, Y' is OH or SH or a group convertible to Y', R' is a group R as previously defined, or a group convertible to R, Q is as previously defined, and Z represents a leaving group such as bromo, iodo, chloro or triflate (Scheme 5) followed by deprotection of Y' if required. Compounds of formula (XXI) are commercially available or can be prepared by standard methodology. Compounds of formula (XXV) can be prepared as shown in Schemes 12, 13, 14 and 15.

It will be appreciated that compounds of formula (XXV) can be pure cis or trans isomers, or a mixture of isomers. If necessary, separation of pure cis and trans isomers after the reaction with (XXI) can be achieved by chromatography or crystallisation.

Scheme 5.

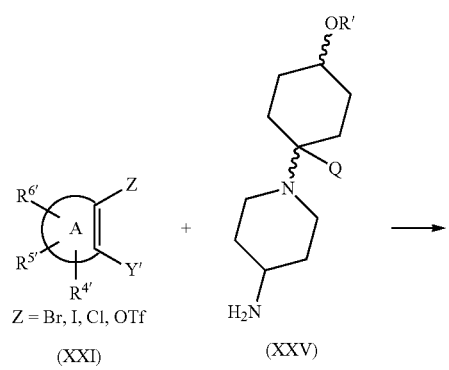

Scheme 6.

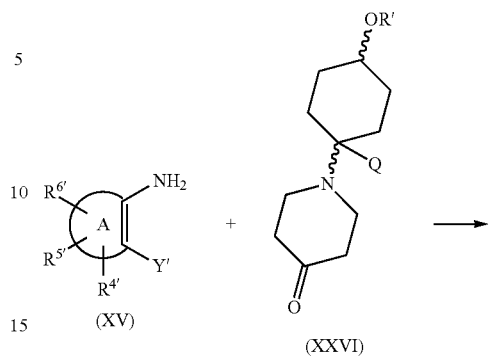

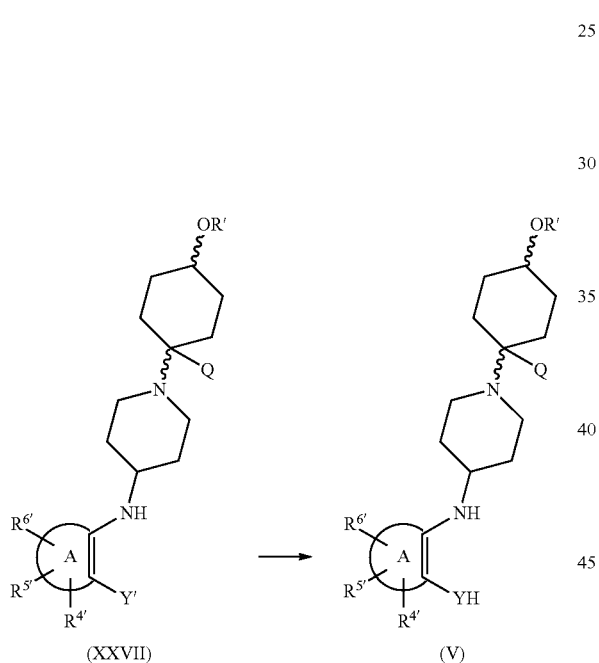

(f) Reductive alkylation of the amine (XV) with the piperidone (XXVI) wherein R$^{6'}$ is a group R$^6$ as previously defined, or a group convertible to R$^6$, R$^{5'}$ is a group R$^5$ as previously defined, or a group convertible to R$^5$, R$^{4'}$ is a group R$^4$ as previously defined, or a group convertible to R$^4$, ring A is as previously defined, Y' is OH or SH or a group convertible to Y', R' is a group R as previously defined, or a group convertible to R, and Q is as previously defined, using for example sodium triacetoxyborohydride in dichloroethane to give the intermediate (XXVII), followed by deprotection of Y' if required (Scheme 6). Compounds of formula (XXVI) can be prepared as shown in Schemes 13, 14 and 15. It will be appreciated that compounds of formula (XXVI) can be pure cis or trans isomers, or a mixture of isomers. If necessary, separation of pure cis and trans isomers after the reaction with (XV) can be achieved by chromatography or crystallisation.

Compounds of formula (VI) are commercially available e.g. carbonyl diimidazole, phosgene, diphosgene, triphosgene, phenyl chloroformate, diethyl carbonate.

Compounds of formula (VII) in which Y' is CH can be prepared as illustrated in Scheme 7.

Displacement of Z from the substituted nitro compound (XXVIII) with the malonate (XXIX) wherein R$^{6'}$ is a group R$^6$ as previously defined, or a group convertible to R$^6$, R$^{6'}$ is a group R$^5$ as previously defined, or a group convertible to R$^5$, R$^{4'}$ is a group R$^4$ as previously defined, or a group convertible to R$^4$, ring A is as previously defined, and R$^7$ is a C$_{1-6}$alkyl or arylalkyl group, using standard conditions for aromatic nucleophilic substitution (Scheme 7) to give (XXX), followed by reduction of the nitro group, and reductive alkylation of the resultant amine (XXXI) with the ketone (XXVI) wherein R' is a group R as previously defined, or a group convertible to R, and Q is as previously defined. Compounds of formula (XXVIII) are commercially available, or can be prepared using standard literature methodology. Compounds of formula (XXIX) are commercially available.

It will be appreciated that compounds of formula (XXVI) can be pure cis or trans isomers, or a mixture of isomers. If necessary, separation of pure cis and trans isomers after the reaction with (XXXI) can be achieved by chromatography or crystallisation.

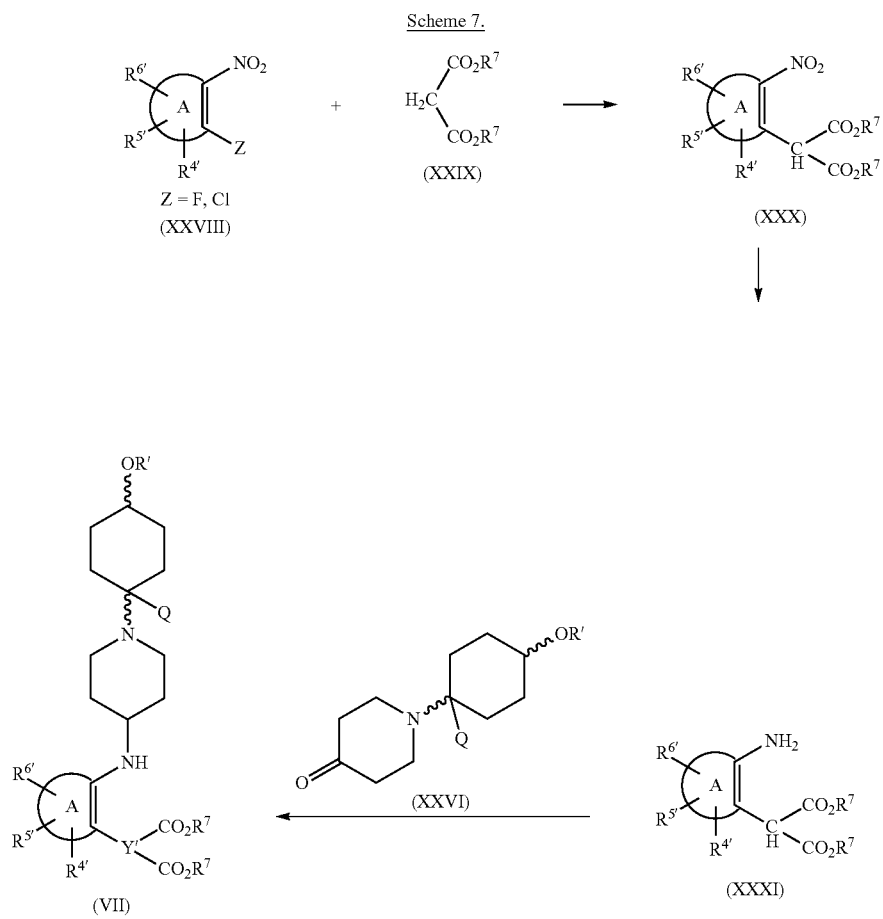

Compounds of formula (VIII) can be prepared as illustrated in Scheme 8.

Wittig-Horner reaction of the aldehyde (XXXII) with the appropriate phosphono acetate (XXXIIb) using standard conditions provides the cinnamate (XXXIII). Reduction of the nitro group and double bond leading to the amine (XXXIV), can be followed by reductive alkylation with ketone (XXVI) to give amine (VIII) (Scheme 8), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, and Q is as previously defined, and $R^7$ is a $C_{1-6}$alkyl group or other acid protecting group. Compounds of formula (XXXII) are commercially available, or can be prepared using standard literature methodology. Compounds of formula (XXXIIb) are commercivially available.

It will be appreciated that compounds of formula (XXVI) can be pure cis or trans isomers, or a mixture of isomers. If necessary, separation of pure cis and trans isomers after the reaction with (XXXIV) can be achieved by chromatography or crystallisation.

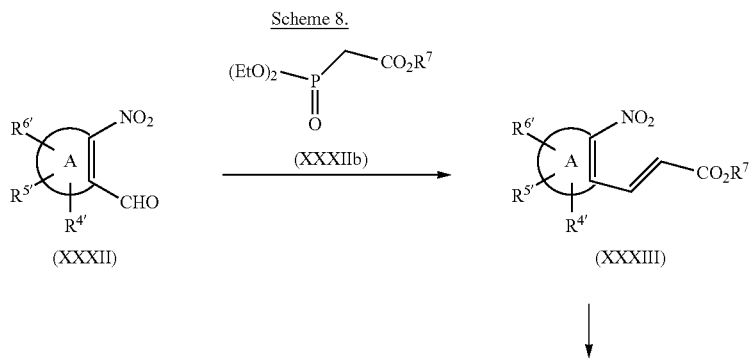

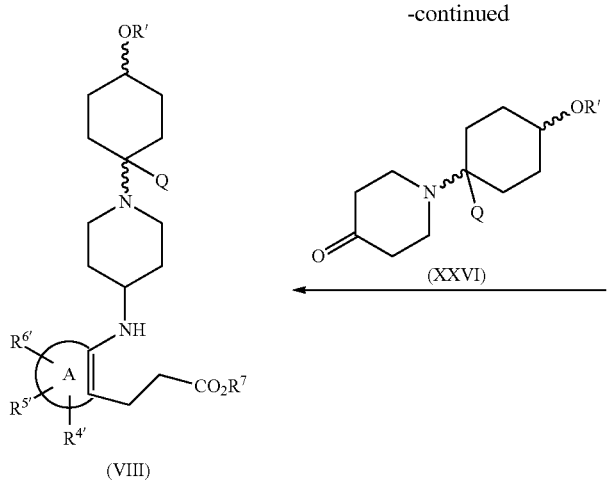

(VIII)

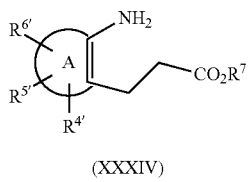

(XXXIV)

Compounds of formula (IX) can be prepared as illustrated in Scheme 9.

Reductive alkylation of the amine (XXXV) with the ketone (XXVI) provides the intermediate (XXXVI), which can then be acylated with the appropriate acid chloride, using standard alkylation conditions to give (IX), wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Q is as previously defined, and Z is a leaving group such as chloro or bromo. Compounds of formula (XXXV) are commercially available, or can be prepared by reduction of the respective commercially available nitrophenol.

It will be appreciated that compounds of formula (XXVI) can be pure cis or trans isomers, or a mixture of isomers. If necessary, separation of pure cis and trans isomers after the reaction with (XXXV) can be achieved by chromatography or crystallisation.

Scheme 9.

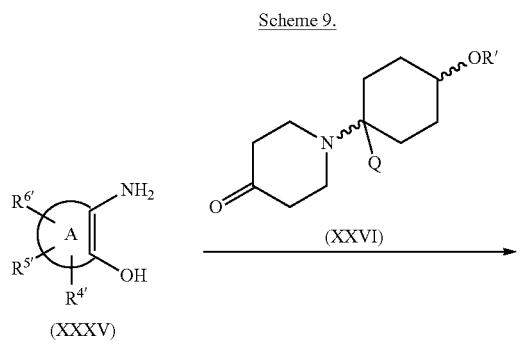

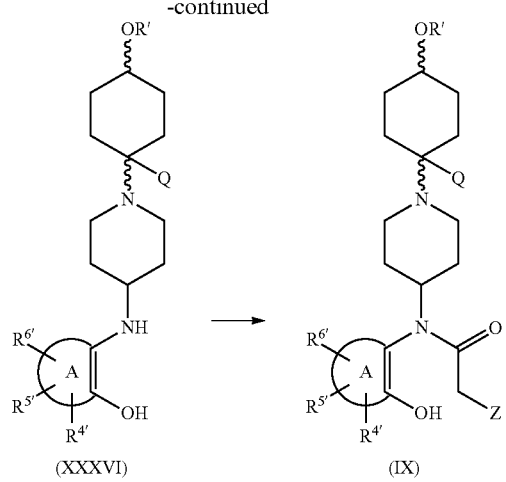

Compounds of formula (X) can be prepared by a variety of processes e.g. as illustrated in Scheme 10 by combining the alcohol/thiol (XIX) and the amine (XXV) with phosgene or a phosgene equivalent using standard conditions. Phosgene equivalents include carbonyl diimidazole, diphosgene, triphosgene, phenyl chloroformate;

or reacting the alcohol/thiol (XIX) with the isocyanate (XXXVII)

wherein $R^{6'}$ is a group $R^6$ as previously defined, or a group convertible to $R^6$, $R^{5'}$ is a group $R^5$ as previously defined, or a group convertible to $R^5$, $R^{4'}$ is a group $R^4$ as previously defined, or a group convertible to $R^4$, ring A is as previously defined, R' is a group R as previously defined, or a group convertible to R, Y is O or S, Z is a leaving group such as bromo, iodo, chloro or triflate, and Q is as previously defined.

The isocyanate (XXXVII) can be prepared from the corresponding amine (XXV) using standard methodology for isocyanate formation.

It will be appreciated that separation of the cis and trans isomers can be achieved at any suitable stage in the synthesis.

Scheme 10.

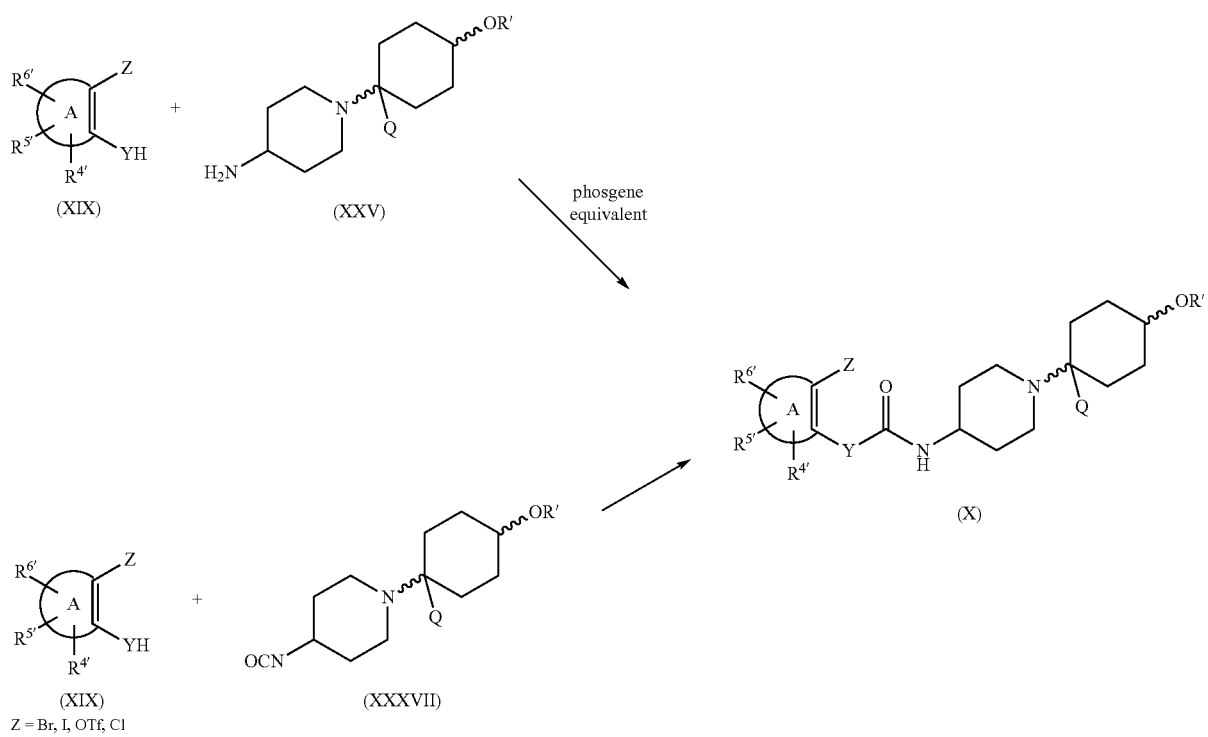

Palladium and copper catalysts (XII) are commercially available or can be prepared as described in the literature (see references in Process F).

Compounds of formula (XIII) are commercially available or can be prepared by literature processes.

Compounds of formula (XIV) where Q=H can be prepared as shown in Scheme 11, by reductive alkylation of (XXXVIII) where Z' represents Z or a group convertible to Z with the ketone (III), and R' is as previously defined. Compounds of formula (XXXVIII) in which Z' is OH can be prepared by reduction of an N-protected piperidone, followed by deprotection. Conversion of a Z' hydroxy group to Z=chloro or bromo can be accomplished using standard methodology e.g. treatment with thionyl chloride or triphenylphosphine/carbon tetrabromide. It will be appreciated that separation of the cis and trans isomers can be achieved at any suitable stage in the synthesis.

Scheme 11.

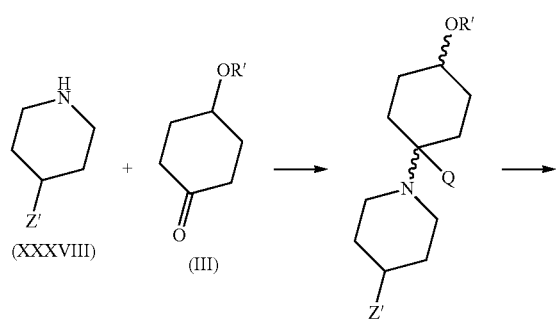

-continued

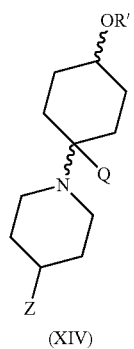

Q = H

The compound (XXV) where Q=H can be prepared as shown in Scheme 12. Reductive alkylation of the commercially available amine (XXXIX) with the cyclohexanone (III) using for example sodium triacetoxyborohydride in dichloroethane provides the intermediate (XL) which is deprotected using HCl in ethanol or trifluoroacetic acid to afford the primary amine (XXV). It will be appreciated that separation of the cis and trans isomers can be achieved at any suitable stage in the synthesis.

Scheme 12.

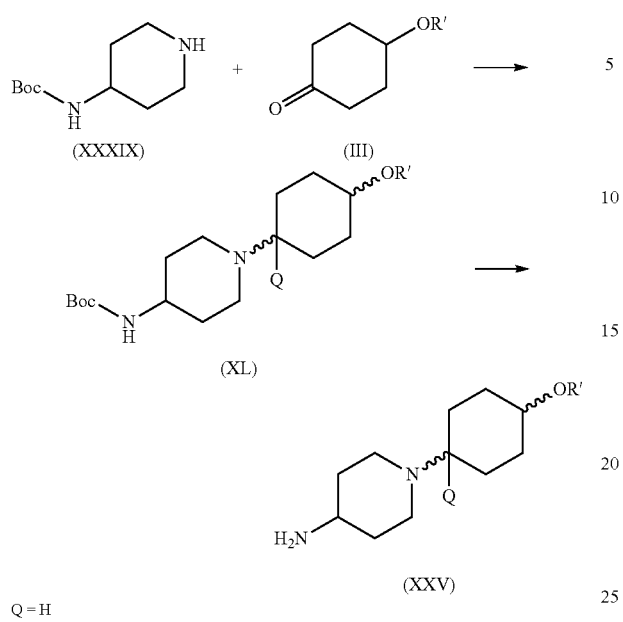

Q = H

The compound (XXV) where Q=alkyl can be prepared from intermediates (XXXIX) and (III) using similar methodology as in process A2, followed by deprotection.

Alternatively the compounds (XXV) and (XXVI) where Q=H can be prepared as shown in Scheme 13. Reductive amination of cyclohexanone (III) using for example ammonia solution under catalytic hydrogenation conditions provides intermediate amine (XLI), which can be converted into piperidinone (XXVI) by reaction with quaternary piperidine salt (XLII). Reductive amination, for example using ammonia and catalytic hydrogenation, affords primary amine (XXV). It will be appreciated that separation of the cis and trans isomers can be achieved at any suitable stage in the synthesis.

Scheme 13.

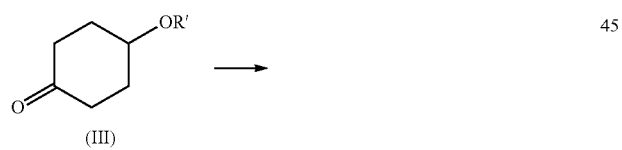

Q = H

Selective preparation of the cis and trans isomers of compound (XXV) where Q=H can be carried out via the process which is illustrated in Scheme 14 for the trans isomer. The commercially available amine (XLIII) is initially N-protected, for example by incorporation in a phthalimide ring, to give (XLIV), then the hydroxyl function converted into a silyl protected group, for example tert-butyldimethylsilyl, to give (XLV), which upon treatment with the appropriate aldehyde or ketone in the presence of triethylsilane and bismuth tribromide affords (XLVI), which after deprotection gives intermediate amine (XLI). Conversion of amine (XLI) to the piperidinone (XXVI) by reaction with the quaternary piperidine salt (XLII), followed by reductive amination, for example using ammonia and catalytic hydrogenation, affords primary amine (XXV).

Scheme 14.

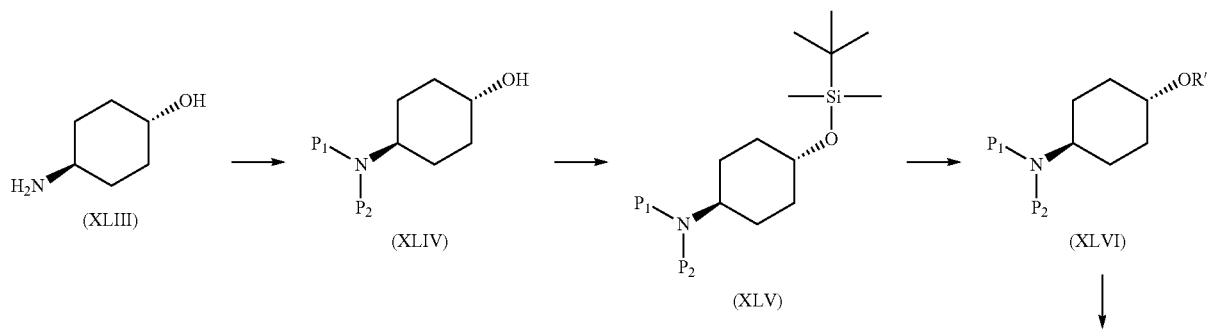

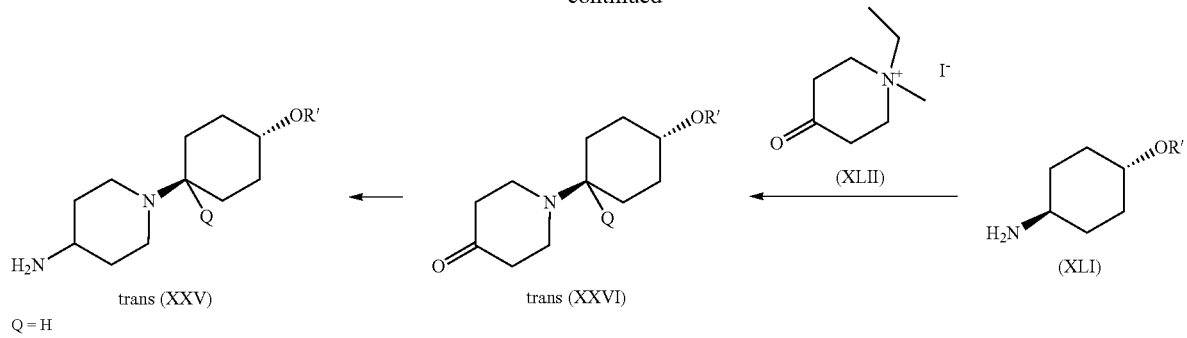

The cis isomer of compound (XXV) can be prepared by a similar procedure from the appropriate cis isomer of the amine (XLIII).

A selective preparation of the trans isomer of compounds (XXV) and (XXVI) where Q=Me is shown in Scheme 15. A suitable ester of 4-hydroxycyclohexane carboxylic acid such as the methyl or ethyl ester (XLVII) wherein R" is methyl or ethyl is protected as a silyl ether, for example the tert-butyldimethylsilyl ether, to give (XLVIII), which on treatment with the appropriate aldehyde or ketone in the presence of triethylsilane and bismuth tribromide affords ether (XLIX). Hydrolysis to acid (L) followed by alkylation using a base such as lithium diisopropylamide with iodomethane affords mixture of cis and trans 1-methylcyclohexane carboxylic acid (LI). The trans isomer (LII) can be isolated by conversion of the mixture to the acid chloride, for example with thionyl chloride, followed by selective hydrolysis of the products by treatment with weak aqueous base such as sodium hydrogen carbonate solution. The trans acid (LII) can be converted to the isocyanate (LIII) by Curtius rearrangement at elevated temperature of an intermediate azide prepared using for example diphenylphosphoryl azide, then the isocyanate hydrolysed to amine (LIV) under acidic conditions. Conversion of amine (LIV) to the piperidinone (XXVI) by reaction with quaternary piperidine salt (XLII) followed by reductive amination, for example using ammonia and catalytic hydrogenation, affords primary amine (XXV). Compounds of formula (XLVII) are commercially available.

Scheme 15.

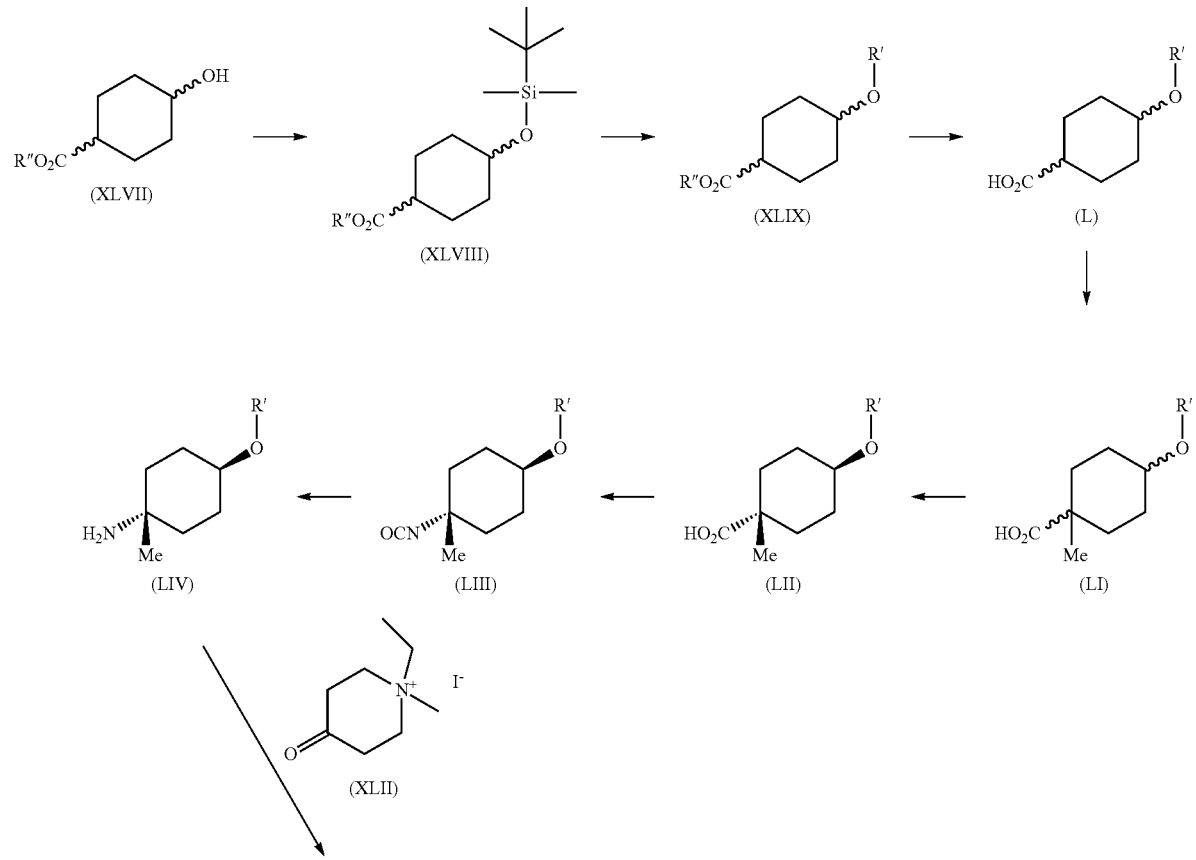

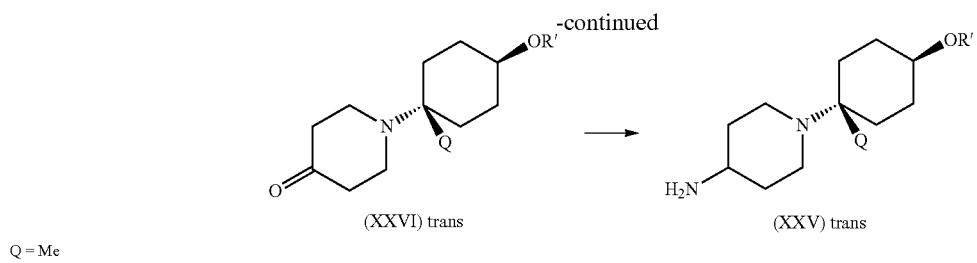

(XXVI) trans → (XXV) trans

Q = Me

An alternative preparation of the cis/trans acids (LI) is shown in Scheme 16.

Diels-Alder reaction of 2-(trimethylsilyloxy)buta-1,3-diene with a suitable ester of methacrylic acid (e.g. R"=isobutyl) affords, after hydrolysis, the cyclohexanone (LVIII). Reductive alkylation using the appropriate alkoxy t-butyl dimethylsilane (R'OTBDMS), anhydrous ferric chloride and triethylsilane (see Iwanami et al, Synthesis 2005, 2669.). generates the ether (LIX) as a mixture of cis/trans isomers. Standard ester hydrolysis using for example aqueous sodium hydroxide leads to the formation of the acids (LI) as a cis/trans mixture. Further synthetic elaboration is as detailed in Scheme 15.

Scheme 16.

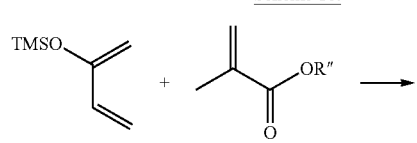

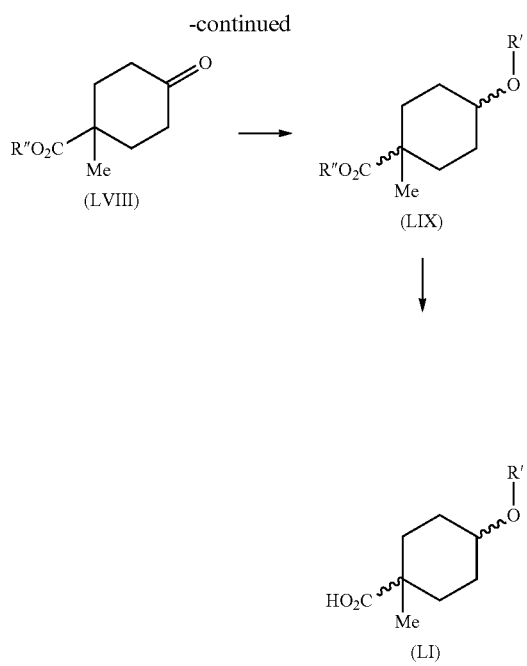

The cis isomer of (XXV) where Q=Me can be obtained as shown in Scheme 17. The mixture of acids (LI) is converted to a mixture of isocyanates (LV) via Curtius rearrangement of an intermediate azide at elevated temperature prepared using for example diphenylphosphoryl azide. The cis isomer (LVI) can be isolated from this mixture by chromatographic separation, then converted through to amine (XXV) using a similar procedure to that as shown for the trans isomer in Scheme 15 through intermediates (LVII) and (XXVI).

Scheme 17.

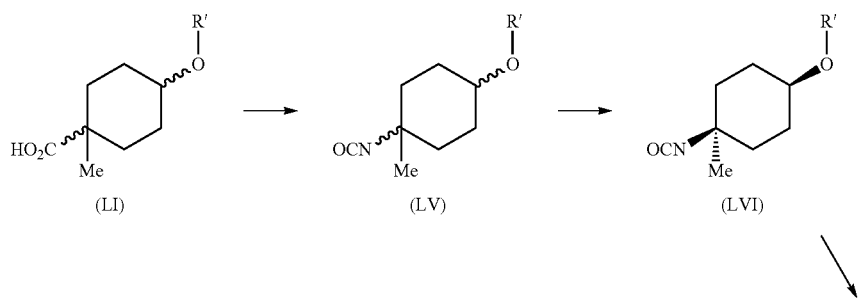

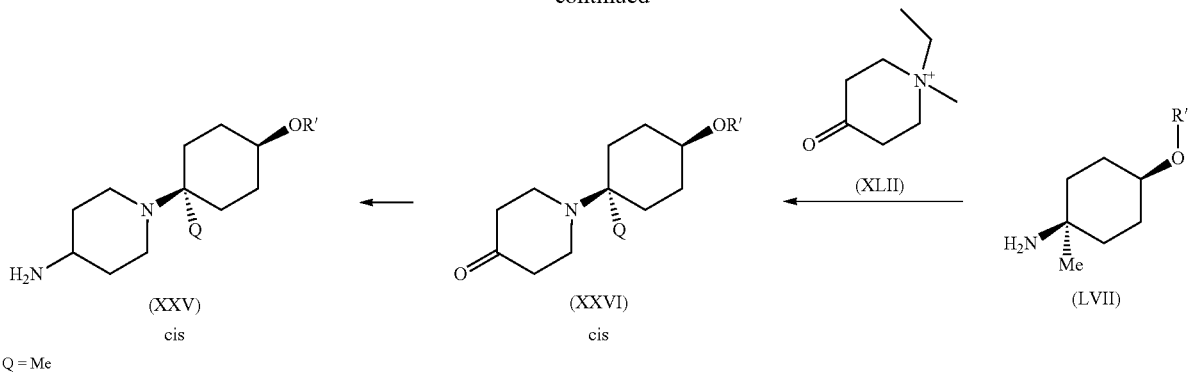

(XXV) cis (XXVI) cis (LVII)

Q = Me

Compounds of the present invention are $M_1$ receptor agonists. Selective $M_1$ receptor agonists are said to be useful to ameliorate positive and cognitive symptoms of psychotic disorders such as schizophrenia, schizo-affective disorders, schizophreniform diseases, psychotic depression, mania, acute mania, paranoid and delusional disorders, and cognitive impairment including memory disorders such as Alzheimer's disease without peripheral cholinergic side effects mediated predominantly through $M_2$ and $M_3$ receptors. $M_1$ receptor agonists may also be suitable for combination with other typical and atypical antipsychotics and other actives such as mood stabilisers, antidepressants, anxiolytics, drugs for extrapyramidal side effects and cognitive enhancers, to provide improved treatment of psychotic disorders.

$M_1$ receptor agonists may also be suitable for treatment of the underlying pathology associated with Alzheimer's Disease, or in a preventative role.

Thus in a further aspect, the invention provides a compound of formula (I) as hereinbefore described or a pharmaceutically acceptable salt thereof for use in therapy.

In another aspect, the invention provides a compound of formula (I) or a pharmaceutically acceptable salt thereof for use in the treatment of a condition wherein agonism of a muscarinic $M_1$ receptor would be beneficial.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). Treatment of the various subtypes of the disorders mentioned herein is contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

Other conditions wherein agonism of the $M_1$ receptor would be beneficial in their treatment include:

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00);

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type;

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50);

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9);

Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9); and Alzheimer's Type Dementia including Dementia of the Alzheimer's Type, With Early Onset, Without Behavioural Disturbance (294.10); Dementia of the Alzheimer's Type, With Late Onset, Without Behavioural Disturbance (294.10); Dementia of the Alzheimer's Type, With Early Onset, With Behavioural Disturbance (294.11); Dementia of the Alzheimer's Type, With Late Onset, With Behavioural Disturbance (294.11).

The compounds of formula (I) may also be useful for the enhancement of cognition, including both the treatment of cognitive impairment on its own and the treatment of cognition impairment in other diseases such as schizophrenia, bipolar disorder, depression, other psychiatric disorders and psychotic conditions associated with cognitive impairment. Where cognitive impairment results from a treatment of a disease, $M_1$ agonists may be beneficial. For example, when the treatment of epilepsy with anticonvulsants results in cognitive impairment, an $M_1$ agonist may be useful for the alleviation or treatment of the cognitive impairment.

Within the context of the present invention, the term cognitive impairment includes, for example, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

Compounds of formula (I) or pharmaceutically accepatble salts thereof may also be used as memory and/or cognition enhancers in healthy humans with no cognitive and/or memory deficit.

In another aspect, the invention provides a compound of formula (I) as hereinbefore described or a pharmaceutically acceptable salt thereof for use in the treatment of a psychotic disorder. In one embodiment, the invention provides a compound of formula (I) as hereinbefore described or a pharmaceutically acceptable salt thereof for use in the treatment of schizophrenia.

The invention also provides a compound of formula (I) as hereinbefore described or a pharmaceutically acceptable salt thereof for use in the treatment of cognitive impairment.

The invention also provides a compound of formula (I) as hereinbefore described or a pharmaceutically acceptable salt thereof for use in the treatment of Alzheimer's Disease.

In another aspect, the invention provides the use of a compound of formula (I) as hereinbefore described or a pharmaceutically acceptable salt thereof in the manufacture of a medicament for the treatment of a condition wherein agonism of the $M_1$ receptor would be beneficial.

In another aspect, the invention provides the use of a compound of formula (I) as hereinbefore described or a pharmaceutically acceptable salt thereof in the manufacture of a medicament for the treatment of a psychotic disorder. In one embodiment, the invention provides the use of a compound of formula (I) as hereinbefore described or a pharmaceutically acceptable salt thereof in the manufacture of a medicament for the treatment of schizophrenia.

In another aspect, the invention provides a compound of formula (I) as hereinbefore described or a pharmaceutically acceptable salt thereof for the treatment of a psychotic disorder. In one embodiment, the invention provides a compound of formula (I) as hereinbefore described or a pharmaceutically acceptable salt thereof for the treatment of schizophrenia.

The invention also provides the use of a compound of formula (I) as hereinbefore described or a pharmaceutically acceptable salt thereof in the manufacture of a medicament for the treatment of cognitive impairment.

The invention also provides a compound of formula (I) as hereinbefore described or a pharmaceutically acceptable salt thereof for the treatment of cognitive impairment.

The invention also provides the use of a compound of formula (I) as hereinbefore described or a pharmaceutically acceptable salt thereof in the manufacture of a medicament for the treatment of Alzheimer's Disease.

The invention also provides a compound of formula (I) as hereinbefore described or a pharmaceutically acceptable salt thereof for the treatment of Alzheimer's Disease.

In another aspect, the invention provides a method of treating a condition where agonism of the $M_1$ receptor would be beneficial, which comprises administering to a mammal in need thereof an effective amount of a compound of formula (I) as hereinbefore described or a pharmaceutically acceptable salt thereof. In one embodiment, the mammal is a human.

In another aspect, the invention provides a method of treating a psychotic disorder which comprises administering to a mammal in need thereof an effective amount of a compound of formula (I) as hereinbefore described or a pharmaceutically acceptable salt thereof. In one embodiment, the invention provides a method of treating schizophrenia, which comprises administering to a mammal in need thereof an effective amount of a compound of formula (I) as hereinbefore described or a pharmaceutically acceptable salt thereof. In one embodiment, the mammal is a human.

The invention also provides a method of treating cognitive impairment, which comprises administering to a mammal in need thereof an effective amount of a compound of formula (I) as hereinbefore described or a pharmaceutically acceptable salt thereof. In one embodiment, the mammal is a human.

The invention also provides a method of treating Alzheimer's Disease, which comprises administering to a mammal in need thereof an effective amount of a compound of formula (I) as hereinbefore described or a pharmaceutically acceptable salt thereof. In one embodiment, the mammal is a human.

The compounds of formula (I) and pharmaceutically acceptable salts thereof may also be suitable for combination with other actives, such as typical and atypical antipsychotics, mood stabilisers, antidepressants, anxiolytics, drugs for extrapyramidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a pharmaceutically acceptable salt thereof and at least one antipsychotic agent, a mood stabiliser, an antidepressant, an anxiolytic, a drug for extrapyrimidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a pharmaceutically acceptable salt thereof may be administered as adjunctive therapeutic treatment to patients who are receiving administration of at least one antipsychotic agent, a mood stabiliser, an antidepressant, an anxiolytic, a drug for extrapyrimidal side effects or a cognitive enhancer, but the scope of the invention also includes the adjunctive therapeutic administration of at least one antipsychotic agent, a mood stabiliser, an antidepressant, an anxiolytic, a drug for extrapyrimidal side effects or a cognitive enhancer to patients who are receiving administration of compounds of formula (I) or a pharmaceutically acceptable salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a pharmaceutically acceptable salt thereof to a patient receiving therapeutic administration of at least one antipsychotic agent. In a further aspect, the invention provides the use of compounds of formula (I) or a pharmaceutically acceptable salt thereof in the manufacture of a medicament for adjunctive therapeutic administration for the treatment of a psychotic disorder in a patient receiving therapeutic administration of at least one antipsychotic agent. In a further aspect, the invention provides compounds of formula (I) or a pharmaceutically acceptable salt thereof for adjunctive therapeutic administration for the treatment of a psychotic disorder in a patient receiving therapeutic administration of at least one antipsychotic agent. The invention further provides compounds of formula (I) or a pharmaceutically acceptable salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I) or a pharmaceutically acceptable salt thereof. In a further aspect, the invention provides the use of at least one antipsychotic agent in the manufacture of a medicament for adjunctive therapeutic administration for the treatment of a psychotic disorder in a patient receiving therapeutic administration of compounds of formula (I) or a pharmaceutically acceptable salt thereof. In a further aspect, the invention provides at least one antipsychotic agent for adjunctive therapeutic administration for the treatment of a psychotic disorder in a pateient recieving therapeutic administration of compounds of formula (I) or a pharmaceutically acceptable salt thereof. The invention further provides at least one antipsychotic agent for adjunctive therapeutic administration for the treatment of a psychotic disorder in a patient receiving therapeutic administration of compounds of formula (I) or a pharmaceutically acceptable salt thereof.

In a further aspect, the invention provides a method of treatment of a psychotic disorder by simultaneous therapeutic administration of compounds of formula (I) or a pharmaceutically acceptable salt thereof in combination with at least one antipsychotic agent. The invention further provides the use of a combination of compounds of formula (I) or a pharmaceutically acceptable salt thereof and at least one antipsychotic agent in the manufacture of a medicament for simultaneous therapeutic administration in the treatment of a psychotic disorder. The invention further provides a combination of compounds of formula (I) or a pharmaceutically acceptable salt thereof and at least one antipsycotic agent for simultaneous therapeutic administration in the treatment of a psychotic disorder. The invention further provides the use of compounds of formula (I) or a pharmaceutically acceptable salt thereof in the manufacture of a medicament for simultaneous therapeutic administration with at least one antipsychotic agent in the treatment of a psychotic disorder. The invention further provides compounds of formula (I) or a pharmaceutically acceptable salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) or a pharmaceutically acceptable salt thereof in the treatment of a psychotic disorder. The invention further provides at least one antipsychotic agent for simultaneous therapeutic administration with compounds of formula (I) or a pharmaceutically acceptable salt thereof in the treatment of a psychotic disorder.

In a further aspect, the invention provides a kit-of-parts for use in the treatment of a psychotic disorder comprising a first dosage form comprising compounds of formula (I) or a pharmaceutically acceptable salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides a compound of the present invention for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyrimidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyrimidal side effects and a cognitive enhancer in the manufacture of a medicament for adjunctive therapeutic administration for the treatment of a psychotic disorder in a patient receiving therapeutic administration of a compound of the present invention.

The invention also provides an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention The invention also provides the use of an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyrimidal side effects and a cognitive enhancer.

The invention further provides the use of a combination of a compound of the present invention and an active ingredient selected from the group consisting of: a mood stabiliser, an antidepressant, an anxiolytic, a drug for extrapyrimidal side effects and a cognitive enhancer in the manufacture of a medicament for simultaneous therapeutic administration in the treatment of a psychotic disorder.

The invention further provides a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration for the treatment of a psychotic disorder.

The invention further provides the use of a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for simultaneous therapeutic administration with an active ingredient selected from the group consisting of: a mood stabiliser, an antidepressant, an anxiolytic, a drug for extrapyrimidal side effects and a cognitive enhancer for the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer in the manufacture of a medicament for simultaneous therapeutic administration with a compound of the present invention in the treatment of a psychotic disorder.

The invention further provides an active ingredient selected from the group consisting of: a mood stabiliser, an antidepressant, an anxiolytic, a drug for extrapyrimidal side effects and a cognitive enhancer for simultaneous therapeutic administration with a compound of the present invention for the treatment of a psychotic disorder.

The invention further provides the use of an active ingredient selected from the group consisting of: a mood stabiliser, an antidepressant, an anxiolytic, a drug for extrapyrimidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyrimidal side effects and a cognitive enhancer for simultaneous therapeutic administration.

In one embodiment, the patient is a human.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antanogist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL®, from Mylan, Zenith Goldline, UDL, Novartis); olanzapine (available under the tradename ZYPREXA®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); sertindole (available under the tradename SERLECT®); amisulpride (available under the tradename SOLION®, from Sanofi-Synthelabo); haloperidol (available under the tradename HALDOL®, from Ortho-McNeil); haloperidol decanoate (available under the tradename HALDOL Decanoate®); haloperidol lactate (available under the tradenames HALDOL® and INTENSOL®); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); fluphenazine decanoate (available under the tradename PROLIXIN decanoate®); fluphenazine enanthate (available under the tradename PROLIXIN®); fluphenazine hydrochloride (available under the tradename PROLIXIN®); thiothixene (available under the tradename NAVANE®, from Pfizer); thiothixene hydrochloride (available under the tradename NAVANE®); trifluoperazine (10-[3-(4-methyl-1-piperazinyl)propyl]-2-(trifluoromethyl)phenothiazine dihydrochloride, available under the tradename STELAZINE®, from SmithKline Beckman); perphenazine (available under the tradename TRILAFON®, from Schering); perphenazine and amitriptyline hydrochloride (available under the tradename ETRAFON TRILAFON®); thioridazine (available under the tradename MELLARIL®; from Novartis, Roxane, HiTech, Teva, and Alpharma); molindone (available under the tradename MOBAN®, from Endo); molindone hydrochloride (available under the tradename MOBAN®); loxapine (available under the tradename LOXITANE®; from Watson); loxapine hydrochloride (available under the tradename LOXITANE®); and loxapine succinate (available under the tradename LOXITANE®). Furthermore, benperidol (Glianimon®), perazine (Taxilan®) or melperone (Eunerpan®)) may be used.

Other suitable antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®;), prochlorperazine (available under the tradename COMPAZINE®), methotrimeprazine (available under the tradename NOZINAN®), pipotiazine (available under the tradename PIPOTRIL®), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, amisulpride, aripiprazole, haloperidol, clozapine, olanzepine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, 5HT7 antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic $M_1$ agonists (such as cevimeline).

For use in medicine, the compounds of the present invention are usually administered as a standard pharmaceutical composition. The present invention therefore provides in a further aspect a pharmaceutical composition comprising a compound of formula (I) as hereinbefore described or a pharmaceutically acceptable salt thereof and a pharmaceutically acceptable carrier. The pharmaceutical composition can be for use in the treatment of any of the conditions described herein. In a further aspect, the invention provides a process for preparing a pharmaceutical composition, the process comprising mixing a compound of formula (I) as hereinbefore described or a pharmaceutically acceptable salt thereof and one or more pharmaceutically acceptable carriers. In a further aspect, the invention provides a pharmaceutical composition comprising a compound of formula (I) as hereinbefore described or a pharmaceutically acceptable salt thereof in combination with at least 1 antipsychotic, and one or more pharmaceutically acceptable carriers. In a further aspect, the invention provides a process for preparing a pharmaceutical composition, the process comprising mixing a compound of formula (I) as hereinbefore described or a pharmaceutically acceptable salt thereof, at least 1 antipsychotic, and one or more pharmaceutically acceptable carriers.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound o the invention or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. The composition may be in unit dose form such as a tablet, capsule or ampoule.

Each dosage unit for oral administration contains, for example, from 1 to 250 mg (and for parenteral administration contains, for example, from 0.1 to 25 mg) of a compound of the formula (I) or a pharmaceutically acceptable salt thereof calculated as the free base.

The daily dosage contains suitably from 0.01 mg/kg to 100 mg/kg of a compound of formula (I) or a pharmaceutically acceptable salt thereof calculated as the free base.

It will be appreciated that the precise dose administered will depend on the age and condition of the patient and the frequency and route of administration and will be at the ultimate discretion of the attendant physician.

The antipsychotic agent component or components used in the adjunctive therapy of the present invention may also be administered in their basic or acidic forms as appropriate or, where appropriate, in the form of a pharmaceutically acceptable salt or other derivative. All solvates and all alternative physical forms of the antipsychotic agent or agents or their salts or derivatives as described herein, including but not limited to alternative crystalline forms, amorphous forms and polymorphs, are also within the scope of this invention. In the case of the antipsychotic agent or agents, the forms and derivatives are, for example, those which are approved for therapeutic administration as monotherapies, including those mentioned above, but all references to antipsychotic agents herein include all salts or other derivatives thereof, and all solvates and alternative physical forms thereof.

For adjunctive therapeutic administration according to the invention, compounds of formula (I) or pharmaceutically acceptable salts thereof and the antipsychotic agent or agents or their salts, derivatives or solvates may each be administered in pure form, but each of the components will, for example, be formulated into any suitable pharmaceutically acceptable and effective composition which provides effective levels of the respective component in the body. The choice of the most appropriate pharmaceutical compositions for each component is within the skill of the art, and may be the same form or different forms for each of the components. Suitable formulations include, but are not limited to tablets, capsules, powders, granules, lozenges, suppositories, reconstitutable powders, or liquid preparations such as oral or sterile parenteral solutions or suspensions.

For simultaneous administration as a combined composition of compounds of formula (I) and the antipsychotic agent or agents according to the invention, compounds of formula (I) or their pharmaceutically acceptable salts and the antipsychotic agent or agents and their salts, derivatives or solvates may be administered together in pure form, but the combined components will, for example, be formulated into any suitable pharmaceutically acceptable and effective composition which provides effective levels of each of the components in the body. The choice of the most appropriate pharmaceutical compositions for the combined components is within the skill of the art. Suitable formulations include, but are not limited to tablets, sub-lingual tablets, buccal compositions, capsules, powders, granules, lozenges, suppositories, reconstitutable powders, or liquid preparations such as oral or sterile parenteral solutions or suspensions.

In order to obtain consistency of adjunctive administration, the compositions of each of the components, or of the combination of the components is, for example, in the form of a unit dose.

The term "treatment" includes prophylaxis, where this is appropriate for the relevant condition(s).

Biological Test Methods

FLIPR Experiments on $M_1$ Receptors to Determine Agonist/Antagonist Potency

Compounds of the invention were characterized in a functional assay to determine their ability to activate the intracellular calcium pathway in CHO cells with stable expression of human muscarinic $M_1$ receptors using FLIPR (Fluorometric Imaging Plate Reader) technology. Briefly, CHO-$M_1$ cells were plated (15,000/well) and allowed to grow overnight at 37 degrees. Media were removed and 30 µL loading buffer (HBSS with 2.5 mM probenicid, 2 µM Fluo-4, 500 µM Brilliant Black, pH 7.4) was added. After incubation at 37 degrees for 90 minutes, 10 µL of the assay buffer (HBSS with 2.5 mM probenecid, pH 7.4) containing test compounds was added to each well on the FLIPR instrument. Calcium response was monitored to determine agonism. Plates were then incubated for another 30 minutes before 10 µL of assay buffer containing acetylcholine was added at an $EC_{80}$, as the agonist challenge. Calcium response was then monitored again to determine compound's antagonism to acetylcholine. Concentration-response curves of both agonism and antagonism on $M_1$ receptors were performed for each compound. Results were imported into ActivityBase data analysis suite (ID Business Solution Inc., Parsippany, N.J.) where the curves were analysed by non-linear curve fitting and the resulting $pEC_{50}$/fpKi were calculated. The maximum asymptotes of agonist compounds were calculated as percentage of maximum FLIPR response induced by carbamoylcholine chloride added as control on the same compound plates.

The example compounds below were tested in the above assay and were found to have average $pEC_{50}$ values of >5.5 at the muscarinic $M_1$ receptor, and intrinsic activity >50%.

FLIPR Experiments on $M_{2-5}$ Receptor to Determine Receptor Subtype Selectivity To determine selectivity of compounds of the invention against other muscarinic receptor subtypes, compounds were characterized in FLIPR experiments in CHO cells with stable expression of human muscarinic receptors, $M_2$, $M_3$, $M_4$ or $M_5$. In the case of $M_2$ and $M_4$ receptors, chimeric G-protein Gqi5 was also co-expressed to couple receptors to the calcium signalling pathway. Briefly, cells were plated (15,000/well) and allowed to grow overnight at 37 degrees. The FLIPR experiment was then carried out on the next day using the same protocol as described above for CHO-M1 cells. Results were imported into ActivityBase data analysis suite where the curves were analysed by non-linear curve fitting and the resulting $pEC_{50}$/fpKi values were calculated.

The example compounds below were tested in the $M_{2-5}$ receptor assays and the majority of the examples were found to be selective for the $M_1$ receptor over $M_2$, $M_3$, $M_4$ and $M_5$ receptors, with typical selectivity (ratio of $pEC_{50}$'s) of ≧10-fold, and in certain cases ≧100-fold.

FLIPR Experiments on $M_1$ Receptor to Determine Agonist Intrinsic Activity

To determine the intrinsic activities of $M_1$ agonist compounds, compounds of the invention were characterized in FLIPR experiments on CHO-K1 cells with transient expression of human muscarinic $M_1$ receptors. Briefly, CHO-K1 cells were transduced with $M_1$ BacMam virus (Ames, R S; Formwald, J A; Nuthulaganti, P; Trill, J J; Foley, J J; Buckley, P T; Kost, T A; Wu, Z and Romanos, M A. (2004) *Use of BacMam recombinant baculoviruses to support G protein-coupled receptor drug discovery*. Receptors and Channels 10 (3-4): 99-109). A functional titration was performed on each batch of cells continuously cultured ahead of experimentation to determine the appropriate multiplicity of infection ratio (MOI) for measuring intrinsic activities of test compounds. After mixing with virus in suspension, cells were plated (10,000/well) and allowed to adhere overnight at 37 degrees.

The FLIPR experiment was carried out on the day following plating using the same protocol as described above for CHO-$M_1$ cells. Data was analysed by non-linear curve fitting using four-parameter logistics contained in XC50 version 2, and the resulting $pEC_{50}$ values were calculated. The intrinsic activities of agonist compounds were measured as percentage of maximum FLIPR response induced by acetylcholine added as control on the same compound plates, and converted to a fraction between 0 and 1 (i.e. calculated using a 100% max response from a fitted acetylcholine standard curve, containing multiple concentrations, as control).

Certain compounds below were tested in this assay, and were found to have average $pEC_{50}$ values of >6.0 at the muscarinic $M_1$ receptor, and intrinsic activity of greater than or equal to 0.3.

The invention is further illustrated by the following non-limiting examples. In the procedures that follow, after each starting material, reference to a Description by number is typically provided. This is provided merely for assistance to the skilled chemist. The starting material may not necessarily have been prepared from the batch referred to.

SCX columns (including SCX, SCX-2, SCX-3) refer to sulfonic acid ion exchange resins supplied by Varian, IST and Radleys.

Amino-doped Silica Columns are Supplied by Biotage

SPE-Si cartridges are silica solid phase extraction columns supplied by Varian.

Flash silica gel chromatography was carried out on, for example, silica gel 230-400 mesh (supplied by Merck AG Darmstadt, Germany) or over pre-packed Biotage silica cartridges (e.g. 12+M, or 65i) on Biotage Horizon, SP1 or SP4 machines.

For specified hydrogenation reactions, an H-cube was used. The H-cube is a continuous flow hydrogenator developed by Thales Nanotechnology. A solution of the sample to be hydrogenated is delivered to the reactor in a continuous stream using an HPLC pump. In the reactor it is mixed with hydrogen (generated from electrolysis of water), heated, and passed through a catalyst (e.g. palladium on charcoal) cartridge (up to 100° C. and 100 bar pressure) to produce a continuous flow of hydrogenated product.

NMR spectra were obtained at 298° K, at the frequency stated using either a Bruker™ DPX400 or an Oxford Instruments™ 250 MHz machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled (singlet), bs, (broad singlet), d (doublet), t (triplet), q (quartet), dd (doublet of doublets), dt (doublet of triplets) and m (multiplet). NMR spectral data, where provided, were obtained for the title substance in each Description or Example (e.g. the hydrochloride salt, or the free base), unless otherwise stated.

Mass spectra (MS) were taken on a 4 II triple quadropole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS-ES (+)]. Analysis was performed on a Waters Atlantis column (50×4.6 mm) with a stationary phase particle size of 3 µM. Mobile phase A (aqueous phase)=water+0.05% formic acid; mobile phase B (organic solvent)=acetonitrile+0.05% formic acid. Method as follows:

| Time/min | % A | % B |
|---|---|---|
| 0 | 97 | 3 |
| 0.1 | 97 | 3 |
| 4 | 3 | 97 |
| 4.8 | 3 | 97 |
| 4.9 | 97 | 3 |
| 5.0 | 97 | 3 |

The above method had a flow rate of 3 mL/min. The injection volume was 5 µL. The column temperature was 30° C. The UV detection range was from 220 to 330 nm.

MDAP (mass-directed auto-preparation) refers to purification by HPLC on a Waters machine, wherein fraction collection is triggered by detection of the programmed mass ion for the compound of interest. High pH separations refer to use of a water/acetonitrile/ammonium carbonate gradient.

MDAP was conducted using a Waters 2525 Binary Gradient Module, a Waters 515 Makeup Pump, a Waters Pump Control Module, a Waters 2767 Inject Collect, a Waters Column Fluidics Manager, a Waters 2996 Photodiode Array Detector, a Waters ZQ Mass Spectrometer, a Gilson 202 fraction collector and a Gilson Aspec waste collector. For low pH, the column was a Waters Atlantis or Sunfire C18 column (19×100 mmm or 30×100 mm, 5 μm packing diameter), solvent A was water plus 0.1% formic acid and solvent B was acetonitrile plus 0.1% formic acid. The gradient used was determined by LCMS retention time.

| LCMS Rt | Gradient |
| --- | --- |
| 1.0-1.5 | 5-30% B |
| 1.5-2.2 | 15-55% B |
| 2.2-2.9 | 30-85% B |
| 2.9-3.6 | 50-99% B |
| 3.6-5.0 | 80-99% B |

For high pH, the column was an X Bridge C18 column (30×100 mm, 5 μm packing diameter), solvent A was 10 mM ammonium carbonate in water adjusted to pH 10 using ammonia solution and solvent B was acetonitrile. The gradient was determined by LCMS retention time:

| LCMS Rt | Gradient |
| --- | --- |
| 1.0-1.5 | 1-99% B |
| 1.5-2.2 | 15-99% B |
| 2.2-2.9 | 30-99% B |
| 2.9-3.6 | 50-99% B |
| 3.6-5.0 | 80-99% B |

For reactions involving microwave irradiation, a Biotage Initiator was used.

Starting materials, reagents and solvents were obtained from commercial suppliers and used without further purification unless otherwise stated. Unless otherwise stated, all compounds with chiral centres are racemic. Where reactions are described as having been carried out in a similar manner to earlier, more completely described reactions, the general reaction conditions used were essentially the same. Work up conditions used were of the types standard in the art, but may have been adapted from one reaction to another. The starting material may not necessarily have been prepared from the batch referred to. Compounds synthesised may have various purities ranging from for example 85% to 98%. However, calculations of number of moles and yield are generally not adjusted for this.

Where applicable, the ratio of cis/trans isomers was assessed by NMR integration. Characterisation of cis and trans was based on NMR shift data and coupling constants for the relevant H.

Abbreviations
NMR Nuclear Magnetic Resonance
THF tetrahydrofuran
DMSO dimethylsulfoxide
DMF dimethylformamide
DCM dichloromethane
DCE 1,2-dichloroethane
EDC 1-ethyl-3-(dimethylaminopropyl)carbodiimide
$Et_2O$ diethyl ether
HOBt 1-hydroxybenzotriazole
MeCN/$CH_3CN$ acetonitrile
MeOH methanol
DIPEA (Hunig's base)diisopropylethylamine
nhex n-hexane
c-hex cyclohexane
iso-hex iso-hexane
EtOAc ethyl acetate
Boc/BOC t-butyloxycarbonyl
MDAP Mass-Directed Auto-Preparation
TLC thin layer chromatography
aq aqueous
eq equivalents
$sat^d$ saturated
LC/MS liquid chromatography/mass spectrometry
Rt/rt/room temp room temperature
SM starting material
RM reaction mixture
FC flash chromatography
PS polymer supported
RB round bottomed
CV column volumes
Pd/C palladium on charcoal
$Pd_2$ $dba_3$ Tris(dibenzylideneacetone)dipalladium (0)
X-Phos 2-dicyclohexylphosphino-2',4',6'-triisopropylbiphenyl
BINAP 2,2'-bis(diphenylphosphino)-1,1'-binaphthyl
mCPBA meta-chloroperoxybenzoic acid
NaI sodium iodide

DESCRIPTION 1 cis/trans-Ethyl 4-{[(1,1-dimethylethyl)(dimethyl)silyl]oxy}cyclohexanecarboxylate. (D1)

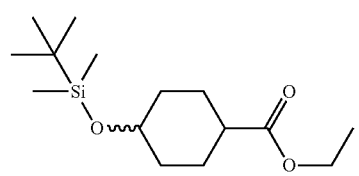

D1

Chloro(1,1-dimethylethyl)dimethylsilane (115 g; 0.76 mol) was added in portions over 1 hour to a solution of commercially available ethyl 4-hydroxycyclohexanecarboxylate (118 g; 0.68 mol), imidazole (103 g; 1.52 mol) and dimethylformamide (400 mL) stirred under an atmosphere of argon. A small exotherm was observed resulting in the reaction mixture temperature increasing to ~40° C. The mixture was stirred at room temperature overnight then poured into 10% citric acid solution (2 L) and extracted with diethyl ether (2×800 mL). The ether extracts were washed with water, brine and then dried ($Na_2SO_4$) and the solvent was removed to give the title compound as an oil (198.4 g)

¹H NMR δ (CDCl₃, 400 MHz): 0.01 (6H, m), 0.85 (9H, s), 1.2 (3H, m), 1.3-1.5 (2H, m), 1.6 (2H, m), 1.85-2 (3H, m), 2.15-2.3 (1H, m) 3.5 (0.4H, m) 3.86 (1H, m) 4.1 (1H, m).

DESCRIPTION 2 cis/trans-Ethyl 4-(ethyloxy)cyclohexanecarboxylate. (D2)

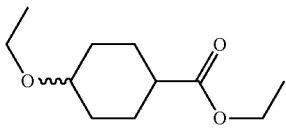

D2 cis/trans Ethyl 4-{[(1,1-dimethylethyl)(dimethyl)silyl]oxy}cyclohexanecarboxylate (D1, 35 g, 122 mmol) was dissolved in CH₃CN (250 mL) and Et₃SiH (1.2 eq., 146 mmol, 23 mL), BiBr₃ (4% mol, 4.9 mmol, 2.2 g) were added portionwise at room temperature followed by acetaldehyde (1.2 eq., 8.2 mL) that was slowly added at 25° C. The mixture was stirred at room temperature for 1 hour. The mixture was subsequently poured onto an aqueous saturated solution of NaHCO₃ and the mixture obtained was then extracted with EtOAc (3×). Organics were combined, washed with brine, dried over Na₂SO₄, filtered and the solvent was evaporated to afford the crude mixture that was purified by silica chromatography (Biotage 65i column, EtOAc-nhex) to afford the title compound, 21 g, 87%.

¹H NMR δ (DMSO-d₆, 400 MHz): 1.1 (3H, m), 1.15 (3H, m), 1.492-3.212 (assume 10H, set of broad signals and multiplets), 3.312 (2H, m), 4.041 (2H, m).

DESCRIPTION 3 cis/trans-4-(Ethyloxy)cyclohexanecarboxylic acid. (D3)

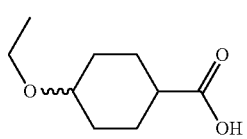

D3

Cis/trans-Ethyl 4-(ethyloxy)cyclohexanecarboxylate (D2, 21 g, 105 mmol) was dissolved in MeOH-THF (100 mL-100 mL) and NaOH (5 eq., 0.5 mol, 40 mL, 12.5 N aqueous solution) was slowly added at room temperature. The mixture was stirred at room temperature overnight. The THF/MeOH was then evaporated and the crude was washed with Et₂O. The aqueous phase was acidified and extracted with EtOAc (2×); organics were dried over Na₂SO₄, filtered and the solvent was evaporated to afford the title compound as a pale-yellow oil, 17.3 g, 96%.

¹H NMR δ (DMSO-d₆, 400 MHz): 1.1 (3H, m), 1.3-3.201 (assume 10H, set of broad signals and multiplets), 3.417 (2H, m), 12.1 (1H, s broad).

DESCRIPTION 4 cis/trans-4-(Ethyloxy)-1-methylcyclohexanecarboxylic acid. (D4)

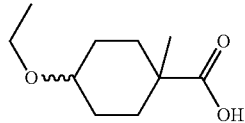

D4

A stirred solution of diisopropylamine (2.3 eq., 0.231 mol, 33 mL) in dry THF (400 mL) at −20° C. under argon was treated over 10 min with 2.5M n-butyllithium in hexane (2.3 eq., 93 mL; 0.231 mol), then allowed to warm to 0° C. and stir for 15 mins. The mixture was re-cooled to −10° C. and treated over 10 min with a solution of cis/trans-4-(ethyloxy)cyclohexanecarboxylic acid (D3, 17.3 g, 0.1 mol) in ~50 mL of dry THF. The resulting yellow solution was heated at 50° C. for 2.5 hr, then cooled to 0° C. and treated with iodomethane (3 eq., 0.3 mol, 19 mL). The mixture was allowed to warm to room temperature and stir overnight. The mixture was cooled to 10° C., treated with 10% citric acid solution (200 mL), and then solvent evaporated to half volume (concentrated under vacuum). The residual mixture was diluted with water (200 mL) and extracted with Et₂O (2 x). The combined extracts were washed with water (150 mL×2), dried (Na₂SO₄), filtered and concentrated under vacuum to leave the title compound as a yellow oil, 16.2 g, 87%, a mixture of cis:trans isomers.

¹H NMR δ (DMSO-d₆, 400 MHz): 1.09 (assume 8H, m), 1.51 (3H, m), 1.70 (1H, m), 1.78 (1H, m), 2.01 (1H, m), 3.19 (1/2H, m), 3.39 (2H, m), 3.61 (1/2H, m), 12.2 (1H, s br).

DESCRIPTION 5 trans-4-(Ethyloxy)-1-methylcyclohexanecarboxylic acid. (D5)

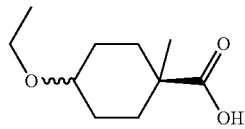

D5 cis/trans-4-(Ethyloxy)-1-methylcyclohexanecarboxylic acid (D4, 16.2 g, 87.1 mmol) was dissolved in thionyl chloride (15 eq., 1.31 mol, ~95 mL) at room temperature and it was subsequently refluxed at 85° C. for 4 hr. The mixture was then allowed to cool to room temperature and the thionyl chloride was azeotropically evaporated with toluene. The residue was dissolved in THF (100 mL), treated with a 5% aqueous solution of Na₂CO₃ (500 mL) and stirred well at room temperature for 20 minutes. The aqueous residue was washed with Et₂O (2×), then acidified and extracted with EtOAc (3×). The combined extracts were dried (Na₂SO₄), filtered and concentrated under vacuum to leave the title compound, 6.5 g, 40%.

¹H NMR δ (DMSO-d₆, 400 MHz): 1.08 (6H, m), 1.51 (6H, m), 1.69 (2H, m), 3.33 (1H, m), 3.39 (2H, q), 12.1 (1H, s br).

DESCRIPTION 6 trans-4-(Ethyloxy)-1-isocyanato-1-methylcyclohexane. (D6)

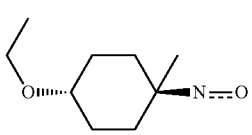

D6

A stirred solution of trans-4-(ethyloxy)-1-methylcyclohexanecarboxylic acid (D5, 5.5 g, 29.5 mmol) in toluene (120 mL) at room temperature under argon was treated with triethylamine (1.3 eq., 37.7 mmol, 5.3 mL) and diphenylphosphoryl azide (1 eq., 29.5 mmol, 6.4 mL) and heated at 85° C. for 1 hr. The mixture was allowed to cool to room temperature, then treated with 1M NaOH solution (300 mL) and extracted with Et₂O (3×). The combined extract was dried (Na₂SO₄), filtered and concentrated under vacuum to leave the title compound, 5 g, 94%.

¹H NMR δ (DMSO-d₆, 400 MHz): 1.09 (3H, t), 1.33 (3H, s), 1.49-1.69 (8H, m), 3.39 (2H, q), 3.48 (1H, m).

DESCRIPTION 7

[trans-4-(Ethyloxy)-1-methylcyclohexyl]amine mono hydrochloride. (D7)

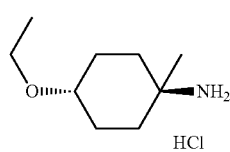

D7

A solution of trans-4-(ethyloxy)-1-isocyanato-1-methylcyclohexane (D6, 5.0 g, 27.3 mmol) in THF (100 mL) was treated with 5M aqueous HCl acid (5.5 eq., 150 mmol, 30 mL) and stirred at room temperature under argon overnight, then concentrated under vacuum. The residual semi-solid was triturated with Et₂O to give a first batch of title compound as a white solid, 2.8 g. The mother liquors were evaporated, dissolved in THF again (50 mL) and treated with 5M aqueous HCl acid (15 mL) and the mixture stirred over a weekend at room temperature. The solvent was then evaporated and the solid obtained was dried in the oven at 50° C. before trituration with Et₂O. This final trituration afforded further 646 mg of title compound.

¹H NMR δ (DMSO-d₆, 400 MHz): 1.08 (3H, t), 1.26 (3H, s), 1.38 (2H, m), 1.62 (4H, m), 1.85 (2H, m), 3.24 (1H, m), 3.42 (2H, q), 8.09 (3H, br s).

DESCRIPTION 8

1-[trans-4-(Ethyloxy)-1-methylcyclohexyl]-4-piperidinone. (D8)

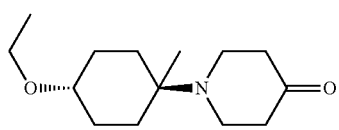

D8

A stirred solution of [trans-4-(ethyloxy)-1-methylcyclohexyl]amine mono hydrochloride (D7, 3.44 g, 17.8 mmol) in a mixture of ethanol (216 mL) and water (108 mL) at room temperature under argon was treated with potassium carbonate (1.1 eq., 19.6 mmol, 2.7 g) followed by 1-ethyl-1-methyl-4-oxopiperidinium iodide (D9, 1.5 eq., 26.7 mmol, 7.1 g), then heated at 80° C. for 2 hours. The mixture was allowed to cool to room temperature then the aqueous residue was treated with sat. NaHCO₃ solution and extracted with dichloromethane (3×). The combined extracts were dried (Na₂SO₄) and concentrated under vacuum to leave the crude compound which was chromatographed on silica gel (Biotage 65i column) eluting with 0-10% MeOH/NH₃/DCM to afford the title compound, 2.3 g, 54%.

¹H NMR δ (DMSO-d₆, 400 MHz): 0.86 (3H, s), 1.10 (3H, t), 1.42 (2H, m), 1.54 (4H, m), 1.79 (2H, m), 2.30 (4H, t), 2.73 (4H, t), 3.38-3.43 (3H, t+m).

DESCRIPTION 9

1-Ethyl-1-methyl-4-oxopiperidinium iodide. (D9)

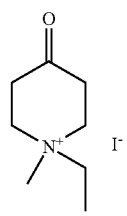

D9

Iodomethane (65 mL; 1.00 mol) was added in portions to a solution of 1-ethyl-4-piperidone (100 g; 0.79 mol) in acetone (1 L) at 20-30° C. (internal, ice cooling). After stirring for 3 h more the title compound was obtained by filtration, and washing with acetone (189 g).

DESCRIPTION 10

2-({1-[trans-4-(Ethyloxy)-1-methylcyclohexyl]-4-piperidinyl}amino)phenol. (D10)

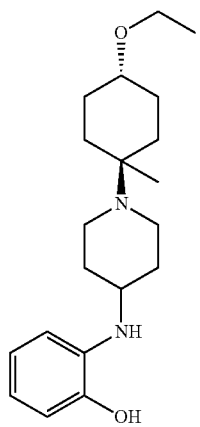

Polymer supported sodium cyanoborohydride (489 mg, 0.997 mmol, 2.04 mmol/g) was added to a solution of 2-aminophenol (52.2 mg, 0.478 mmol), 1-[trans-4-(ethyloxy)-1-methylcyclohexyl]-4-piperidinone (D8, 135 mg, 0.564 mmol) and acetic acid (0.27 mL, 4.72 mmol) in dichloromethane (2.5 mL). The mixture was heated by microwave at 100° C. for 10 min before being filtered and concentrated by rotary evaporation to give a yellow oil. The residue was purified via chromatography (silica, dichloromethane to 0.5% ammonia/9.5% methanol/90% dichloromethane) to give 2-({1-[trans-4-(ethyloxy)-1-methylcyclohexyl]-4-piperidinyl}amino)phenol (D10, 91.6 mg, 54%), which was isolated in two batches, as a colourless solid.
M+H$^+$ 333

DESCRIPTION 11 cis/trans-Ethyl 4-(propyloxy)cyclohexanecarboxylate. (D11)

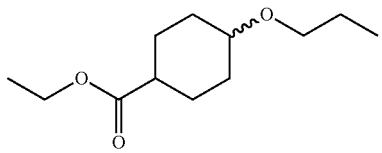

Propionaldehyde (6.4 g) in acetonitrile (50 mL) was added over 30 minutes to a solution of cis/trans ethyl 4-{[(1,1-dimethylethyl)(dimethyl)silyl]oxy}cyclohexanecarboxylate (D1, 25.2 g), bismuth tribromide (4.4 g) and triethylsilane (17.5 mL) in acetonitrile (300 mL) and the mixture was stirred for a further 1.5 hours. The solvent was partially removed then the residue was treated with ethyl acetate and saturated sodium bicarbonate solution. The organic layer was separated, washed with brine, dried with anhydrous sodium sulphate and the solvent was removed to give the title compounds contaminated with silicone residues (39.1 g).

DESCRIPTION 12 cis/trans-4-(Propyloxy)cyclohexanecarboxylic acid. (D12)

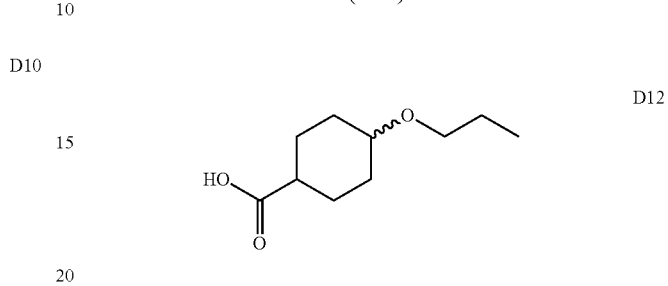

cis/trans-Ethyl 4-(propyloxy)cyclohexanecarboxylate (D11) (39.1 g), 40% w/w sodium hydroxide solution (150 mL), tetrahydrofuran (200 mL) and methanol (150 mL) was stirred for approx. 72 hours. The solvent was partially removed then the resulting mixture was treated with ethyl acetate and water. The aqueous layer was separated, acidified with concentrated hydrochloric acid and extracted with diethyl ether. The ether layer was washed with brine, dried with anhydrous sodium sulphate and the solvent was removed to give the title compounds as oil (15.42 g).

DESCRIPTION 13 cis/trans-1-Methyl-4-(propyloxy)cyclohexanecarboxylic acid. (D13)

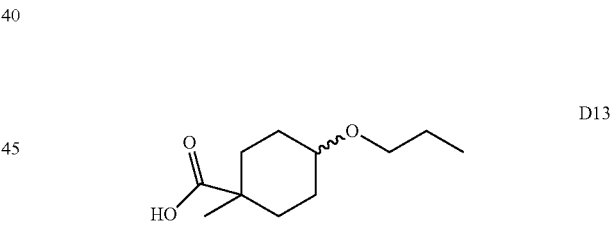

A stirred solution of diisopropylamine (24 mL, 0.17 mol) in THF (300 mL) at −20° C. under argon was treated over 10 mins with 2.5M n-butyllithium in hexane (68 mL, 0.17 mol), then allowed to warm to 0° C. and stir for 15 mins. The mixture was re-cooled to −10° C. and treated over 10 mins with a solution of 4-(propyloxy)cyclohexanecarboxylic acid (D12, 13.8 g, 0.074 mol) in THF. The resulting yellow solution was heated at 50° C. for 2.5 hr, then cooled to 0° C. and treated with iodomethane (13.8 mL, 0.22 mol). The mixture was allowed to warm to room temperature and stir for 20 hr when a yellow precipitate had formed. The mixture was cooled to 10° C., treated with 10% citric acid solution (200 mL), then concentrated under vacuum to approx. 250 mL volume. The residual mixture was diluted with water (200 mL) and extracted with Et$_2$O (3×250 mL). The combined extract was dried (Na$_2$SO$_4$) and concentrated under vacuum to leave a yellow oil (15.0 g) which was approx. 60:40 mixture of cis:trans isomers.

DESCRIPTION 14 trans-1-Methyl-4-(propyloxy)cyclohexanecarboxylic acid. (D14)

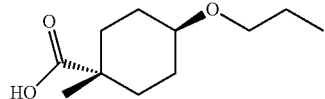

D14 cis/trans-1-Methyl-4-(propyloxy)cyclohexanecarboxylic acid (D13, 13 g, 0.070 mol) was added to stirred thionyl chloride (50 mL), 0.68 mol) at 10° C. and then allowed to warm to room temperature, followed by heating at 85° C. for 3 hr. The mixture was concentrated under vacuum and the residue concentrated twice with toluene to remove excess thionyl chloride. The residue was dissolved in THF (100 mL), treated with dil. NaHCO$_3$ solution (250 mL) and stirred well at room temperature for 24 hr, followed by standing at room temperature for 3 days. The mixture from the same stage of a smaller scale reaction on 2 g of cis/trans-1-methyl-4-(propyloxy)cyclohexanecarboxylic acid was combined at this time. The combined mixture was concentrated under vacuum to approx. 300 mL and the aqueous residue washed with Et$_2$O (2×120 mL), then acidified with 2M HCl acid and extracted with EtOAc (2×150 mL). The combined extract was dried (Na$_2$SO$_4$) and concentrated under vacuum to leave the title compound as a pale yellow solid (5.1 g, 34%).

$^1$H NMR δ (CDCl$_3$, 400 MHz): 0.92 (3H, t), 1.24 (3H, s), 1.54-1.74 (8H, m), 1.78-1.88 (2H, m), 3.33-3.40 (3H, m). 1H not discernible from spectrum.

DESCRIPTION 15 trans-1-Isocyanato-1-methyl-4-(propyloxy)cyclohexane. (D15)

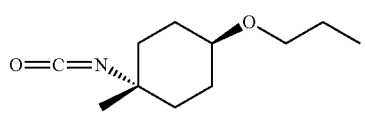

D15

A stirred solution of trans-1-methyl-4-(propyloxy)cyclohexanecarboxylic acid (D14, 5.1 g, 0.027 mol) in toluene (120 mL) at room temperature under argon was treated with triethylamine (4.9 mL, 0.035 mol) and diphenylphosphoryl azide (5.8 mL, 0.027 mol) and heated at 85° C. for 1 hr. The mixture was allowed to cool to room temperature, then treated with 1M NaOH solution (200 mL) and extracted with Et$_2$O (2×150 mL). The combined extract was dried (Na$_2$SO$_4$) and concentrated under vacuum to leave the title compound as a yellow oil (5.0 g, 100%).

$^1$H NMR δ (CDCl$_3$, 400 MHz): 0.91 (3H, t), 1.36 (3H, s), 1.50-1.60 (4H, m), 1.65-1.80 (6H, m), 3.33 (2H, t), 3.46-3.52 (1H, m).

DESCRIPTION 16

[trans-1-Methyl-4-(propyloxy)cyclohexyl]amine hydrochloride. (D16)

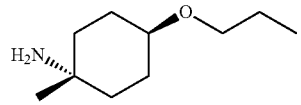

D16

A solution of trans-1-isocyanato-1-methyl-4-(propyloxy)cyclohexane (D15, 5.0 g, 0.027 mol) in THF (100 mL) was treated with 5M HCl acid (25 mL) and stirred at room temperature under argon for 20 hr, then concentrated under vacuum and the residue azeotroped with toluene to remove traces of water. The residual semi-solid was triturated with Et$_2$O (120 mL) to give a solid, which was filtered off, washed with Et$_2$O and dried at 50° C. under vacuum to afford the title compound as a white solid (4.5 g, 85%).

$^1$H NMR δ (CDCl$_3$, 400 MHz): 0.91 (3H, t), 1.47 (3H, s), 1-45-1.70 (4H, m), 1.75-2.00 (6H, m), 3.52 (2H, t), 3.40-3.48 (1H, m), 8.38 (3H, br s).

DESCRIPTION 17

1-[trans-1-Methyl-4-(propyloxy)cyclohexyl]-4-piperidinone. (D17)

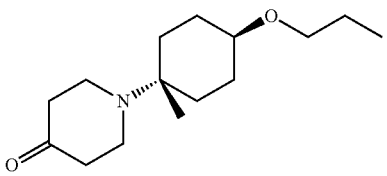

D17

A stirred solution of [trans-1-methyl-4-(propyloxy)cyclohexyl]amine hydrochloride (D16, 4.5 g, 0.022 mol) in a mixture of ethanol (100 mL) and water (60 mL) at room temperature under argon was treated with potassium carbonate (3.31 g, 0.024 mol) followed by 1-ethyl-1-methyl-4-oxopiperidinium iodide (D9, 8.91 g, 0.033 mol), then heated at 80° C. for 2.5 hr. The mixture was allowed to cool, concentrated under vacuum to approx. 60 mL, then the aqueous residue was treated with sat. NaHCO$_3$ solution and extracted with DCM (3×80 mL). The combined extract was dried (Na$_2$SO$_4$) and concentrated under vacuum to leave an orange oil (6.1 g), which was chromatographed on silica gel eluting with 0-10% MeOH/DCM to afford the title compound as a yellow oil (3.45 g, 63%).

¹H NMR δ (CDCl₃, 400 MHz): 0.93 (3H, s+3H, t), 1.48-1.72 (8H, m), 1.80-1.92 (2H, m), 2.41 (4H, t), 2.82 (4H, t), 3.35-3.45 (3H, t+m).

DESCRIPTION 18

2-({1-[trans-1-Methyl-4-(propyloxy)cyclohexyl]-4-piperidinyl}amino)phenol. (D18)

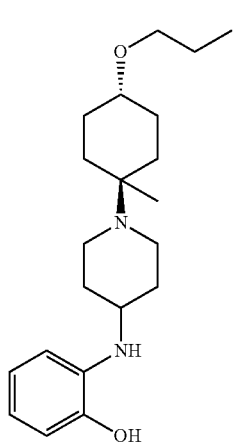

2-Aminophenol (43.1 mg, 0.395 mmol) was dissolved in dichloromethane (2.5 mL) and 1-[trans-1-methyl-4-(propyloxy)cyclohexyl]-4-piperidinone (D17, 100 mg, 0.395 mmol), acetic acid (0.113 mL, 1.97 mmol), and polymer supported sodium cyanoborohydride (387 mg, 0.789 mmol, 2.04 mmol/g) were all added at rt. The mixture was reacted at 100° C. in the microwave for 10 min. The mixture was then cooled to rt, filtered and concentrated by rotary evaporation. The crude product was then purified via chromatography (silica, dichloromethane to 0.5% ammonia/9.5% methanol/90% dichloromethane) to give 2-({1-[trans-1-methyl-4-(propyloxy)cyclohexyl]-4-piperidinyl}amino)phenol (D18, 54.7 mg, 36% yield) as a white solid.

M+H⁺ 347

DESCRIPTION 19

3-Amino-4-hydroxybenzonitrile. (D19)

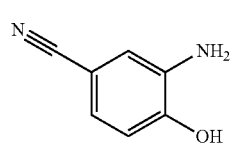

4-Hydroxy-3-nitrobenzonitrile (0.5 g, 3.05 mmol) was dissolved in ethanol (20 mL) and methanol (10 mL), and Raney-Nickel (1 mL, 10% aqueous solution) was added at rt followed by hydrazine mono hydrate (0.296 mL, 6.09 mmol). The mixture was stirred at rt overnight. The mixture was then filtered through celite and concentrated by rotary evaporation. The residue was purified via chromatography (silica, n-hexane to ethyl acetate) to give 3-amino-4-hydroxybenzonitrile (D19, 200 mg, 49%) as an orange solid.

M+H⁺ 135

¹H NMR: δ (DMSO-d₆, 400 MHz) 4.99 (2 H, br. s), 6.74 (1 H, d, J 7.9), 6.82-6.89 (2 H, m), 10.23 (1 H, br. s).

DESCRIPTION 20

3-({1-[trans-4-(Ethyloxy)-1-methylcyclohexyl]-4-piperidinyl}amino)-4-hydroxybenzonitrile. (D20)

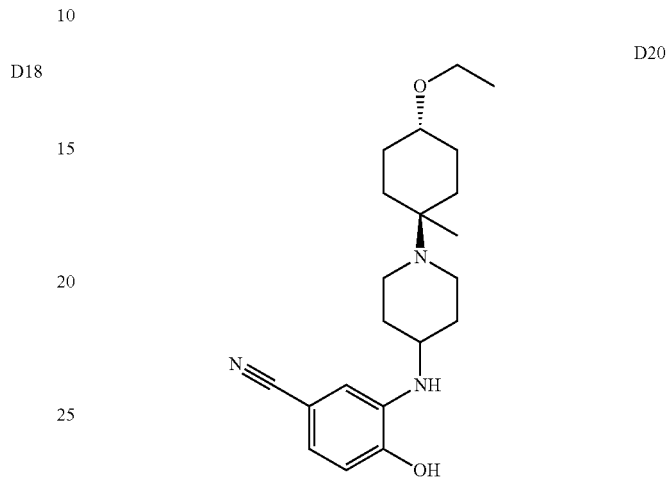

Polymer supported sodium cyanoborohydride (419 mg, 0.854 mmol, 2.04 mmol/g) was added to a solution of 3-amino-4-hydroxybenzonitrile (D19, 55.2 mg, 0.412 mmol), 1-[trans-4-(ethyloxy)-1-methylcyclohexyl]-4-piperidinone (D8, 123 mg, 0.514 mmol) and acetic acid (120 μl, 2.10 mmol) in dichloromethane (2.5 mL). The mixture was heated by microwave at 100° C. for 10 min before being filtered and concentrated by rotary evaporation to give an orange/brown oil. The residue was purified via chromatography (silica, dichloromethane to 0.5% ammonia/9.5% methanol/90% dichloromethane) to give 3-({1-[trans-4-(ethyloxy)-1-methylcyclohexyl]-4-piperidinyl}amino)-4-hydroxybenzonitrile (D20, 96.9 mg, 59% yield) as a yellow oil.

M+H⁺ 358

DESCRIPTION 21

5-Fluoro-4-methyl-2-nitrophenol. (D21)

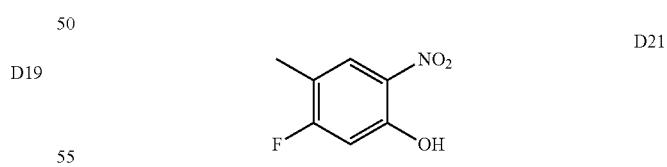

70% Nitric acid (0.759 mL, 8.42 mmol) was added dropwise to a solution of 3-fluoro-4-methylphenol (966 mg, 7.66 mmol) in dichloromethane (25 mL) at rt. The reaction was stirred for 30 min before being washed with water. The aqueous layer was extracted with dichloromethane (1×) and the combined organics were dried (Na₂SO₄) and concentrated by rotary evaporation to give a yellow/orange solid. The residue was purified via chromatography (silica, dichloromethane to 0.5% ammonia/9.5% methanol/90% dichloromethane) to give 5-fluoro-4-methyl-2-nitrophenol (D21, 873 mg, 67% yield) as a yellow solid.

¹H NMR δ (CDCl₃, 400 MHz) 2.60 (3 H, s), 6.80 (1 H, d, J 10), 7.99 (1H, dd, J 10 and 0.8).

DESCRIPTION 22

2-Amino-5-fluoro-4-methylphenol. (D22)

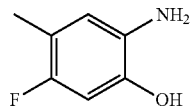

5-Fluoro-4-methyl-2-nitrophenol (D21, 162 mg, 0.946 mmol) was reduced using H-Cube™ hydrogenator (full H₂ mode, 25° C., 1 mL/min). The reaction was concentrated by rotary evaporation to give 2-amino-5-fluoro-4-methylphenol (D22, 117 mg, 88% yield) as a pale yellow solid.

¹H NMR δ (CDCl₃, 400 MHz) 2.13 (3 H, s), 6.51 (1 H, d, J 10), 6.61 (1 H, d, J 7.6).

DESCRIPTION 23

2-({1-[trans-4-(Ethyloxy)-1-methylcyclohexyl]-4-piperidinyl}amino)-5-fluoro-4-methylphenol. (D23)

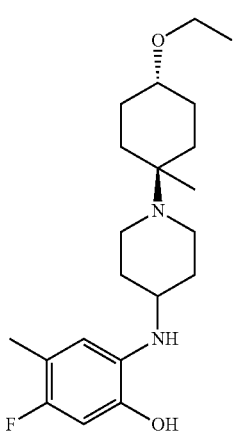

Polymer supported sodium cyanoborohydride (439 mg, 0.896 mmol, 2.04 mmol/g) was added to a solution of 2-amino-5-fluoro-4-methylphenol (D22, 61.4 mg, 0.435 mmol), 1-[trans-4-(ethyloxy)-1-methylcyclohexyl]-4-piperidinone (D8, 105 mg, 0.440 mmol) and acetic acid (0.12 mL, 2.10 mmol) in dichloromethane (2.5 mL). The mixture was heated by microwave at 100° C. for 10 min and then for a further 10 min before being filtered and concentrated by rotary evaporation to give a green oil. The residue was purified via chromatography (silica, dichloromethane to 0.5% ammonia/9.5% methanol/90% dichloromethane) to give 2-({1-[trans-4-(ethyloxy)-1-methylcyclohexyl]-4-piperidinyl}amino)-5-fluoro-4-methylphenol (D23, 128 mg, 72% yield) as a white solid.

M+H⁺ 365

DESCRIPTION 24

2-({1-[trans-4-(Ethyloxy)-1-methylcyclohexyl]-4-piperidinyl}amino)-4-(methylsulfonyl)phenol. (D24)

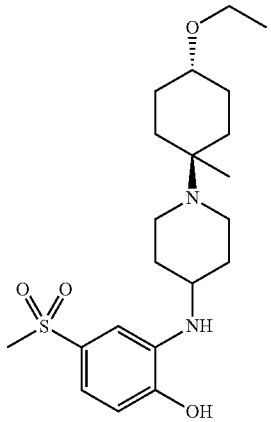

Polymer supported cyanoborohydride (158 mg, 0.679 mmol, 4.3 mmol/g) was added to a solution of 2-amino-4-(methylsulfonyl)phenol (63.6 mg, 0.34 mmol), 1-[trans-4-(ethyloxy)-1-methylcyclohexyl]-4-piperidinone (D8, 84.6 mg, 0.353 mmol) and acetic acid (0.1 mL, 1.75 mmol) in tetrahydrofuran (2.5 mL). The mixture was heated by microwave at 100° C. for 30 min before being filtered and concentrated by rotary evaporation to give a pale yellow oil. The residue was purified via chromatography (silica, dichloromethane to 0.5% ammonia/9.5% methanol/90% dichloromethane) to give 2-({1-[trans-4-(ethyloxy)-1-methylcyclohexyl]-4-piperidinyl}amino)-4-(methylsulfonyl)phenol (D24, 93.3 mg, 67% yield) as a white solid.

¹H NMR δ (CDCl₃, 400 MHz) 1.10-1.22 (6 H, m), 1.33-2.08 (10 H, m), 2.38-2.59 (2 H, m), 2.90-3.13 (6 H, m), 3.16-3.37 (2 H, m), 3.41-3.52 (3 H, m), 6.64 (1 H, d, J 8), 7.09 (2 H, m).

DESCRIPTION 25

2-({1-[trans-4-(Ethyloxy)-1-methylcyclohexyl]-4-piperidinyl}amino)-4-(ethylsulfonyl)phenol. (D25)

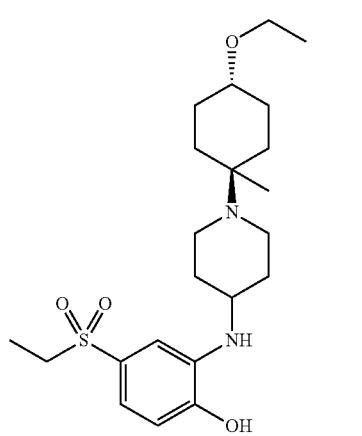

2-Amino-4-(ethylsulfonyl)phenol (91 mg, 0.451 mmol) was dissolved in tetrahydrofuran (3 mL) and 1-[trans-4-(ethyloxy)-1-methylcyclohexyl]-4-piperidinone (D8, 108 mg, 0.451 mmol), polymer supported sodium cyanoborohydride (442 mg, 0.902 mmol, 2.04 mmol/g), and acetic acid (0.129 mL, 2.26 mmol) were all added at rt. The mixture was reacted at 100° C. in the microwave for 95 min. The mixture was then cooled to rt, filtered and concentrated to give 2-({1-[trans-4-(ethyloxy)-1-methylcyclohexyl]-4-piperidinyl}amino)-4-(ethylsulfonyl)phenol (D25, 211 mg, 66% yield) as a brown oil.
M+H⁺ 425

DESCRIPTION 26

4-Fluoro-2-({1-[trans-1-methyl-4-(propyloxy)cyclohexyl]-4-piperidinyl}amino)phenol. (D26)

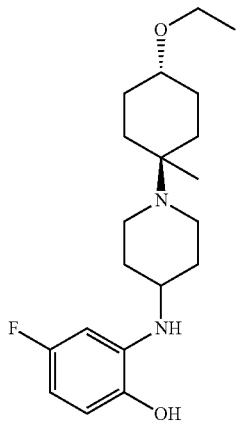

2-Amino-4-fluorophenol (55.2 mg, 0.434 mmol) was dissolved in dichloromethane (3 mL) and 1-[trans-1-methyl-4-(propyloxy)cyclohexyl]-4-piperidinone (D17, 110 mg, 0.434 mmol), polymer supported sodium cyanoborohydride (426 mg, 0.868 mmol, 2.04 mmol/g) and acetic acid (0.124 mL, 2.17 mmol) were all added at rt. The mixture was reacted at 100° C. in the microwave for 10 min. The mixture was then cooled to rt, filtered and evaporated to give 4-fluoro-2-({1-[trans-1-methyl-4-(propyloxy)cyclohexyl]-4-piperidinyl}amino)phenol (D26, 216 mg, 82% yield) as a brown solid.
M+H⁺ 365

DESCRIPTION 27

2-({1-[trans-4-(Ethyloxy)-1-methylcyclohexyl]-4-piperidinyl}amino)-4-fluorophenol. (D27)

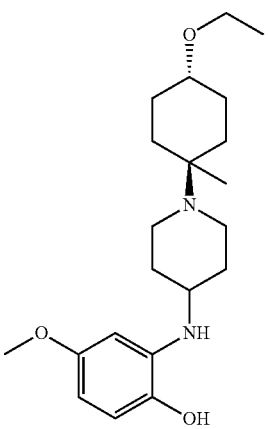

2-Amino-4-fluorophenol (74.0 mg, 0.582 mmol) was dissolved in dichloromethane (3 mL) and 1-[trans-4-(ethyloxy)-1-methylcyclohexyl]-4-piperidinone (D8, 139 mg, 0.582 mmol), polymer supported sodium cyanoborohydride (571 mg, 1.16 mmol, 2.04 mmol/g) and acetic acid (0.167 mL, 2.91 mmol) were all added at rt. The mixture was reacted at 100° C. in the microwave for 10 min. The mixture was then cooled to rt, filtered and concentrated by rotary evaporation to give 2-({1-[trans-4-(ethyloxy)-1-methylcyclohexyl]-4-piperidinyl}amino)-4-fluorophenol (D27, 299 mg, 88% yield) as a brown oil.
M+H⁺ 351

DESCRIPTION 28

2-({1-[trans-4-(ethyloxy)-1-methylcyclohexyl]-4-piperidinyl}amino)-4-(methyloxy)phenol. (D28)

2-Amino-4-(methyloxy)phenol monohydrochloride (503 mg, 2.86 mmol) was treated with saturated aqueous NaHCO₃

(50 mL) and the aqueous layer was extracted with dichloromethane (2×). The combined organics were then dried (Na$_2$SO$_4$) and concentrated by rotary evaporation to give the free base. The free base was then dissolved in dichloromethane (3 mL) and 1-[trans-4-(ethyloxy)-1-methylcyclohexyl]-4-piperidinone (D8, 99.2 mg, 0.414 mmol), acetic acid (0.119 mL, 2.07 mmol) and polymer supported sodium cyanoborohydride (406 mg, 0.829 mmol) were all added at rt. The mixture was reacted at 100° C. in the microwave for 10 min. The mixture was then cooled to rt, filtered and concentrated by rotary evaporation. The crude product was then purified via chromatography (silica, dichloromethane to 0.5% ammonia/9.5% methanol/90% dichloromethane) to give 2-({1-[trans-4-(ethyloxy)-1-methylcyclohexyl]-4-piperidinyl}amino)-4-(methyloxy)phenol (D28, 79.7 mg, 42% yield) as a brown solid.

M+H$^+$ 363

DESCRIPTION 29

2-({1-[trans-4-(Ethyloxy)cyclohexyl]-4-piperidinyl}amino)-4-methyl phenol. (D29)

DESCRIPTION 30

2-({1-[trans-4-(Ethyloxy)-1-methylcyclohexyl]-4-piperidinyl}amino)-4-methylphenol. (D30)

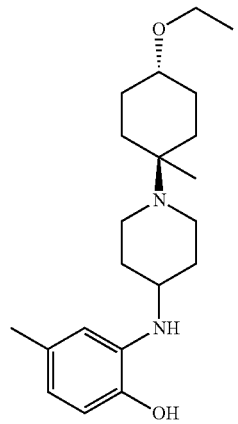

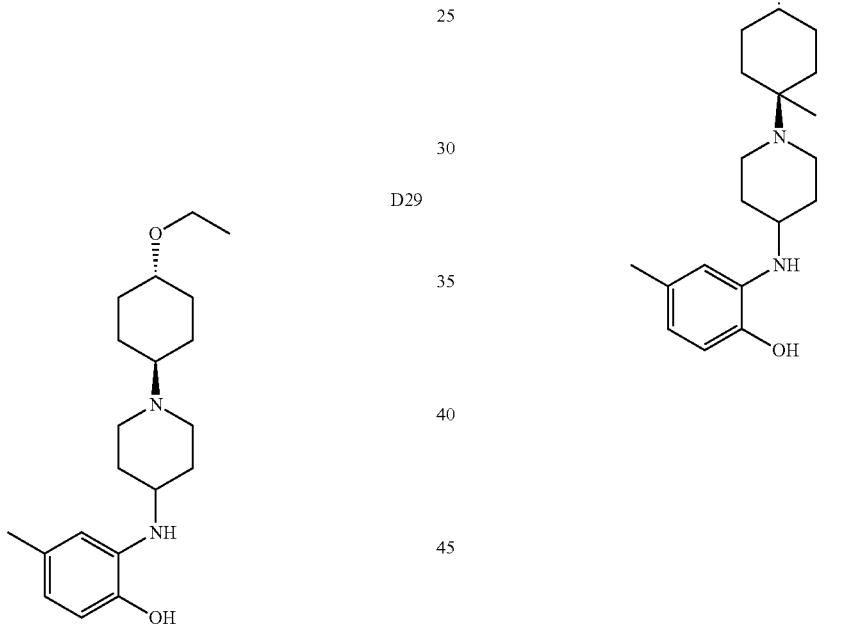

2-Amino-4-methylphenol (56.1 mg, 0.456 mmol) was dissolved in dichloromethane (3 mL) and 1-[trans-4-(ethyloxy)cyclohexyl]-4-piperidinone (D66, 103 mg, 0.456 mmol), polymer supported sodium cyanoborohydride (212 mg, 0.912 mmol, 4.3 mmol/g) and acetic acid (0.13 mL, 2.28 mmol) were all added at rt. The mixture was reacted at 100° C. in the microwave for 10 min. The mixture was then cooled to rt, filtered and concentrated by rotary evaporation to give 2-({1-[trans-4-(ethyloxy)cyclohexyl]-4-piperidinyl}amino)-4-methylphenol (D29, 215 mg, 92% yield) as a white solid.

M+H$^+$ 333

Polymer supported sodium cyanoborohydride (592 mg, 1.21 mmol, 2.04 mmol/g) was added to a solution 1-[trans-4-(ethyloxy)-1-methylcyclohexyl]-4-piperidinone (D8, 145 mg, 0.604 mmol), 2-amino-4-methylphenol (79.9 mg, 0.649 mmol) and acetic acid (0.2 mL, 3.49 mmol) in dichloromethane (2.5 mL). The mixture was heated by microwave at 100° C. for 10 min before being filtered and concentrated by rotary evaporation to give a yellow oil. The residue was purified via chromatography (silica, dichloromethane to 0.5% ammonia/9.5% methanol/90% dichloromethane) to give 2-({1-[trans-4-(ethyloxy)-1-methylcyclohexyl]-4-piperidinyl}amino)-4-methylphenol (D30, 143 mg, 65% yield) as a white solid.

M+H$^+$ 347

DESCRIPTION 31

2-Chloro-N-{1-[trans-4-(ethyloxy)-1-methylcyclohexyl]-4-piperidinyl}-N-(2-hydroxy-5-methylphenyl)acetamide. (D31)

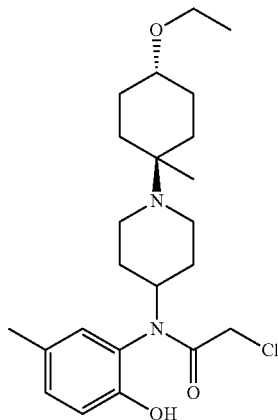

Chloroacetyl chloride (0.1 mL, 1.25 mmol) was added to a mixture of 2-({1-[trans-4-(ethyloxy)-1-methylcyclohexyl]-4-piperidinyl}amino)-4-methylphenol (D30, 163 mg, 0.471 mmol) in ethyl acetate (5 mL) and potassium carbonate solution (5 mL, 2.5 mmol, 0.5 M in water). The reaction was stirred for 1 h and then the 2 phases were separated and the organic phase was dried (Na$_2$SO$_4$) and concentrated by rotary evaporation to give 2-chloro-N-{1-[trans-4-(ethyloxy)-1-methylcyclohexyl]-4-piperidinyl}-N-(2-hydroxy-5-methylphenyl)acetamide (D31, 186 mg, 93% yield) as a pale yellow oil. M+H$^+$ 423

DESCRIPTION 32

1,1-Dimethylethyl 4-[(5-cyano-2-hydroxyphenyl)amino]-1-piperidinecarboxylate. (D32)

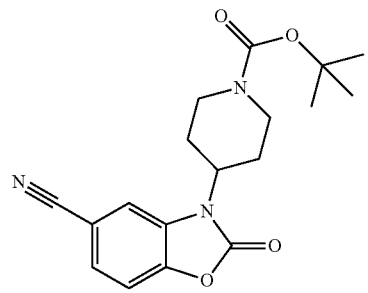

Polymer supported sodium cyanoborohydride (3531 mg, 7.20 mmol, 2.04 mmol/g) was added to a solution of 3-amino-4-hydroxybenzonitrile (D19, 477 mg, 3.56 mmol), 1,1-dimethylethyl 4-oxo-1-piperidinecarboxylate (709 mg, 3.56 mmol) and acetic acid (1 mL, 17.5 mmol) in tetrahydrofuran (10 mL). The mixture was heated by microwave at 100° C. for 30 min and then for a further 30 min before being filtered and concentrated by rotary evaporation to give 1,1-dimethylethyl 4-[(5-cyano-2-hydroxyphenyl)amino]-1-piperidinecarboxylate (D32, 982 mg, 3.09 mmol, 87% yield) as a yellow solid. M−H$^+$ 316

$^1$H NMR: δ (CDCl$_3$; 400 MHz) 1.32-1.53 (11 H, m), 2.03 (2 H, m), 2.86-3.14 (2 H, m), 3.41 (1 H, m), 4.03 (2 H, m), 6.77 (1 H, d, J 1.8), 6.82 (1 H, d, J 8.0), 6.90 (1 H, dd, J 8.0 and 1.8).

DESCRIPTION 33

1,1-Dimethylethyl 4-(5-cyano-2-methylidene-1,3-benzoxazol-3(2H)-yl)-1-piperidinecarboxylate. (D33)

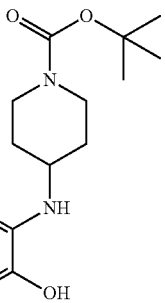

Hünig's base (1 mL, 5.73 mmol) was added to a solution of 1,1-dimethylethyl 4-[(5-cyano-2-hydroxyphenyl)amino]-1-piperidinecarboxylate (D32, 977 mg, 3.08 mmol) in dichloromethane (20 mL) at rt under argon. The reaction was cooled to 0° C. and triphosgene (373 mg, 1.26 mmol) was added. The reaction was then stirred for 30 min at 0° C. and quenched with saturated aqueous NaHCO$_3$ (20 mL) before being partitioned between dichloromethane and water. The aqueous layer was extracted with dichloromethane (2×) and the combined organics were dried (Na$_2$SO$_4$) and concentrated by rotary evaporation to give a yellow oil. The crude residue was purified via chromatography (silica, Biotage 40+S column, dichloromethane to 0.5% ammonia/9.5% methanol/90% dichloromethane) to give 1,1-dimethylethyl 4-(5-cyano-2-methylidene-1,3-benzoxazol-3(2H)-yl)-1-piperidinecarboxylate (D33, 1.22 g, 92% yield, 82% purity by LC-MS) as a yellow oil.

[M−O$^t$Bu] 270

¹H NMR: δ (CDCl₃; 400 MHz) 1.51 (9 H, s), 1.93 (2 H, m), 2.28 (2 H, m), 2.92 (2 H, m), 4.28-4.44 (3 H, m), 7.35 (1 H, d, J 8.8), 7.48-7.54 (2 H, m).

DESCRIPTION 34

2-oxo-3-(4-piperidinyl)-2,3-dihydro-1,3-benzoxazole-5-carbonitrile monohydrochloride. (D34)

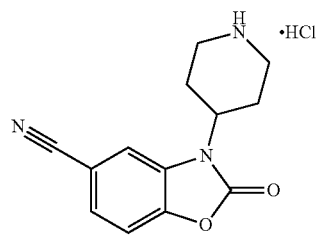

1,1-Dimethylethyl 4-(5-cyano-2-oxo-1,3-benzoxazol-3(2H)-yl)-1-piperidinecarboxylate (D33, 1.22 g, 2.84 mmol, 80% wt.) was dissolved in dichloromethane (20 mL) at rt to give a yellow solution and HCl (20 mL, 80 mmol, 4 M in 1,4-dioxane) was added whereupon the mixture turned orange. The reaction was stirred for 2 h (precipitate formed after 15 minutes). The reaction was diluted with diethyl ether (20 mL) and filtered. The solid was washed with diethyl ether (2×) and dried under high vacuum to give 2-oxo-3-(4-piperidinyl)-2,3-dihydro-1,3-benzoxazole-5-carbonitrile monohydrochloride (D34, 557 mg, 70% yield) as a pale pink solid.
[M+H]⁺ 244
¹H NMR δ (DMSO-d₆; 400 MHz) 2.01 (2 H, m), 3.07 (2 H, m), 3.44 (2 H, m), 4.54 (1 H, m), 7.59 (1 H, d, J 8.3), 7.70 (1 H, dd, J 8.3 and 1.5), 8.07 (1 H, d, J1.5), 8.94 (2 H, m). 2 H obscured by solvent peak.

DESCRIPTION 35

3-[1-(1-Cyano-4-{[2-(methyloxy)ethyl]oxy}cyclohexyl)-4-piperidinyl]-2-oxo-2,3-dihydro-1,3-benzoxazole-5-carbonitrile. (D35)

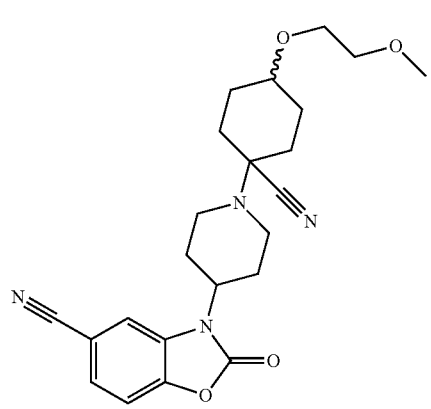

2-Oxo-3-(4-piperidinyl)-2,3-dihydro-1,3-benzoxazole-5-carbonitrile monohydrochloride (D34, 254.4 mg, 0.909 mmol) was purified by SCX (5 g, eluting with MeOH followed by 2 M NH₃ in MeOH) to give the free base (225 mg). The free base was then dissolved in N,N-dimethylacetamide (10 mL) at rt under argon. MgSO₄ (560 mg, 4.66 mmol), 4-{[2-(methyloxy)ethyl]oxy}cyclohexanone (D61, 259 mg, 1.51 mmol) and acetone cyanohydrin (0.17 mL, 1.86 mmol) were added and the reaction was heated at 70° C. overnight under a gentle stream of argon. The mixture was then cooled to rt, diluted with 1:1 dichloromethane:water (30 mL) and sonicated for 15 min. The phases were allowed to separate and the organic phase was dried by filtering through a hydrostatic cartridge. A further 10 mL of dichloromethane was added to the aqueous phase and the mixture stirred vigorously for 10 min. The 2 phases were again separated and the organic phase was dried by filtering through a hydrostatic cartridge. The combined organic layer was concentrated by rotary evaporation to give 3-[1(1-cyano-4-{[2-(methyloxy)ethyl]oxy}cyclohexyl)-4-piperidinyl]-2-oxo-2,3-dihydro-1,3-benzoxazole-5-carbonitrile (D35, 490 mg, 15% yield, 12% purity) as a yellow oil.

Isomer 1: [M-CN]⁺ 398; retention time 2.75.
Isomer 2: [M-CN]⁺ 398; retention time 2.85.

DESCRIPTIONS 36 and 37

4-Hydroxy-3-{[1-(trans-1-methyl-4-{[2-(methyloxy)ethyl]oxy}cyclohexyl)-4-piperidinyl]amino}benzonitrile. (D36) and 4-Hydroxy-3-{[1-(cis-1-methyl-4-{[2-(methyloxy)ethyl]oxy}cyclohexyl)-4-piperidinyl]amino}benzonitrile. (D37)

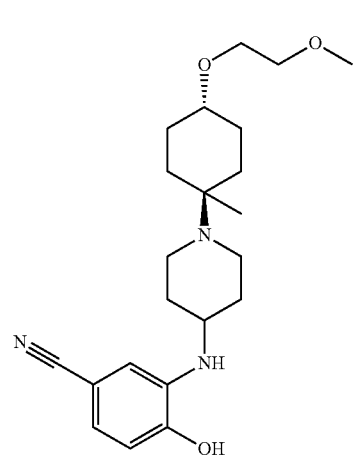

-continued

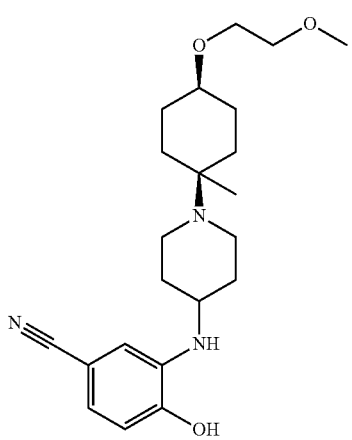

Methylmagnesium iodide (2.3 mL, 6.90 mmol, 3 M in diethyl ether) was added to a suspension of 3-[1(1-cyano-4-{[2-(methyloxy)ethyl]oxy}cyclohexyl)-4-piperidinyl]-2-oxo-2,3-dihydro-1,3-benzoxazole-5-carbonitrile (D35, 490 mg, 0.808 mmol, 70% wt.) in tetrahydrofuran (5 mL) at rt under argon. The reaction was diluted with a further portion of tetrahydrofuran (5.00 mL) and stirred for 2 h before being cooled to 0° C. and being quenched with saturated aqueous NH$_4$Cl (5 mL). The mixture was partitioned between ethyl acetate and water and the aqueous layer was extracted with ethyl acetate (2×). The combined organics were dried (Na$_2$SO$_4$) and concentrated by rotary evaporation to give an orange/yellow oil. The mixture was separated by high pH MDAP to give 4-hydroxy-3-{[1-(trans-1-methyl-4-{[2-(methyloxy)ethyl]oxy}cyclohexyl)-4-piperidinyl]amino}benzonitrile (D36, 37.5 mg, 70% yield) as a colourless oil and 4-hydroxy-3-{[1-(cis-1-methyl-4-{[2-(methyloxy)ethyl]oxy}cyclohexyl)-4-piperidinyl]amino}benzonitrile (D37, 22.6 mg, 42% yield) as an off white solid.

Assignment of cis or trans geometry was by conversion to the benzoxazolone and then use of distinctive chemical shift
trans: [M+H]$^+$ 388; Rt=5.61
cis: [M+H]$^+$ 388; Rt=7.07

DESCRIPTION 36

Alternative Procedure. 4-Hydroxy-3-{[1-(trans-1-methyl-4-{[2-(methyloxy)ethyl]oxy}cyclohexyl)-4-piperidinyl]amino}benzonitrile. (D36)

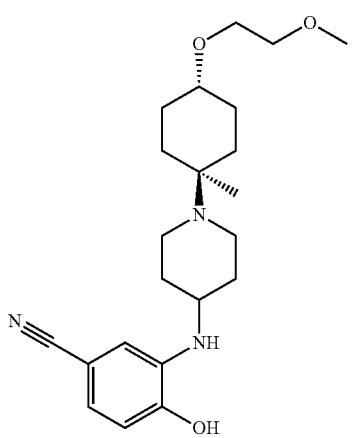

Polymer supported cyanoborohydride (908 mg, 3.90 mmol, 4.3 mmol/g) was added to a solution of 3-amino-4-hydroxybenzonitrile (D19, 265 mg, 1.98 mmol), 1-(trans-1-methyl-4-{[2-(methyloxy)ethyl]oxy}cyclohexyl)-4-piperidinone (D73, 526 mg, 1.95 mmol) and acetic acid (0.56 mL, 9.76 mmol) in THF (8 mL). The mixture was heated by microwave at 100° C. for 1 h and then for a further 1 hour. The reaction was then filtered and concentrated by rotary evaporation to give a yellow/brown oil which was purified via flash column chromatography (silica, Biotage 40+S column, DCM to 0.5% NH$_3$/9.5% MeOH/90% DCM) to give 4-hydroxy-3-{[1-(trans-1-methyl-4-{[2-(methyloxy)ethyl]oxy}cyclohexyl)-4-piperidinyl]amino}benzonitrile (D36, 554 mg, 73%) as a cream solid.

LCMS: [M+H]$^+$ 388

$^1$H NMR: δ (CDCl$_3$; 400 MHz) 1.04 (3 H, s), 1.34-1.48 (2 H, m), 1.50-1.77 (6 H, m), 1.81-1.98 (2 H, m), 2.05-2.16 (2 H, m), 2.33-2.48 (2 H, m), 3.04-3.29 (4 H, m), 3.39 (3 H, s), 3.51-3.61 (4 H, m), 6.58 (1 H, d, J 8.1), 6.70 (1 H, d, J 1.9), 6.85 (1 H, dd, J 8.1 and 1.9).

DESCRIPTION 38

Bis(1,1-dimethylethyl) (4-methyl-2-nitrophenyl)propanedioate. (D38)

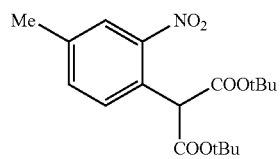

A stirred solution of di-tert-butyl malonate (1.5 mL, 6.70 mmol) in N,N-dimethylformamide (15 mL) at 0° C. under argon was treated portionwise over 10 minutes with sodium hydride (276 mg of 60% oil dispersion, 6.90 mmol) and stirred at 0° C. for 15 minutes before allowing to warm to room temperature over 1 hour. A white precipitate was produced. The stirred mixture was cooled to 0° C. and treated with a solution of 4-fluoro-3-nitrotoluene (1.0 g, 6.45 mmol) in N,N-dimethylformamide (2 mL) and a deep purple colour was immediately formed. This mixture was stirred at room temperature for 28 hours then heated at 70° C. for 6 hours. The mixture was cooled, then diluted with water (100 mL) and extracted with Et$_2$O (2×50 mL). The combined extract was washed with water (70 mL), dried (Na$_2$SO$_4$) and concentrated under vacuum. The residue was purified by chromatography on silica gel (40 g) eluting with toluene to afford the title compound as a yellow oil (660 mg, 29%).

$^1$H NMR δ (CDCl$_3$, 400 MHz): 1.48-1.53 (18H, m), 2.43 (3H, s), 5.06 (1H, s), 7.40-7.48 (2H, m), 7.84 (1H, d).

DESCRIPTION 39

Bis(1,1-dimethylethyl) (2-amino-4-methylphenyl)propanedioate. (D39)

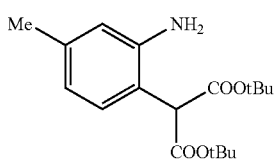
D39

A solution of bis(1,1-dimethylethyl) (4-methyl-2-nitrophenyl)propanedioate (D38, 660 mg, 1.88 mmol) in ethyl acetate (25 mL) was treated with 10% Pd/C (0.5 g) and shaken under hydrogen at atmospheric pressure and room temperature for 20 hours. The mixture was filtered through Kieselguhr and the filtrate concentrated under vacuum to afford the title compound as a colourless oil (606 mg, 100%).

$^1$H NMR δ (CDCl$_3$, 400 MHz): 1.40-1.52 (18H, m), 2.24 (3H, s), 4.03 (2H, br s), 4.43 (1H, s), 6.50-6.60 (2H, m), 7.04 (1H, d).

DESCRIPTION 40

Bis(1,1-dimethylethyl) [4-methyl-2-({1-[trans-1-methyl-4-(propyloxy)cyclohexyl]-4-piperidinyl}amino)phenyl]propanedioate. (D40)

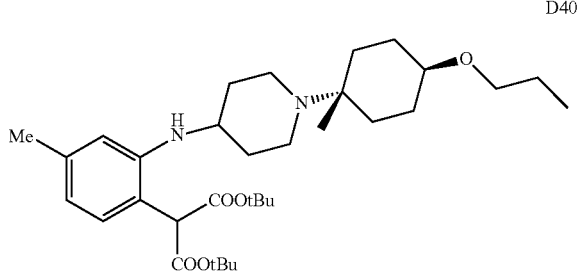
D40

A stirred solution of 1-[trans-1-methyl-4-(propyloxy)cyclohexyl]-4-piperidinone (D17, 165 mg, 0.65 mmol) in dichloromethane (5 mL) at room temperature under argon was treated with bis(1,1-dimethylethyl) (2-amino-4-methylphenyl)propanedioate (D39, 200 mg, 0.62 mmol), sodium triacetoxyborohydride (190 mg, 0.90 mmol) and acetic acid (1 drop) and maintained at room temperature for 19 hours. Further 1-[trans-1-methyl-4-(propyloxy)cyclohexyl]-4-piperidinone (165 mg) and sodium triacetoxyborohydride (190 mg) were then added and the mixture stirred at room temperature for 10 days. The reaction mixture was treated with Na$_2$CO$_3$ solution and extracted with dichloromethane. The extract was dried (Na$_2$SO$_4$) and concentrated under vacuum to leave a yellow oil (340 mg) containing the title compound. This was used in the next step without further purification.

DESCRIPTION 41

2-Fluoro-4-methyl-6-nitrophenol. (D41)

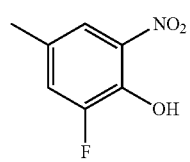
D41

To 2-fluoro-4-methylphenol (500 mg, 3.96 mmol) in dichloromethane (5 mL) at room temperature was added dropwise nitric acid 70% (0.4 mL, 4.44 mmol) [exotherm observed]. After 15 min more washed with water, dried, evaporated to give 2-fluoro-4-methyl-6-nitrophenol (400 mg, 2.337 mmol, 59.0% yield) as a yellow solid.

DESCRIPTION 42

2-Fluoro-4-methyl-6-aminophenol (D42)

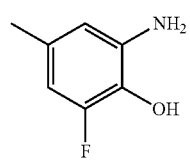
D42

A solution of 2-fluoro-4-methyl-6-nitrophenol D41 (400 mg, 2.337 mmol) (D41) in ethanol (50 mL) was hydrogenated using a Pd/C cartridge in the H-cube™ hydrogenator at 1 mL/min and full hydrogen. Evaporation gave 2-fluoro-4-methyl-6-aminophenol (250 mg, 1.771 mmol, 76% yield) as a fawn solid.

DESCRIPTION 43

2-({1-[trans-4-Ethoxy-1-methylcyclohexyl]-4-piperidinyl}amino)-6-fluoro-4-methylphenol. (D43)

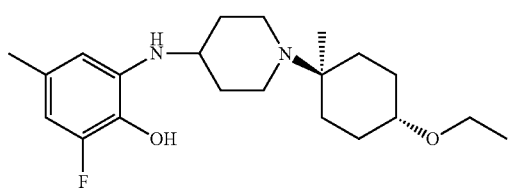
D43

A mixture of 2-fluoro-4-methyl-6-aminophenol (60 mg, 0.425 mmol) (D42), 1-[trans-4-ethoxy-1-methylcyclohexyl]-4-piperidinone (D8, 100 mg, 0.418 mmol), polymer supported cyanoborohydride (450 mg, 0.918 mmol), acetic acid (0.14 mL, 2.448 mmol), and dichloromethane (2.5 mL) was heated in the microwave reactor at 100° C. for 10 min, then filtered and evaporated. Chromatography (20 g silica, 0-10% 2M ammonia-methanol in dichloromethane) gave 2-({1-[trans-4-ethoxy-1-methylcyclohexyl]-4-piperidinyl}amino)-6-fluoro-4-methylphenol (100 mg, 0.274 mmol, 65.7% yield) as a foam.

DESCRIPTION 44

2,3-Difluoro-4-methyl-6-nitrophenol. (D44)

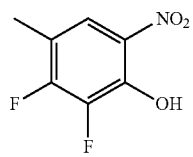

D44

To 2,3-difluoro-4-methylphenol (1 g, 6.94 mmol) in dichloromethane at 0° C. was added nitric acid 70% (0.7 mL, 7.77 mmol). After 1 h at room temperature the solution was washed with water, dried and evaporated to give 2,3-difluoro-4-methyl-6-nitrophenol (1.2 g, 6.35 mmol, 91% yield) (D44) as yellow solid.

DESCRIPTION 45

2,3-Difluoro-4-methyl-6-aminophenol. (D45)

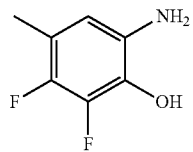

D45

A solution of 2,3-difluoro-4-methyl-6-nitrophenol (1.2 g, 6.35 mmol) (D44) in ethanol (120 mL) was hydrogenated using a 10% Pd/C cartridge in the H-cube™ hydrogenator at 1 mL/min and full hydrogen at 25° C. Evaporation gave 2,3-difluoro-4-methyl-6-aminophenol (1.0 g, 6.28 mmol, 99% yield) as a fawn solid.

DESCRIPTION 46

2-({1-[trans-4-Ethoxy-1-methylcyclohexyl]-4-piperidinyl}amino)-5,6-difluoro-4-methylphenol. (D46)

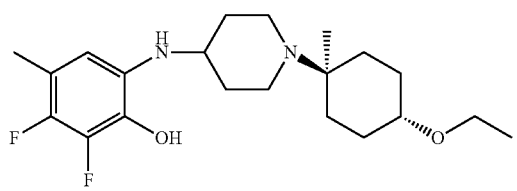

D46

A mixture of 2,3-difluoro-4-methyl-6-aminophenol (D45, 75 mg, 0.471 mmol), 1-[trans-4-ethoxy-1-methylcyclohexyl]-4-piperidinone (D8, 100 mg, 0.418 mmol), polymer supported cyanoborohydride (400 mg, 0.816 mmol), acetic acid (0.15 mL, 2.62 mmol), and dichloromethane (2.5 mL) was heated in the microwave reactor at 100° C. for 10 min, then filtered and evaporated. Chromatography on silica (20 g), eluting with 0-15% 2M ammonia in methanol-dichloromethane, gave 6-({1-[trans-4-ethoxy-1-methylcyclohexyl]-4-piperidinyl}amino)-2,3-difluoro-4-methylphenol (110 mg, 0.288 mmol, 68.8% yield) as a white solid.

DESCRIPTION 47

1-[trans-1-Methyl-4-(methyloxy)cyclohexyl]-4-piperidinone (D47)

D47

(i) cis/trans-1-Methyl-4-(methyloxy)cyclohexanecarboxylic acid

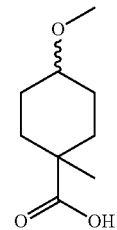

A stirred solution of diisopropylamine (16.1 mL, 115 mmol, 2.1 eq.) in tetrahydrofuran (200 mL) at 0° C. under argon was treated with 2.5M n-butyllithium in hexane (1.05 eq., 110 mmol, 44 mL) and it was then stirred at the same temperature for 10 minutes. The mixture was then treated with a solution of 4-(methyloxy)cyclohexanecarboxylic acid (1 eq., 55 mmol, 8.7 g) in 50 mL of dry tetrahydrofuran. The resulting yellow solution was heated at 50° C. for 2 hr, then cooled to 0° C. and treated with iodomethane (3 eq., 12 mL). The mixture was allowed to warm to room temperature and was stirred for 2 hr. The mixture was partitioned between citric acid (10% aqueous solution) and Et$_2$O, the two phases were separated and the aqueous was extracted with Et$_2$O (2×). Organics were combined, dried (Na$_2$SO$_4$), filtered and concentrated under vacuum to leave a yellow solid (9.8 g) a mixture of cis:trans isomers.

$^1$H NMR δ (DMSO-d$_6$, 400 MHz): 1.08-2.09 (11 H, cis/trans isomers), 3.07 (0.5H, m single isomer), 3.19 (1.5H, s single isomer), 3.21 (1.5H, s single isomer), 3.61 (0.5H, s broad, single isomer), >12.5 (1H, s broad, cis/trans isomers).

(ii) trans-1-Methyl-4-(methyloxy)cyclohexanecarboxylic acid

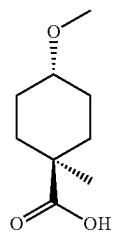

cis/trans-1-methyl-4-(methyloxy)cyclohexanecarboxylic acid from part (i) (41.3 mmol, 7.7 g) was dissolved in thionyl chloride (15.3 eq., 631 mmol, 46 mL). The mixture was refluxed at 90° C. for 4 hours. The solvent was evaporated and the crude product treated with toluene and concentrated in vacuo. The residual brown oil was treated with 5% $Na_2CO_3$ solution (400 mL) and tetrahydrofuran (40 mL) and the mixture was stirred at room temperature for 30 minutes. The aqueous solution was washed with $Et_2O$ (2×) and the aqueous phase was acidified with 2M HCl acid and extracted with ethyl acetate (2×). The combined organics were dried over $Na_2SO_4$, filtered and the solvent was evaporated to afford the titled compound (2.8 g, 40%).

$^1$H NMR δ (DMSO-$d_6$, 400 MHz): 1.09 (3H, s), 1.42 (2H, m), 1.49 (4H, m), 1.70 (2H, m), 3.23 (4H, m), 3.34 (1H, s).

(iii) trans-1-Isocyanato-1-methyl-4-(methyloxy)cyclohexane

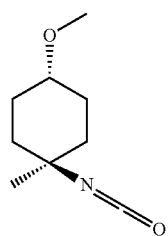

To a solution of trans-1-methyl-4-(methyloxy)cyclohexanecarboxylic acid from part (ii) (15.0 mmol, 2.8 g) in dry toluene (70 mL), $Et_3N$ (1.3 eq., 19.6 mmol, 2.7 mL), and diphenylphosphoryl azide (1.0 eq., 15.0 mmol, 3.2 mL) were added at room temperature. The mixture was refluxed at 80° C. for 2 hours. The mixture was cooled to room temperature and poured onto 1M NaOH (70 mL); the aqueous solution was extracted with EtOAc (2×). The organics were combined dried over $Na_2SO_4$, filtered and the solvent was evaporated to afford the crude compound. The crude product was then purified by chromatography (EtOAc-n-hexane) on silica column to afford the title compound (1.33 g, 48%).

$^1$H NMR δ (DMSO-$d_6$, 400 MHz): 1.33 (3H, s), 1.61 (8H, m), 3.20 (3H, s) 3.36 (1H, m).

(iv) trans-1-Methyl-4-(methyloxy)cyclohexanamine monohydrochloride

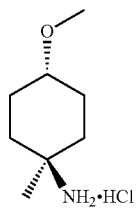

To a solution of trans-1-isocyanato-1-methyl-4-(methyloxy)cyclohexane from part (iii) (7.27 mmol, 1.33 g) in THF (30 mL), concentrated HCl (6 mL) was added at room temperature. The mixture was stirred for 4 hours at room temperature and concentrated HCl (a few drops) was added. The reaction was left overnight and the solvent evaporated to afford the title compound (0.9 g, 69%).

$^1$H NMR δ (DMSO-$d_6$, 400 MHz): 1.26 (3H, s), 1.39 (2H, m), 1.63 (4H, m), 1.87 (2H, m), 3.16 (1H, m), 3.22 (3H, s), 8.22 (3H, br s).

(v) 1-[trans-1-Methyl-4-(methyloxy)cyclohexyl]-4-piperidinone (D47)

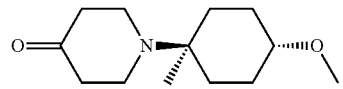

D47 trans-1-Methyl-4-(methyloxy)cyclohexanamine monohydrochloride from part (iv) (7.69 mmol, 1.1 g), 1-ethyl-1-methyl-4-oxopiperidinium iodide (D9, 1.7 eq., 13.1 mmol), 3.5 g, $K_2CO_3$ (1.5 eq., 11.5 mmol, 1.5 g), water (40 mL) and ethanol (80 mL) were refluxed at 80° C. until the starting material was not observed on TLC. The mixture was partitioned between $NaHCO_3$ and dichloromethane. Some product was lost due to mechanical spillage. The work up was repeated. The crude product was then purified by chromatography (MeOH—$NH_3$-dichloromethane) on silica column to afford the title compound (650 mg, 35%).

$^1$H NMR δ (DMSO-$d_6$, 400 MHz) 0.85 (3H, s), 1.50 (6H, m), 1.76 (2H, m), 2.30 (4H, t), 2.72 (4H, t), 3.21 (3H, s), 3.27 (1H, m).

DESCRIPTION 48

4-Methyl-2-({1-[trans-1-methyl-4-(methyloxy)cyclohexyl]-4-piperidinyl}amino)phenol. (D48)

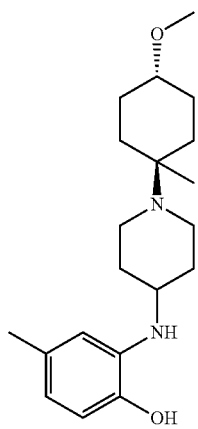

D48

Macroporous triethylammonium triacetoxyborohydride (1.0 g, 2.0 mmol/g) was added to a solution of 2-amino-4-methylphenol (86 mg) and 1-[trans-1-methyl-4-(methyloxy)cyclohexyl]-4-piperidinone (D47, 120 mg) in dry THF (3.0 mL) in a 5 mL microwave vial. The resulting suspension was heated to 100° C. for 30 min. After cooling the reaction was diluted with DCM and partitioned into NaHCO$_3$ (sat$^d$ aq), the organic layers separated, dried over MgSO$_4$, filtered and the solvent removed under reduced pressure to afford essentially pure product, 174 mg.

(M+H)$^+$333.

DESCRIPTION 49

2-({1-[trans-4-(Ethyloxy)-1-methylcyclohexyl]-4-piperidinyl}amino)-4,6-difluorophenol. (D49)

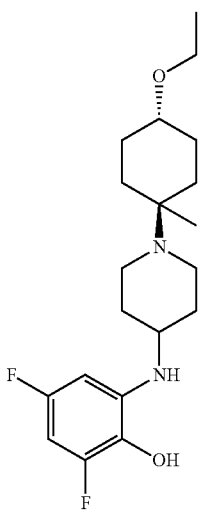

D49

2-Amino-4,6-difluorophenol (100 mg, 0.689 mmol), 1-[trans-4-(ethyloxy)-1-methylcyclohexyl]-4-piperidinone (D8, 127 mg, 0.530 mmol), macroporous triethylammonium methylpolystyrene triacetoxyborohydride (182 mg, 0.440 mmol) and 10% acetic acid in tetrahydrofuran (3 mL) were combined in a 5 mL microwave vial, sealed and heated at 110° C. for 30 min. LC/MS showed the reaction to be incomplete. The reaction mixture was heated for a further 30 min at 110° C., but the reaction had not progressed any further. The reaction mixture was filtered, then diluted with dichloromethane (10 mL). The solution was washed with saturated aqueous sodium bicarbonate (12 mL), dried and evaporated to give a brown gum. Recrystallisation from hexane and diethyl ether failed to purify the product. The product solution was evaporated to give the title compound as a brown oil (175 mg), which was estimated as being 30% pure by LC/MS. The crude material was carried forward without further purification.

(M+H)$^+$=369.

DESCRIPTION 50

2-({1-[trans-4-(Ethyloxy)-1-methylcyclohexyl]-4-piperidinyl}amino)-4-[(trifluoromethyl)oxy]phenol. (D50)

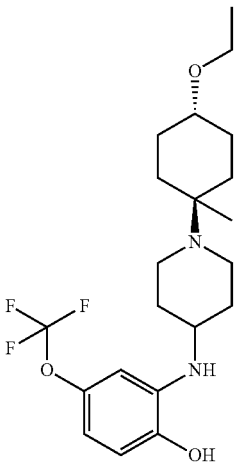

D50

1-[trans-4-(Ethyloxy)-1-methylcyclohexyl]-4-piperidinone (D8; 113 mg, 0.472 mmol) was dissolved in dichloromethane (DCM) (2.5 mL) and acetic acid (0.250 mL) and 2-amino-4-(trifluoromethoxy)phenol (109 mg, 0.567 mmol) was added, followed by macroporous triethylammonium methylpolystyrene cyanoborohydride (409 mg, 0.944 mmol). The reaction mixture was heated in a microwave reactor at 100° C. for 15 min. The reaction mixture was diluted with DCM (12.5 mL) and washed with sodium bicarbonate solution (15 mL). The organic layer was dried with magnesium sulphate to give the title compound as a brown solid (102 mg), which was estimated as being 20% pure by LC/MS. The crude material was carried forward without further purification.

(M+H)$^+$=417.

DESCRIPTION 51

2-({1-[trans-4-(Ethyloxy)-1-methylcyclohexyl]-4-piperidinyl}amino)-4,5-difluorophenol acetate. (D51)

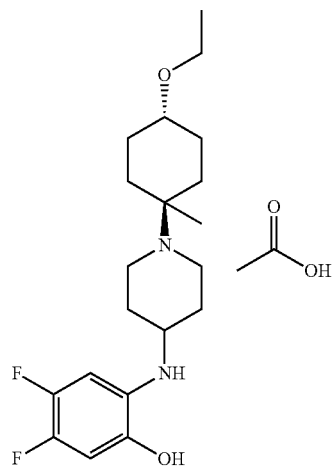

1-[trans-4-(Ethyloxy)-1-methylcyclohexyl]-4-piperidinone (D8, 99 mg, 0.414 mmol) was dissolved in dichloromethane (2.5 mL) and acetic acid (0.250 mL) and 2-amino-4,5-difluorophenol (72.0 mg, 0.496 mmol) was added, followed by macroporous triethylammonium methylpolystyrene cyanoborohydride (179 mg, 0.414 mmol). The reaction mixture was heated in a microwave reactor at 100° C. for 10 min. The reaction mixture was filtered and evaporated to dryness to give the title compound as a brown oil (253 mg), with residual acetic acid. The crude material was carried forward without further purification.

(M−H)$^+$=367.

$^1$H NMR δ (CDCl$_3$): 1.19 (3H, m), 1.34 (4H, m), 1.90 (2H, m), 2.02-2.07 (equivalent to 20H, br. m., contains acetic acid contaminant), 2.82 (1H, br. s), 3.28 (1H, s), 3.45-3.54 (3H, br. m), 6.32 (1H, m), 6.70 (1H, m).

DESCRIPTION 52

2-Amino-4-(trifluoromethyl)phenol. (D52)

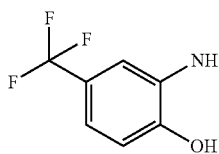

A solution of 2-nitro-4-(trifluoromethyl)phenol (100 mg, 0.483 mmol) in ethanol (10 mL) was pumped through an H-cube™ hydrogenator CatCart (Pd/C, 30×4 mm) at a flow rate of 1 mL/min at 40° C. and 40 psi, topping up the solution with methanol (10×1 mL) when it was running low. The collected solution was evaporated to dryness to give an off-white solid (88 mg, assume quantitative yield). The material was carried forward without further purification.

(M$^+$=178.

$^1$H NMR δ (CDCl$_3$): 6.76 (1H, d, J=8.4 Hz), 6.94 (1H, d, J=8.4 Hz), 6.98 (1H, s).

DESCRIPTION 53

2-({1-[trans-4-(Ethyloxy)-1-methylcyclohexyl]-4-piperidinyl}amino)-4-(trifluoromethyl)phenol acetate. (D53)

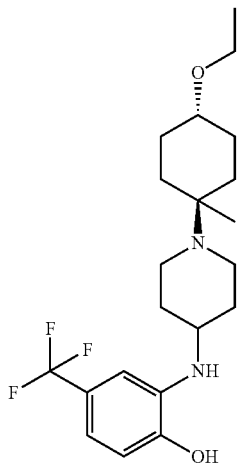

1-[trans-4-(Ethyloxy)-1-methylcyclohexyl]-4-piperidinone (D8, 99 mg, 0.414 mmol) was dissolved in dichloromethane (2.5 mL) and acetic acid (0.250 mL) and 2-amino-4-trifluoromethylphenol (D52, 88 mg, 0.497 mmol) was added, followed by macroporous triethylammonium methylpolystyrene cyanoborohydride (179 mg, 0.414 mmol). The reaction mixture was heated in a microwave reactor at 100° C. for 15 min. The reaction mixture was filtered and evaporated thoroughly to give the title compound as a yellow oil (225 mg), with residual acetic acid. The crude material was carried forward without further purification.

(M+H)$^+$=401.

$^1$H NMR δ (CDCl$_3$): 1.19 (3H, m), 1.35 (3H, br. m), 1.88 (2H, m), 2.05-2.07 (equivalent to 15H, m, contains acetic acid contaminant), 2.17 (2H, m), 2.82 (1H, br. m), 3.36 (1H, br. m), 3.40 (1H, br. m), 3.52 (3H, br. m), 6.67 (1H, s), 6.80-6.93 (2H, m).

DESCRIPTION 54 bis(1,1-Dimethylethyl) [4-methyl-2-({1-[trans-1-methyl-4-(methyloxy)cyclohexyl]-4-piperidinyl}amino)phenyl]propanedioate. (D54)

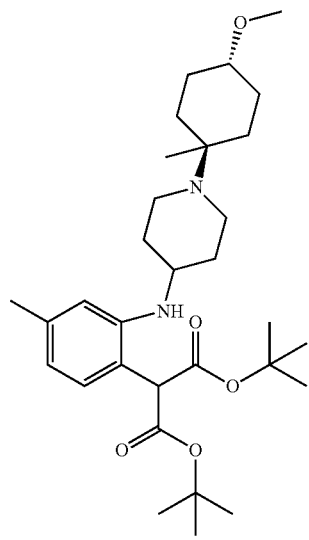

D54

1-[trans-1-Methyl-4-(methyloxy)cyclohexyl]-4-piperidinone D47 (0.8 eq., 0.25 mmol, 56 mg) and bis(1,1-dimethylethyl) (2-amino-4-methylphenyl)propanedioate D39 (1 eq., 0.31 mmol, 100 mg) were dissolved in isopropyl acetate (4 mL) and trifluoroacetic acid (2 eq., 0.62 mmol, 45 microliters) was added at Rt. NaBH(OAc)$_3$ (1.4 eq., 0.43 mmol, 92 mg) was then added at Rt and the mixture was stirred at Rt for 3 hours. The mixture was then diluted with water, basified to pH=10 (2M aq. NaOH) and it was extracted with EtOAc (3 x); organics were combined, dried (Na$_2$SO$_4$), concentrated under vacuum and the residue chromatographed (12M amino column, EtOAc-n-hexane) to afford 100 mg of a mixture containing the desired product that was used for the next step.
MH$^+$=531.

DESCRIPTION 55

4-Hydroxy-3-({1-[trans-1-methyl-4-(methyloxy)cyclohexyl]-4-piperidinyl}amino)benzonitrile. (D55)

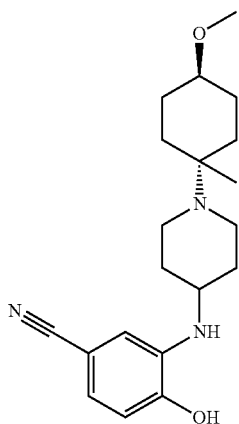

D55

3-Amino-4-hydroxybenzonitrile (D19) (100 mg, 0.746 mmol) was dissolved in dichloromethane (DCM) (4 mL) and 1-[trans-1-methyl-4-(methyloxy)cyclohexyl]-4-piperidinone D47 (336 mg, 1.491 mmol), acetic acid (0.064 mL, 1.118 mmol), polymer supported sodium cyanoborohydride (520 mg, 2.237 mmol) were all added at room temperature. The mixture was reacted at 90° C. in the microwave. Sample was then cooled to Rt, purified on 5 g SCX column first and then by chromatography (40S silica cartridge, MeOH—NH$_3$-DCM) to afford the title compound, 70%.
MH$^+$=344

DESCRIPTION 56 bis(1,1-Dimethylethyl) [2-({1-[trans-4-(ethyloxy)-1-methylcyclohexyl]-4-piperidinyl}amino)-4-methylphenyl]propanedioate. (D56)

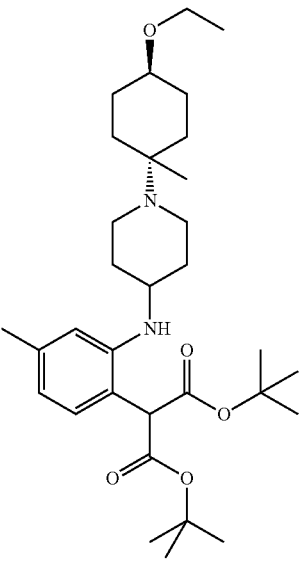

D56

1-[trans-4-(Ethyloxy)-1-methylcyclohexyl]-4-piperidinone (D8) (1 eq., 0.38 mmol, 90 mg) and bis(1,1-dimethylethyl) (2-amino-4-methylphenyl)propanedioate (D39) (1.3 eq., 0.5 mmol, 158 mg) were dissolved in isopropyl acetate (3 mL) and trifluoroacetic acid (2.5 eq., 0.95 mmol, 68 microliters) were added at Rt; NaBH(OAc)$_3$ (1.7 eq., 0.65 mmol, 138 mg) was then added at Rt and the mixture was stirred at Rt for 3 hours. The mixture was then diluted with water, basified to pH=10 (2M aq. NaOH) and it was extracted with EtOAc (3 x); organics were combined, dried (Na$_2$SO$_4$), concentrated under vacuum and the residue chromatographed (12M amino column, EtOAc-n-hexane) to afford 134 mg of a mixture containing the desired product that was used for the next step.
MH$^+$=545.

DESCRIPTION 57

2-({1-[trans-1-Methyl-4-(propyloxy)cyclohexyl]-4-piperidinyl}amino)-4-(methylsulfonyl)phenol. (D57)

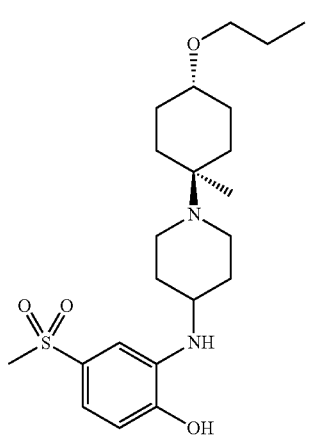

D57

Polymer supported cyanoborohydride (98 mg, 0.421 mmol) was added to a solution of 2-amino-4-(methylsulfonyl)phenol (39.4 mg, 0.210 mmol), 1-[trans-1-methyl-4-(propyloxy)cyclohexyl]-4-piperidinone (D17, 54.8 mg, 0.216 mmol) and acetic acid (0.06 mL, 1.05 mmol) in tetrahydrofuran (2.5 mL). The mixture was heated by microwave at 100° C. for 30 min and then for a further 30 min before a further solution of 1-[trans-1-methyl-4-(propyloxy)cyclohexyl]-4-piperidinone (35.1 mg) in tetrahydrofuran (0.5 mL) was added and the reaction heated for another 30 min. The mixture was then filtered and concentrated by rotary evaporation to give a pale yellow solid. The residue was purified via chromatography (silica, dichloromethane to 0.5% ammonia/9.5% methanol/90% dichloromethane) to give 2-({1-[trans-1-methyl-4-(propyloxy)cyclohexyl]-4-piperidinyl}amino)-4-(methylsulfonyl)phenol (D57, 31.4 mg, 0.074 mmol, 35% yield) as an off-white solid.

$MH^+$=425

DESCRIPTION 58

3-[2-({1-[trans-4-(Ethyloxy)-1-methylcyclohexyl]-4-piperidinyl}amino)-4-methylphenyl]propanoic acid. (D58)

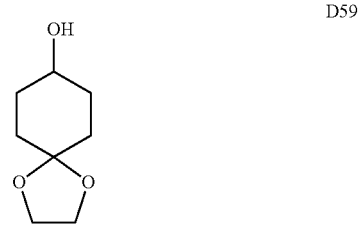 [SMILES: OC1CCC2(CC1)OCCO2]

D58

A mixture of ethyl 3-[2-({1-[trans-4-(ethyloxy)-1-methylcyclohexyl]-4-piperidinyl}amino)-4-methylphenyl]propanoate D144 (80 mg, 0.186 mmol) and LiOH (15.59 mg, 0.372 mmol) in methanol (2 mL) and water (2.000 mL) was heated to reflux for 4 hr. LC/MS of the mixture indicated no SM to be present and a product with the desired mol. wt to be the main component in the RM. The mixture was treated with 2N HCl to adjust the pH to 4; the mixture was concentrated to dryness to afford a yellow gum, 94 mg, >100%, which was used without further purification.

LC/MS 403 ($MH^+$), 401(M−H).

DESCRIPTION 59a 1,4-Dioxaspiro[4.5]decan-8-ol. (D59)

D59

1,4-Dioxaspiro[4.5]decan-8-one (64 mmol, 10 g) was dissolved in ethanol (125 mL) and treated with $NaBH_4$ (1.2 eq., 76.8 mmol, 2.9 g), at 0° C. portionwise and the mixture was stirred at room temperature for 1 hour. Reaction was quenched with NaOH (25 mL, 2N aqueous solution). The aqueous solution was extracted with dichloromethane (2×). The organics were combined, dried over $Na_2SO_4$, filtered and the solvent was evaporated to afford the title compound, 8.3 g, 82%, as a colourless oil.

$^1$H NMR δ (DMSO-d$_6$, 400 MHz) 1.44 (4H, m), 1.64 (4H, m), 3.54 (1H, d broad), 3.82 (4H, m), 4.48 (1H, d).

DESCRIPTION 59b

Scale-up procedure. 1,4-Dioxaspiro[4.5]decan-8-ol. (D59)

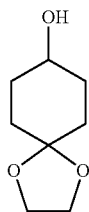
D59

1,4-Dioxaspiro[4.5]decan-8-one (60 g, 384 mmol) was dissolved in methanol (600 mL) under Argon, then sodium borohydride (15.99 g, 423 mmol) was added portionwise (the addition was exothermic and a huge gas evolution was observed). The resulting mixture was stirred for 30 min. The reaction was quenched with water (200 mL) and stirred for 10 min. Solvent was removed under reduced pressure and the residue taken-up with DCM (600 mL) and water (300 mL). Phases were separated then the aqueous phase extracted with DCM (1×600 mL). Combined organic phases were dried on Na$_2$SO$_4$ and concentrated under vacuum to obtain title material (58 g; 95%) as colourless oil.

$^1$H NMR δ (CDCl$_3$, 400 MHz): 1.64 (4H, m), 1.87 (4H, m), 3.83 (1H, m), 3.97 (4H, dt).

DESCRIPTION 60a

8-{[2-(Methyloxy)ethyl]oxy}-1,4-dioxaspiro[4.5]decane. (D60)

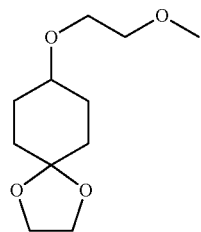
D60

1,4-Dioxaspiro[4.5]decan-8-ol (D59, 10 g, 58 mmol) was dissolved in 200 mL of dry DMF and NaH (60% dispersion in mineral oil, 1.01 eq., 58.7 mmol, 2.3 g) was added at 0° C.

The mixture was stirred at the same temperature for 30 min and 1-bromo-2-(methyloxy)ethane (1.5 eq., 87 mmol, 8.2 mL) was added followed by NaI (cat, 500 mg) at 0° C. The mixture was stirred at Rt overnight. The mixture was then gently warmed to 40° C. and stirred overnight. The mixture was then quenched with MeOH, diluted with water and extracted with EtOAc (3×). Organics were diluted with hexane and extracted with brine and water respectively (2×). Organics were then dried over Na$_2$SO$_4$, filtered and the solvent was evaporated to afford 3.7 g of crude product that was purified by silica chromatography (40 M column, EtOAc-nhex) to afford 1.6 g of the title compound, 12%.

$^1$H NMR δ (CDCl$_3$, 400 MHz): 1.51-1.56 (2H, m), 1.69-1.87 (6H, m), 3.40 (3H,s), 3.43 (1H, m), 3.54 (2H, m), 3.59 (2H, m), 3.93 (4H, m).

DESCRIPTION 60b

Scale-up procedure. 8-{[2-(Methyloxy)ethyl]oxy}-1,4-dioxaspiro[4.5]decane. (D60)

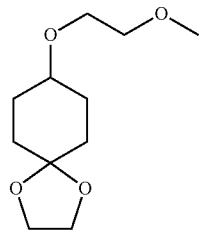
D60

Two different batches of material were reacted separately and then worked up together. In a 1 L round-bottomed flask 1,4-dioxaspiro[4.5]decan-8-ol D59 (45 g, 284 mmol) was dissolved in dimethyl sulfoxide (DMSO) (320 mL) to give a colourless solution. Potassium hydroxide (64 g, 1138 mmol) was added and the mixture was allowed to stir under argon for 20 minutes then a catalytic amount of sodium iodide was added. 2-Bromoethyl methyl ether (106 mL, 1138 mmol) was added dropwise keeping the internal temperature below +35° C. and the mixture was allowed to stir at room temperature overnight. The reaction was 80% complete by TLC after 5 hours. A further 32 g of potassium hydroxide and 54 mL of 2 bromoethyl methyl ether were added consequently and the reaction was allowed to stir at room temperature for 72 h.

In a similar way, in a 2 L round-bottomed flask 1,4-dioxaspiro[4.5]decan-8-ol D59 (65.6 g, 415 mmol) was dissolved in dimethyl sulfoxide (DMSO) (400 mL) to give a colourless solution. Potassium hydroxide (93.3 g, 1659 mmol) was added and the mixture was allowed to stir under argon for 20 minutes then a catalytic amount of NaI was added. 2-bromoethyl methyl ether (156 mL, 1659 mmol) was added dropwise keeping the internal temperature below +35° C. and the mixture was allowed to stir at room temperature overnight. After 5 h, reaction was 80% complete by TLC. Potassium hydroxide (46.7 g) and 2-bromoethyl methyl ether (78 ml) were added and the reaction allowed to stir at rt for a further 72 h.

The two reaction mixtures were combined and the overall resulting mixture was carefully portionwise added to a well stirred mixture of 1 L of water and 2 L of diethyl ether. The aqueous layer was back extracted with diethyl ether (2×500 mL). The organic phase was dried over anhydrous Na$_2$SO$_4$, filtered and concentrated to obtain 210 g of an oil residue that was purified via Biotage® 75 L SiO$_2$ column eluting with 8/2 c-hex/EtOAc. Collected fractions were evaporated under vacuum to afford title material (155.3 g; 102% uncorrected) as yellow oil.

¹H NMR δ (CDCl₃, 400 MHz): 1.55 (2H, m), 1.80 (6H, m), 3.40 (3H, s), 3.44 (1H, m), 3.62-3.53 (4H, m), 3.95 (4H, d t).

DESCRIPTION 61a

4-{[2-(Methyloxy)ethyl]oxy}cyclohexanone. (D61)

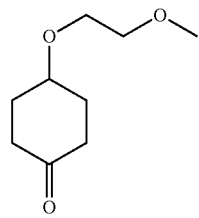

D61

8-{[2-(Methyloxy)ethyl]oxy}-1,4-dioxaspiro[4.5]decane (D60) (1.6 g, 7 mmol), was dissolved in 20 mL of THF and HCl (25 eq., 5M, 35 mL) was added at Rt. The mixture was stirred at Rt for 5 hr. THF was then evaporated and the aqueous was extracted with dichloromethane (2×). Organics were washed once with water, dried over Na₂SO₄, filtered and the solvent was evaporated to afford the title compound, 1.3 g, complete conversion as a pale yellow oil.

¹H NMR δ (CDCl₃, 400 MHz): 1.92-2.00 (2H, m), 2.10-2.14 (2H, m), 2.23-2.30 (2H, m), 2.55-2.63 (2H, m), 3.41 (3H, s), 3.58 (2H, m), 3.64 (2H, m), 3.76 (1H, m).

DESCRIPTION 61b

Scale-up procedure. 4-{[2-(Methyloxy)ethyl]oxy}cyclohexanone. (D61)

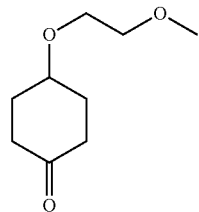

D61

In a 10 L round-bottomed flask 8-{[2-(methyloxy)ethyl]oxy}-1,4-dioxaspiro[4.5]decane D60 (151 g, 700 mmol) was dissolved in tetrahydrofuran (THF) (3000 mL) to give a colourless solution. 3M hydrochloric acid (2333 mL, 7000 mmol) was added. Reaction was allowed to stir at room temperature overnight. The organic solvent was partially evaporated under vacuum and then the aqueous layer was back extracted with DCM (3×500 mL). The organic phase was dried over Na₂SO₄, filtered and concentrated to obtain 121 g of crude material as yellow oil. The crude product was purified by Biotage® 75 L SiO₂ column eluting with c-hex/EtOAc 8/2 to get title material (76 g; 63%).

¹H NMR δ (CDCl₃, 400 MHz): 1.98 (2H, m), 2.11 (2H, m), 2.28 (2H, m), 2.60 (2H, m), 3.41 (3H, s), 3.59 (2H, m), 3.68 (2H, m), 3.77 (1H, m).

DESCRIPTION 62 trans-N-(4-Hydroxycyclohexyl)phthalimide. (D62)

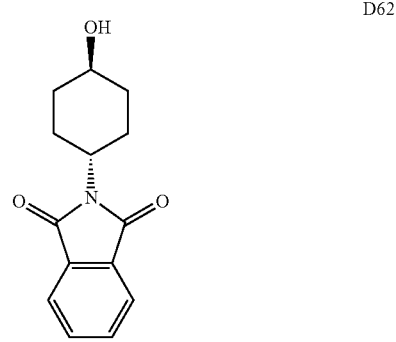 [SMILES: O=C1c2ccccc2C(=O)N1[C@H]1CC[C@H](O)CC1]

D62

N-Ethoxycarbonylphthalimide (100 g; 0.46 mol) was added to a mixture of trans-4-hydroxycyclohexylamine hydrochloride (69 g; 0.46 mol), potassium carbonate (158 g; 1.15 mol) and water (1 L) at room temperature. After stirring for 3 h the title compound (95 g) was isolated by filtration, washing with water then ethyl acetate.

DESCRIPTION 63 trans-N-(4-tert-Butyldimethylsilyloxycyclohexyl)phthalimide. (D63)

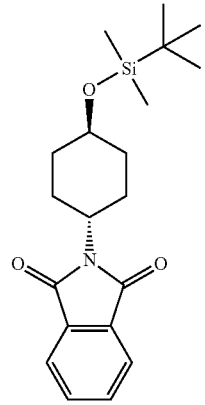

D63 tert-Butyldimethylsilyl chloride (60 g; 0.39 mol) was added in portions to a mixture of trans N-(4-hydroxycyclohexyl)phthalimide (D62, 95 g; 0.39 mol), imidazole (55 g; 0.78 mol), and DMF (200 mL) at 20-30° C. (internal, ice cooling). After stirring for 3 h more at 40° C. the mixture was partitioned between water/hexane. Drying and evaporation of the organic layer gave the title compound (92 g) crystallised from pentane.

DESCRIPTION 64 trans-N-(4-Ethoxycyclohexyl)phthalimide (D64)

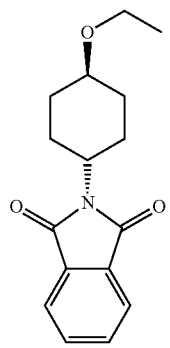

D64

Acetaldehyde (10 mL; 0.17 mol) in acetonitrile (50 mL) was added over 30 minutes to a solution of trans-N-(4-tert-butyldimethylsilyloxycyclohexyl)phthalimide (D63; 50.0 g; 0.14 mol), bismuth tribromide (6.7 g; 0.015 mol) and triethylsilane (27 mL; 0.18 mol) in acetonitrile (500 mL) stirred at ice bath temperature and the mixture was allowed to warm to room temperature overnight. The mixture was filtered and the resulting grey solid and filtrate were worked up separately. The filtrate was evaporated and treated with hexane to give the title compound as a white solid (16.35 g). The grey solid was washed with dichloromethane, the dichloromethane extract was evaporated and the residue was stirred with hexane (200 mL) to give a second crop of the title compound as a white solid (17.47 g).

DESCRIPTION 65 trans-4-Ethoxycyclohexylamine (D65)

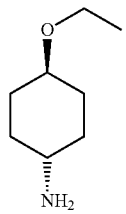

D65

A solution of trans-N-(4-ethoxycyclohexyl)phthalimide (D64, 16.35 g), hydrazine hydrate (12 mL) in ethanol (300 mL) and methanol (200 mL) was stirred at reflux for 3 hours. The solvent was removed to give a slurry, which was treated with diethyl ether and filtered. The filtrate was evaporated to afford the title compound as a viscous oil contaminated with ether (8.16 g).

DESCRIPTION 66 trans-1-(4-Ethoxycyclohexyl)-4-piperidone (D66)

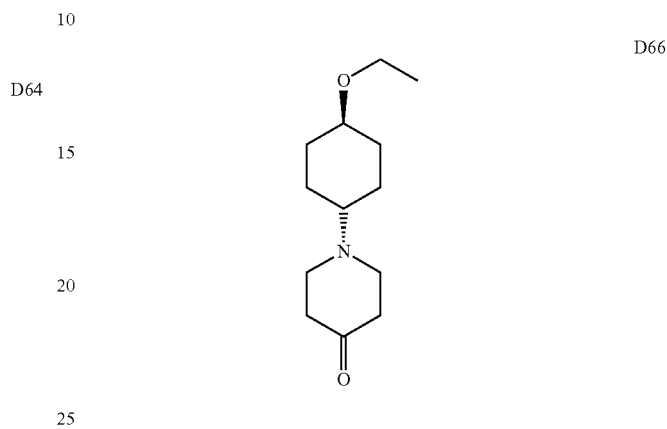

D66

A mixture of 1-ethyl-4-piperidone methiodide (D9, 27 g), trans-4-ethoxycyclohexylamine (D65, 8.16 g, 0.065 mol), potassium carbonate (13.5 g), water (100 mL), and ethanol (200 mL) was heated for 3 hours at 80° C., then cooled overnight. The mixture was partitioned with aqueous sodium bicarbonate and dichloromethane. The dichloromethane layer was separated, washed with brine and solvent removed to give the title compound as an amber coloured oil (13.2 g).

DESCRIPTION 67

2-Methylpropyl 1-methyl-4-oxocyclohexanecarboxylate. (D67)

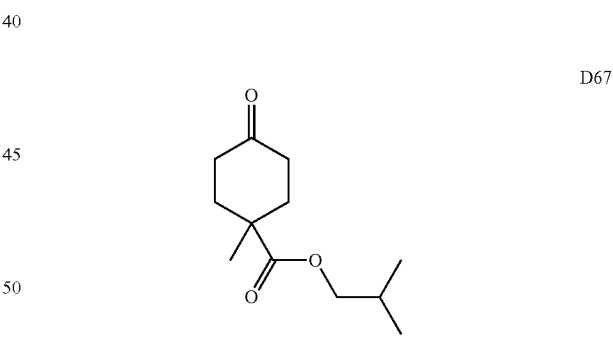

D67

2-(Trimethylsilyloxy)buta-1,3-diene (40 g, 281 mmol) was weighed into a Teflon™ microwave container. Isobutyl methacrylate (50.8 mL, 317 mmol) was added followed by 4,4'-methylenebis(2,6-di-tert-butylphenol) (0.5 g, 1.177 mmol), finally 1-butyl-3-methylimidazolium hexafluorophosphate (0.5 mL) was added, the vessel transferred to the Advancer microwave and heated for 4 hr (normal absorption, no fixed hold time, 190° C.). After 1 hr 20 min an error message was seen for the temperature probe, the error was cleared and heating was continued for a further hour. At this time the software had frozen forcing a shutdown at the mains. The reaction mixture was allowed to cool to RT. Tetrahydrofuran (THF) (200 mL) was added and the solution transferred to a round bottomed flask. 2M HCl was added and the reaction mixture left to stir overnight. DCM was added to the reaction mixture, whereupon an emulsion formed. An attempt to filter this was unsuccessful, and the mixture was left to stand overnight. The organic layer was separated, dried (Na$_2$SO$_4$) and evaporated to give a sticky oil. Flash column chromatography, eluting with ethyl acetate/isohexane gave 2-methylpropyl 1-methyl-4-oxocyclohexanecarboxylate as a yellow oil (12.74 g, 60.0 mmol, 21.35% yield).

DESCRIPTION 68

Isobutyl 1-methyl-4-(2-methoxyethoxy)cyclohexanecarboxylate. (D68)

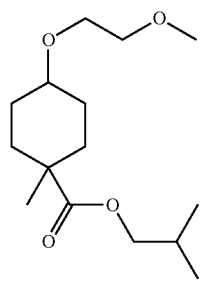

D68

A solution of isobutyl 1-methyl-4-oxocyclohexanecarboxylate (D67, 12.7 g, 59.8 mmol), t-butyl dimethyl 2-methoxyethoxy silane (11.4 g, 59.9 mmol), and anhydrous ferric chloride (250 mg, 1.541 mmol) in acetonitrile (150 mL) at 0° C. was treated with triethylsilane (12 mL, 75 mmol). The mixture was stirred for 1 h at room temperature, then partitioned between saturated sodium bicarbonate and dichloromethane, and the organic layer was dried and evaporated to give isobutyl 1-methyl-4-(2-methoxyethoxy)cyclohexanecarboxylate (27 g, 49.6 mmol, 83% yield) as a cis/trans mixture containing one equivalent of t-butyldimethyl triethyl siloxane.

DESCRIPTION 69

1-Methyl-4-(2-methoxyethoxy)cyclohexanecarboxylic acid. (D69)

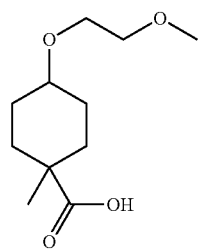

D69

A mixture of isobutyl 1-methyl-4-(2-methoxyethoxy)cyclohexanecarboxylate (D68, 27 g, 49.6 mmol), 1,4-dioxane (100 mL) and 3M aqueous sodium hydroxide (100 mL, 300 mmol) was heated at 100° C. for 18 h then cooled and partitioned between water and diethyl ether. The aqueous phase was acidified and extracted with ethyl acetate to give the desired product. Unreacted starting material remained in the ether wash, so the ether was evaporated and the residue dissolved in a mixture of THF (100 mL), methanol (100 mL), and 6M aqueous sodium hydroxide (100 mL) and heated at 65° C. for 18 h then worked up as before to give additional product, which was combined to give 1-methyl-4-(2-methoxyethoxy)cyclohexanecarboxylic acid (9.5 g, 43.9 mmol, 89% yield) as a pale yellow oil.

DESCRIPTION 70 trans 1-Methyl-4-(2-methoxyethoxy)cyclohexanecarboxylic acid. (D70)

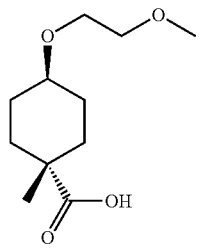

D70

A solution containing 1-methyl-4-(2-methoxyethoxy)cyclohexanecarboxylic acid (D69, 9.5 g, 43.9 mmol), thionyl chloride (50 mL, 685 mmol), and toluene (25 mL) was heated at 90° C. for 4 h then cooled and evaporated. The residue was stirred with aqueous sodium bicarbonate for 30 min then washed with diethyl ether. Acidification and extraction with ethyl acetate gave trans 1-methyl-4-(2-methoxyethoxy)cyclohexanecarboxylic acid (3.2 g, 14.80 mmol, 33.7% yield) as an oil.

DESCRIPTION 71 trans 1-Methyl-4-(2-methoxyethoxy)cyclohexyl isocyanate. (D71)

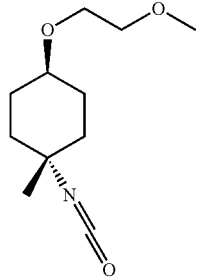

D71

A mixture of trans 1-methyl-4-(2-methoxyethoxy)cyclohexanecarboxylic acid (D70, 3.3 g, 15.26 mmol), diphenylphosphoryl azide (3.4 mL, 15.75 mmol), triethylamine (4.0 mL, 28.6 mmol), and toluene (50 mL) was heated at 100° C. for 1 h, then cooled and washed with water to give trans 1-methyl-4-(2-methoxyethoxy)cyclohexyl isocyanate (3.2 g, 15.00 mmol, 98% yield) as a mobile oil.

DESCRIPTION 72 trans 1-Methyl-4-(2-methoxyethoxy)cyclohexylamine hydrochloride. (D72)

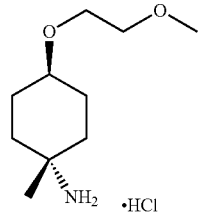

A mixture of trans 1-methyl-4-(2-methoxyethoxy)cyclohexyl isocyanate (D71, 3.2 g, 15.00 mmol), 5M hydrochloric acid (50 mL, 250 mmol), and THF (50 mL) was stirred at room temperature for 18 h then evaporated to give trans 1-methyl-4-(2-methoxyethoxy)cyclohexylamine hydrochloride (3.5 g, 15.64 mmol, 104% yield) as a pale brown foam.

DESCRIPTION 73

1-(trans-1-Methyl-4-{[2-(methyloxy)ethyl]oxy}cyclohexyl)-4-piperidinone. (D73)

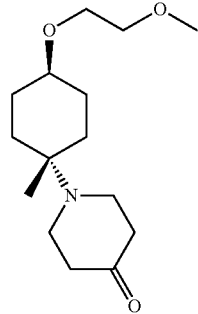

A solution of trans 1-methyl-4-(2-methoxyethoxy)cyclohexylamine hydrochloride (D72, 3.5 g, 15.64 mmol) in ethanol (80 mL) and water (40 mL) was treated with potassium carbonate (3.0 g, 21.71 mmol). The mixture was heated to 80° C. and then a solution of 1-ethyl-1-methyl-4-oxopiperidinium iodide (D9, 7.0 g, 26.0 mmol) in ethanol (20 mL) and water (10 mL) added. After 2 h at the same temperature the reaction was partitioned between aqueous sodium bicarbonate and dichloromethane. Chromatography on silica (20 g), eluting with 0-10% 2M ammonia in methanol-dichloromethane, gave 1-(trans-1-methyl-4-{[2-(methyloxy)ethyl]oxy}cyclohexyl)-4-piperidinone (1.9 g, 7.05 mmol, 45.1% yield) as a straw coloured oil.

DESCRIPTION 74

1,1-Dimethylethyl 4-[bis(phenylmethyl)amino]-1-piperidinecarboxylate. (D74)

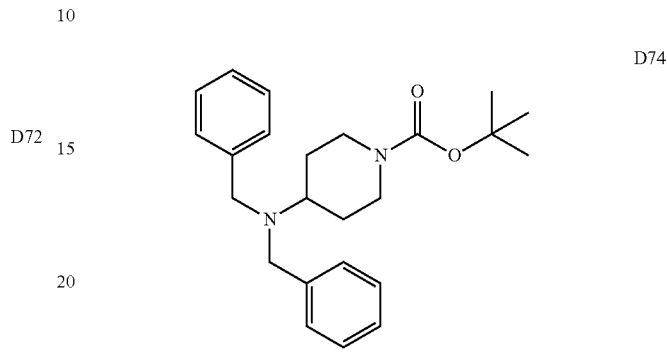

1,1-Dimethylethyl 4-amino-1-piperidinecarboxylate (100 g, 499 mmol) was dissolved in 1,2-dichloroethane (DCE) (1000 mL), 55 mL (1.1 eq) of benzaldehyde were added and finally 127 g (1.2 eq.) of sodium triacetoxyborohydride were added portionwise.

The suspension was stirred overnight, then further 55 mL (1.1 eq) of benzaldehyde were added and 127 g (1.2 eq.) of sodium triacetoxyborohydride were added portionwise and stirred for 5 h, then further 28 mL (0.55 eq) of benzaldehyde were added and finally 64 g (0.6 eq.) of sodium triacetoxyborohydride were added portionwise and stirred overnight.

The reaction was treated with 3 L of NaHCO$_3$ saturated solution until pH was basic, resulting mixture was diluted with water (500 mL) and DCM (1.5 L). Phases were separated, the organic layer was washed with brine (2×1 L), dried over Na$_2$SO$_4$ and concentrated under vacuum. The residue was triturated with methanol (700 mL). The suspension was filtered through sintered glass funnel and the solid washed with methanol (100 mL). Obtained white solid was dried under vacuum to give title material (161 g; 85%).

$^1$H NMR δ (CDCl$_3$, 400 MHz): 1.47 (9H, s), 1.56 (2H, m), 1.82 (2H, m), 2.72-2.50 (3H, m), 3.66 (4H, m), 4.17 (2H, bs), 7.23 (2H, m), 7.31 (4H, m), 7.38 (4H, m).

DESCRIPTION 75

N,N-bis(Phenylmethyl)-4-piperidinamine. (D75)

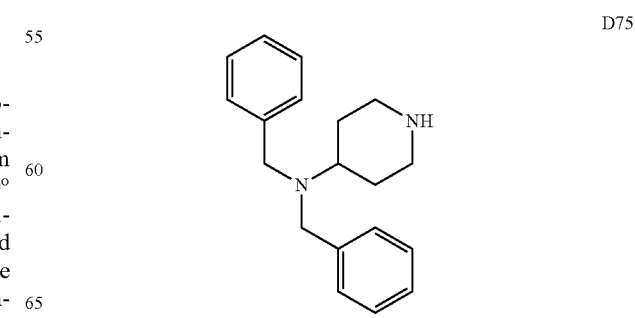

1,1-Dimethylethyl 4-[bis(phenylmethyl)amino]-1-piperidinecarboxylate D74 (160 g, 420 mmol) was dissolved in dichloromethane (DCM) (1 L) and TFA (188 mL, 2443 mmol) was added dropwise at room temperature. The resulting mixture was stirred for 3 h then further 100 mL of TFA was added and stirred for 2 h. The mixture was concentrated under reduced pressure and the residue treated with saturated solution NaHCO$_3$ (1.5 L) and NaOH (3M solution; 200 mL) to basic pH. The aqueous phase was extracted with DCM (2×1.5 L). Combined organic layers were diluted with ethyl acetate (100 mL), washed with water (1×1 L) and brine (1×1 L) then dried on Na$_2$SO$_4$ and concentrated to obtain title material (118 g; 100%).

$^1$H NMR δ (CDCl$_3$, 400 MHz): 1.56 (2H, qd), 1.83 (2H, m), 2.49 (2H, td), 2.60 (1H, tt), 3.12 (2H, d), 3.66 (4H, s), 7.22 (2H, m), 7.30 (4H, t), 7.38 (4H, d).

DESCRIPTION 76

1-(trans-1-Methyl-4-{[2-(methyloxy)ethyl]oxy}cyclohexyl)-N,N-bis(phenylmethyl)-4-piperidinamine. (D76)

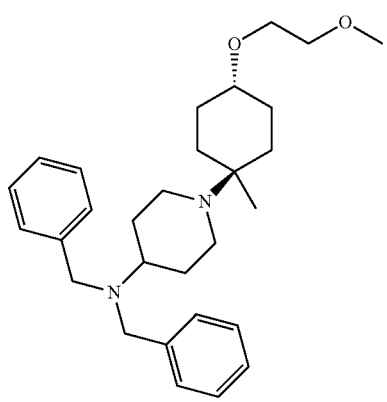

D76

In a 4000 mL round-bottomed flask 4-{[2-(methyloxy)ethyl]oxy}cyclohexanone D61 (78.7 g, 457 mmol) was dissolved in 1,2-dichloroethane (DCE) (2000 mL) to give a colourless solution. N,N-bis(phenylmethyl)-4-piperidinamine D75 (96.3 g, 343 mmol) was added, then titanium (IV) isopropoxide (174 mL, 584 mmol) was added and the mixture was stirred at room temperature. After 22 h cyano(diethyl)aluminium 1M in toluene (650 mL, 650 mmol) was added and the mixture was allowed to stir at room temperature for 20 h. The reaction was quenched by dropwise addition of 1.5 L of saturated sodium bicarbonate solution under mechanical stirring; the resulting mixture was filtered over a Celite® pad washing the panel with 800 mL of DCM. The organic layer was dried over anhydrous sodium sulphate and finally concentrated to dryness to afford 151.4 g of a crude oil that was dissolved in tetrahydrofuran (THF) (1500 mL) in a 4 L pear flask to give a colourless solution. The solution was chilled to 0° C. and methylmagnesium bromide 3M in diethyl ether solution (601 mL, 1804 mmol) was added dropwise. The reaction was allowed to stir at room temperature.

The day after, the work up was performed in the following way: the mixture was chilled to 0° C. and quenched by dropwise addition of 300 mL of water (strong gas evolution, salt precipitation was observed). The resulting mixture was diluted with 1.5 L of diethyl ether. The suspension was filtered and the solid was washed with 2×400 mL of DCM. The two organic phases were combined and dried over anhydrous sodium sulphate and finally concentrated under vacuum to afford 129 g of a crude white solid. The crude product was added to a silica gel column (1400 g) and was eluted with DCM/MeOH/NH$_3$ 2M in methanol from 2000/0/0 to 2000/150/0 ending with 2000/150/30. Collected fractions were evaporated under vacuum to give cis,trans-[1'-methyl-4-{[2-(methyloxy)ethyl]oxy}-1,1'-bi(cyclohexyl)-4-yl] bis(phenylmethyl)amine mixture (120.4 g, yield=77% considering cis/trans mixture) as white solid. 119 g of this material were purified by preparative HPLC. Evaporation of collected fraction afforded title material (35.6 g; 30% considering only preparative HPLC separation step) as white solid.

Preperative HPLC Conditions:
Preparative instrument: Hipersep LC110 lab unit and Novasep LC50 mm DAC column.
Column: Kromasil Silica 10 um 60 angstrom (50 mm×27 cm)
Mobile phase: 50% C7: 50% MTBE with 0.25% v/v DEA
Flow rate: 200 mL/min
Main Pump stroke length: 5 mm
Sample pump stroke length: 2 mm
Mixer valve: 60 mm
UV detection wavelength: 254 nm
Overall run time: 6 mins
Sample preparation: 50 g/L cis/trans mixture dissolved in DCM
Sample load: 2 g.

$^1$H NMR δ (CDCl$_3$, 400 MHz): 0.86 (3H, s), 1.44 (4H, m), 1.61 (4H, m), 1.84 (4H, m), 1.97 (2H, t), 2.47 (1H, t), 3.00 (2H, d), 3.37 (1H, m), 3.39 (3H, s), 3.55 (4H, m), 3.66 (4H, m), 7.20 (2H, t), 7.30 (4H, t), 7.37 (4H, d).

DESCRIPTION 77

1-(trans-1-Methyl-4-{[2-(methyloxy)ethyl]oxy}cyclohexyl)-4-piperidinamine. (D77)

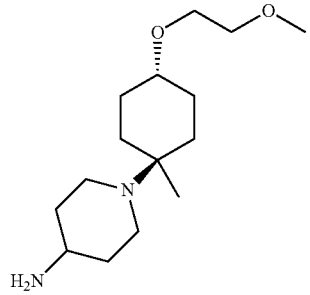

D77

1-(trans-1-Methyl-4-{[2-(methyloxy)ethyl]oxy}cyclohexyl)-N,N bis(phenylmethyl)-4-piperidinamine D76 (42.5 g, 94 mmol) was dissolved in dry methanol (425 mL). Pd/charcoal 10% w/w (16.05 g, 15.09 mmol) and ammonium formate (59.5 g, 943 mmol) were added (caution, flammable; operation carried out under Argon) and the mixture heated at 80° C. for 1 h. Reaction mixture was cooled down to room temperature and filtered, washing with MeOH. Volatiles were evaporated to dryness under reduced pressure to afford title compound (25.2 g, 93 mmol, yield=99%) as pale grey oil.

$^1$H NMR δ (DMSO-d$_6$, 400 MHz): 0.79 (3H, s), 1.13 (2H, m), 1.44 (8H, m), 1.69 (4H, m), 2.00 (2H, dt), 2.43 (1H, m), 2.79 (2H, d), 3.25 (3H, s), 3.53-3.34 (5H, m). MH$^+$=271.0

DESCRIPTION 78

3-Bromo-4-[(phenylmethyl)oxy]benzonitrile. (D78)

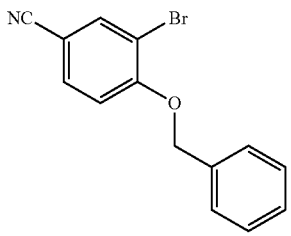

To a solution of 3-bromo-4-hydroxybenzonitrile (60 g, 303 mmol) in acetone (600 mL) under nitrogen, potassium carbonate (62.8 g, 455 mmol) was added followed by potassium iodide (0.503 g, 3.03 mmol). To the mixture benzyl chloride (49.3 mL, 424 mmol) was added dropwise and the mixture was heated at 50° C. (48° C. internal temp) for 16 h. Reaction mixture was cooled down to room temperature, taken up with water (500 mL)/Et$_2$O (1 L). Phases were separated and the aqueous phase back extracted with Et$_2$O (2×500 mL). Combined organics were washed with NaHCO$_3$ saturated solution (400 mL), then with 1M HCl solution (400 mL) and brine. Crude solution was then dried over Na$_2$SO$_4$ and evaporated under reduced pressure to give crude material (110 g) as brown solid that was triturated with c-hex (500 mL) for 30 min. The solid was collected by filtration and washed with c-hex/EtOAc 9/1 (200 mL). Evaporation of residual solvents under high vacuum afforded title material (75.5 g; 261 mmol; 86%) as pale brown solid.

$^1$H NMR δ (CDCl$_3$, 400 MHz): 5.25 (2H, s), 6.99 (1H, d), 7.43 (5H, m), 7.58 (1H, dd), 7.88 (1H, d).

DESCRIPTION 79

3-{[1-(trans-1-Methyl-4-{[2-(methyloxy)ethyl]oxy}cyclohexyl)-4-piperidinyl]amino}-4-[(phenylmethyl)oxy]benzonitrile. (D79)

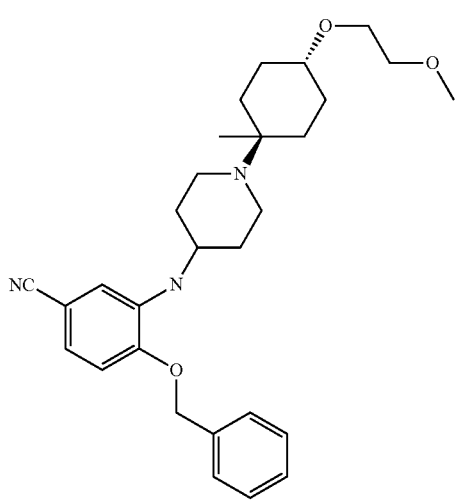

To a solution of 1-(trans-1-methyl-4-{[2-(methyloxy)ethyl]oxy}cyclohexyl)-4-piperidinamine D77 (26.8 g, 99 mmol) and 3-bromo-4-[(phenylmethyl)oxy]benzonitrile D78 (26 g, 90 mmol) in dry toluene (520 mL) under argon, sodium tert-butoxide (13.01 g, 135 mmol) and BINAP (5.62 g, 9.02 mmol) were added at room temperature. The resulting slurry was degassed (vacuum/Argon) 3 times, then Pd$_2$dba$_3$ (4.13 g, 4.51 mmol) was added and the mixture heated at 70° C. for 3 h. Slurry was cooled down to room temperature, then taken up with EtOAc (500 mL)/water (500 mL). Phases were separated and the aqueous one was back extracted with EtOAc (2×500 mL). Combined organics were dried over Na$_2$SO$_4$ then evaporated to dryness to get crude material as brown orange oil 62 g, which was purified by SiO$_2$ FC eluting with DCM/MeOH 98/2 to 95/5 to get title material (42 g, 88 mmol; yield 97%) as thick yellow oil.

$^1$H NMR δ (CDCl$_3$, 400 MHz): 0.94 (3H, s), 1.46 (6H, m), 1.67 (2H, m), 1.86 (2H, m), 2.05 (2H, m), 2.28 (2H, m), 2.95 (2H, m), 3.26 (1H, m), 3.41 (4H, bs), 3.58 (4H, m), 4.37 (1H, d), 5.13 (2H, s), 6.79 (1H, d), 6.82 (1H, d), 6.94 (1H, dd), 7.40 (5H, m). MH$^+$=478.17

DESCRIPTION 80

(Alternative Procedure for Preparation of D36)

4-Hydroxy-3-{[1-(trans-1-methyl-4-{[2(methyloxy)ethyl]oxy}cyclohexyl)-4-piperidinyl]amino}benzonitrile. (D80)

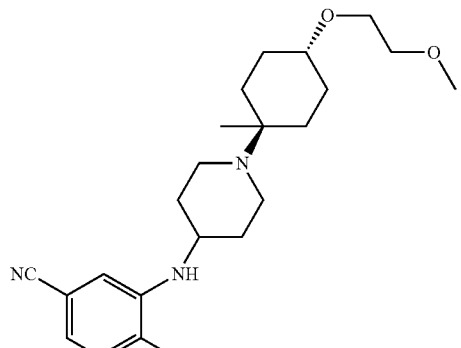

To a solution of 3-{[1-(trans-1-methyl-4-{[2-(methyloxy)ethyl]oxy}cyclohexyl)-4-piperidinyl]amino}-4-[(phenylmethyl)oxy]benzonitrile D79 (37 g, 77 mmol) in ethyl acetate (555 mL) under a nitrogen atmosphere, palladium on carbon 10% w/w (9.25 g, 8.69 mmol) was carefully added. The resulting slurry was hydrogenated at atmospheric pressure and room temperature for 15 h. Reaction mixture was filtered over Sterimat® under an Argon atmosphere, washing the solid with EtOAc. Solvent was evaporated under vacuum to give crude material, (33 g) as yellow foam that was purified by SiO$_2$ FC eluting with DCM/MeOH/NH$_4$OH from 95/5/0 to 9/1/0 to 90/10/0.5 to 90/10/1 to 85/15/2. Evaporation of volatiles afforded title material (26.33 g, 67.9 mmol, yield 88%) as off white foamy solid.

$^1$H NMR δ (CDCl$_3$, 400 MHz): 1.07 (3H, s), 1.46 (2H, m), 1.65 (4H, m), 1.76 (2H, m), 1.94 (2H, m), 2.13 (2H, m), 2.43 (2H, m), 3.13 (3H, m), 3.28 (3H, m), 3.42 (3H, s), 3.59 (4H, m), 6.64 (1H, d), 6.75 (1H, d), 6.90 (1H, dd). MH$^+$=388.14

DESCRIPTION 81 bis(1,1-Dimethylethyl) (4-methyl-2-{1-(trans-1-methyl-4-{[2-(methyloxy)ethyl]oxy}cyclohexyl)-4-piperidinyl]amino}phenyl)propanedioate. (D81)

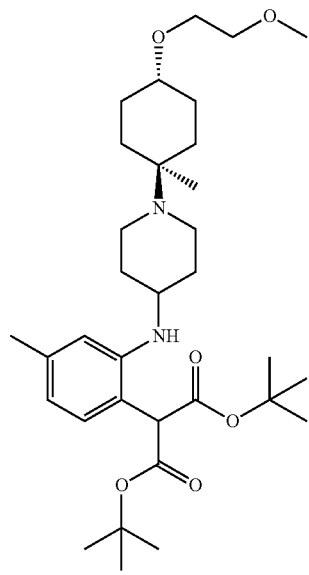

Polymer supported cyanoborohydride (86 mg, 0.37 mmol, 4.3 mmol/g) was added to a solution of 1-(trans-1-methyl-4-{[2-(methyloxy)ethyl]oxy}cyclohexyl)-4-piperidinone (D73, 49 mg, 0.18 mmol), bis(1,1-dimethylethyl) (2-amino-4-methylphenyl)propanedioate (D39, 59 mg, 0.19 mmol) and acetic acid (0.06 mL, 1.05 mmol) in DCM (2.5 mL). The mixture was heated by microwave at 100° C. for 10 min before being filtered and concentrated by rotary evaporation to give bis(1,1-dimethylethyl) (4-methyl-2-{[1-(trans-1-methyl-4-{[2-(methyloxy)ethyl]oxy}cyclohexyl)-4-piperidinyl]amino}phenyl)propanedioate (D81, 106 mg, 58%) as a colourless oil, which was used without further purification.

LCMS: [M+H]⁺ 575

DESCRIPTION 82

2-Nitro-4-[(trifluoromethyl)sulfonyl]phenol. (D82)

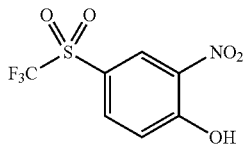

Sodium hydroxide (211 mg, 5.28 mmol) was added to a suspension of 1-chloro-2-nitro-4-[(trifluoromethyl)sulfonyl]benzene (297 mg, 1.03 mmol) in H$_2$O (5 mL) at rt, followed by methanol (0.5 mL) to solubilise the starting material, and the reaction was heated at 110° C. for 1 h. The mixture was allowed to cool to rt, diluted with H$_2$O (10 mL) and neutralised with 5 M HCl. DCM was added, the 2 layers were partitioned and the aqueous layer was extracted with DCM (2×). The combined organics were dried (Na$_2$SO$_4$) and concentrated by rotary evaporation to give 2-nitro-4-[(trifluoromethyl)sulfonyl]phenol (D82, 70 mg, 25%) as a colourless oil.

LCMS: [M–H]⁻ 270

DESCRIPTION 83

2-Amino-4-[(trifluoromethyl)sulfonyl]phenol. (D83)

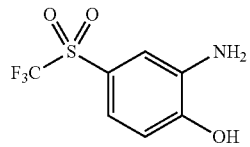

A solution of 2-nitro-4-[(trifluoromethyl)sulfonyl]phenol (D3, 40 mg, 0.13 mmol) in ethanol (2.5 mL) was reduced using an H-Cube (full H$_2$ mode, 25° C., 1 mL/min). The reaction mixture was concentrated by rotary evaporation to give 2-amino-4-[(trifluoromethyl)sulfonyl]phenol (D83, 35 mg, 97%) as a colourless oil.

LCMS: [M–H]⁻ 240

DESCRIPTION 84

2-({1-[trans-1-Methyl-4-(propyloxy)cyclohexyl]-4-piperidinyl}amino)-4-[(trifluoromethyl)sulfonyl]phenol. (D84)

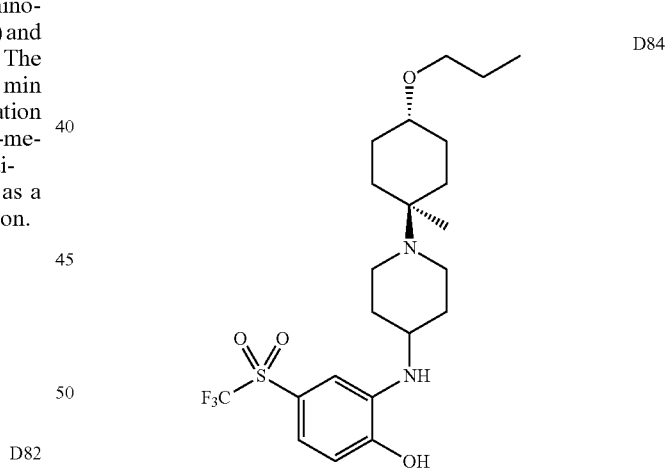

Polymer supported cyanoborohydride (61 mg, 0.26 mmol, 4.3 mmol/g) was added to a solution of 2-amino-4-[(trifluoromethyl)sulfonyl]phenol (D83, 35 mg, 0.12 mmol), 1-[trans-1-methyl-4-(propyloxy)cyclohexyl]-4-piperidinone (D17, 35 mg, 0.14 mmol) and acetic acid (0.04 mL, 0.61 mmol) in THF (2.5 mL). The mixture was heated by microwave at 100° C. for 30 min and then for a further 1 h. A further portion of 1-[trans-1-methyl-4-(propyloxy)-cyclohexyl]-4-piperidinone (D17, 10 mg) was added and the reaction was heated in the microwave for a 2 h and then for a further 4×1 h. The reaction was then filtered and concentrated by rotary evaporation to give a yellow oil which was purified via flash column chromatography (silica, DCM to 0.5% NH$_3$/9.5%

MeOH/90% DCM) to give 2-({1-[trans-1-methyl-4-(propyloxy)cyclohexyl]-4-piperidinyl}amino)-4-[(trifluoromethyl)sulfonyl]phenol (D84, 22 mg, 36%) as a white solid.

LCMS: [M+H]⁺479

DESCRIPTION 85

3-Methyl-4-(methylsulfonyl)phenol. (D85)

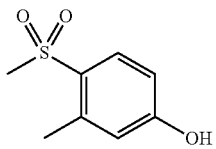

A solution of mCPBA (1.97 g, 8.01 mmol, 70% wt. in H₂O) in DCM (10 mL) was added to a solution of 3-methyl-4-(methylthio)phenol (590.8 mg, 3.83 mmol) in DCM (10 mL) at 0° C. under Ar. The reaction was stirred for 1 h (during which time a white precipitate formed) and then quenched with sat. NaHCO₃ (10 mL). The 2 phases were separated and the aqueous phase was extracted with DCM (2×). The combined organics were washed with H₂O and sat. NaCl, dried (Na₂SO₄) and concentrated by rotary evaporation to give 3-methyl-4-(methylsulfonyl)phenol (D85, 503 mg, 60%) as a yellow gum.

LCMS: [M+H]⁺ 187

DESCRIPTION 86

5-Methyl-4-(methylsulfonyl)-2-nitrophenol. (D86)

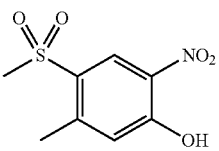

3-Methyl-4-(methylsulfonyl)phenol (D85, 503 mg, 2.29 mmol) was dissolved in DCM (5 mL) and 70% nitric acid (0.16 mL, 3.58 mmol) was added dropwise to the reaction. The mixture was stirred o/n. A further 2 mL of 70% nitric acid was then added. The reaction was stirred for 4 h, then H₂O (20 mL) was added and the 2 phases were separated. The aqueous layer was extracted with DCM and the combined organics were dried (Na₂SO₄) and concentrated by rotary evaporation to give a yellow solid, which was purified via flash column chromatography (silica, iso-hexane to 50% EtOAc/50% iso-hexane) to give a yellow solid. This solid was triturated with Et₂O (2×) to give 5-methyl-4-(methylsulfonyl)-2-nitrophenol (D86, 103 mg, 19%) as a yellow solid.

LCMS: [M−H]⁻ 230

DESCRIPTION 87

2-Amino-5-methyl-4-(methylsulfonyl)phenol. (D87)

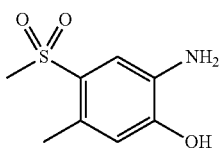

5-Methyl-4-(methylsulfonyl)-2-nitrophenol (D86, 103 mg, 0.45 mmol) was dissolved in EtOH:EtOAc (20 mL, 1:1) and was reduced using an H-Cube (full H₂ mode, 25° C., 1 mL/min). The reaction was concentrated by rotary evaporation and the crude residue was purified via flash column chromatography (silica, DCM to 0.5% NH₃/9.5% MeOH/ 90% DCM) to give 2-amino-5-methyl-4-(methylsulfonyl) phenol (D87, 48 mg, 41%) as a yellow solid.

LCMS: [M+H]⁺ 202

DESCRIPTIONS 88 and 89

5-Methyl-2-({1-[trans-1-methyl-4-(propyloxy)cyclohexyl]-4-piperidinyl}amino)-4-(methylsulfonyl)phenol. (D88)

and

5-Methyl-4-(methylsulfonyl)-2-({1-[trans-4-(propyloxy)cyclohexyl]-4-piperidinyl}amino)phenol. (D89)

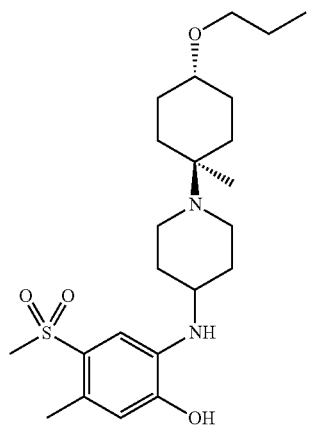

-continued

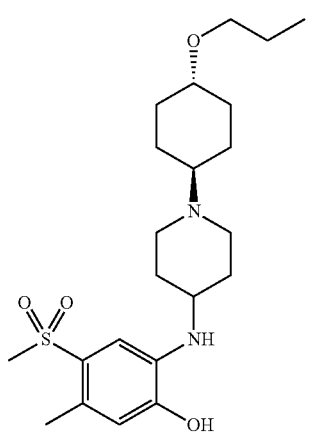

D89

Polymer supported cyanoborohydride (110 mg, 0.47 mmol, 4.3 mmol/g) was added to a solution of 2-amino-5-methyl-4-(methylsulfonyl)phenol (D87, 48 mg, 0.24 mmol), 1-[trans-1-methyl-4-(propyloxy)cyclohexyl]-4-piperidinone (D17, 65 mg, 0.26 mmol, this specific batch contained-25% 1-[trans-4-(propyloxy)cyclohexyl]-4-piperidinone) and acetic acid (0.07 mL, 1.19 mmol) in THF (2.5 mL). The mixture was heated by microwave at 100° C. for 30 min and then for a further 3×30 min. The reaction was then filtered and concentrated by rotary evaporation to give a yellow oil, which was purified by high pH MDAP to give 5-methyl-2-({1-[trans-1-methyl-4-(propyloxy)cyclohexyl]-4-piperidinyl}amino)-4-(methylsulfonyl)phenol (D88, 49 mg, 46%) as a cream solid and 5-methyl-4-(methylsulfonyl)-2-({1-[trans-4-(propyloxy)cyclohexyl]-4-piperidinyl}amino) phenol (D89, 14 mg, 13%) as a yellow oil.

D88—LCMS: $[M+H]^+$ 439
D89—LCMS: $[M+H]^+$ 425

DESCRIPTION 90

5-Hydroxy-2-methylbenzonitrile. (D90)

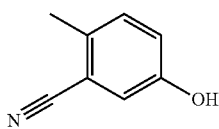

D90

Concentrated sulfuric acid (5 mL, 94 mmol) was added to $H_2O$ (10 mL) (causing an exotherm). While the diluted acid was still hot, 5-amino-2-methylbenzonitrile (826 mg, 6.25 mmol) was added giving a clear solution. This was cooled to 15° C. (during which time a precipitate occurred) and 8 g of ice was added. As soon as the temperature was below 5° C., a solution of sodium nitrite (522 mg, 7.57 mmol) in $H_2O$ (5 mL) was added from a syringe (with the needle extended below the surface of the liquid) keeping the internal temperature below 5° C. The solution went clear after 5 min of stirring and then cold $H_2O$ (5 mL), urea (59 mg, 0.97 mmol) and ice (5 g) were added sequentially. In a separate flask $H_2O$ (5 mL) was added to sodium sulfate (4.75 g, 33.4 mmol) under an atmosphere of argon. Concentrated sulfuric acid (10 mL) was cautiously added and the reaction heated to reflux. The diazonium species was added to the refluxing mixture in portions and the heating continued for 2 h (NOTE: Blast shield used during heating). The mixture was cooled to rt and extracted with $Et_2O$ (2×). The combined organics were washed with $H_2O$ and 10% $Na_2CO_3$ solution before being extracted with 10% NaOH solution. The NaOH solution was acidified with concentrated HCl and then extracted with $Et_2O$ (2×). The combined organics from this second extraction were dried ($Na_2SO_4$) and concentrated by rotary evaporation to give a light brown solid which was purified via flash column chromatography (silica, DCM to 0.5% $NH_3$/9.5% MeOH/90% DCM) to give 5-hydroxy-2-methylbenzonitrile (D90, 476 mg, 52%) as an orange solid.

LCMS: $[M-H]^-$ 132

DESCRIPTION 91

5-Hydroxy-2-methyl-4-nitrobenzonitrile. (D91)

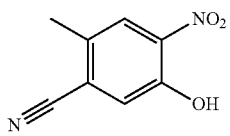

D91

5-Hydroxy-2-methylbenzonitrile (D90, 475 mg, 3.57 mmol) was dissolved in DCM (5 mL) and 70% nitric acid (1 mL, 22 mmol) was added dropwise to the reaction. The mixture was stirred for 45 min before the addition of $H_2O$ (15 mL). The two phases were separated and the aqueous phase was extracted with DCM (2×). The combined organics were dried ($Na_2SO_4$) and concentrated by rotary evaporation to give a yellow solid. The crude residues were purified by flash column chromatography (silica, 10% EtOAc/90% iso-hexane to 50% EtOAc/50% iso-hexane) to give 5-hydroxy-2-methyl-4-nitrobenzonitrile (D91, 186 mg, 26%) as a yellow solid.

LCMS: $[M-H]^-$ 177

DESCRIPTION 92

4-Amino-5-hydroxy-2-methylbenzonitrile. (D92)

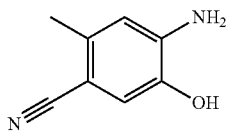

D92

5-hydroxy-2-methyl-4-nitrobenzonitrile (D91, 185 mg, 1.04 mmol) was dissolved in EtOH:EtOAc (24 mL, 1:1) and was reduced using an H-Cube (full $H_2$ mode, 25° C., 1 mL/min). The reaction was concentrated by rotary evaporation to give 4-amino-5-hydroxy-2-methylbenzonitrile (D92, 152 mg, 95%) as a pale yellow solid.

LCMS: $[M+H]^+$ 149

DESCRIPTION 93

5-Hydroxy-2-methyl-4-{[1-(trans-1-methyl-4-{[2-(methyloxy)-ethyl]oxy}cyclohexyl)-4-piperidinyl]amino}benzonitrile. (D93)

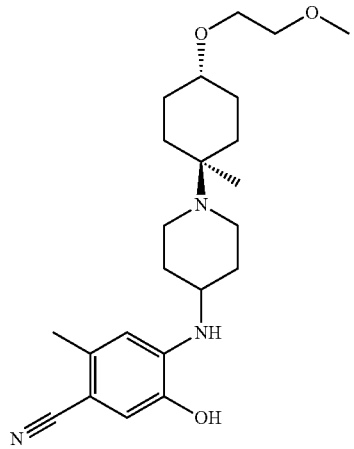

D93

Polymer supported cyanoborohydride (199 mg, 0.86 mmol, 4.3 mmol/g) was added to a solution of 4-amino-5-hydroxy-2-methylbenzonitrile (D92, 65 mg, 0.44 mmol), 1-(trans-1-methyl-4-{[2-(methyloxy)ethyl]oxy}cyclohexyl)-4-piperidinone (D73, 117 mg, 0.43 mmol) and acetic acid (0.12 mL, 2.17 mmol) in THF (2.5 mL). The mixture was heated by microwave at 100° C. for 1 h and then for a further 2 h. An extra 50 mg of polymer supported cyanoborohydride was added and the reaction heated by microwave at 100° C. for 2×1 h. The reaction was then filtered and concentrated by rotary evaporation to give a yellow oil, which was purified via high pH MDAP to give 5-hydroxy-2-methyl-4-{[1-(trans-1-methyl-4-{[2-(methyloxy)ethyl]oxy}cyclohexyl)-4-piperidinyl]amino}benzonitrile (D93, 62 mg, 36%) as a green oil.

LCMS: [M+H]$^+$402

DESCRIPTION 94

4-(Difluoromethoxy)-2-nitrophenol. (D94)

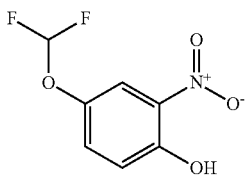

D94

4-(Difluoromethoxy)phenol (500 mg, 3.12 mmol) was dissolved in DCE (3 mL). The reaction mixture was cooled to 0° C. and nitric acid (0.488 mL, 10.92 mmol) was added dropwise over 10 min. The reaction mixture was stirred for a further hour at 0° C., then poured into an ice/water mix (5 g in 5 mL). DCE (10 mL) was added and the layers separated. The organic layer was dried (MgSO$_4$) and evaporated to dryness to give a crude brown oil (550 mg). Material was carried forward without further purification, as no separation between products was found in TLC solvent systems used. (M−H)$^−$=204.

$^1$H NMR δ (CDCl$_3$): 6.51 (1H, t, J=71.2 Hz), 7.18 (1H, d, J=7.2 Hz), 7.3 (1H, dd, J=9.2, 2.8 Hz), 7.91 (1H, s), 10.45 (1H, s).

DESCRIPTION 95

4-(Difluoromethoxy)-2-aminophenol. (D95)

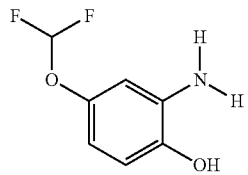

D95

A mixture of 4-(difluoromethoxy)-2-nitrophenol (D94, 450 mg, 1.974 mmol), Raney-nickel (est. 200 mg), 1,4-dioxane (10 mL) and water (5 mL) was stirred at room temperature in a hydrogen atmosphere for 20 h. The reaction mixture was filtered through kieselguhr under an argon atmosphere and evaporated to dryness. The unreacted starting material was sufficiently volatile that most of it was removed by using a rotary evaporator. The residue was purified by flash column chromatography on a pre-packed silica cartridge (column size 50 g), eluting with 0-30% ethyl acetate in hexane, followed by 10-50% 2 M ammonia in methanol in DCM. The residue was further purified on an IST SCX-2 cartridge 20 g, washing with methanol (125 mL) and eluting with 2 M ammonia in methanol (125 mL). The basic eluent was evaporated to dryness to afford the desired product (D95) as a brown solid (200 mg). (M+H)$^+$=176.

$^1$H NMR δ (CDCl$_3$): 6.38 (1H, t, J=74.6 Hz), 6.41 (1H, dd, J=8.6 Hz, 2.6 Hz), 6.55 (1H, d, J=8.0 Hz), 6.67 (1H, d, J=8.4 Hz).

DESCRIPTION 96

4-(Difluoromethoxy)-2-({1-[trans-4-(ethyloxy)-1-methylcyclohexyl]-4-piperidinyl}amino)phenol. (D96)

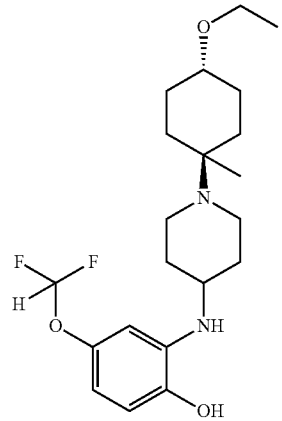

D96

1-[trans-4-(Ethyloxy)-1-methylcyclohexyl]-4-piperidinone (D8, 114 mg, 0.476 mmol) was dissolved in DCM (2.5 mL) and acetic acid (0.25 mL) and 2-amino-4-(difluoromethoxy)phenol (D95, 100 mg, 0.572 mmol) was added, followed by macroporous triethylammonium methylpolystyrene cyanoborohydride (412 mg, 0.953 mmol). The reaction mixture was heated in a microwave reactor at 100° C. for 10 min. The reaction mixture was filtered and evaporated to dryness. The crude product was purified by flash column chromatography on a pre-packed silica cartridge (column size 10 g), eluting with 0-10% 0.2 M ammonia in methanol in DCM to afford the desired compound D96 as a pale brown oil (118 mg). $(M+H)^+=399$.

DESCRIPTION 97

4-Methyl-2-{[1-(trans-1-methyl-4-{[2-(methyloxy)ethyl]oxy}cyclohexyl)-4-piperidinyl]amino}phenol. (D97)

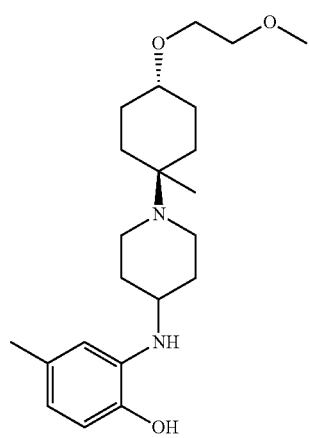

D97

1-(trans-1-Methyl-4-{[2-(methyloxy)ethyl]oxy}cyclohexyl)-4-piperidinone (D73, 60 mg, 0.223 mmol) was dissolved in DCM (1.25 mL) and acetic acid (0.125 mL) and 2-amino-4-methylphenol (32.9 mg, 0.267 mmol) was added, followed by macroporous triethylammonium methylpolystyrene cyanoborohydride (193 mg, 0.445 mmol). The reaction mixture was heated in a microwave reactor at 100° C. for 10 min. The reaction mixture was filtered and evaporated to dryness. The crude product was purified by flash column chromatography on a pre-packed silica cartridge (column size 10 g), eluting with 5-10% 0.2 M ammonia in methanol in DCM to afford the desired compound as a colourless oil (56 mg). $(M+H)^+=377$.

DESCRIPTION 98

2-{[1-(trans-1-Methyl-4-{[2-(methyloxy)ethyl]oxy}cyclohexyl)-4-piperidinyl]amino}-4-(methyloxy)phenol. (D98)

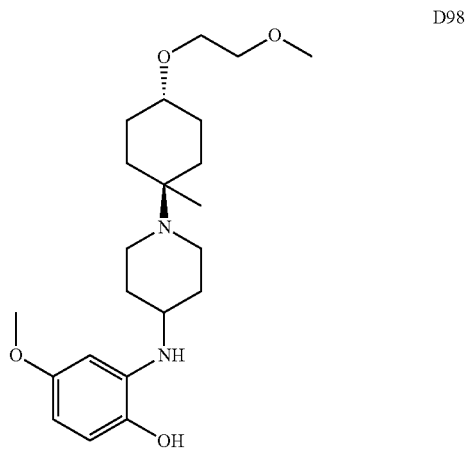 [SMILES: COCCO[C@H]1CC[C@](C)(N2CCC(Nc3cc(OC)ccc3O)CC2)CC1]

D98

1-(trans-1-Methyl-4-{[2-(methyloxy)ethyl]oxy}cyclohexyl)-4-piperidinone (D73, 55 mg, 0.204 mmol) was dissolved in DCM (1.25 mL) and acetic acid (0.125 mL) and 2-amino-4-methoxyphenol (37 mg, 0.266 mmol) was added, followed by macroporous triethylammonium methylpolystyrene cyanoborohydride (177 mg, 0.408 mmol). The reaction mixture was heated in a microwave reactor at 100° C. for 10 min. The reaction mixture was filtered and evaporated to dryness. The crude product was purified by flash column chromatography on a pre-packed silica cartridge (column size 10 g), eluting with 5-10% 0.2 M ammonia in methanol in DCM to afford the desired compound as a yellow oil (12 mg). Due to the poor recovery, the remaining fractions were combined and evaporated to give a yellow oil (20 mg). The yellow oils were combined to give the desired product as a crude yellow oil (31 mg). The material was carried forward without further purification.

$^1$H NMR δ (CDCl$_3$): 1.26 (3H, s), 1.40 (3H, br. m), 1.88 (6H, br. m), 2.04 (4H, m), 2.24 (2H, br. m), 2.83 (2H, br.m), 3.30 (2H, br. m), 3.38 (3H, s), 3.42 (3H, br. m), 3.53 (2H, m), 3.60 (2H, m), 3.72 (2H, br. m), 6.18 (1H, m), 6.72 (1H, m).

DESCRIPTION 99

Ethyl 4-[(cyclopropylmethyl)oxy]cyclohexanecarboxylate. (D99)

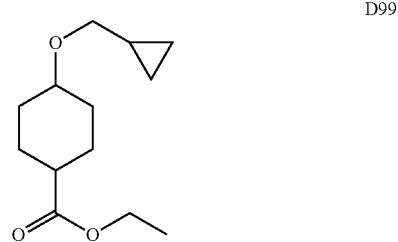 [SMILES: CCOC(=O)C1CCC(OCC2CC2)CC1]

D99

Triethylsilane (10 mL, 63 mmol) was added to a solution of ethyl 4-{[(1,1-dimethylethyl)(dimethyl)silyl]oxy}cyclohexanecarboxylate (D1, 13.6 g, 47.4 mmol), bismuth tribromide (923 mg, 2.06 mmol) and cyclopropanecarbaldehyde (4.25 mL, 56.8 mmol) in acetonitrile (60 mL) at rt under Ar. A black precipitate and an exotherm occurred on the addition of the triethylsilane. The mixture was stirred for 1 h before being poured on to sat. NaHCO₃ (200 mL). The reaction was extracted with EtOAc (2×) and the combined organics were washed (sat. NaCl), dried (Na₂SO₄) and concentrated by rotary evaporation to give a mixture of cis and trans ethyl 4-[(cyclopropylmethyl)oxy]cyclohexanecarboxylate (D99, 20.8 g, 97%, contained silyl residues) as a colourless oil.

¹H NMR δ (CDCl₃, 400 MHz) mixture of approx. 1:1 cis:trans 0.15-0.20 (2 H, m), 0.47-0.54 (2 H, m), 1.02 (1 H, m), 1.20-1.28 (3 H, m), 1.39-2.10 (8 H, m), 2.23 (0.5 H, m), 2.34 (0.5 H, m), 3.17-3.30 (2.5 H, m), 3.45 (0.5 H, m), 4.06-4.15 (2 H, m).

DESCRIPTION 100

4-[(Cyclopropylmethyl)oxy]cyclohexanecarboxylic acid. (D100)

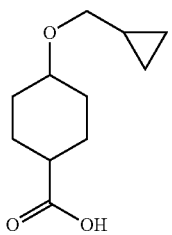

D100

Ethyl 4-[(cyclopropylmethyl)oxy]cyclohexanecarboxylate (D99, 20.8 g, 45.8 mmol) was taken up in THF (50 mL)/methanol (50 mL). Sodium hydroxide (20 mL, 250 mmol, concentrated) was added to the solution which was left to stir o/n. The THF/methanol was evaporated and the crude residue washed with Et₂O. The aqueous layer was acidified with 5 M HCl and extracted with EtOAc (2×). The EtOAc organics were combined, dried (Na₂SO₄) and the solvent evaporated to give a mixture of cis and trans 4-[(cyclopropylmethyl)oxy]cyclohexanecarboxylic acid (D100, 9.47 g, 94%) as a yellow oil.

¹H NMR δ (CDCl₃, 400 MHz) mixture of approx. 1:1 cis:trans 0.12-0.19 (2 H, m), 0.45-0.53 (2 H, m), 0.95-1.06 (1 H, m), 1.19-1.32 (1 H, m), 1.38-1.69 (3.5 H, m), 1.72-1.83 (1 H, m), 1.84-2.10 (2.5 H, m), 2.27 (0.5 H, m), 2.38 (0.5 H, m), 3.17-3.29 (2.5 H, m), 3.44 (0.5 H, m), 10.85 (1 H, br. s).

DESCRIPTION 101

4-[(Cyclopropylmethyl)oxy]-1-methylcyclohexanecarboxylic acid—mixture of cis and trans. (D101)

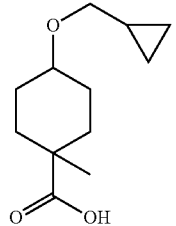

D101

Diisopropylamine (15 mL, 105 mmol) in THF (100 mL) was cooled to 0° C. under Ar. n-Butyllithium (38 mL, 95 mmol, 2.5M in hexane) was added dropwise over 10 min. The reaction mixture was left to stir for 15 min at 0° C. A solution of 4-[(cyclopropylmethyl)oxy]cyclohexanecarboxylic acid (D100, 9.47 g, 43.0 mmol) in THF (50 mL) was added and the resulting yellow solution was heated at 50° C. for 2 h. The reaction mixture was cooled to 0° C. and iodomethane (8 mL, 128 mmol) was added dropwise, the reaction was then allowed to warm to rt and left to stir for 3 days. 10% Citric acid (200 mL) was then added and the reaction mixture was concentrated by rotary evaporation. The residual mixture was diluted with H₂O and extracted with Et₂O (2×). The organics were combined, dried (Na₂SO₄) and concentrated by rotary evaporation to give a mixture of cis and trans 4-[(cyclopropylmethyl)oxy]-1-methylcyclohexanecarboxylic acid (D101, 10.0 g, 93%) as a brown oil.

¹H NMR δ (DMSO-d₆, 400 MHz) mixture of approx. 1:1 cis:trans 0.09-0.17 (2 H, m), 0.39-0.47 (2 H, m), 0.83-2.03 (12 H, m), 3.16-3.24 (2 H, m), 3.33 (0.5 H, m), 3.60 (0.5 H, m), 12.12 (1 H, br. s).

DESCRIPTION 102 trans-4-[(Cyclopropylmethyl)oxy]-1-methylcyclohexanecarboxylic

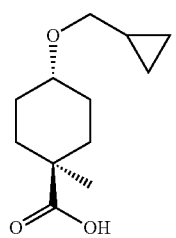

D102

4-[(Cyclopropylmethyl)oxy]-1-methylcyclohexanecarboxylic acid—mixture of cis and trans (D101, 10.0 g, 40.0 mmol) was azeotroped with PhMe (2×) to remove any trace H₂O and then dissolved in toluene (50 mL). Thionyl chloride (50 mL, 685 mmol) was added and the reaction heated at 90° C. for 4 h. Excess thionyl chloride was removed by rotary evaporation and the residue was azeotroped with toluene to remove the final traces. THF (50 mL) was added and the solution poured on to 5% $Na_2CO_3$ solution (200 mL). The mixture was stirred vigorously for 20 min before being washed with $Et_2O$ (2×). The aqueous layer was then acidified with concentrated HCl and extracted with EtOAc (2×). The combined EtOAc organics were dried ($Na_2SO_4$) and concentrated by rotary evaporation to give a brown oil. This residue was purified by being divided into 4 roughly equal portions, each of which was purified via flash column chromatography (silica, 5% EtOAc/95% iso-hexane to 25% EtOAc/75% iso-hexane). The desired fractions were combined to give trans-4-[(cyclopropylmethyl)oxy]-1-methylcyclohexanecarboxylic acid (D102, 893 mg, 10%) as a colourless oil.

$^1$H NMR δ ($CDCl_3$, 400 MHz) 0.16-0.23 (2 H, m), 0.49-0.56 (2 H, m), 1.05 (1 H, m), 1.25 (3 H, s), 1.60-1.87 (8 H, m), 3.26 (2 H, d, J 6.8), 3.40 (1 H, m).

DESCRIPTION 103 trans-4-[(Cyclopropylmethyl)oxy]-1-isocyanato-1-methylcyclo-hexane. (D103)

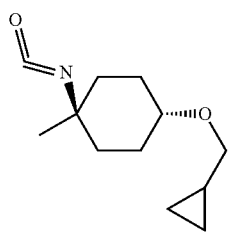

trans-4-[(Cyclopropylmethyl)oxy]-1-methylcyclohexanecarboxylic acid (D102, 890 mg, 4.19 mmol) was dissolved in toluene (25 mL) and triethylamine (0.760 mL, 5.45 mmol) was added, followed by diphenyl phosphoryl azide (0.903 mL, 4.19 mmol). The reaction mixture was heated at 85° C. for 2 h, then allowed to cool to room temperature overnight. The reaction mixture was treated with 1 M aq. sodium hydroxide (75 mL), then extracted with diethyl ether (3×50 mL). The combined organics were dried ($MgSO_4$) and evaporated to afford the desired product (D103) as a colourless oil (934 mg).

$^1$H NMR δ ($CDCl_3$): 0.18 (2H, m), 0.52 (2H, m), 1.03 (1H, m), 1.37 (3H, s), 1.54 (2H, m), 1.74 (6H, m), 3.23 (2 H, d, J=6.8 Hz), 3.53 (1H, br. s).

DESCRIPTION 104 trans-4-[(Cyclopropylmethyl)oxy]-1-methylcyclo-hexanamine hydrochloride. (D104)

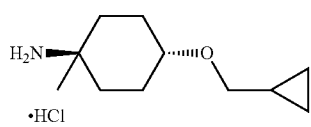

trans-4-[(Cyclopropylmethyl)oxy]-1-isocyanato-1-methylcyclohexane (D103, 877 mg, 4.19 mmol) was dissolved THF (25 mL) and 5 M hydrochloric acid (0.127 mL, 4.19 mmol) was added. The reaction mixture was stirred at room temperature for 3 h in an argon atmosphere. The reaction mixture was evaporated to dryness, redissolved in THF and evaporated. This was repeated until a white solid was obtained. This solid was triturated with ethanol and dried in a vacuum oven to afford the desired product (D104, 700 mg, 76% yield).

$^1$H NMR δ ($CD_3OD$): 0.20 (2H, m), 0.51 (2H, m), 1.01 (1H, m), 1.37 (3H, s), 1.59 (4H, m), 1.87 (4H, m), 1.32 (2H, d, J=5.2 Hz), 3.42 (1H, m).

DESCRIPTION 105

1-{trans-4-[(Cyclopropylmethyl)oxy]-1-methylcyclohexyl}-4-piperidinone. (D105)

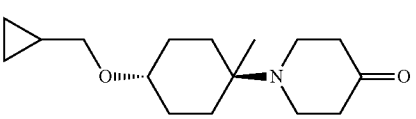

To a solution of trans-4-[(cyclopropylmethyl)oxy]-1-methylcyclohexanamine hydrochloride (D104, 700 mg, 3.19 mmol) in ethanol (20 mL) was added a solution of potassium carbonate (572 mg, 4.14 mmol) in water (10 mL), followed by 1-ethyl-1-methyl-4-oxopiperidinium iodide (D9, 1500 mg, 5.57 mmol). The reaction mixture was heated at 80° C. for 3 h. The reaction mixture was evaporated to dryness and partitioned between DCM and saturated sodium bicarbonate (25 mL of each). The aqueous layer was extracted with further DCM (2×25 mL). The combined organics were dried ($MgSO_4$) and evaporated to give an orange oil. The crude product was purified by flash column chromatography on a Biotage SP4 (column size 24+S), eluting with 0-10% methanol in DCM to afford the product (D105) as an orange oil (340 mg).

¹H NMR δ (CDCl₃): 0.20 (2H, m), 0.53 (2H, m), 0.94 (3H, s), 1.05 (1H, m), 1.48-1.61 (4H, m), 1.69 (2H, m), 1.86 (2H, m), 2.41 (4H, t, J=6 Hz), 2.82 (4H, t, J=6 Hz), 3.27 (2H, d, J=6.4 Hz), 3.44 (1H, m).

DESCRIPTION 106

2-[(1-{trans-1-Methyl-4-[(2-methylbutyl)oxy]cyclohexyl}-4-piperidinyl)amino]-4-(methylsulfonyl)phenol. (D106)

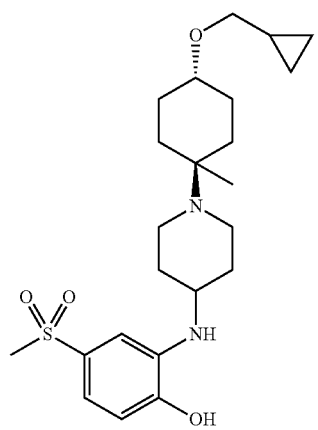

(D106)

1-{trans-4-[(Cyclopropylmethyl)oxy]-1-methylcyclohexyl}-4-piperidinone (D105, 170 mg, 0.641 mmol) was dissolved in THF (5 mL) and 2-amino-4-(methylsulfonyl)phenol (120 mg, 0.641 mmol) was added, followed by acetic acid (0.158 mL, 2.75 mmol) and macroporous triethylammonium methylpolystyrene cyanoborohydride (555 mg, 1.281 mmol). The reaction mixture was heated in a microwave reactor at 100° C. for 90 minutes. The reaction filtered, washing with methanol to dissolve a precipitate which formed. The collected solution was evaporated to give an orange oil-solid mixture. This was triturated with THF to give the desired product (D106) as a white solid (85 mg). (M+H)⁺=437.

DESCRIPTION 107

Phenylmethyl 1-methyl-4-oxocyclohexanecarboxylate. (D107)

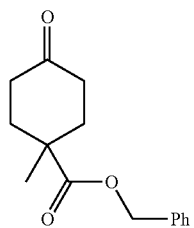

(D107)

2-(Trimethylsilyloxybutadiene (6.46 g, 45.4 mmol), phenylmethyl 2-methyl-2-propenoate (8.00 g, 45.4 mmol), and 4,4'-methanediylbis[2,6-bis(1,1-dimethylethyl)phenol] (0.019 g, 0.045 mmol) were combined together in a 20.0 mL microwave vessel and heated to 200° C. for 300 mins. Sample recovered and removed from vessel using THF (~3×10 mL). The solvent was removed under reduced pressure and the residual oil taken up in 10% 2N HCl/THF (100 mL) and stirred overnight. After this time a clear solution formed, which was diluted with water (50 mL), partitioned into DCM (2×100 mL) and the organic layers separated, dried over MgSO₄, filtered and the solvent removed under reduced pressure. The residue was purified by FC over Silica (150 g: 5-10% EtOAc/iso-hex) to afford a clear oil. Confirmed by NMR to be phenylmethyl 1-methyl-4-oxocyclohexanecarboxylate (3.48 g, 11.30 mmol, 24.89% yield).

¹H NMR δ (CDCl₃, 400 MHz): 1.32 (3 H, s), 1.64-1.69 (2H, m), 1.71-1.85 (6H, m), 5.19 (2H, s), 7.32-7.39 (5H, m).

DESCRIPTION 108

Phenylmethyl 1-methyl-4-[(1-methylethyl)oxy]-cyclohexanecarboxylate. (D108)

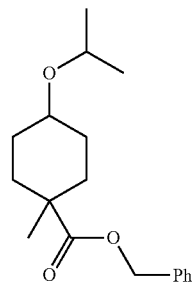

(D108)

Neat triethylsilane (1.518 g, 13.06 mmol) was added to a stirred, cooled (0° C.) solution of phenylmethyl 1-methyl-4-oxocyclohexanecarboxylate (D107) (2.68 g, 10.88 mmol), trimethyl[(1-methylethyl)oxy]silane (1.439 g, 10.88 mmol) and iron (III) chloride (0.176 g, 1.088 mmol) in acetonitrile (100 mL). The solution was stirred for 1 hour at 0° C. TLC (SiO₂ 10% EtOAc/is-hex) showed the presence of two close running products, less polar than starting material and little else but some baseline impurity. The reaction was diluted with water (100 mL), extracted into DCM (2×50 mL), the organic layers dried, filtered and the solvent removed under reduced pressure to afford a yellow oil. Chromatography (SiO₂ 10-20% EtOAc/is-hex) afforded, phenylmethyl 1-methyl-4-[(1-methylethyl)oxy]-cyclohexanecarboxylate (2.3 g, 7.92 mmol, 72.8% yield) as a clear oil. NMR shows the product to be a trans:cis mix, approx 2:1.

Where possible trans and cis NMR data are identified $^1$H NMR δ (CDCl$_3$, 400 MHz): 1.12 (6H, d, J=4.0 Hz), 1.21 (3H, s), 1.5-1.7 (6H, m), 1.75-1.9 (2H, m), 3.2-3.3 (1H, m cis), 3.35-3.45 (1H m trans), 3.6-3.7 (1H, sept J=4.0 Hz), 5.1 (2H, s), 7.4-7.3 (5H, m)

DESCRIPTION 109

1-Methyl-4-[(1-methylethyl)oxy]cyclohexanecarboxylic acid. (D109)

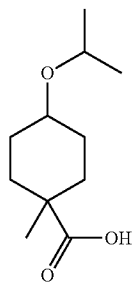
(D109)

Phenylmethyl 1-methyl-4-[(1-methylethyl)oxy]cyclohexanecarboxylate (D108) (2.3 g, 7.92 mmol) was suspended in water (30 mL) and tetrahydrofuran (THF) (10 mL) along with lithium hydroxide (0.759 g, 31.7 mmol). The resulting solution was warmed to reflux overnight, TLC (SiO$_2$ 10% EtOAc/is-hex) showed some of more polar SM present but none of less polar SM. Reaction cooled and extracted with ether (2×20 mL) to remove unhydrolysed SM. Aqueous layer acidified with 2 N HCl (acid to pH stick) and extracted into DCM (2×15 mL). DCM layers combined and dried over MgSO$_4$, filtered and solvent removed under reduced pressure. NMR confirmed 1-methyl-4-[(1-methylethyl)oxy]cyclohexanecarboxylic acid (1.13 g, 5.64 mmol, 71.2% yield) as a mixture of cis and trans isomers. As suspected from the TLC one of the isomers, suspected to be the trans (ether:carboxylate) had hydrolysed faster. This resulted in a ~2:1 ratio of the acids.

Where possible trans and cis NMR data are identified $^1$H NMR δ (CDCl$_3$, 400 MHz): 1.14 (6H, d, J=4.0 Hz), 1.20 (3H, s), 1.5-1.7 (6H, m), 1.80-1.9 (2H, m), 3.3-3.4 (1H, m cis), 3.4-3.5 (1H m trans), 3.6-3.7 (1H, sept J=4.0 Hz), 9.5-10.0 (1H, s).

DESCRIPTION 110 trans-1-Methyl-4-[(1-methylethyl)oxy]cyclohexanecarboxylic acid. (D110)

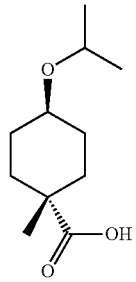
(D110)

1-Methyl-4-[(1-methylethyl)oxy]cyclohexanecarboxylic acid (D109) (1.13 g, 5.64 mmol) was dissolved in neat thionyl chloride (2.059 mL, 28.2 mmol) and warmed to reflux for three hours. The mixture was then allowed to cool to room temp and the thionyl chloride removed under reduced pressure. All thionyl chloride residue was removed by repeated azeotropic evaporation from toluene. The residue was taken up in THF (20 mL) and treated with 5% aq sodium carbonate (10 mL) for 1 hour. The reaction was then diluted with water (20 mL), extracted with ether (2×10 mL), the aqueous layer separated, acidified with 2N HCl, (pH stick) and extracted with DCM (2×10 mL). The DCM layers were combined and dried over MgSO$_4$, filtered and the solvent removed under reduced pressure to afford trans-1-methyl-4-[(1-methylethyl)oxy]cyclohexanecarboxylic acid (556 mg, 2.78 mmol, 49.2% yield). NMR show clean isolation of the trans acid.

$^1$H NMR δ (CDCl$_3$, 400 MHz): 1.14 (6H, d, J=4.0 Hz), 1.20 (3H, s), 1.5-1.7 (6H, m), 1.80-1.9 (2H, m), 3.4 (1H m), 3.64 (1H, sept J=4.0 Hz), 9.5-10.0 (1H, s).

DESCRIPTION 111 trans 1-Methyl-4-(2-methoxyethoxy)cyclohexylamine hydrochloride. (D111)

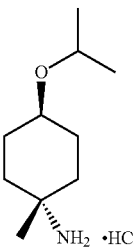
(D111)

A solution of trans-1-methyl-4-[(1-methylethyl)oxy]cyclohexanecarboxylic acid (D110) (556 mg, 2.78 mmol), diphenyl azidophosphate (764 mg, 2.78 mmol), and triethylamine (0.387 mL, 2.78 mmol) in toluene (10 mL) was warmed to reflux for 2 hr. The solution was then cooled to room temp, and treated with 1 N NaOH (aq, 10 mL) for three hours. After this time ether (50 mL) was added, the organic layers separated, dried over MgSO$_4$, filtered and the solvent removed under reduced pressure to give a clear oil. NMR is consistent with the intermediate isocyanate. The recovered material was taken up in tetrahydrofuran (THF) (10.00 mL) and treated with hydrochloric acid 5N (0.084 mL, 2.78 mmol) and stirred at room temperature for 48 hr. The solvent was removed under reduced pressure and the residue triturated from ether to afford trans-1-methyl-4-[(1-methylethyl)oxy]-cyclohexanamine (335 mg, 1.956 mmol, 70.5% yield). NMR is consistent with the structure of the desired product.

$^1$H NMR δ (d$_4$-MeOH, 400 MHz): 1.14 (6H, d, J=4.0 Hz), 1.4 (3H, s), 1.5-1.6 (6H, m), 1.6-1.7 (2H, m), 3.5 (1H m), 3.74 (1H, sept J=4.0 Hz).

DESCRIPTION 112

1-{trans-1-Methyl-4-[(1-methylethyl)oxy]cyclohexyl}-4-piperidinone

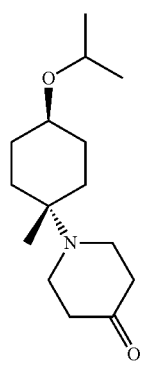

(D112)

1-Ethyl-1-methyl-4-oxopiperidinium iodide (D9; 354 mg, 1.315 mmol) was added to a stirred solution of trans-1-methyl-4-[(1-methylethyl)oxy]cyclohexylamine hydrochloride (D111) (227 mg, 1.315 mmol) and potassium carbonate (132 mg, 0.955 mmol) in ethanol (14 mL)/water (7 mL) and the resulting solution warmed to reflux for three hours. The mixture was then allowed to cool to room temp and partitioned into NaHCO$_3$ solution (aq sat. 25 mL) and extracted into DCM (3×20 mL). The combined extracts were dried over MgSO$_4$, filtered and the solvent removed under reduced pressure to afford a yellow oil. Purification by FC, SiO$_2$ (3-5% 2N NH$_3$/MeOH/DCM) afforded 1-{trans-1-methyl-4-[(1-methylethyl)oxy]cyclohexyl}-4-piperidinone (140 mg, 0.553 mmol, 42.0% yield). NMR consistent with desired product.

$^1$H NMR δ (CDCl$_3$, 400 MHz): 0.9 (3H, s), 1.12 (6H, d, J=4.0 Hz), 1.4-1.5 (2H, m), 1.5-1.6 (2H, m), 1.6-1.7 (2H, m), 1.7-1.8 (2 h, m), 2.4 (4H, t J=8.0 Hz), 2.85 4H, t J=8.0 Hz) 3.45 (1H m), 3.65 (1H, sept J=4.0 Hz).

DESCRIPTION 113

2-[(1-{trans-1-Methyl-4-[(1-methylethyl)oxy]cyclohexyl}-4-piperidinyl)amino]-4-(methylsulfonyl)phenol. (D113)

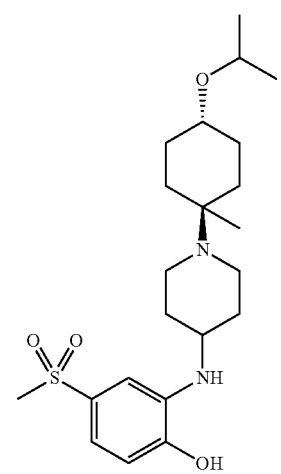

D113

1-{trans-1-Methyl-4-[(1-methylethyl)oxy]cyclohexyl}-4-piperidinone (D112, 140 mg, 0.553 mmol) was dissolved in THF (5 mL) and 2-amino-4-(methylsulfonyl)phenol (103 mg, 0.550 mmol) was added, followed by acetic acid (0.135 mL, 2.366 mmol) and macroporous triethylammonium methylpolystyrene cyanoborohydride (595 mg, 1.375 mmol). The reaction mixture was heated in a microwave reactor at 100° C. for 60 minutes. The reaction mixture was scratched, causing a precipitate to form. The reaction mixture was filtered. Methanol was added to the collected solid to dissolve the precipitate, leaving behind the insoluble resin. The methanol solution was evaporated to give the desired product as a tan solid (125 mg).

$^1$H NMR δ (CD$_3$OD): 1.14 (6H, d, J=6.0 Hz), 1.38 (3H, s), 1.45 (2H, m), 1.73 (4H, m), 2.02 (4H, m), 2.30 (2H, m), 3.05 (3H, s), 3.12 (2H, m), 3.34 (2H, s), 3.39 (1H, m), 3.57 (2H, m), 3.67 (2H, m), 3.77 (1H, septet, J=6.2 Hz), 6.83 (1H, d, J=8.0 Hz), 7.10 (1H, s), 7.13 (1H, d, J=8.0 Hz).

DESCRIPTION 114

2-{[1-(trans-1-Methyl-4-{[2-(methyloxy)ethyl]oxy}cyclohexyl)-4-piperidinyl]amino}-4-(trifluoromethyl)phenol. (D114)

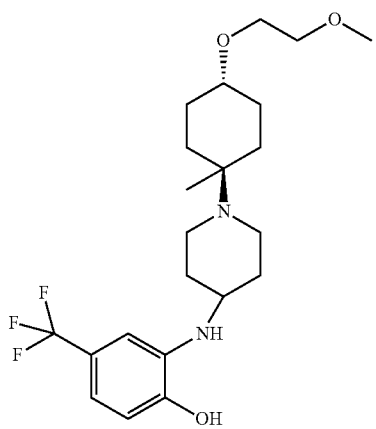

2-Amino-4-(trifluoromethyl)phenol (65.8 mg, 0.371 mmol), 1-(trans-1-methyl-4-{[2-(methyloxy)ethyl]oxy}cyclohexyl)-4-piperidinone (D73) (100 mg, 0.371 mmol), PS-CNBH₃ (354 mg, 0.817 mmol) were placed in a 5 mL microwave tube, AcOH (0.13 mL, 2.271 mmol) and dichloromethane (DCM) (2.5 mL) were added. The tube was sealed and heated to 100° C. for 15 min, fixed hold time. The reaction mixture was filtered and the filtrate evaporated to give a clear oil. The oil was purified on a 10 g silica column, eluent —NH3/MeOH/DCM. This gave a clear oil 2-{[1-(trans-1-methyl-4-{[2-(methyloxy)ethyl]oxy}cyclohexyl)-4-piperidinyl]amino}-4-(trifluoromethyl)phenol (109 mg, 0.253 mmol, 68.2% yield).

¹H NMR δ (CDCl₃, 400 MHz) 0.9 (3H,$), 1.4-1.6 (6H, br m), 1.7 (3H, br m), 1.9 (2H, br m), 2.1 (2H, br m), 2.35 (2H, t, J=12.0 Hz), 3.05 (2H, d, J=12.0 Hz), 3.25 (2H, br m), 3.4 (3H, s), 3.55 (4H, m), 4.5 (1H, br s), 6.70 (1H, d, J=8.0 Hz), 6.76 (1H, s), 6.82 (1H, d, J=8.0 Hz).

DESCRIPTION 115

2-Fluoro-4-methyl-6-nitrophenol. (D115) (Scale-up Preparation of D41)

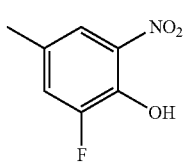

2-Fluoro-4-methylphenol (2.6 g, 20.61 mmol) was dissolved in dichloromethane (DCM) and placed in a 100 mL RB flask. Nitric acid, 70% (1.576 mL, 24.74 mmol) was added dropwise (exotherm observed). The reaction mixture was left to stir for ~1 hr, washed with water, the organic dried and evaporated to give a yellow solid, 2-fluoro-4-methyl-6-nitrophenol (3.276 g, 19.14 mmol, 93% yield).

¹H NMR δ (CDCl₃, 400 MHz) 2.35 (3H,$), 7.26 (1H, d, J=1.0 Hz), 7.71 (1H, d, J=1.0 Hz), 10.3 (1H, s).

DESCRIPTION 116

2-Fluoro-4-methyl-6-aminophenol. (D116) (Scale-Up Preparation of D42)

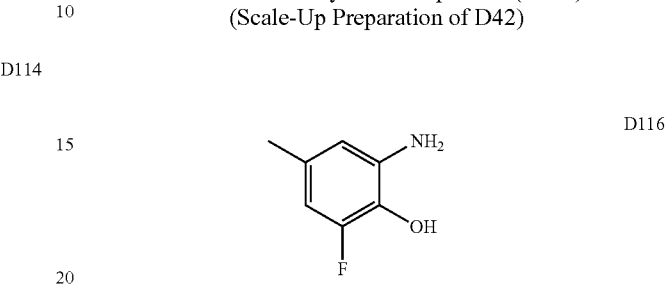

2-Fluoro-4-methyl-6-nitrophenol (D115, 3.276 g, 19.14 mmol) was dissolved in ethanol (100 mL). 10% Pd/C (0.323 g, 0.304 mmol) was added and the reaction mixture hydrogenated for ~18 hr. Catalyst was filtered off and the filtrate evaporated to dryness. TLC showed only a small amount of material had been reduced. Solid was redissolved in 350 mL ethanol, 150 mL of this solution was passed down the H-cube at 1 mL/min with full hydrogen. After ~2 hr the cartridge had been exhausted. A new cartridge was used and the reaction mixture was left recycling through the instrument for ~4 hr. ~30% of nitro compound was still remaining. The reaction mixture was evaporated to dryness.

Redissolved in EtOH and passed through the H-cube with a new cartridge to give fully reduced material 2-fluoro-4-methyl-6-aminophenol (907 mg, 6.43 mmol, 33.6% yield) as a brown solid. The remaining nitro compound was passed down the H-cube at 1 mL/min with full hydrogen—still only 58% conversion. Redissolved in EtOH and passed through the H-cube with a new cartridge. Evaporated to dryness redissolved in MeOH and loaded onto an SCX-2 cartridge (50 g) washed with MeOH and eluted with 1M NH₃/MeOH, evaporated to dryness to give a brown solid batch 2 (1.319 g, 9.35 mmol, 48.8% yield).

¹H NMR δ (CDCl₃, 400 MHz) 2.18 (3H,$), 3.5 (2H, br s), 6.33 (2H, br m), 7.47 (1H, s).

DESCRIPTION 117

[4-({[4-(Methyloxy)phenyl]methyl}oxy)-3-nitrophenyl]methanol. (D117)

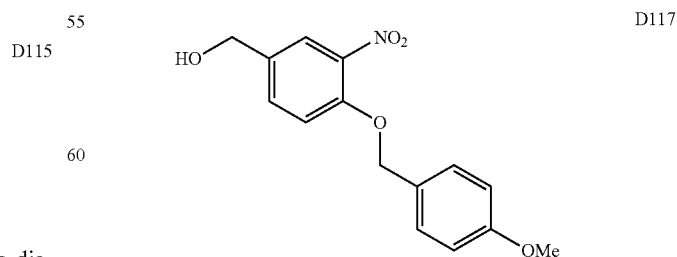

To a solution of 4-(hydroxymethyl)-2-nitrophenol (2.20 g, 13.01 mmol) in DMF (60 mL) was added cesium carbonate (8.48 g, 26.0 mmol) followed by the portionwise addition of 4-methoxybenzyl chloride (3.06 g, 19.51 mmol). After stirring at rt for 45 mins additional 4-methoxybenzyl chloride (2.037 g, 13.01 mmol) was added followed by tetrabutylammonium iodide (2.402 g, 6.50 mmol). The reaction mixture was stirred at rt for 18 hr and then diluted with EtOAc (200 mL) and washed successively with water, 10% aq. $K_2CO_3$, water and finally brine, dried ($MgSO_4$), filtered and concentrated to dryness in vacuo. The residue was purified by silica gel chromatography eluting with 10-50% EtOAc in isohexane to afford the title compound as a cream solid, 2.17 g, 57.7%.

$^1$H NMR δ ($CDCl_3$): 1.81 (1H, t, J=5.6 Hz), 3.81 (3H, s), 4.67 (2H, d), 5.15 (2H, s), 6.90 (2H, d), 7.10 (1H, d), 7.37 (2H, d), 7.50 (1H, m), 7.85 (1H, d).

DESCRIPTION 118

4-[(Methyloxy)methyl]-1-({[4-(methyloxy)phenyl]methyl}oxy)-2-nitrobenzene. (D118)

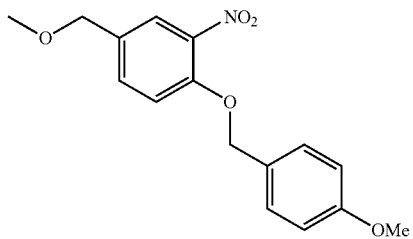

D118

To a solution of [4-({[4-(methyloxy)phenyl]methyl}oxy)-3-nitrophenyl]methanol D117 (2.16 g, 7.47 mmol) in THF (100 mL) was added iodomethane (0.700 mL, 11.20 mmol) followed by the portionwise addition of a 0.5M solution of potassium hexamethyldisilazide (22.40 mL, 11.20 mmol) in toluene. After stirring at rt for 2 hr the mixture was diluted with EtOAc (150 mL) and washed with water (2×50 mL) and brine (2×50 mL). The organic phase was dried ($MgSO_4$) filtered and concentrated in vacuo. The residue was purified by silica gel chromatography eluting with 10-40% EtOAc in isohexane to afford the title compound as a pale orange oil which solidified on standing, 1.57 g, 69.3%.

$^1$H NMR δ ($CDCl_3$): 3.39 (3H, s), 3.81 (3H, s), 4.41 (2H, s), 5.16 (2H, s), 6.92 (2H, d), 7.10 (1H, d, J=8.0 Hz), 7.38 (2H, d), 7.45 (1H, m), 7.82 (1H, d).

DESCRIPTION 119

2-Methyl-4-[(methyloxy)methyl]phenol. (D119)

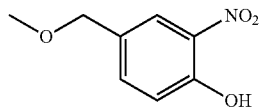

D119

To a solution of 4-[(methyloxy)methyl]-1-({[4-(methyloxy)phenyl]methyl}oxy)-2-nitrobenzene D118 (1.57 g, 5.18 mmol) in DCM (80 mL) was added trifluoroacetic acid (3.99 mL, 51.80 mmol). After 1 hr the mixture was washed with water (3×25 mL) and then extracted with 10% aq potassium carbonate solution (3×20 mL). The combined extracts were back washed with diethyl ether (20 mL) and then the pH was adjusted to 1 with 2N HCl, the mixture was extracted with DCM (3×25 mL), the combined extracts were washed with water (25 mL) and brine (25 mL), dried($MgSO_4$), filtered and concentrated in vacuo. The residue was purified by silica gel chromatography eluting with 5-40% EtOAc in isohexane to afford the title compound as a bright yellow oil. 0.72 g, 76%

$^1$H NMR δ ($CDCl_3$): 3.41 (3H, s), 4.42 (2H, d), 7.15 (1H, d, J=8.4 Hz), 7.56 (1H, m), 8.08 (1H, d).

DESCRIPTION 120

2-Amino-4-[(methyloxy)methyl]phenol. (D120)

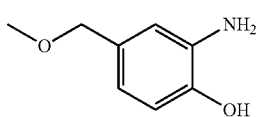

D120

A mixture of 4-[(methyloxy)methyl]-2-nitrophenol D119 (0.72 g, 3.93 mmol) and platinum (IV) oxide (0.089 g, 0.393 mmol) in ethanol (15 mL) was stirred under an atmosphere of hydrogen for 16 hr. The catalyst was removed by filtration through celite and the filtrate concentrated to dryness in vacuo to afford the title compound as a green/brown solid 0.51 g, 85%.

$^1$H NMR δ ($CDCl_3$): 3.35 (3H, s), 3.7-4.5 (2H, br s+2H, s), 6.62 (2H, m), 6.74 (1H, d).

DESCRIPTION 121

2-{[1-(trans-1-Methyl-4-{[2-(methyloxy)ethyl]oxy}cyclohexyl)-4-piperidinyl]amino}-4-[(methyloxy)methyl]phenol. (D121)

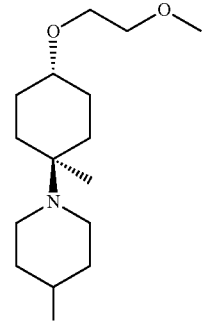

D121

A mixture of 2-amino-4-[(methyloxy)methyl]phenol (D120) (37.5 mg, 0.245 mmol), 1-(trans-1-methyl-4-{[2-(methyloxy)ethyl]oxy}cyclohexyl)-4-piperidinone (D73, 60 mg, 0.223 mmol), Polymer supported cyanoborohydride (185 mg, 0.445 mmol) and acetic acid (0.064 mL, 1.114 mmol) in THF (3 mL) was heated to 100° C. for 40 mins (2×20 mins) in a microwave reactor. The mixture was diluted with EtOAc (5 mL) washed with dilute aq potassium bicarbonate, water and brine, dried (MgSO₄) and concentrated to dryness in vacuo. The reside was purified by silica gel chromatography eluting with DCM to 20% of 1:10 2M NH₃ in MeOH/DCM to yield the title compound as a thick pale yellow oil. 58 mg, 57.6%

¹H NMR δ (CDCl₃): 1.35-1.61 (8H, m), 1.66-1.71 (2H, m), 1.86-1.91 (2H, m), 2.23-2.40 (2H, m), 2.89-2.98 (2H, m), 3.21 (1H, m), 3.37 (3H, s), 3.43 (3H, s), 3.49 (3H, s), 3.53-3.66 (5H, m), 4.34 (2H, s), 6.55 (1H, br s), 6.67 (1H, br s). LC/MS 407 (MH+), 405(M−H).

DESCRIPTION 122

4-[(Methyloxy)methyl]-2-nitrophenyltrifluoromethanesulfonate. (D122)

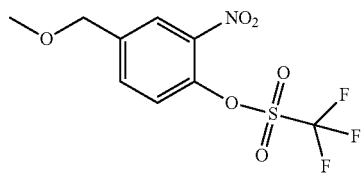

A stirred mixture of 4-[(methyloxy)methyl]-2-nitrophenol D119 (1.15 g, 6.28 mmol) and pyridine (0.762 mL, 9.42 mmol) in DCM (50 mL) under argon was cooled to 0° C. and trifluoromethanesulfonic anhydride (1.167 mL, 6.91 mmol) was added dropwise over 5 mins. The mixture was stirred at 0° C. for 10 mins and then at room temp for 1 hr before cooling back to 0° C. whereupon it was treated with 1N HCl (15 mL). the mixture was allowed to warm to rt, the organic phase separated washed with further 1N HCl and brine, dried over MgSO₄, and then concentrated to dryness under vacuum to afford the title compound as a pale brown oil 1.95 g, 99%.

¹H NMR δ (CDCl₃): 3.47 (3H, s), 4.55 (2H, s), 7.42 (1H, d, J=8.4 Hz), 7.68 (1H, d, J=8.4 Hz), 8.14 (lH, d).

DESCRIPTION 123 bis(1,1-Dimethylethyl) {4-[(methyloxy)methyl]-2-nitrophenyl}propanedioate. (D123)

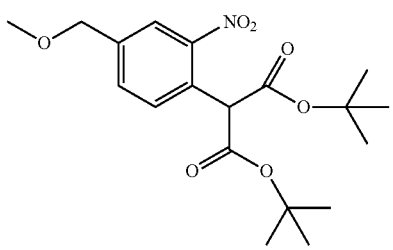

A stirred solution of bis(1,1-dimethylethyl) propanedioate (1.672 g, 7.73 mmol) in anhydrous DMF (25 mL) under argon was cooled to 0° C. and treated, portionwise with sodium hydride (0.297 g, 7.42 mmol) which was added over 10 mins. The resultant mixture was stirred at 0° C. for 15 mins and then allowed to warm to rt. After 1 hr the mixture was cooled back to 0° C. and treated with a solution of 4-[(methyloxy)methyl]-2-nitrophenyl trifluoromethanesulfonate D122 (1.95 g, 6.19 mmol) in DMF (5 mL) which was added slowly over 10 mins. After the addition was complete the cooling bath was removed and the mixture allowed to warm to rt. After 1 hr TLC indicated little or no reaction. The mixture was then warmed to 70° C. for 16 hr, then cooled to room temp and the solvent was removed under vacuum. The dark brown oily reside was dissolved in EtOAc (100 mL) and washed thoroughly with water (6×50 mL) and brine (50 mL), dried (MgSO₄) and concentrated to dryness under vacuum. The residue was subjected to silica gel chromatography eluting with 0-5% MeOH in DCM to give the title compound as a yellow oil (1.32 g, 55.9%).

¹H NMR δ (CDCl₃, 400 MHz): 1.45-1.51 (18H, m), 3.42 (3H, s), 4.52 (2H, s), 5.09 (1H, s), 7.51 (1H, d), 7.59 (1H, m), 8.01 (1H, d).

DESCRIPTION 124 bis(1,1-Dimethylethyl) {2-amino-4-[(methyloxy)methyl]phenyl}propanedioate. (D124)

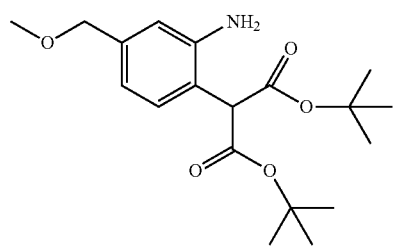

A mixture of bis(1,1-dimethylethyl) {4-[(methyloxy)methyl]-2-nitrophenyl}propanedioate (D123) (1.30 g, 3.41 mmol) and palladium on carbon (0.181 g, 0.170 mmol) in ethanol (30 mL) was stirred under hydrogen at atmospheric pressure for 16 hr. The catalyst was removed by filtration through celite and the filtrate concentrated to dryness under vacuum to afford the crude title compound as a thick yellow oil 1.15 g, 96%.

¹H NMR δ (CDCl₃, 400 MHz): 1.42-1.51 (18H, m), 3.37 (3H, s), 4.12 (2H, br s), 4.35 (2H, s), 4.46 (1H, s), 6.71 (2H, m), 7.13 (1H, d).

DESCRIPTION 125

4-Hydroxy-3-nitrobenzamide. (D125)

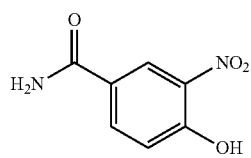

A mixture of methyl 4-hydroxy-3-nitrobenzoate (1.00 g, 5.07 mmol) and concentrated aq ammonia (10.0 mL, 162 mmol) was heated to 100° C. for 90 mins (3×30 mins) in a microwave reactor. The mixture was poured into water (70 mL), acidified with 6N HCl and extracted with EtOAc (4×25 mL). The combined extracts were dried (MgSO₄) and concentrated in vacuo. The residue was triturated with DCM (20 mL) filtered and washed with DCM before drying under vacuum to afford the crude title compound as a yellow solid 0.49 g, 53.0%

$^1$H NMR δ (DMSO-d$_6$, 400 MHz): 7.15 (1H, d), 7.36 (1H, s), 8.00-8.05 (2H, m), 8.42 (1H, s), 11.75 (lH, br s)

DESCRIPTION 126

3-Amino-4-hydroxybenzamide. (D126)

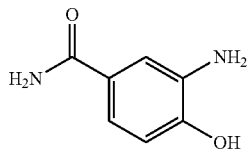

D126

A mixture of 4-hydroxy-3-nitrobenzamide D125 (0.49 g, 2.69 mmol), cyclohexene (1.105 g, 13.45 mmol) and 10% palladium on carbon (0.143 g, 0.135 mmol) in ethanol (20 mL) was heated to reflux under argon for 3 hr. The cooled mixture was filtered through celite and the filtrate concentrated to dryness in vacuo to afford a yellow/brown solid. The product was purified by silica gel chromatography eluting with 0-15% 2M ammonia in MeOH/DCM. The title compound was isolated as a pale brown powder, 0.26 g, 57.2%.

$^1$H NMR δ (d$^6$DMSO, 400 MHz): 4.36 (2H, br s), 6.63 (1H, d), 6.89 (1H, s), 6.96 (1H, m), 7.13 (1H, d), 7.53 (1H, s), 9.50 (lH, br s)

DESCRIPTION 127

3-({1-[trans-4-(Ethyloxy)-1-methylcyclohexyl]-4-piperidinyl}amino)-4-hydroxybenzamide. (D127)

D127

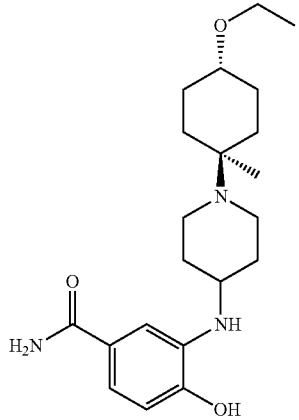

A mixture of 3-amino-4-hydroxybenzamide (D126) (47.7 mg, 0.313 mmol), 1-[trans-4-(ethyloxy)-1-methylcyclohexyl]-4-piperidinone (75 mg, 0.313 mmol), polymer supported cyanoborohydride (260 mg, 0.627 mmol) and acetic acid (0.090 mL, 1.567 mmol) in THF (3 mL) was heated to 100° C. for 40 mins (2×20 mins) in a microwave reactor. The mixture was diluted with EtOAc (5 mL) washed with dilute aq potassium bicarbonate, water and brine, dried (MgSO$_4$) and concentrated to dryness in vacuo. The reside was purified by silica gel chromatography eluting with DCM to 20% 3:10 2M NH$_3$ in MeOH/DCM. The title compound was isolated as a colourless solid, 51 mg, 41.2%.

$^1$H NMR δ (CD$_3$OD): 1.18 (3H, t), 1.23-1.58 (7H, m), 1.73 (2H, m), 1.95 (2H, m), 2.10 (2H, d), 2.44 (2H, t), 3.12 (2H, d), 3.29-3.41 (7H, m), 3.47-3.52 (2H, m), 6.68 (1H, d J=8.4 Hz), 7.11 (1H, d J=8.4 Hz), 7.16 (1H, d), [OH not visible].

LC/MS 376 (MH$^+$), 374(M−H).

DESCRIPTION 128

4-Hydroxy-3-{[1-(trans-1-methyl-4-{[2-(methyloxy) ethyl]oxy}cyclohexyl)-4-piperidinyl] amino}benzamide. (D128)

D128

A mixture of 3-amino-4-hydroxybenzamide (D126) (33.9 mg, 0.223 mmol),1-(trans-1-methyl-4-{[2-(methyloxy) ethyl]oxy}cyclohexyl)-4-piperidinone (60 mg, 0.223 mmol), polymer supported cyanoborohydride (185 mg, 0.445 mmol) and acetic acid (0.064 mL, 1.114 mmol) in THF (3 mL) was heated to 100° C. for 40 mins (2×20 mins) in a microwave reactor. The mixture was filtered, diluted with EtOAc (5 mL) washed with dilute aq potassium bicarbonate, water and brine, dried (MgSO$_4$) and concentrated to dryness in vacuo. The residue was purified by silica gel chromatography eluting with 0-10% 2M NH$_3$ in MeOH/DCM. The title compound was isolated as a colourless solid 29 mg, 28.9%.

$^1$H NMR δ (CDCl$_3$): 1.49-1.70 (10H, m), 1.85-1.91 (4H, m), 2.23-2.32 (4H, m) 3.14 (2H, m), 3.40-3.54 (5H, m), 3.56 (4H, dd), 4.10 (1H, m), 4.47 (2H, s), 7.04 (1H, d), 7.15 (2H, m).

LC/MS 406 (MH+), 404(M−H).

DESCRIPTION 129

4-(2-Methyl-1,3-dioxolan-2-yl)-2-nitrophenol. (D129)

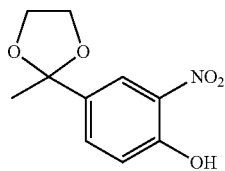

A stirred mixture of 1-(4-hydroxy-3-nitrophenyl)ethanone (3.00 g, 16.56 mmol), ethylene glycol (1.385 mL, 24.84 mmol) and p-toluenesulfonic acid monohydrate (0.158 g, 0.828 mmol) in toluene (60 mL) was heated to reflux for 18 hr in a 250 mL round bottom flask fitted with a Dean-Stark apparatus. The mixture was cooled and diluted with EtOAc (80 mL) and then washed with water (3×30 mL) and brine (20 mL), dried (Na$_2$SO$_4$) and concentrated to dryness in vacuo to afford a thick brown oily residue. This was purified by silica gel chromatography eluting with 5-50% Et$_2$O in isohexane. The title product was isolated as a yellow oil (2.41 g, 64.6%).

$^1$H NMR δ (CDCl$_3$, 400 MHz): 1.64 (3H, s), 3.83 (4H, q), 4.06 (4H, q), 7.14 (1H, d), 7.69 (1H, d), 8.23 (1H, d), 10.57 (1H, s).

DESCRIPTION 130

2-Amino-4-(2-methyl-1,3-dioxolan-2-yl)phenol. (D130)

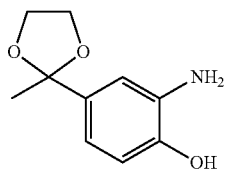

A stirred mixture of 4-(2-methyl-1,3-dioxolan-2-yl)-2-nitrophenol D129 (2.40 g, 10.66 mmol), cyclohexene (4.38 g, 53.3 mmol) and 10% palladium on carbon (0.227 g, 0.213 mmol) in ethanol (75 mL) was heated to reflux for 6 hr under argon. The mixture was cooled to rt and the catalyst was removed by filtration through celite. The filtrate was concentrated to dryness in vacuo and the reside dissolved in 10% MeOH in DCM (20 mL) and passed through a SCX-2 cartridge (25 g) which was then eluted with further 10% MeOH in DCM to wash through any unreacted starting material and then with 2M ammonia in MeOH. The basic eluate was concentrated under vacuum to give the title compound as a yellow-brown solid (1.58 g, 76%).

$^1$H NMR δ (DMSO-d$_6$, 400 MHz) 2.44 (3H, s), 3.44 (4H, s) (note: partly obscured by water signal), 3.74 (2H, br s), 6.69 (1H, d), 7.53 (1H, s), 7.12 (1H, d), 7.21 (1H, s), 9.30 (1H, br s)

DESCRIPTION 131

1-(4-Hydroxy-3-{[1-(trans-1-methyl-4-{[2-(methyloxy)ethyl]oxy}-cyclohexyl)-4-piperidinyl]amino}phenyl)ethanone. (D131)

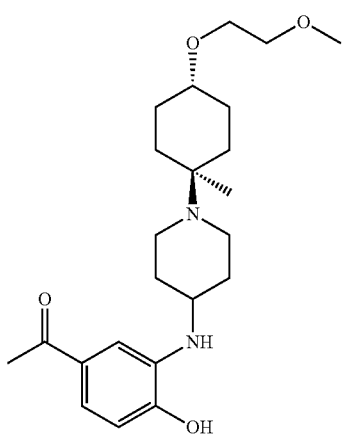

A mixture of 2-amino-4-(2-methyl-1,3-dioxolan-2-yl)phenol D130 (43.5 mg, 0.223 mmol), 1-(trans-1-methyl-4-{[2-(methyloxy)ethyl]oxy}cyclohexyl)-4-piperidinone (D73, 60 mg, 0.223 mmol), polymer supported cyanoborohydride (185 mg, 0.445 mmol) and acetic acid (0.019 mL, 0.334 mmol) in THF (3 mL) was heated in a microwave reactor to 100° C. for 60 mins (3×20 mins). The cooled mixture was diluted with EtOAc (5 mL) and washed with dilute aq potassium carbonate and brine, dried (MgSO$_4$), then concentrated to dryness in vacuo. The residue was subjected to chromatography on silica gel eluting with DCM to DCM/MeOH/NH$_4$OH (90/9/1). The crude title product was isolated as a sticky brown gum (32 mg, 32.0%), the product was taken forward to the next step in the synthesis without further purification.

LC/MS 405 (MH)$^+$, 403(M−H)$^+$.

DESCRIPTION 132

1-(3-Amino-4-hydroxyphenyl)ethanone O-methyloxime. (D132)

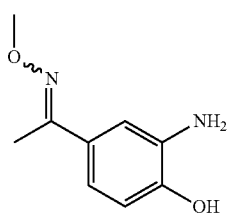

A mixture of O-methylhydroxylamine hydrochloride (535 mg, 6.40 mmol), 2-amino-4-(2-methyl-1,3-dioxolan-2-yl)

phenol D130 (250 mg, 1.28 mmol) and potassium carbonate (442 mg, 3.20 mmol) in ethanol (10 mL) was heated to reflux for 2 hr. The mixture was cooled to rt and concentrated to dryness under vacuum and the residue partitioned between DCM and water. The organic phase was separated washed with brine, dried (MgSO$_4$) and concentrated to dryness in vacuo. The residue was purified using silica gel chromatography eluting with 0 to 10% MeOH in DCM. The title product was isolated as a pale brown solid, 224 mg, 97%.

$^1$H NMR δ (CDCl$_3$, 400 MHz): 2.03 (3H, s), 3.84 (3H, s), 4.61 (2H, br s), 6.62 (1H, d), 6.69 (1H, d), 6.89 (1H, d), 9.33 (1H, br s).

DESCRIPTION 133

1-(4-Hydroxy-3-{[1-(trans-1-methyl-4-{[2-(methyloxy)ethyl]oxy}cyclohexyl)-4-piperidinyl]amino}phenyl)ethanone O-methyloxime. (D133)

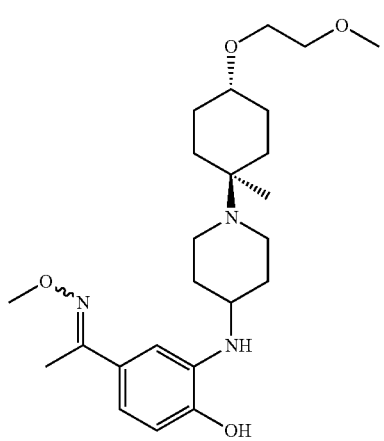

A mixture of 1-(3-amino-4-hydroxyphenyl)ethanone O-methyloxime (D132) (33 mg, 0.183 mmol), 1-(trans-1-methyl-4-{[2-(methyloxy)ethyl]oxy}cyclohexyl)-4-piperidinone (D73, 49.3 mg, 0.183 mmol), polymer supported cyanoborohydride (152 mg, 0.366 mmol) and acetic acid (0.052 mL, 0.916 mmol) in dichloromethane (DCM) (3 mL) was heated to 100° C. for 30 mins in a microwave reactor. The mixture was washed with dilute aq potassium carbonate dried (MgSO$_4$) and concentrated to dryness under vacuum. The residue was purified by silica gel chromatography eluting with DCM/MeOH/NH$_4$OH (90:9:1). The title product was isolated as a v pale yellow gum, 40 mg, 50.4%.

LC/MS 434 (MH)$^+$, 432(M−H)$^+$.

DESCRIPTION 134

2-Bromo-4-cyanophenylacetic acid. (D134)

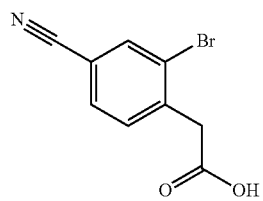

A solution of 4-cyanophenylacetic acid (1.6 g, 9.93 mmol) in 50% aqueous sulfuric acid (10 mL) was treated with N-bromosuccinimide (1.8 g, 10.11 mmol). The mixture was stirred in the dark for 18 h then diluted with water and extracted with diethyl ether to give 2-bromo-4-cyanophenylacetic acid (2.1 g, 7.00 mmol, 70.5% yield) as a white solid containing about 25% of starting material.

[M—CO$_2$H]$^-$ 194 and 196

DESCRIPTION 135

N-Boc 4-{[(2-Bromo-4-cyanophenyl)acetyl]amino}piperidine. (D135)

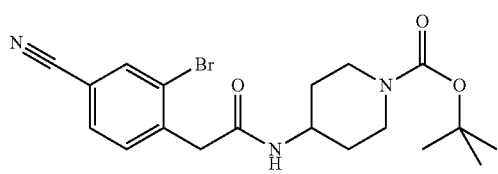

A mixture of 3-bromo-4-cyanophenylacetic acid (D134, 2.1 g, 7.00 mmol), 1-Boc 4-aminopiperidine (1.5 g, 7.49 mmol), EDC hydrochloride (1.5 g, 7.82 mmol), diisopropylethylamine (3.0 mL, 17.22 mmol), and DMF (25 mL) was stirred for 2 h at room temperature then diluted with ethyl acetate and washed with aqueous citric acid, aqueous sodium bicarbonate, water, and brine. Crystallisation from diethyl ether gave N-Boc 4-{[(2-bromo-4-cyanophenyl)acetyl]amino}piperidine (1.5 g, 2.84 mmol, 40.6% yield) as a white solid containing about 20% of N-Boc 4-{[(4-cyanophenyl)acetyl]amino}piperidine.

M−H$^-$ 420 and 422

DESCRIPTION 136

N-Boc 4-(6-Cyano-2-oxo-2,3-dihydro-1H-indol-1-yl)-piperidine. (D136)

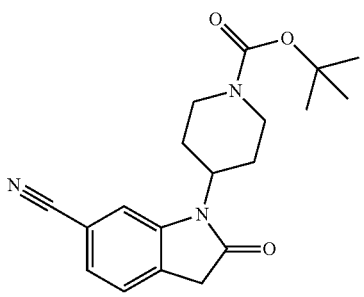

A solution of N-Boc 4-{[(2-bromo-4-cyanophenyl)acetyl]amino}piperidine (D135, 100 mg, 0.189 mmol) in anhydrous degassed tert-butanol (2 mL) was treated with X-PHOS (10 mg, 0.021 mmol), potassium carbonate (70 mg, 0.506 mmol), palladium (II) acetate (2 mg, 8.91 μmol), and phenylboronic acid (2 mg, 0.016 mmol), then heated at 85° C. for 1 h then cooled and evaporated. Chromatography on silica (20 g), eluting with 10-50% ethyl acetate—isohexane, gave N-Boc-4-(6-cyano-2-oxo-2,3-dihydro-1H-indol-1-yl)-piperidine (40 mg, 0.117 mmol, 61.8% yield) as a colourless oil.

[M−H]⁻ 340.

DESCRIPTION 137

4-(6-Cyano-2-oxo-2,3-dihydro-1H-indol-1-yl)-piperidine hydrochloride. (D137)

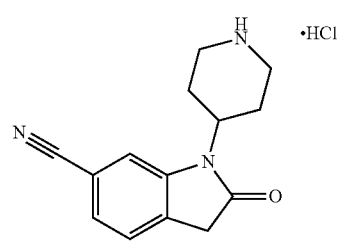

A solution of N-Boc 4-(6-cyano-2-oxo-2,3-dihydro-1H-indol-1-yl)-piperidine (D136, 400 mg, 1.172 mmol) in dichloromethane (5 mL) was treated with 4M HCl in dioxane (5 mL, 20.00 mmol). After 4 h at room temperature, evaporation and crystallisation from diethyl ether gave white crystals of 4-(6-cyano-2-oxo-2,3-dihydro-1H-indol-1-yl)-piperidine hydrochloride (270 mg, 0.972 mmol, 83% yield).

MH⁺ 242

DESCRIPTION 138

5-Fluoro-3-(4-piperidinyl)-1,3-benzoxazol-2(3H)-one hydrochloride. (D138)

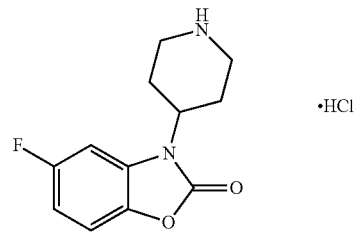

The title compound can be prepared using a similar methodology to that described for the 6-chloro analogue (E82 in WO9528397).

DESCRIPTION 139

(4-Methyl-2-nitrophenyl)methanol. (D139)

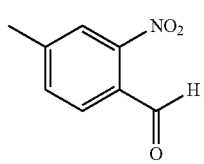

To a stirred solution of 4-methyl-2-nitrobenzoic acid (5 g, 27.6 mmol) in tetrahydrofuran (THF) (27 mL) was added borane tetrahydrofuran complex (35.9 mL, 35.9 mmol) and the mixture stirred at reflux for 3 hours. After cooling, the reaction mixture was extracted with water and DCM. The combined organic layers were dried over MgSO₄ and then evaporated to dryness to give the alcohol (D139) as a pale yellow solid (4.52 g, 98%) which was used without further purification.

¹H-NMR (CDCl₃) δ: 2.45 (s, 3H), 4.89-4.91 (d, 2H), 7.44-7.48 (dd, 1H), 7.55-7.59 (d, 1H), 7.90-7.91 (s, 1H).

LC/MS Retention time=2.67 min. (100%) (no ionisation)

DESCRIPTION 140

4-Methyl-2-nitrobenzaldehyde. (D140)

(4-Methyl-2-nitrophenyl)methanol D139 (1.028 g, 6.15 mmol), pyridinium dichromate (3.47 g, 9.22 mmol)+molecular sieves (7 g, 6.15 mmol) in dry dichloromethane (DCM) (14 mL) was stirred under argon at R.T. overnight. The reaction mixture was filtered by silica/kieselguhr (1:1) and extracted with water and DCM. Organic layers were combined and evaporated to give a pale yellow solid which was used without further purification (0.665 g, 65.5%).

$^1$H-NMR (CDCl$_3$): δ2.54 (s, 3H), 7.57-7.6 (m, 1H), 7.86-7.9 (m, 2H), 10.49 (s, 1H).

LC/MS Retention time=3.01 min. (100%) (no ionisation)

DESCRIPTION 141

Ethyl (2E)-3-(4-methyl-2-nitrophenyl)-2-propenoate. (D141)

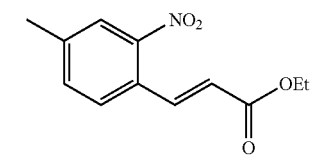

To sodium hydride (1.593 g, 39.8 mmol) was added THF (39 mL) dropwise and the reaction mixture cooled to −10° C. Triethyl phosphonoacetate (7.90 mL, 39.8 mmol) was added dropwise to give a colourless solution, maintaining the temperature at −10° C. The reaction mixture was allowed to warm to R.T. and the reaction mixture stirred for 30 mins. A solution of 4-methyl-2-nitrobenzaldehyde D140 (2.192 g, 13.27 mmol) in THF (39 mL) was added to give a dark yellow solution and the reaction mixture was heated at reflux for 90 mins. The solution turned a dark red/brown. After this time, the reaction mixture was allowed to cool to R.T. TLC showed all s.m. disappeared, product and a baseline impurity (DCM). The reaction mixture was diluted with water (32 mL) and extracted into diethyl ether (3×30 mL) and the organic layer dried over MgSO$_4$. The reaction mixture was filtered and evaporated to dryness. The crude product was purified by flash chromatography and was eluted with DCM to give the title compound as a yellow oil. Oil was triturated with isohexane to give a pale yellow solid (1.18 g, 37.8%).

$^1$H-NMR (CDCl$_3$) δ: 1.31-1.39 (t, 3H), 2.47 (s, 3H), 4.26 (q, 2H), 6.32-6.36 (d, 1H), 7.25-7.26 (d, 1H), 7.43-7.45 (d, 1H), 7.83-7.84 (d, 1H), 8.04-8.09 (d, 1H).

DESCRIPTION 142

Ethyl (2E)-3-(2-amino-4-methylphenyl)-2-propenoate. (D142)

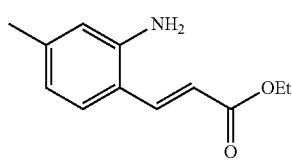

Ethyl (2E)-3-(4-methyl-2-nitrophenyl)-2-propenoate D141 (0.500 g, 2.126 mmol), iron (0.593 g, 10.63 mmol) and ammonium chloride (0.057 g, 1.063 mmol) in ethanol (11 mL) and water (2 mL) was heated at reflux for 2 hours. The mixture was cooled and filtered through a pad of kieselguhr. The filtrate was concentrated and the residue diluted with ethyl acetate, washed with water and dried (MgSO$_4$). Filtration and evaporation of solvent afforded a bright yellow solid (0.417 g, 96%).

$^1$H-NMR (CDCl$_3$) δ: 1.31-1.34 (t, 3H), 2.27 (s, 3H), 3.92 (s, br, 2H), 4.19-4.31 (q, 2H), 6.29-6.36 (d, 1H), 6.58 (s, 1H), 6.58-6.6 (dd, 1H), 7.28-7.32 (dd, 1H), 7.77-7.83 (d, 1H).

LC/MS Retention time=3.32 min. (92%) (no ionisation).

DESCRIPTION 143

Ethyl (2E)-3-[2-({1-[4-(ethyloxy)-1-methylcyclohexyl]-4-piperidinyl}-amino)-4-methylphenyl]-2-propenoate. (D143)

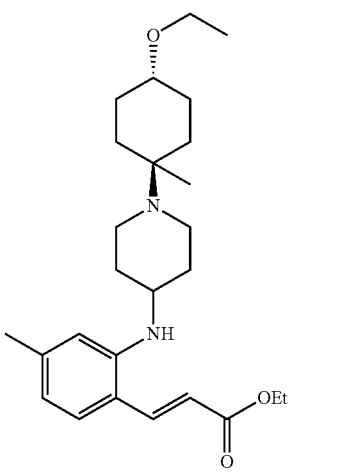

1-[4-(Ethyloxy)-1-methylcyclohexyl]-4-piperidinone (D8) (0.350 g, 1.462 mmol)+ethyl (2E)-3-(2-amino-4-methylphenyl)-2-propenoate (D142) (0.1 g, 0.487 mmol) were placed in a microwave vial with 1,2-dichloroethane (DCE) (0.974 mL) and stirred for 10 mins. Sodium triacetoxyborohydride (0.387 g, 1.827 mmol) was added and the mixture heated at 140° C. for 10 mins. LCMS of the crude reaction mixture showed product (67% by u.v.). The reaction was quenched with NaHCO$_3$ (10 mL, sat. aq) and then extracted with DCM (3×20 mL). The organic phases were combined, dried (phase sep. cartridge) and passed through a SCX-3 cartridge, eluting with DCM/MeOH to remove any neutral/acidic by-products. The product was eluted from the cartridge with 0.5 M NH$_3$/MeOH to give a dark yellow oil. The crude product was purified by column chromatography using a 5 g cartridge and eluting with DCM-8% NH$_3$/MeOH/DCM to give the product as a bright yellow/green oil (0.117 g, 56%).

LC/MS 429 (MH$^+$), retention time=2.69 mins.

DESCRIPTION 144

Ethyl 3[2-({1-[trans-4-(ethyloxy)-1-methylcyclohexyl]-4-piperidinyl}amino)-4-methylphenyl]propanoate. (D144)

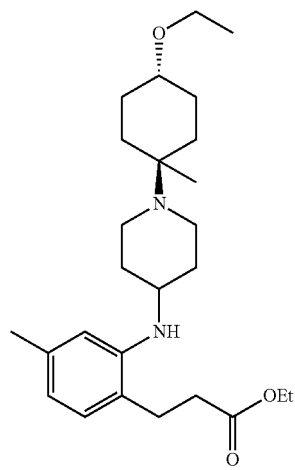

Ethyl (2E)-3-[2-({1-[trans-4-(ethyloxy)-1-methylcyclohexyl]-4-piperidinyl}amino)-4-methyl-phenyl]-2-propenoate D143 (0.117 g, 0.273 mmol) was dissolved in ethanol (16 mL) and passed over a Pd/C cartridge on the H-cube, temp. 45° C., pressure 50 psi. with a flow rate of 0.5 mL/min. LCMS showed double bond reduced and some s.m. remaining. The solution was passed through the H-cube again, same temp. and pressure as before. LCMS showed reaction had gone to completion. The solvent was removed in vacuo to give a pale brown oil.

LC/MS 431 (MH+), retention time=2.64 min.

DESCRIPTION 145

2-Amino-6-methyl-3-pyridinol. (D145)

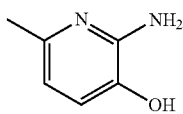

A mixture of 3-hydroxy-6-methyl-2-nitropyridine (4.2 g, 27 mmol) and 10% palladium on carbon (0.25 g, 0.24 mmol) in ethanol (75 mL) was stirred at rt under an atmosphere of hydrogen for 24 hr. The catalyst was removed by filtration through celite and the filtrate concentrated to dryness under vacuum. The residue was subjected to chromatography on silica gel using Biotage SP1 employing a 40+M cartridge and eluting with MeOH/DCM 10% 2 CV, 10-35% in 10 CV, 35% 2 CV. The purified product 2-amino-6-methyl-3-pyridinol (D145, 2.72 g, 80%) was isolated as pale brown solid.

[M+H]$^+$125

DESCRIPTION 146

2-({1-[trans-4-(Ethyloxy)-1-methylcyclohexyl]-4-piperidinyl}amino)-6-methyl-3-pyridinol. (D146)

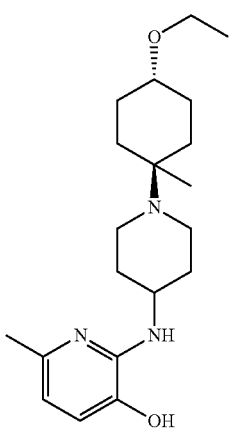

Polymer supported sodium cyanoborohydride (99 mg, 0.43 mmol) was added to a solution of 1-[trans-4-(ethyloxy)-1-methylcyclohexyl]-4-piperidinone (D8, 51 mg, 0.21 mmol), 2-amino-6-methyl-3-pyridinol (D145, 26 mg, 0.21 mmol) and acetic acid (0.061 mL, 1.07 mmol) in THF (2.5 mL). The mixture was heated by microwave at 100° C. for 30 min and then for a further 30 min before being filtered and concentrated by rotary evaporation to give 2-({1-[trans-4-(ethyloxy)-1-methylcyclohexyl]-4-piperidinyl}amino)-6-methyl-3-pyridinol (D146, 82 mg, 100%) as a yellow oil, which was used without further purification.

$^1$H NMR (CDCl$_3$) δ: 1.16-1.24 (4 H, m), 1.45-1.74 (6 H, m), 1.82-1.96 (3 H, m), 2.32 (3 H, s), 2.43 (3 H, m), 2.85 (3 H, m), 3.41 (1 H, m), 3.45-3.52 (3 H, m), 6.24 (1 H, d, J 8.1), 6.99 (1 H, d, J 8.1).

DESCRIPTION 147

2-Fluoro-4-hydroxy-5-nitrobenzonitrile. (D147)

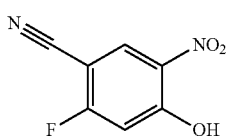

Nitric acid (0.326 mL, 7.29 mmol) 70% was added dropwise to a stirred solution of 2-fluoro-4-hydroxybenzonitrile (1 g, 7.29 mmol) in acetic acid (20 mL). The resulting solution was warmed to 40° C. for 24 hr. Solvent removed under reduced pressure to afford a yellow solid. Recrystallisation from EtOH (~15 mL) afforded 2-fluoro-4-hydroxy-5-nitrobenzonitrile (401 mg, 2.202 mmol, 30.2% yield) as a yellow solid.

$^1$H NMR δ (CDCl$_3$): 7.04 (1 H, d, J=9.6 Hz), 8.52 (1H, d, J=6.4 Hz), 11.10 (1H, s).

DESCRIPTION 148

5-Amino-2-fluoro-4-hydroxybenzonitrile. (D148)

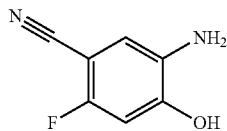

D148

A solution of 2-fluoro-4-hydroxy-5-nitrobenzonitrile (D147; 270 mg, 1.483 mmol) in ethanol (35 mL) was passed through an H-Cube flow hydrogenator at room temperature and atmospheric pressure on full H$_2$ mode, with a flow rate of 1 mL min$^{-1}$ and using a CatCart30 (approx. 140 mg catalyst). The residual solution was diluted with further ethanol (8 mL) to ensure maximum recovery of material. The collected product solution was evaporated to dryness to give the desired product as a tan solid (215 mg).

$^1$H NMR δ (CD$_3$OD): 6.58 (1H, dd, J=7.6, 3 Hz), 6.85 (1H, d, J=6.8 Hz).

EXAMPLE 1

3-{1-[trans-4-(Ethyloxy)-1-methylcyclohexyl]-4-piperidinyl}-1,3-benz oxazol-2(3H)-one hydrochloride. (E1)

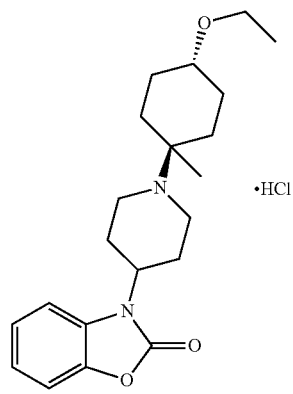

E1

Hünig's base (DIPEA) (100 μl, 0.573 mmol) was added to a solution of 2-({1-[trans-4-(ethyloxy)-1-methylcyclohexyl]-4-piperidinyl}amino)phenol (D10, 82.6 mg, 0.248 mmol) in dichloromethane (4 mL) at rt under argon. The reaction was cooled to 0° C. and the triphosgene (35.6 mg, 0.120 mmol) was added. The mixture was stirred for 1 h at 0° C. and then the reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a pale yellow oil. The residue was purified via chromatography (silica, dichloromethane to 0.5% ammonia/9.5% methanol/90% dichloromethane) to give the free base of the title compound as a pale yellow solid. HCl (500 μl, 0.500 mmol, 1 M in diethyl ether) was added to a solution of the free base in dichloromethane (2 mL) at rt. The reaction was stirred for 30 min before the solvent was removed by rotary evaporation to give 3-{1-[trans-4-(ethyloxy)-1-methylcyclohexyl]-4-piperidinyl}-1,3-benzoxazol-2(3H)-one hydrochloride (E1, 82.4 mg, 80% yield) as a cream solid.

$^1$H NMR δ (DMSO-d$_6$, 400 MHz) 1.10 (3 H, t, J 6.8), 1.28-1.40 (5 H, m), 1.78 (2 H, m), 1.95-2.11 (6 H, m), 2.64-2.78 (2 H, m), 3.16-3.28 (3 H, m), 3.48 (2 H, q, J 6.8), 3.67 (2 H, m), 4.56 (1 H, m), 7.16 (1 H, t, J 7.8), 7.26 (1 H, t, J 7.8), 7.37 (1 H, d, J 8), 7.63 (1 H, m), 9.54 (1 H, m).

M+H$^+$ 359

EXAMPLE 2

3-{1-[trans-1-Methyl-4-(propyloxy)cyclohexyl]-4-piperidinyl}-1,3-benzoxazol-2(3H)-one hydrochloride. (E2)

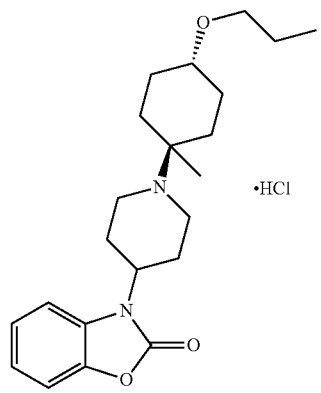

E2

Diisopropylethylamine (57.3 μl, 0.328 mmol) was added to a solution of 2-({1-[trans-1-methyl-4-(propyloxy)cyclohexyl]-4-piperidinyl}amino)phenol (D18, 53.8 mg, 0.155 mmol) in dichloromethane (2.28 mL) at rt under argon. The reaction was cooled to 0° C. and the triphosgene (20.0 mg, 0.067 mmol) was added. The mixture was stirred for 30 min at 0° C., followed by a further 15 min at rt. The reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a pale yellow oil. The residue was purified via chromatography (silica, dichloromethane to 0.5% ammonia/9.5% methanol/90% dichloromethane) to give the free base of the title compound as a white solid. The free base was dissolved in dichloromethane (1.45 mL) and methanol (724 μl) at 25° C. HCl (252 μl, 0.252 mmol, 1 M in diethyl ether) was then added and the reaction was stirred for 15 min. The solvent was removed by rotary evaporation to give 3-{1-[trans-1-methyl-4-(propyloxy)cyclohexyl]-4-piperidinyl}-1,3-benzoxazol-2(3H)-one hydrochloride (E2, 49.5 mg, 70% yield) as a white solid.

$^1$H NMR δ (DMSO-d$_6$, 400 MHz) 0.868 (3 H, t, J 7.2), 1.28-1.40 (5 H, m), 1.44-1.55 (2 H, m), 1.79 (2 H, m), 1.97-2.11 (6 H, m), 2.65-2.79 (2 H, m), 3.14-3.27 (3 H, m), 3.83 (2 H, q, J 7.2), 3.67 (2 H, m), 4.57 (1 H, m), 7.16 (1 H, m), 7.26 (1 H, m), 7.37 (1 H, d, J 8), 7.65 (1 H, d, J 7.6), 9.57 (1 H, m).

M+H$^+$ 373

EXAMPLE 3

3-{1-[trans-4-(Ethyloxy)-1-methylcyclohexyl]-4-piperidinyl}-2-oxo-2,3-dihydro-1,3-benzoxazole-5-carbonitrile hydrochloride. (E3)

EXAMPLE 4

3-{1-[trans-4-(Ethyloxy)-1-methylcyclohexyl]-4-piperidinyl}-6-fluoro-5-methyl-1,3-benzoxazol-2(3H)-one hydrochloride. (E4)

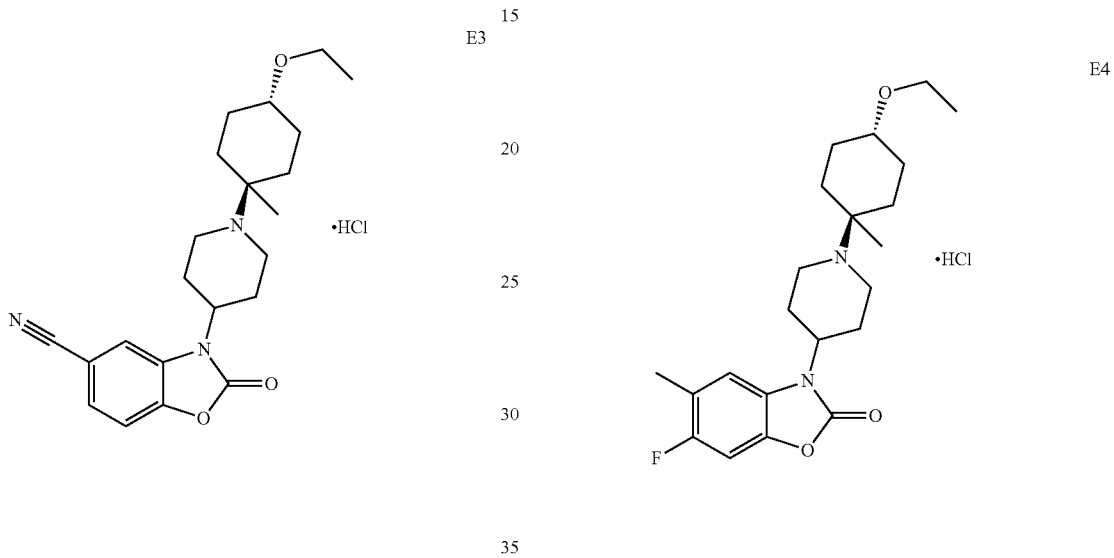

Diisopropylethylamine (0.1 mL, 0.573 mmol) was added to a solution of 3-({1-[trans-4-(ethyloxy)-1-methylcyclohexyl]-4-piperidinyl}amino)-4-hydroxybenzonitrile (D20, 96.9 mg, 0.271 mmol) in dichloromethane (4 mL) at rt under argon. The reaction was cooled to 0° C. and the triphosgene (34.8 mg, 0.117 mmol) was added. The mixture was stirred for 30 min at 0° C., followed by a further 15 min at rt. The reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a pale yellow oil. The residue was purified via chromatography (silica, dichloromethane to 0.5% ammonia/9.5% methanol/90% dichloromethane) to give the free base of the title compound as a white solid. The free base was dissolved in dichloromethane (2.0 mL) and methanol (1 mL) at rt. HCl (0.35 mL, 0.350 mmol, 1 M in diethyl ether) was added and the reaction stirred for 30 min. The solvent was removed by rotary evaporation to give 3-{1-[trans-4-(ethyloxy)-1-methylcyclohexyl]-4-piperidinyl}-2-oxo-2,3-dihydro-1,3-benzoxazole-5-carbonitrile hydrochloride (E3, 72.3 mg, 61% yield) as a white solid.

$^1$H NMR δ (DMSO-d$_6$, 400 MHz) 1.10 (3 H, t, J 6.8), 1.22-1.40 (5 H, m), 1.89-2.11 (8 H, m), 2.87 (2 H, m), 3.13-3.29 (3 H, m), 3.47 (2 H, q, J 6.8), 3.68 (2 H, m), 4.61 (1 H, m), 7.58 (1 H, d, J 8.4), 7.69 (1 H, dd, J 8.4 and 1.2), 8.43 (1 H, d, J 1.2), 10.62 (1 H, m).

M+H$^+$ 384

Hünig's base (0.12 mL, 0.687 mmol) was added to a solution of 2-({1-[trans-4-(ethyloxy)-1-methylcyclohexyl]-4-piperidinyl}amino)-5-fluoro-4-methylphenol (D23, 120 mg, 0.328 mmol) in dichloromethane (5 mL) at rt under argon. The reaction was cooled to 0° C. and the triphosgene (39.2 mg, 0.132 mmol) was added. The mixture was stirred for 40 min at 0° C. and then the reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a yellow oil. The residue was purified via chromatography (silica, dichloromethane to 0.5% ammonia/9.5% methanol/90% dichloromethane) to give the free base of the title compound as a colourless oil. HCl (0.53 mL, 0.53 mmol, 1 M in diethyl ether) was added to a solution of the free base in diethyl ether (5 mL) at rt. The reaction was stirred for 5 min before the solvent was removed by rotary evaporation to give 3-{1-[trans-4-(ethyloxy)-1-methylcyclohexyl]-4-piperidinyl}-6-fluoro-5-methyl-1,3-benzoxazol-2(3H)-one hydrochloride (E4, 108 mg, 73% yield) as a cream solid.

$^1$H NMR δ (DMSO-d$_6$, 400 MHz) 1.10 (3 H, t, J 6.8), 1.23-1.14 (5 H, m), 1.89-2.08 (8 H, m), 2.27 (3 H, s), 2.85 (2 H, m), 3.13-3.27 (3 H, m), 3.47 (2 H, q, J 6.8), 3.66 (2 H, m), 4.55 (1 H, m), 7.36 (1 H, d, J 9.2), 7.95 (1 H, d, J 6.4), 10.42 (1 H, m).

M+H$^+$ 391

EXAMPLE 5

3-{1-[trans-4-(Ethyloxy)-1-methylcyclohexyl]-4-piperidinyl}-5-(methylsulfonyl)-1,3-benzoxazol-2(3H)-one hydrochloride. (E5)

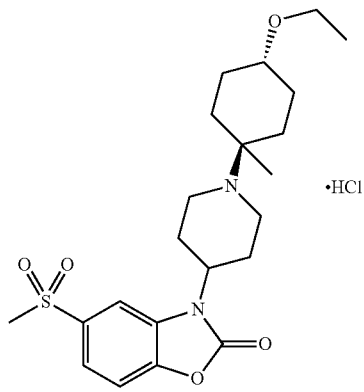

Diisopropylethylamine (0.079 mL, 0.454 mmol) was added to a solution of 2-({1-[trans-4-(ethyloxy)-1-methylcyclohexyl]-4-piperidinyl}amino)-4-(methylsulfonyl)phenol (D24, 93.3 mg, 0.227 mmol) in dichloromethane (2.5 mL) at rt under argon. The reaction was cooled to 0° C. and the triphosgene (26.8 mg, 0.09 mmol) was added. The mixture was stirred for 30 min at 0° C. The reaction was quenched with saturated aqueous $NaHCO_3$ (5 mL) and partitioned between dichloromethane and water. The aqueous layer was extracted with dichloromethane (2×) and the combined organics were dried ($Na_2SO_4$) and concentrated by rotary evaporation to give a yellow oil. The residue was purified via chromatography (silica, dichloromethane to 0.5% ammonia/9.5% methanol/90% dichloromethane) to give the free base of the title compound as a pale yellow solid. HCl (0.32 mL, 0.32 mmol, 1 M in diethyl ether) was added to a solution of the free base in dichloromethane (2 mL) and the mixture stirred for 15 min. The solvent was removed by rotary evaporation and the residue triturated with diethyl ether to give 3-{1-[trans-4-(ethyloxy)-1-methylcyclohexyl]-4-piperidinyl}-5-(methylsulfonyl)-1,3-benzoxazol-2(3H)-one hydrochloride (E5, 64 mg, 57% yield) as a white solid.

$^1$H NMR δ (DMSO-$d_6$, 400 MHz) 1.10 (3 H, t, J 6.8), 1.27-1.41 (5 H, m), 1.83 (2 H, m), 1.99 (4 H, m), 2.11 (2 H, m), 2.75 (2 H, m), 3.14-3.28 (3 H, m), 3.35 (3 H, s), 3.70 (2 H, m), 4.65 (1 H, m), 7.62 (1 H, d, J 8.4), 7.75 (1 H, dd, J 8.4 and 1.6), 8.18 (1 H, s), 9.83 (1 H, m). Note: 2 H not visible in NMR spectrum as obscured by solvent or water.

M+H$^+$ 437.

EXAMPLE 6

3-{1-[trans-4-(Ethyloxy)-1-methylcyclohexyl]-4-piperidinyl}-5-(ethylsulfonyl)-1,3-benzoxazol-2(3H)-one hydrochloride. (E6)

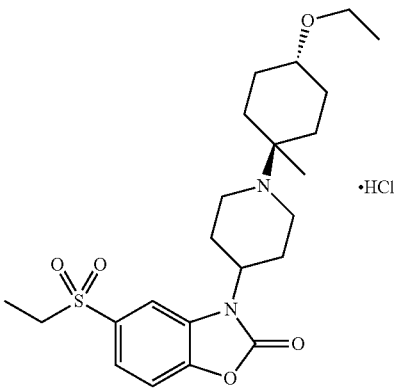

Diisopropylethylamine (0.184 mL, 1.05 mmol) was added to a solution of 2-({1-[trans-4-(ethyloxy)-1-methylcyclohexyl]-4-piperidinyl}amino)-4-(ethylsulfonyl)phenol (D25, 211 mg, 0.497 mmol) in dichloromethane (9 mL) at rt under argon. The reaction was cooled to 0° C. and the triphosgene (60.9 mg, 0.205 mmol) was added. The mixture was stirred for 30 min at 0° C., followed by a further 15 min at rt. The reaction was quenched with saturated aqueous $NaHCO_3$ (15 mL) and partitioned between dichloromethane and water. The aqueous layer was extracted with dichloromethane (2×) and the combined organics were dried ($Na_2SO_4$) and concentrated by rotary evaporation to give a brown oil. The residue was purified via chromatography (silica, dichloromethane to 0.5% ammonia/9.5% methanol/90% dichloromethane followed by amino-doped silica, iso-hexane-ethyl acetate) to give the free base of the title compound as a white solid. HCl (0.1 mL, 0.100 mmol, 1 M in diethyl ether) was added to a solution of the free base in dichloromethane (1 mL) at rt. The solvent was removed by rotary evaporation and the resulting solid triturated with diethyl ether (2×) to give 3-{1-[trans-4-(ethyloxy)-1-methylcyclohexyl]-4-piperidinyl}-5-(ethylsulfonyl)-1,3-benzoxazol-2(3H)-one hydrochloride (E6, 19.7 mg, 8% yield) as a white solid.

$^1$H NMR δ (DMSO-$d_6$, 400 MHz) 1.08-1.17 (6 H, m), 1.27-1.41 (5 H, m), 1.80 (2 H, m), 1.99 (4 H, m), 2.12 (2 H, m), 2.69 (2 H, m), 3.12-3.26 (3 H, m), 3.69 (2 H, m), 4.64 (1 H, m), 7.63 (1 H, d, J 8), 7.71 (1 H, dd, J 8 and 1.6), 8.05 (1 H, d, J 2), 9.62 (1 H, m). Note: 4 H not visible in NMR spectrum as obscured by solvent or water.

M+H$^+$ 451.

EXAMPLE 7

5-Fluoro-3-{1-[trans-1-methyl-4-(propyloxy)cyclohexyl]-4-piperidinyl}-1,3-benzoxazol-2(3H)-one hydrochloride. (E7)

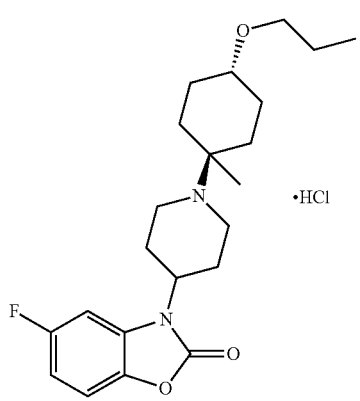

EXAMPLE 8

3-{1-[trans-4-(Ethyloxy)-1-methylcyclohexyl]-4-piperidinyl}-5-fluoro-1,3-benzoxazol-2(3H)-one hydrochloride. (E8)

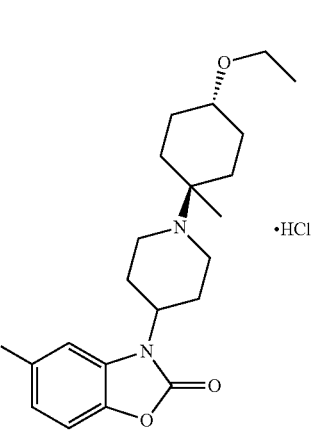

Diisopropylethylamine (0.219 mL, 1.25 mmol) was added to a solution of 4-fluoro-2-({1-[trans-1-methyl-4-(propyloxy)cyclohexyl]-4-piperidinyl}amino)phenol (D26, 216 mg, 0.591 mmol) in dichloromethane (9 mL) at rt under argon. The reaction was cooled to 0° C. and the triphosgene (75 mg, 0.254 mmol) was added. The mixture was stirred for 30 min at 0° C., followed by a further 15 min at rt. The reaction was quenched with saturated aqueous NaHCO$_3$ (15 mL) and partitioned between dichloromethane and water. The aqueous layer was extracted with dichloromethane (2×) and the combined organics were dried (Na$_2$SO$_4$) and concentrated by rotary evaporation to give a pale yellow oil. The residue was purified via chromatography (silica, dichloromethane to 0.5% ammonia/9.5% methanol/90% dichloromethane followed by amino-doped silica, iso-hexane to ethyl acetate) to give the free base of the title compound as a white solid. The free base was dissolved in dichloromethane (702 µl) at 25° C. HCl (81 µl, 0.081 mmol, 1 M in diethyl ether) was then added and the reaction was stirred for 15 min. The solvent was removed by rotary evaporation to give a white solid that was then triturated with diethyl ether to give 5-fluoro-3-{1-[trans-1-methyl-4-(propyloxy)cyclohexyl]-4-piperidinyl}-1,3-benzoxazol-2(3H)-one hydrochloride (E7, 17.8 mg, 6% yield) as a white solid.

$^1$H NMR δ (DMSO-d$_6$, 400 MHz) 0.87 (3 H, t, J 7.2), 1.26-1.41 (5 H, m), 1.49 (2 H, m), 1.80 (2 H, m), 1.96-2.12 (4 H, m), 2.69 (2 H, m), 3.12-3.26 (3 H, m), 3.38 (3 H, d, J 6.6), 3.68 (2 H, m), 4.57 (1 H, m), 6.99 (1 H, m), 7.40 (1 H, m), 7.68 (1 H, dd, J 8.8 and 2.4), 9.68 (1 H, m).

M+H$^+$ 391.

Diisopropylethylamine (0.316 mL, 1.81 mmol) was added to a solution of 2-({1-[trans-4-(ethyloxy)-1-methylcyclohexyl]-4-piperidinyl}amino)-4-fluorophenol (D27, 299 mg, 0.853 mmol) in dichloromethane (9 mL) at rt under argon. The reaction was cooled to 0° C. and the triphosgene (104 mg, 0.352 mmol) was added. The mixture was stirred for 30 min at 0° C., followed by a further 15 min at room temperature. The reaction was quenched with saturated aqueous NaHCO$_3$ (15 mL) and partitioned between dichloromethane and water. The aqueous layer was extracted with dichloromethane (2×) and the combined organics were dried (Na$_2$SO$_4$) and concentrated by rotary evaporation to give a brown oil. The residue was purified via chromatography (silica, dichloromethane to 0.5% ammonia/9.5% methanol/90% dichloromethane followed by amino-doped silica, iso-hexane to ethyl acetate) to give the free base of the title compound as a white solid. The free base was dissolved in diethyl ether (1.5 mL) at 25° C. HCl (0.154 mL, 0.154 mmol, 1 M in diethyl ether) was then added and the reaction was stirred for 15 min. The solvent was removed by rotary evaporation to give 3-{1-[trans-4-(ethyloxy)-1-methylcyclohexyl]-4-piperidinyl}-5-fluoro-1,3-benzoxazol-2(3H)-one hydrochloride (E8, 33.4 mg, 9% yield) as a white solid.

$^1$H NMR δ (DMSO-d$_6$, 400 MHz) 1.10 (3 H, t, J 6.8), 1.25-1.42 (5 H, m), 1.87 (2 H, m), 1.95-2.12 (6 H, m), 2.77 (2 H, m), 3.12-3.27 (3 H, m), 3.47 (2 H, q, J 6.8), 3.67 (2 H, m), 4.57 (1 H, m), 6.99 (1 H, m), 7.39 (1 H, m), 7.82 (1 H, dd, J 9.2 and 2.8), 10.12 (1 H, m).

M+H$^+$ 377.

EXAMPLE 9

3-{1-[trans-4-(Ethyloxy)-1-methylcyclohexyl]-4-piperidinyl}-5-(methyloxy)-1,3-benzoxazol-2(3H)-one hydrochloride. (E9)

EXAMPLE 10

3-{1-[trans-4-(Ethyloxy)cyclohexyl]-4-piperidinyl}-5-methyl-1,3-benzoxazol-2(3H)-one hydrochloride. (E10)

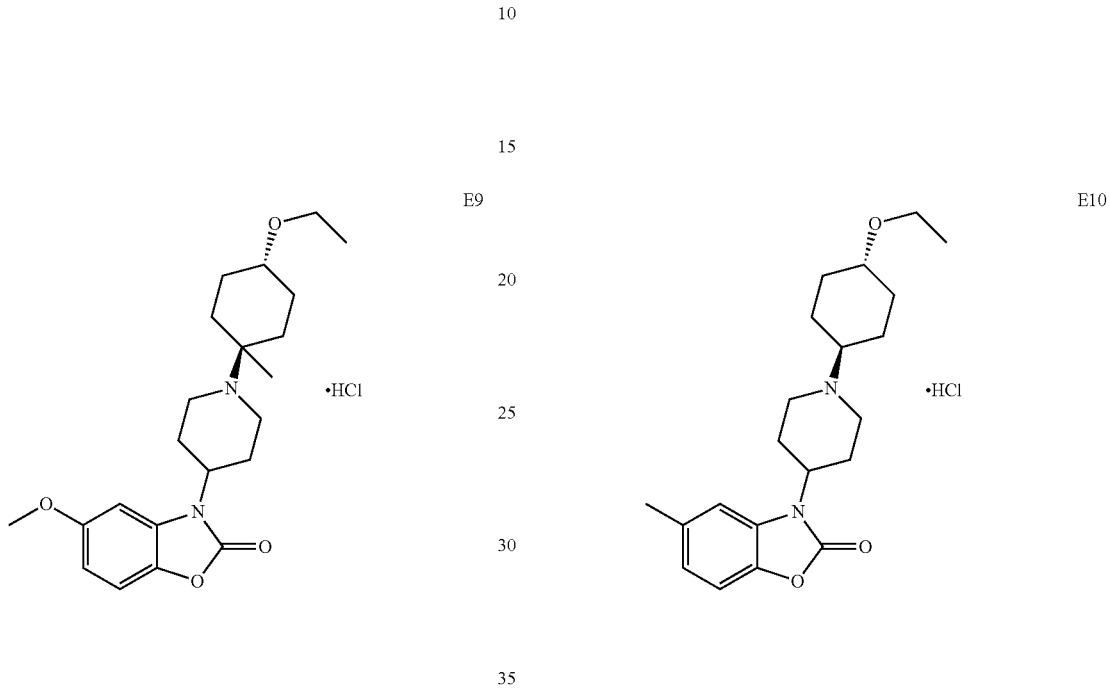

Diisopropylethylamine (81 µl, 0.466 mmol) was added to a solution of 2-({1-[trans-4-(ethyloxy)-1-methylcyclohexyl]-4-piperidinyl}amino)-4-(methyloxy)phenol (D28, 79.7 mg, 0.22 mmol) in dichloromethane (3.23 mL) at rt under argon. The reaction was cooled to 0° C. and the triphosgene (28.1 mg, 0.095 mmol) was added. The mixture was stirred for 30 min at 0° C., followed by a further 15 min at rt. The reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a pale yellow oil. The residue was purified via chromatography (silica, dichloromethane to 0.5% ammonia/9.5% methanol/90% dichloromethane) to give the free base of the title compound as an orange-yellow oil. The free base was dissolved in diethyl ether (2.34 mL) at 25° C. HCl (272 µl, 0.272 mmol, 1 M in diethyl ether) was then added and the reaction was stirred for 15 min. The solvent was removed by rotary evaporation to give a white solid that was then triturated with diethyl ether to give 3-{1-[trans-4-(ethyloxy)-1-methylcyclohexyl]-4-piperidinyl}-5-(methyloxy)-1,3-benzoxazol-2(3H)-one hydrochloride (E9, 46.9 mg, 45% yield) as a white solid.

$^1$H NMR δ (CDCl$_3$, 400 MHz) 1.2 (3 H, m), 1.35-1.49 (5 H, m), 1.98-2.11 (4 H, m), 2.15 (2 H, m), 2.43 (2 H, m), 2.90 (2 H, m), 3.38-3.59 (5 H, m), 3.82 (2 H, m), 4.00 (3 H, s), 4.57 (1 H, m), 6.68 (1 H, dd, J 8.8 and 2.4), 7.08 (1 H, d, J 8.8), 7.71 (1 H, d, J 2.4).

M+H$^+$ 389.

Diisopropylethylamine (0.24 mL, 1.37 mmol) was added to a solution of 2-({1-[trans-4-(ethyloxy)cyclohexyl]-4-piperidinyl}amino)-4-methylphenol (D29, 215 mg, 0.648 mmol) in dichloromethane (8 mL) at rt under argon. The reaction was cooled to 0° C. and the triphosgene (79 mg, 0.267 mmol) was added. The mixture was stirred for 30 min at 0° C., followed by a further 15 min at rt. The reaction was quenched with saturated aqueous NaHCO$_3$ (10 mL) and partitioned between dichloromethane and water. The aqueous layer was extracted with dichloromethane (2×) and the combined organics were dried (Na$_2$SO$_4$) and concentrated by rotary evaporation to give a white solid. The residue was purified via chromatography (silica, dichloromethane to 0.5% ammonia/9.5% methanol/90% dichloromethane) to give the free base of the title compound as a white solid. The free base was dissolved in diethyl ether (1.5 mL) at 25° C. HCl (0.207 mL, 0.207 mmol, 1 M in diethyl ether) was then added and the reaction was stirred for 15 min. The solvent was removed by rotary evaporation to give 3-{1-[trans-4-(ethyloxy)cyclohexyl]-4-piperidinyl}-5-methyl-1,3-benzoxazol-2(3H)-one hydrochloride (E10, 39.3 mg, 14% yield) as a white solid.

$^1$H NMR δ (DMSO-d$_6$, 400 MHz) 1.10 (3 H, t, J 6.8), 1.24-1.40 (2 H, m), 1.54 (2 H, m), 2.0-2.16 (6 H, m), 2.66 (3 H, s), 2.73 (2 H, m), 3.15-3.30 (4 H, m), 3.42-3.58 (4 H, m), 4.15 (1 H, m), 6.96 (1 H, d, J 8), 7.23 (1 H, d, J 8), 7.55 (1 H, s), 10.22 (1 H, m).

M+H$^+$ 359.

EXAMPLE 11

4-{1-[trans-4-(Ethyloxy)-1-methylcyclohexyl]-4-piperidinyl}-6-methyl-2H-1,4-benzoxazin-3(4H)-one hydrochloride. (E11)

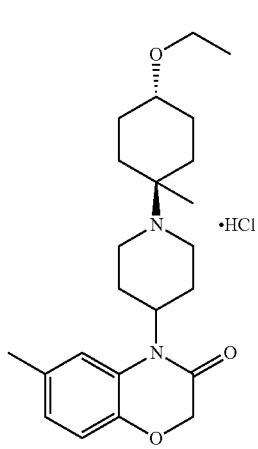

E11

Sodium tert-butoxide (123 mg, 1.28 mmol) was added to a solution of 2-chloro-N-{1-[trans-4-(ethyloxy)-1-methylcyclohexyl]-4-piperidinyl}-N-(2-hydroxy-5-methylphenyl)acetamide (D31, 186 mg, 0.439 mmol) in tetrahydrofuran (5 mL) at rt under argon. The mixture was stirred overnight and then partitioned between dichloromethane and saturated aqueous NaHCO$_3$. The aqueous layer was extracted with dichloromethane (2×) and the combined organics were dried (Na$_2$SO$_4$) and concentrated by rotary evaporation to give a brown solid. The residue was purified via chromatography (silica, dichloromethane to 0.5% ammonia/9.5% methanol/90% dichloromethane followed by amino-doped silica, isohexane to ethyl acetate) to give the free base of the title compound as a pale yellow solid. HCl (0.33 mL, 0.330 mmol, 1 M in diethyl ether) was added to a solution of the free base in dichloromethane (2 mL) at rt. The solvent was removed by rotary evaporation and the resulting solid triturated with diethyl ether to give 4-{1-[trans-4-(ethyloxy)-1-methylcyclohexyl]-4-piperidinyl}-6-methyl-2H-1,4-benzoxazin-3(4H)-one hydrochloride (E11, 60.7 mg, 31% yield) as a pale yellow solid.

$^1$H NMR δ (DMSO-d$_6$, 400 MHz) 1.10 (3 H, t, J 7.2), 1.24-1.39 (5 H, m), 1.79 (2 H, m), 1.96 (6 H, m), 2.33 (3 H, s), 2.95 (2 H, m), 3.11-3.22 (3 H, m), 3.47 (2 H, q, J 7.2), 3.57-3.66 (2 H, m), 4.42-4.54 (3 H, m), 6.84 (1 H, d, J 8), 6.92 (1 H, d, J 8), 7.35 (1 H, s), 9.38 (1 H, m).

M+H$^+$ 387.

EXAMPLE 12a

3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile hydrochloride. (E12a)

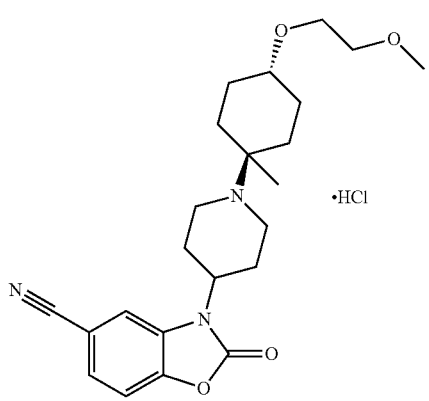

E12a

Diisopropylethylamine (0.04 mL, 0.229 mmol) was added to a solution of 4-hydroxy-3-{[1-(trans-1-methyl-4-{[2-(methyloxy)ethyl]oxy}cyclohexyl)-4-piperidinyl]amino}benzonitrile (D36, 37.5 mg, 0.097 mmol) in dichloromethane (2.5 mL) at rt under argon. The reaction was cooled to 0° C. and triphosgene (13.6 mg, 0.046 mmol) was added. The mixture was stirred for 1 h at 0° C. The reaction was quenched with saturated aqueous NaHCO$_3$ (5 mL) and partitioned between dichloromethane and water. The aqueous layer was extracted with dichloromethane (2×) and the combined organics were dried (Na$_2$SO$_4$) and concentrated by rotary evaporation to give a pale yellow solid. The residue was purified via chromatography (silica, Biotage 12S column, dichloromethane to 0.5% ammonia/9.5% methanol/90% dichloromethane) to give the free base of the title compound as a colourless oil. HCl (0.1 mL, 0.1 mmol, 1 M in diethyl ether) was added to a solution of the free base in dichloromethane (0.5 mL) and the solvent removed by rotary evaporation. The resulting residue was triturated with diethyl ether (2×) to give 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride (E12a, 11.2 mg, 24% yield) as a cream solid.

$^1$H NMR δ (DMSO-d$_6$, 400 MHz) 1.25-1.40 (5 H, m), 1.84 (2 H, m), 1.96-2.12 (6 H, m), 2.74 (2 H, m), 3.13-3.29 (6 H, m), 3.42 (2 H, m), 3.55 (2 H, m), 3.69 (2 H, m), 4.59 (1 H, m), 7.59 (1 H, d, J 8.4), 7.69 (1 H, dd, J 8.4 and 1.6), 8.22 (1 H, d, J 1.6), 9.95 (1 H, m).

M+H$^+$ 414.

EXAMPLE 12b

3-[1-(trans-1-Methyl-4-{[2-(methyloxy)ethyl]
oxy}cyclohexyl)-4-piperidinyl]-2-oxo-2,3-dihydro-1,
3-benzoxazole-5-carbonitrile free base. (E12b)

EXAMPLE 12c

3-[1-(trans-1-Methyl-4-{[2-(methyloxy)ethyl]
oxy}cyclohexyl)-4-piperidinyl]-2-oxo-2,3-dihydro-1,
3-benzoxazole-5-carbonitrile hydrochloride. (E12c)

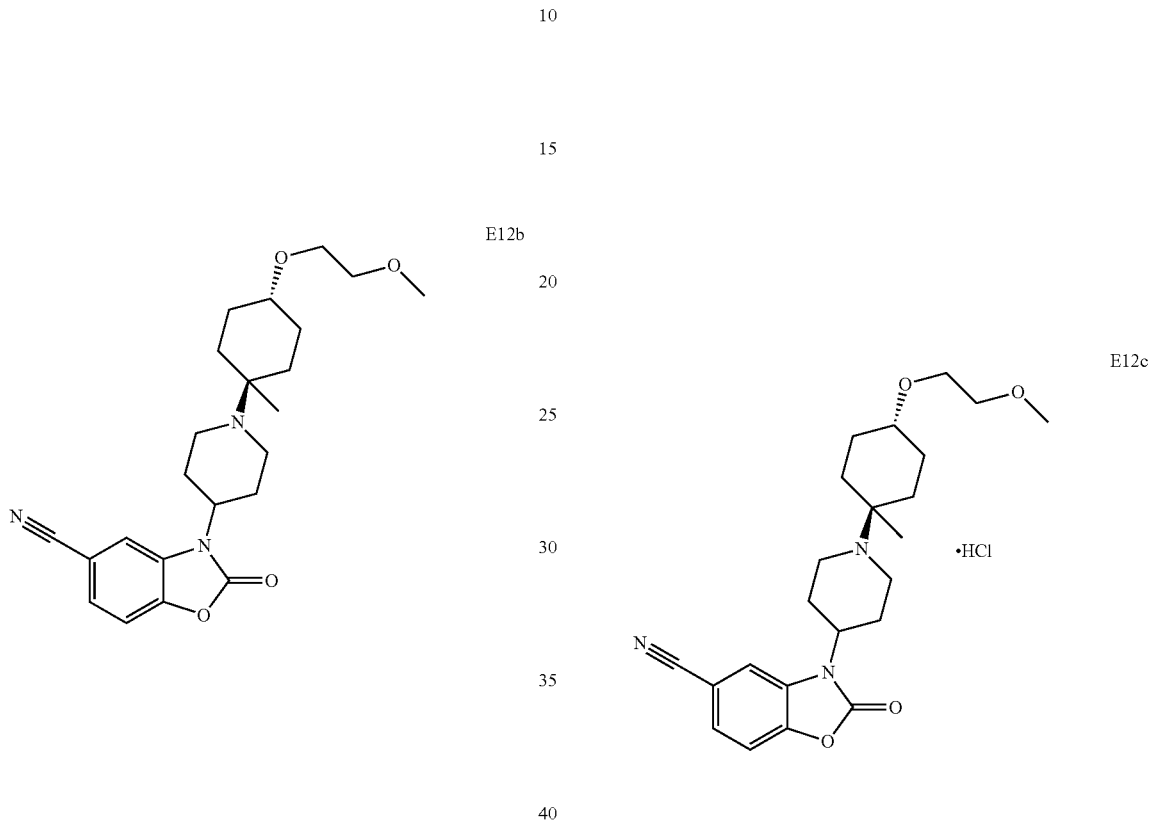

N.B. free base was also isolated en route to the HCl salt produced in E12a.

Hunig's Base (0.5 mL, 2.86 mmol) was added to a solution of 4-hydroxy-3-{[1-(trans-1-methyl-4-{[2-(methyloxy) ethyl]oxy}cyclohexyl)-4-piperidinyl]amino}benzonitrile (D36-alternative procedure, 554 mg, 1.43 mmol) in DCM (10 mL) at rt under Ar. The reaction was cooled to 0° C. and triphosgene (180 mg, 0.61 mmol) was added. The mixture was stirred for 2 h at 0° C. The reaction was quenched with sat. NaHCO₃ (10 mL) and partitioned between DCM and H₂O. The aqueous layer was extracted with DCM (2×) and the combined organics were dried (Na₂SO₄) and concentrated by rotary evaporation to give a yellow solid. The residues were purified via flash column chromatography (silica, Biotage 40+S column, DCM to 0.5% NH₃/9.5% MeOH/90% DCM) to give 3-[1-(trans-1-methyl-4-{[2 (methyloxy)ethyl] oxy}cyclohexyl)-4-piperidinyl]-2-oxo-2,3-dihydro-1,3-benzoxazole-5-carbonitrile free base (E12b, 421 mg, 64%) as an off-white solid.

$^1$H NMR δ (DMSO-d₆, 400 MHz) 0.87 (3 H, s), 1.36-1.59 (6 H, m), 1.73-1.86 (4 H, m), 2.12-2.24 (4 H, m), 3.00-3.07 (2 H, m), 3.26 (3 H, s), 3.40-3.51 (5 H, m), 4.07 (1 H, m), 7.54 (1 H, d, J 8.3), 7.65 (1 H, dd, J 8.3 and 1.5), 7.97 (1 H, d, J1.5).

LCMS: [M+H]⁺ 414.

HCl (1.3 mL, 1.3 mmol, 1 M in Et₂O) was added to a solution of 3-[1-(trans-1-methyl-4-{[2-(methyloxy)ethyl] oxy}cyclohexyl)-4-piperidinyl]-2-oxo-2,3-dihydro-1,3-benzoxazole-5-carbonitrile free base (E12b, 270 mg, 0.65 mmol) in DCM (3 mL) at rt. The reaction was stirred for 5 min, then the solvent was removed by rotary evaporation and the residue triturated with Et₂O to give 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride (E12c, 265 mg, 81%) as an off-white solid.

$^1$H NMR δ (DMSO-d₆, 400 MHz) 1.27-1.39 (5 H, m), 1.78-1.89 (2 H, m), 1.95-2.12 (6 H, m), 2.68-2.81 (2 H, m), 3.12-3.28 (6 H, m), 3.40-3.45 (2 H, m), 3.53-3.58 (2 H, m), 3.65-3.73 (2 H, m), 4.60 (1 H, m), 7.59 (1 H, d, J 8.4), 7.70 (1 H, dd, J 8.4 and 1.4), 8.22 (1 H, d, J 1.4), 9.95 (1 H, m).

LCMS: [M+H]⁺ 414.

EXAMPLE 12d

3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile free base. (E12d)

EXAMPLE 12e

3-[1-(trans-1-Methyl-4-{[2-(methyloxy)ethyl]oxy}cyclohexyl)-4-piperidinyl]-2-oxo-2,3-dihydro-1,3-benzoxazole-5-carbonitrile hydrochloride. (E12e)

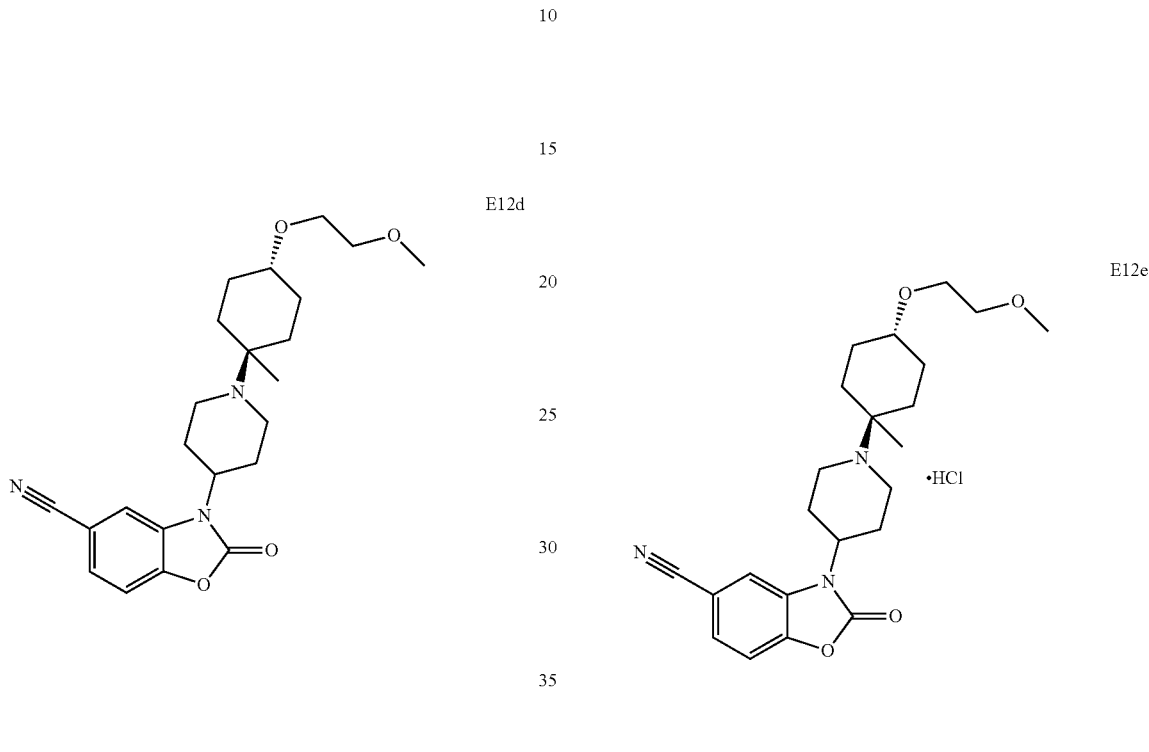

To a solution of 4-hydroxy-3-{[1-(trans-1-methyl-4-{[2-(methyloxy)ethyl]oxy}cyclohexyl)-4-piperidinyl]amino}benzonitrile (D80) (26.33 g, 67.9 mmol) in dry dichloromethane (DCM) (400 mL), DIPEA (23.73 mL, 136 mmol) was added at room temperature under argon. The reaction was chilled at 0° C. and then triphosgene (8.67 g, 29.2 mmol) was added portionwise. Reaction mixture was allowed to stir at 0° C. for 1 h then at room temperature for an additional hour. Reaction mixture was quenched with saturated solution NaHCO$_3$ (200 mL), phases were separated and the aqueous one back extracted with DCM (2×300 mL). Combined organics were dried over Na$_2$SO$_4$ and evaporated to dryness to give crude material, 31 g, as pale yellow semi-solid. Further 3.4 g of crude material were obtained in a similar way starting from 3.24 g of 4-hydroxy-3-{[1-(trans-1-methyl-4-{[2-(methyloxy)ethyl]oxy}cyclohexyl)-4-piperidinyl]amino}benzonitrile. The two crude batches were combined and purified by SiO$_2$ FC eluting with DCM/MeOH/NH$_4$OH from 98/2/05 to 96/4/0.5 to 90/10/1. Evaporation of volatiles afforded title material (E12d, 27 g; 85%) as white crystalline solid.

$^1$H NMR δ (CDCl$_3$, 400 MHz): 0.95 (3H, s), 1.58 (4H, m), 1.68 (2H, m), 1.89 (4H, m), 2.23 (4H, m), 3.18 (2H, d), 3.41 (3H, s), 3.50 (1H, m), 3.57 (2H, m), 3.62 (2H, m), 4.13 (1H, m), 7.29 (1H, d), 7.47 (1H, dd), 7.47 (1H, s).

MH$^+$=414.1.

To a solution of 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile (E12d) (10 g, 24.18 mmol) in dichloromethane (DCM) (100 mL), cooled at 0° C. under an Argon atmosphere, HCl 1M in Et$_2$O (48.4 mL, 48.4 mmol) was added dropwise. The slurry was left stirring 30 min at 0° C. then 30 min. at room temperature. White solid precipitation occurred. Slurry was then cautiously evaporated under reduced pressure with no bath heating. Obtained solid was triturated with Et$_2$O (100 mL) for 20 minutes and collected by filtration over a sintered glass filter. Product was dried at high vacuum overnight at room temperature then for 30 min at 40° C. under vacuum to get title material (E12e, 10.58 g, 97% yield) as white solid.

$^1$H NMR δ (DMSO-d$_6$, 400 MHz): 1.32 (2H, m) 1.34 (3H, s), 1.98 (8H, m), 2.79 (2H, m), 3.21 (3H, m), 3.25 (3H, s), 3.43 (2H, m), 3.56 (2H, m), 3.68 (2H, m), 4.61 (1H, m), 7.59 (1H, d), 7.62 (1H, dd), 8.30 (1H, d), 10.19 (1H, m).

MH$^+$=414.1.

EXAMPLE 12f

3-[1-(trans-1-Methyl-4-{[2-(methyloxy)ethyl]
oxy}cyclohexyl)-4-piperidinyl]-2-oxo-2,3-dihydro-1,
3-benzoxazole-5-carbonitrile 4-methylbenzene-
sulfonate. (E12f)

EXAMPLE 12g

3-[1-(trans-1-Methyl-4-{[2-(methyloxy)ethyl]
oxy}cyclohexyl)-4-piperidinyl]-2-oxo-2,3-dihydro-1,
3-benzoxazole-5-carbonitrile methanesulfonate.
(E12 g)

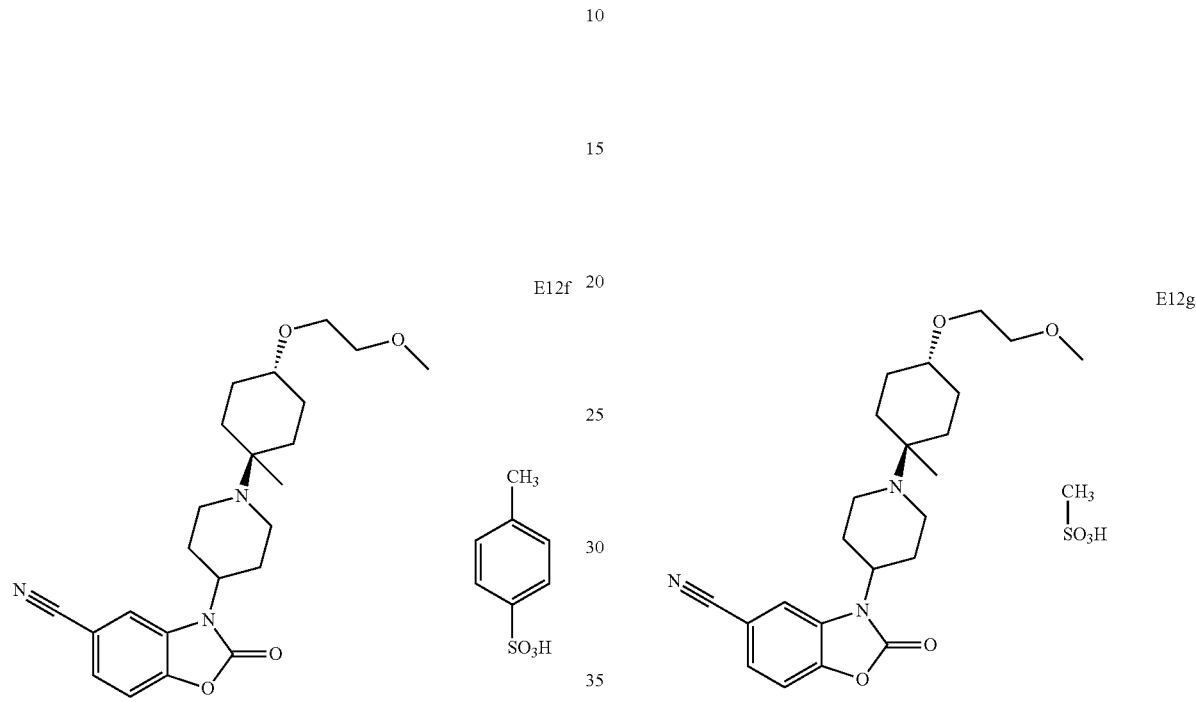

p-Toluenesulfonic acid monohydrate (11 mg, 0.06 mmol) was added to a solution of 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile free base (23 mg, 0.06 mmol) in DCM (0.5 mL):Et$_2$O (0.5 mL) at rt. The reaction was stirred for 3 h before the addition of Et$_2$O (10 mL) which caused the precipitation of a white solid. The solid was isolated by filtration, washing with Et$_2$O (2×) and EtOAc (2×) to give 3-[1-(trans-1-methyl-4-{[2-(methyloxy)ethyl]oxy}cyclohexyl)-4-piperidinyl]-2-oxo-2,3-dihydro 1,3-benzoxazole-5-carbonitrile 4-methylbenzenesulfonate (E12f, 27 mg, 74%) as a white solid.

$^1$H NMR δ (DMSO-d$_6$, 400 MHz) 1.28-1.40 (5 H, m), 1.60-1.70 (2 H, m), 1.96-2.06 (4 H, m), 2.09-2.17 (2 H, m), 2.29 (3 H, s), 3.10-3.28 (6 H, m), 3.40-3.46 (2 H, m), 3.52-3.59 (2 H, m), 3.66-3.75 (2 H, m), 4.57 (1 H, m), 7.11 (2 H, d, J 8.0), 7.47 (2 H, d, J 8.0), 7.60 (1 H, d, J 8.3), 7.71 (1 H, dd, J 8.3 and 1.2), 7.84 (1 H, d, J 1.2), 8.71 (1 H, m). Note: 2 H not visible in NMR spectrum as obscured by solvent or water.

LCMS: [M+H]$^+$ 414.

Methanesulfonic acid (4 μl, 0.06 mmol) was added to a solution of 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile free base (24 mg, 0.06 mmol) in DCM (1 mL) at rt. The reaction was stirred for 30 min before the addition of Et$_2$O (10 mL) which caused the precipitation of a white solid. The solid was isolated by filtration, washing with Et$_2$O (2×) and EtOAc (2×) to give 3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile methanesulfonate (E12g, 9.6 mg, 31% yield) as a white solid.

$^1$H NMR δ (DMSO-d$_6$, 400 MHz) 1.27-1.41 (5 H, m), 1.61-1.73 (2 H, m), 1.96-2.19 (6 H, m), 2.30 (3 H, s), 3.11-3.29 (6 H, m), 3.53-3.59 (2 H, m), 3.67-3.76 (2 H, m), 4.57 (1 H, m), 7.60 (1 H, d, J 8.2), 7.71 (1 H, d, J 8.2), 7.86 (1 H, s), 8.80 (1 H, m). Note: 4 H not visible in NMR spectrum as obscured by solvent or water.

LCMS: [M+H]$^+$ 414.

EXAMPLE 13

3-[1-(cis-1-methyl-4-{[2-(methyloxy)ethyl]oxy}cyclohexyl)-4-piperidinyl]-2-oxo-2,3-dihydro-1,3-benzoxazole-5-carbonitrile hydrochloride. (E13)

EXAMPLE 14

6-Methyl-1-{1-[trans-1-methyl-4-(propyloxy)cyclohexyl]-4-piperidinyl}-1,3-dihydro-2H-indol-2-one hydrochloride. (E14)

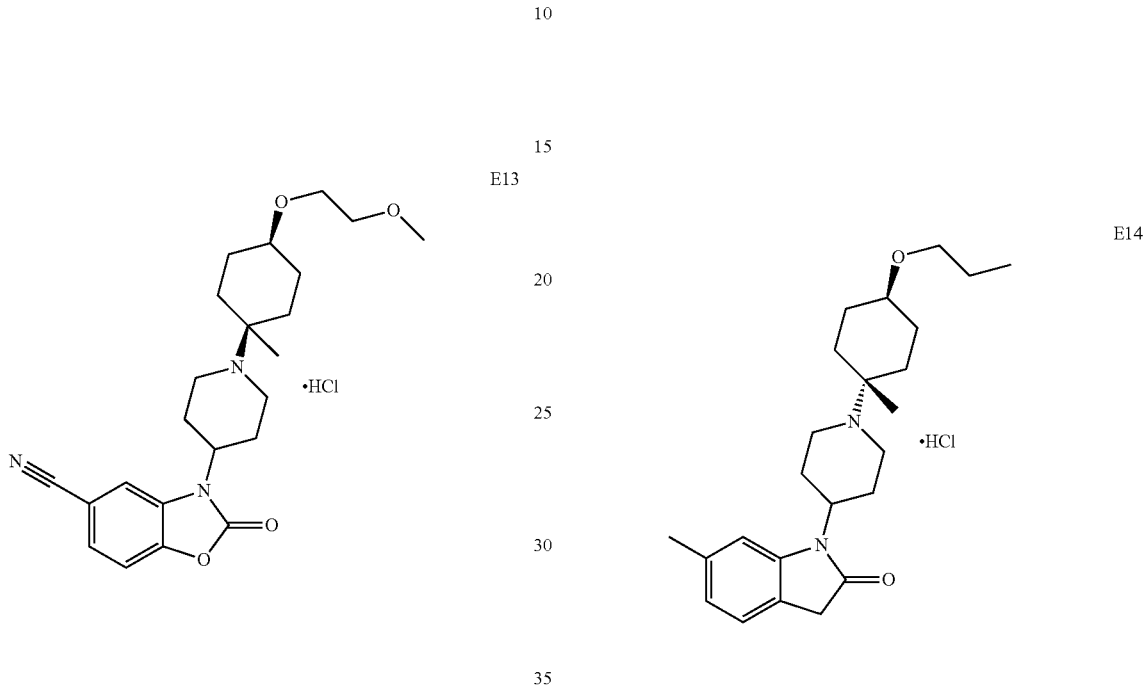

Diisopropylethylamine (0.02 mL, 0.115 mmol) was added to a solution of 4-hydroxy-3-{[1-(cis-1-methyl-4-{[2-(methyloxy)ethyl]oxy}cyclohexyl)-4-piperidinyl]amino}benzonitrile (D37, 22.6 mg, 0.058 mmol) in dichloromethane (2.5 mL) at rt under argon. The reaction was cooled to 0° C. and the triphosgene (9 mg, 0.03 mmol) was added. The mixture was stirred for 30 min at 0° C. The reaction was quenched with saturated aqueous NaHCO$_3$ (5 mL) and partitioned between dichloromethane and water. The aqueous layer was extracted with dichloromethane (2×) and the combined organics were dried (Na$_2$SO$_4$) and concentrated by rotary evaporation to give a pale yellow solid. The residue was purified via chromatography (silica, dichloromethane to 0.5% ammonia/9.5% methanol/90% dichloromethane) to give the free base of the title compound as a pale yellow solid. HCl (0.1 mL, 0.1 mmol, 1 M in diethyl ether) was added to a solution of the free base in dichloromethane (0.5 mL) and the solvent removed by rotary evaporation. The resulting residue was triturated with diethyl ether (2×) to give 3-[1-(cis-1-methyl-4-{[2-(methyloxy)ethyl]oxy}cyclohexyl)-4-piperidinyl]-2-oxo-2,3-dihydro-1,3-benzoxazole-5-carbonitrile hydrochloride (E13, 14.8 mg, 53.6% yield) as a pale yellow solid.

$^1$H NMR δ (DMSO-d$_6$, 400 MHz) 1.33 (3 H, s), 1.52-1.63 (2 H, m), 1.75 (2 H, m), 1.82-1.96 (4 H, m), 2.09 (2 H, m), 2.65 (2 H, m), 3.16 (2 H, m), 3.27 (3 H, s), 3.43-3.58 (5 H, m), 3.71 (2 H, m), 4.60 (1 H, m), 7.60 (1 H, d, J 8), 7.71 (1 H, dd, J 8 and 1.2), 8.37 (1 H, d, J 1.2), 9.30 (1 H, m).

M+H$^+$ 414.

A stirred solution of bis(1,1-dimethylethyl) [4-methyl-2-({1-[trans-1-methyl-4-(propyloxy)cyclohexyl]-4-piperidinyl}amino)phenyl]propanedioate (D40, 340 mg, 0.61 mmol) in toluene (12 mL) at room temperature under argon was treated with 4-toluenesulphonic acid monohydrate (150 mg, 0.80 mmol) and then heated at 110° C. for 2 hours. The mixture was allowed to cool, concentrated under vacuum and the residue treated with 10% Na$_2$CO$_3$ solution (15 mL) and extracted with ethyl acetate (2×15 mL). The combined extract was dried (Na$_2$SO$_4$) and concentrated under vacuum. The residue was initially purified by chromatography on silica gel (20 g) eluting with 0-8% MeOH/dichloromethane, followed by purification using mass-directed HPLC to afford the free base of the title compound as a colourless oil (170 mg). This material was dissolved in dichloromethane (2 mL), treated with 1M HCl/Et$_2$O (0.5 mL) and concentrated to afford the title compound E14 as a white solid (145 mg).

$^1$H NMR HCl salt δ (DMSO-d$_6$, 400 MHz): 0.88 (3H, t), 1.25-1.40 (2H, m+3H, s), 1.44-1.55 (2H, m), 1.80 (2H, br d), 1.90-2.10 (6H, br m), 2.33 (3H, s), 2.88-3.00 (2H, m), 3.10-3.26 (3H, m), 3.39 (2H, t), 3.50 (2H, s), 3.63 (2H, br d), 4.53-4.63 (1H, m), 6.81 (1H, d), 7.12 (1H, d), 7.59 (1H, s), 10.36 (1H, br s).

MH$^+$=385.

EXAMPLE 15

3-{1-[trans-4-Ethoxy-1-methylcyclohexyl]-4-piperidinyl}-7-fluoro-5-methyl-1,3-benzoxazol-2(3H)-one hydrochloride. (E15)

EXAMPLE 16

3-{1-[TRANS-4-ETHOXY-1-METHYLCYCLO-HEXYL]-4-PIPERIDINYL}-6,7-DIFLUORO-5-methyl-1,3-benzoxazol-2(3H)-one hydrochloride. (E16)

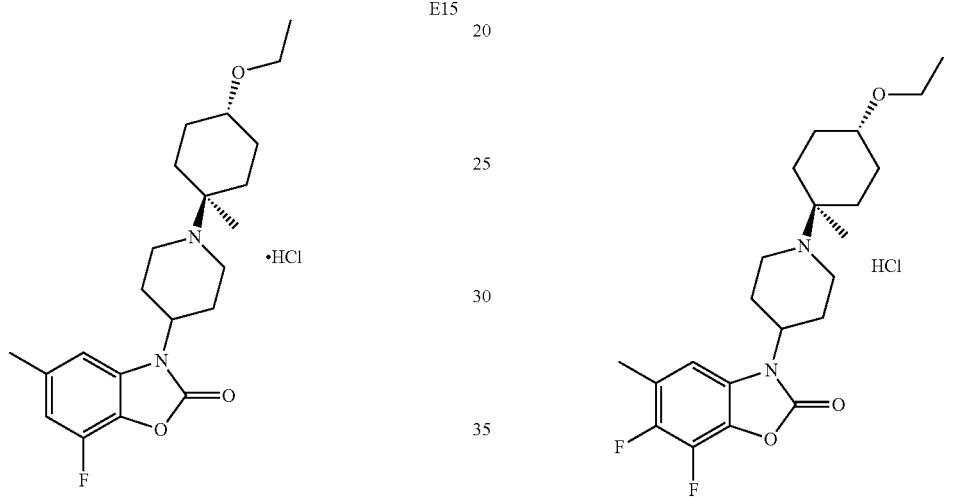

To 2-({1-[trans-4-ethoxy-1-methylcyclohexyl]-4-piperidinyl}amino)-6-fluoro-4-methylphenol (100 mg, 0.274 mmol) (D43) in dichloromethane (5 mL) at 0° C. were added diisopropylethylamine (0.15 mL, 0.859 mmol) and triphosgene (35 mg, 0.118 mmol). After 30 min at 0° C. and 30 min at room temperature, the mixture was washed with aqueous sodium bicarbonate, dried, and evaporated. Chromatography on silica (5 g), eluting with 0-10% 2M ammonia in methanol-dichloromethane, and conversion to the hydrochloride gave 3-{1-[trans-4-ethoxy-1-methylcyclohexyl]-4-piperidinyl}-7-fluoro-5-methyl-1,3-benzoxazol-2(3H)-one (E15, 48 mg, 0.112 mmol, 41.0% yield) as the hydrochloride salt.

$^1$H NMR (HCl salt) δ (DMSO-$d_6$): 1.1 (3H, t), 1.35 (5H, m), 2.0 (8H, m), 2.35 (3H, s), 2.8 (2H, b q), 3.2 (3H, m), 3.4 (2H, q), 3.7 (2H, m), 4.6 (1H, m), 6.9 (1H, d), 7.6 (1H, s), 10.3 (1H, br s).

MH$^+$ 391.

To 6-({1-[trans-4-ethoxy-1-methylcyclohexyl]-4-piperidinyl}amino)-2,3-difluoro-4-methyl-phenol (110 mg, 0.288 mmol) (D46) in dichloromethane (5 mL) at 0° C. were added diisopropylethylamine (0.15 mL, 0.859 mmol) and triphosgene (35 mg, 0.118 mmol). After 30 min at 0° C. and 30 min at room temperature, the mixture was washed with aqueous sodium bicarbonate, dried, and evaporated. Chromatography on silica (5 g), eluting with 0-5% 2M ammonia in methanol-dichloromethane, and conversion to the hydrochloride, gave 3-{1-[trans-4-ethoxy-1-methylcyclohexyl]-4-piperidinyl}-6,7-difluoro-5-methyl-1,3-benzoxazol-2(3H)-one (E16, 62 mg, 0.132 mmol, 46.0% yield) as the hydrochloride salt.

$^1$H NMR (HCl salt) δ (DMSO-$d_6$): 1.1 (3H, t), 1.35 (5H, m), 2.0 (8H, m), 2.3 (3H, s), 2.85 (2H, b q), 3.2 (3H, m), 3.4 (2H, q), 3.7 (2H, m), 4.6 (1H, m), 7.8 (1H, d), 10.45 (1H, br s).

MH$^+$ 409.

EXAMPLE 17

5-Methyl-3-{1-[trans-1-methyl-4-(methyloxy)cyclohexyl]-4-piperidinyl}-1,3-benzoxazol-2(3H)-one hydrochloride. (E17)

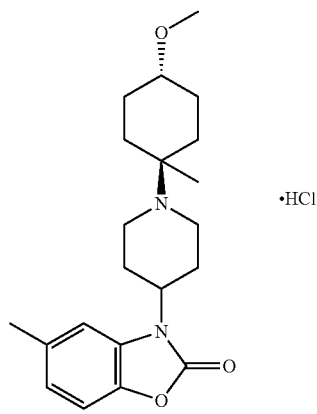

E17

4-Methyl-2-({1-[trans-1-methyl-4-(methyloxy)cyclohexyl]-4-piperidinyl}amino)phenol (D48, 174 mg) was taken up in dry DCM (5.0 mL) containing diisopropylethylamine (133 μl) and treated with triphosgene (120 mg). After two hours the reaction mixture was partitioned between DCM and NaHCO$_3$ (sat$^d$ aq), the organic layers separated, dried over MgSO$_4$, filtered and the solvent removed under reduced pressure to afford a white solid. Recrystallisation from ethanol afforded the title compound (E17, 72 mg).

$^1$H NMR δ (d$_4$-MeOH): 1.48 (4H m), 2.19 (2H, m), 2.67 (6H, m), 2.76 (3H, s), 3.15 (2H, m), 3.26 (4H, m), 3.32 (3H,s), 3.83 (2H, m), 4.48 (1H, m), 6.99 (1H, dd, J=8.0 and 0.8 Hz), 7.07 (1H, d, J=8.0 Hz), 7.31 (1H, s).
(M+H)$^+$ 359.

EXAMPLE 18

3-{1-[trans-4-(Ethyloxy)-1-methylcyclohexyl]-4-piperidinyl}-5,7-difluoro-1,3-benzoxazol-2(3H)-one hydrochloride. (E18)

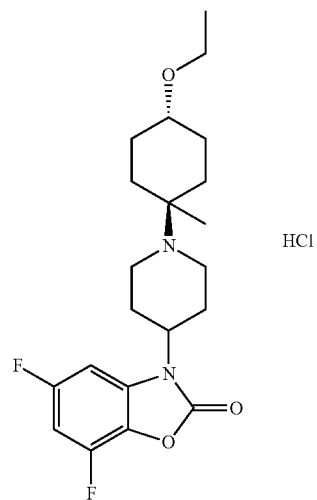

E18

2-({1-[trans-4-(Ethyloxy)-1-methylcyclohexyl]-4-piperidinyl}amino)-4,6-difluorophenol (D49; assumed 0.530 mmol crude) was dissolved in dichloromethane (3 mL) and diisopropylethylamine (203 μl) was added, followed by triphosgene (173 mg, 0.583 mmol) in dichloromethane (2 mL). The reaction mixture was stirred at room temperature for 5 h. The reaction mixture was treated with aqueous saturated sodium bicarbonate (5 mL) and stirred for 10 min. The layers were separated via phase separator and the organic layer evaporated to give a brown oil. This was purified by mass-directed LC/MS in 2 batches. The fractions containing product were treated with 2M ammonia in methanol (1 mL) then evaporated thoroughly. Both fractions when evaporated gave white-yellow solids. These were dissolved in methanol and loaded onto SCX-3 cartridges (1 g). The cartridges were eluted with methanol (6 mL each), followed by 0.5 M ammonia in methanol (8 mL each). The basic eluants were combined and evaporated to dryness to give a yellow solid. This material was obtained as an HCl salt by dissolving in 4.0M HCl in 1,4-dioxane, stirring for 20 min, then evaporating to dryness to give the title compound E18 as a yellow solid (17 mg, 7.5%).

$^1$H NMR (HCl salt) δ (DMSO-d$_6$, 400 MHz): 1.08 (3H, t, J=8.6 Hz), 1.35 (2H, br. s), 1.87-2.06 (8H, br. m), 2.75-2.84 (2H, br. s), 3.19 (3H, br. s), 3.47 (2H, q, J=6.8 Hz), 3.65-3.73 (4H, br. m), 4.15 (1H, br. m), 4.646 (1H, br. m), 7.20 (1H, m), 7.76 (1H, m), 10.35 (1H, br. s).

(M+H)$^+$=395.

EXAMPLE 19

3-{1-[trans-4-(Ethyloxy)-1-methylcyclohexyl]-4-piperidinyl}-5-[(trifluoromethyl)oxy]-1,3-benzoxazol-2(3H)-one hydrochloride. (E19)

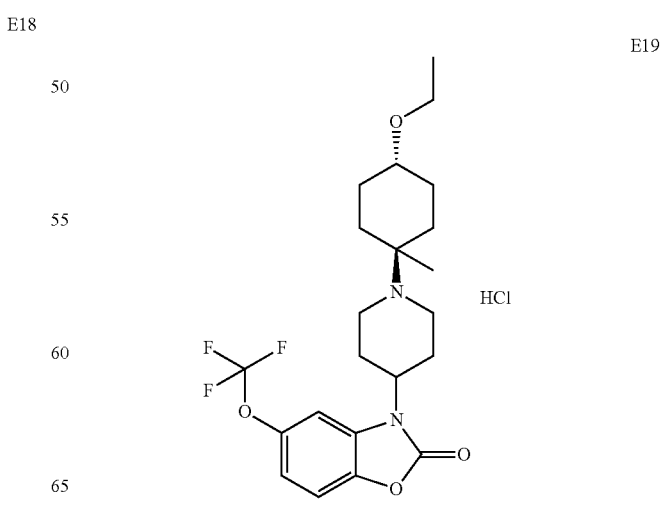

E19

2-({1-[trans-4-(Ethyloxy)-1-methylcyclohexyl]-4-piperidinyl}amino)-4-[(trifluoromethyl) oxy]phenol (D50, 90 mg, 0.216 mmol) was dissolved in anhydrous dichloromethane (DCM) (3 mL) and diisopropylethylamine (0.075 mL, 0.432 mmol) was added. The reaction mixture was cooled to 0° C. and triphosgene (25.7 mg, 0.086 mmol) was added. The reaction mixture was stirred for 1 h. The reaction mixture was treated with saturated sodium bicarbonate solution (4 mL) and diluted with DCM (7 mL) and water (6 mL). The layers were separated. The organic layer was dried with magnesium sulphate and evaporated to dryness. The residue was purified by mass-directed LC/MS (MDAP). Fraction 1 was deemed to be the only pure one, so this was basified with ammonia and evaporated to dryness. The residual salts were removed on an IST SCX-2 (5 g) cartridge, washing with methanol (40 mL) and 0.5 M ammonia in methanol (40 mL). The basic eluant was evaporated to dryness to give a colourless oil. This was redissolved in methanol (4 mL) and 2.0 M HCl in diethyl ether (4 mL). The solution was stirred for 15 min at room temperature and evaporated to dryness to give the title compound (E19) as a tan solid (22 mg, 21%).

$^1$H NMR δ (d$_4$-MeOH, 400 MHz): 1.18 (3H, t, J=6.8 Hz), 1.41-1.49 (5H, br. m), 1.80-1.86 (2H, br. m), 2.11 (4H, m), 2.22 (2H, m), 2.75-2.84 (2H, br. m), 3.24-3.37 (3 h, br. m, obscured by methanol peak), 3.57 (2H, qm J=6.8 Hz), 3.83 (2H, m), 4.41 (1H, m), 7.11 (1H, d, J=8.4 Hz), 7.34 (1H, d, J=8.8 Hz), 7.57 (1H, s).

(M+H)$^+$=443. Rt 2.56

EXAMPLE 20

3-{1-[trans-4-(Ethyloxy)-1-methylcyclohexyl]-4-piperidinyl}-5,6-difluoro-1,3-benzoxazol-2(3H)-one hydrochloride. (E20)

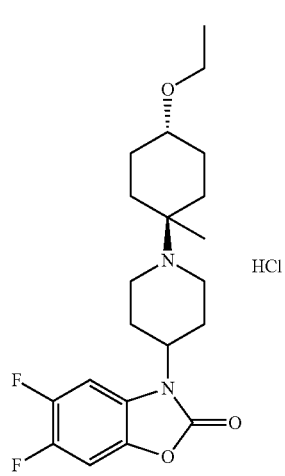

2-({1-[trans-4-(Ethyloxy)-1-methylcyclohexyl]-4-piperidinyl}amino)-4,5-difluorophenol (D51, 253 mg, 0.401 mmol) was dissolved in dichloromethane (DCM) (5 mL) and diisopropylethylamine (0.437 mL, 2.5 mmol) was added. The reaction mixture was cooled to 0° C. under argon and triphosgene (89 mg, 0.301 mmol) was added. The reaction mixture was stirred for 1 h. The reaction mixture was treated with saturated sodium bicarbonate solution (4 mL), then diluted with DCM and water (6 mL) of each. The layers were separated and the organic layer dried (magnesium sulphate) and evaporated. The residue was purified by flash column chromatography, using an IST pre-packed silica cartridge (20 g) and a gradient of 100% DCM to 0.3% ammonia, 5.7% methanol, 94% DCM, giving the crude product as an orange oil. This was further purified by mass-directed LC/MS (MDAP).

Fraction 1 was neutralised and evaporated to dryness. The resulting solid was purified on an IST SCX-2 cartridge (5 g), washing with methanol (30 mL) and eluting with 0.5M ammonia in methanol (30 mL). The basic wash was evaporated to dryness.

Fraction 2 was neutralised with ammonia and evaporated to dryness. The resulting solid was partitioned between dichloromethane and saturated sodium bicarbonate solution (4 mL of each). The layers were separated with a phase separator, and the organic layer evaporated to dryness.

The products obtained from work-up of fractions 1 and 2 were combined and evaporated to dryness. The resulting white solid was dissolved in DCM (1 mL) and 2.0 M HCl in diethyl ether was added (159 µl, 5 eq.). The solution was stirred for 30 min, then evaporated to dryness. The material was re-evaporated from 1:1 DMSO-d$^6$: methanol (after NMR was unresolved), giving the title compound E20 as a white solid (22 mg, 13%).

(M+H)$^+$=395, Rt 2.36

$^1$H NMR (HCl salt) δ (DMSO-d$_6$, 400 MHz): 1.10 (3H, t, J=6.8 Hz), 1.32 (3H, br. s), 1.92-2.04 (8H, br. m), 2.83 (2H, m), 3.19 (3H, m), 3.34 (2H, br. s), 3.47 (2H, m), 3.67 (2H, m), 4.57 (1H, m), 7.73 (1H, m), 8.21 (1H, m), 10.5 (1H, br. s).

EXAMPLE 21

3-{1-[trans-4-(Ethyloxy)-1-methylcyclohexyl]-4-piperidinyl}-5-(trifluoromethyl)-1,3-benzoxazol-2 (3H)-one hydrochloride. (E21)

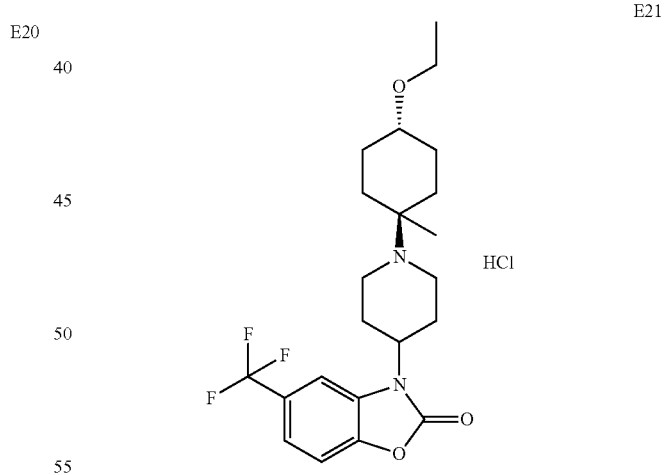

2-({1-[trans-4-(Ethyloxy)-1-methylcyclohexyl]-4-piperidinyl}amino)-4-(trifluoromethyl)phenol (D53, 225 mg, 0.406 mmol) was dissolved in dichloromethane (5 mL) and diisopropylethylamine (0.248 mL, 1.419 mmol) was added. The reaction mixture was cooled to 0° C. under argon and triphosgene (90 mg, 0.304 mmol) was added. The reaction mixture was stirred for 1 h. The reaction mixture was treated with saturated sodium bicarbonate solution (4 mL), then diluted with dichloromethane and water (6 mL) of each. The layers were separated and the organic layer dried (magnesium sulphate) and evaporated.

The residue was purified by flash column chromatography on a Biotage SP4 (12+M cartridge) using a dichloromethane to 0.5% ammonia/9.5% Methanol/90% dichloromethane gradient, to give a colourless oil.

The oil was purified by mass-directed LC/MS (MDAP). Fraction 1 was collected, neutralised with ammonia and evaporated to dryness. The residue was purified on an IST SCX-2 cartridge (5 g), washing with methanol (30 mL) and eluting with 0.5 M ammonia in methanol (30 mL). The basic wash was evaporated to dryness to give a white solid.

The solid was dissolved in dichloromethane (2 mL) and 2.0 M hydrogen chloride in diethyl ether (2 mL) was added. The solution was stirred for 15 min, then evaporated thoroughly to give a white solid (43 mg). This was re-evaporated from 1:2 DMSO-$d^6$: ethanol (3 mL) giving the title compound (E21) as a white solid (37 mg, 20%).

$(M+H)^+=427$.

$^1$H NMR (HCl salt) δ (DMSO-$d_6$, 400 MHz): 1.10 (3H, t, J=6.8 Hz), 1.33 (3H, br. s), 1.90-2.08 (8H, br. m), 2.85 (2H, m) 3.19 (3H, m), 3.33 (2H, br. s), 3.47 (2H, q, J=6.8 Hz), 3.68 (2H, m), 4.63 (1H, m), 7.55 (2H, m), 8.17 (1H, s), 10.5 (1H, br. s).

EXAMPLE 22

6-Methyl-1-{1-[trans-1-methyl-4-(methyloxy)cyclohexyl]-4-piperidinyl}-1,3-dihydro-2H-indol-2-one hydrochloride. (E22)

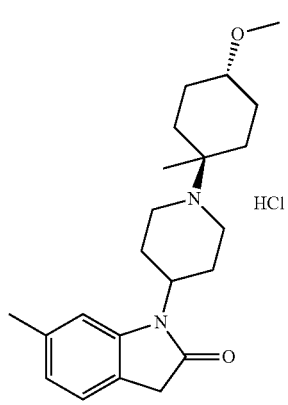

E22 bis(1,1-Dimethylethyl) [4-methyl-2-({1-[trans-1-methyl-4-(methyloxy)cyclohexyl]-4-piperidinyl}amino)phenyl]propanedioate (D54) (1 eq., 0.19 mmol, 100 mg), 4-methylbenzenesulfonic acid monohydrate (1.3 eq., 0.24 mmol, 46 mg) were dissolved in toluene (4 mL) and heated at 120° C. for 2 hours. The mixture was then cooled to Rt, the solvent was evaporated and the crude was then partitioned between $Na_2CO_3$ (10% aq. solution) and EtOAc. The two phases were separated and the aqueous phase was extracted with EtOAc (2×); organics were combined, dried ($Na_2SO_4$) and concentrated under vacuum to leave a beige solid, which was purified by silica chromatography (12M column, EtOAc-nhex) to afford the product as a free base, (50 mg, 74%). This was dissolved in MeOH (3 mL) and treated with a 1M solution (in $Et_2O$) of HCl (2 eq., 0.28 mmol, 0.28 mL). The mixture was stirred at Rt for 5 min, the solvent was evaporated and the solid obtained was triturated with $Et_2O$ to afford the title compound E22, (47 mg, 89%).

$H^+=357$.

$^1$H NMR (HCl salt) δ ($d_6$-DMSO, 400 MHz): 1.24-1.34 (5H, m), 1.79-2.02 (8H, m), 2.34 (3H, s), 2.89 (2H, q), 3.06-3.21 (3H, m), 3.26 (3H, s), 3.49 (2H, s), 3.64 (2H, d), 4.54 (1H, m), 6.82 (1H, d), 7.13 (1H, d), 7.48 (1H, s), 10.1 (1H, s br).

EXAMPLE 23

3-{1-[trans-1-Methyl-4-(methyloxy)cyclohexyl]-4-piperidinyl}-2-oxo-2,3-dihydro-1,3-benzoxazole-5-carbonitrile hydrochloride. (E23)

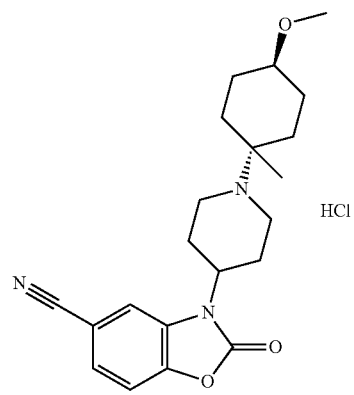

E23

4-Hydroxy-3-({1-[trans-1-methyl-4-(methyloxy)cyclohexyl]-4-piperidinyl}amino)benzonitrile (D55, 200 mg, 0.582 mmol) was dissolved into dry dichloromethane (DCM) (4 mL) and DIPEA (0.135 mL, 0.757 mmol) was added at Rt followed by triphosgene (69.1 mg, 0.233 mmol) at Rt. The mixture was stirred at Rt for 2 hours. The mixture was quenched with saturated aqueous solution of $NaHCO_3$, diluted with DCM (10 mL), stirred vigorously for 10 min and the organic phase was separated from the aqueous by hydrophobic filter to afford the crude product, which was purified by chromatography (25S silica column, MeOH—$NH_3$-DCM) to afford the free base, a pale-yellow solid, (60%). This was dissolved in a mixture of methanol (1 mL) and dichloromethane (DCM) (0.5 mL) and treated with hydrochloric acid (0.352 mL, 0.352 mmol) at 25° C. The mixture was stirred at 25° C. for 10 minutes and the solvent was then evaporated to afford the title compound 3-{1-[trans-1-methyl-4-(methyloxy)cyclohexyl]-4-piperidinyl}-2-oxo-2,3-dihydro-1,3-benzoxazole-5-carbonitrile hydrochloride (E23, 118 mg, 0.276 mmol, 78% yield) as a pale-yellow solid that was triturated with $Et_2O$ and filtered to afford the title compound.

$MH^+=370$.

$^1$H NMR δ (d$_6$-DMSO, 250 MHz, T=349K): 1.36 (4H, m), 1.90-2.10 (6H, m), 2.75-3.2 (m), 3.27 (3H, s), 3.69 (2H, d), 4.58 (1H, m), 7.50 (1H, d), 7.60 (1H, dd), 8.22 (1H, s br), 10.1 (1H, s br).

EXAMPLE 24

1-{1-[trans-4-(Ethyloxy)-1-methylcyclohexyl]-4-piperidinyl}-6-methyl-1,3-dihydro-2H-indol-2-one hydrochloride. (E24)

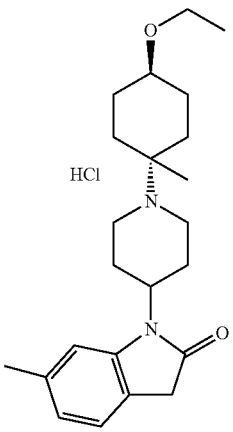

bis(1,1-Dimethylethyl) [2-({1-[trans-4-(ethyloxy)-1-methylcyclohexyl]-4-piperidinyl}amino)-4-methylphenyl]propanedioate (D56) (1 eq., 0.25 mmol, 134 mg), was dissolved in toluene (4 mL) and 4-methylbenzenesulfonic acid monohydrate (1.3 eq., 0.320 mmol, 61 mg) was added and the mixture was heated at 120° C. for 2 hours. The mixture was then cooled to Rt, the solvent was evaporated and the crude was then partitioned between Na$_2$CO$_3$ (10% aq. solution) and EtOAc. The two phases were separated and the aqueous was extracted with EtOAc (2×); organics were combined, dried (Na$_2$SO$_4$) and concentrated under vacuum to leave a beige solid, which was purified by silica chromatography (12M column, EtOAc-nhex) to afford the product as a free base, (70 mg in 76% yield). This material was dissolved in MeOH/dichloromethane mixture and treated with a 1M solution (in Et$_2$O) of HCl (2 eq.). The mixture was stirred at Rt for 10 min, the solvent was evaporated and the solid obtained was triturated with Et$_2$O to afford the title compound E24, (64 mg, 79% yield).

MH$^+$=371.

$^1$H NMR (HCl salt) δ (d$_6$-DMSO, 250 MHz): 1.10 (3H, m), 1.17-1.33 (4H, m), 1.80-2.00 (7H, m), 2.34 (3H, s), 2.85 (2H, q), 3.18-3.51 (m), 4.52 (1H, m), 6.82 (1H, d), 7.13 (1H, d), 7.42 (1H, s), 9.9 (1H, s br).

EXAMPLE 25

3-{1-[trans-1-Methyl-4-(propyloxy)cyclohexyl]-4-piperidinyl}-5-(methylsulfonyl)-1,3-benzoxazol-2(3H)-one hydrochloride. (E25)

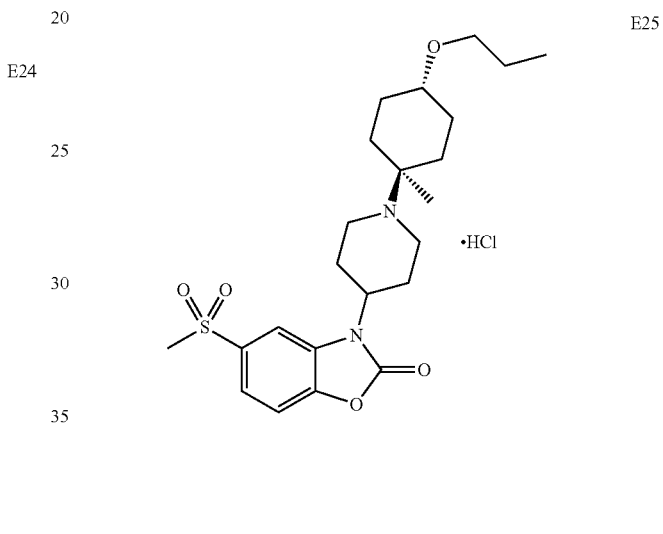

Diisopropylethylamine (0.03 mL, 0.172 mmol) was added to a solution of 2-({1-[trans-1-methyl-4-(propyloxy)cyclohexyl]-4-piperidinyl}amino)-4-(methylsulfonyl)phenol (D57, 31.4 mg, 0.074 mmol) in dichloromethane (5 mL) at rt under argon. The reaction was cooled to 0° C. and the triphosgene (16 mg, 0.054 mmol) was added. The mixture was stirred for 1 h at 0° C. The reaction was quenched with saturated aqueous NaHCO$_3$ (5 mL) and partitioned between dichloromethane and water. The aqueous layer was extracted with dichloromethane (2×) and the combined organics were dried (Na$_2$SO$_4$) and concentrated by rotary evaporation to give a pale yellow solid. The residue was purified via chromatography (silica, dichloromethane to 0.5% ammonia/9.5% methanol/90% dichloromethane) to give the free base of the title compound as a white solid. HCl (0.1 mL, 0.1 mmol, 1 M in diethyl ether) was added to a solution of the free base in dichloromethane (0.5 mL). The solvent was removed by rotary evaporation and the residue triturated with diethyl ether to give 3-{1-[trans-1-methyl-4-(propyloxy)cyclohexyl]-4-piperidinyl}-5-(methylsulfonyl)-1,3-benzoxazol-2(3H)-one hydrochloride E25 (23.2 mg, 0.045 mmol, 61% yield) as a cream solid.

MH$^+$ 451.

$^1$H NMR δ (DMSO-d$_6$, 400 MHz) 0.87 (3 H, t, J 7.2), 1.25-1.40 (5 H, m), 1.47-1.53 (2 H, m), 1.78 (2 H, m), 1.99 (4 H, m), 2.12 (2 H, m), 2.69 (2 H, m), 3.12-3.28 (3 H, m), 3.82

(2 H, q, J 7.2), 3.70 (2 H, m), 4.64 (1 H, m), 7.63 (1 H, d, J 8.6), 7.76 (1 H, dd, J 8.6 and 1.6), 8.08 (1 H, d, J 1.6), 9.53 (1 H, m).

EXAMPLE 26

1-{1-[trans-4-(Ethyloxy)-1-methylcyclohexyl]-4-piperidinyl}-7-methyl-3,4-dihydro-2(1H)-quinolinone. (E26)

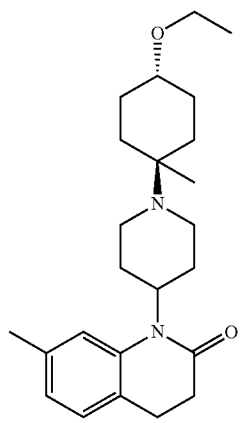

E26

A stirred solution of the crude 3-[2-({1-[trans-4-(ethyloxy)-1-methylcyclohexyl]-4-piperidinyl}amino)-4-methylphenyl]propanoic acid (D58, 75 mg, 0.186 mmol) in N,N-dimethylformamide (DMF) (3 mL) under argon was treated with EDC (39.3 mg, 0.205 mmol), HOBT (31.4 mg, 0.205 mmol) and finally triethylamine (0.057 mL, 0.410 mmol) and the resulting solution stirred o/n at rt. The mixture was concentrated to dryness under vacuum and the residue partitioned between 1:1 dilute potassium carbonate solution and DCM (20 mL). The organic phase was separated washed with brine (5 mL), dried ($MgSO_4$) and concentrated to dryness in vacuo. LC/MS indicated that the residue consisted of a mixture of components including the putative product (45.45%). This was then subjected to silica gel chromatography using Biotage SP1 with a 12+M cartridge and eluting with 0-10% MeOH in DCM over 15 CV. Fractions containing the desired product were concentrated to dryness in vacuo to give a colourless gum. After triturating the product in diethyl ether/isohexane a colourless solid was produced which was collected by filtration and dried at 40° C. under vacuum (E26, 4 mg, 5.58%).

$^1$H NMR δ ($CDCl_3$, 400 MHz) 1.20 (3H, t), 1.38-1.73 (8H, m), 1.88 (3H, m), 2.18 (2H, t), 2.36 (3H, s), 2.45-2.62 (5H, m), 2.76 (2H, m), 3.08 (2H, d), 3.42 (1H, m), 3.48 (2H, q), 3.76 (1H, m), 4.08 (1H, m), 6.80 (1H, d), 7.02 (2H, m).

LC/MS ES+1.94 (94.06%) 385 ($MH^+$).

EXAMPLE 27

3,3,6-Trimethyl-1-{1-[trans-1-methyl-4-(propyloxy)cyclohexyl]-4-piperidinyl}-1,3-dihydro-2H-indol-2-one hydrochloride. (E27)

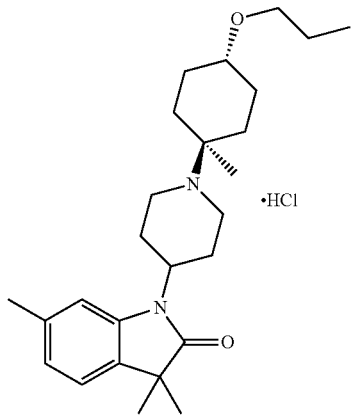

E27

6-Methyl-1-{1-[trans-1-methyl-4-(propyloxy)cyclohexyl]-4-piperidinyl}-1,3-dihydro-2H-indol-2-one hydrochloride (E14, 46 mg, 0.11 mmol) was suspended in DMF (3 mL) under Ar and cooled to 0° C. Sodium hydride (18 mg, 0.45 mmol, 60% wt. suspension in oil) was added and the reaction stirred for 20 min at 0° C. Methyl iodide (0.014 mL, 0.23 mmol) was then added and the reaction stirred for a further 1 h at 0° C. A further portion of sodium hydride (5 mg, 0.13 mmol, 60% wt. suspension in oil) and methyl iodide (6 μl, 0.10 mmol) were added and stirring continued for 1 h. The reaction was quenched by the addition of sat. $NaHCO_3$ (10 mL) and extracted with EtOAc (2×). The combined organics were washed sequentially with sat. NaCl, $H_2O$ and sat. NaCl, dried ($Na_2SO_4$) and concentrated by rotary evaporation to give a yellow/brown oil. The crude residue was purified via flash column chromatography (silica, DCM to 0.5% $NH_3$/9.5% MeOH/90% DCM) to give a brown oil which was further purified by high pH MDAP to give the free base of the title compound. HCl (50 μl, 0.05 mmol, 1 M in $Et_2O$) was added to a solution of the free base in methanol (0.5 mL) and the solvent was then removed by rotary evaporation to give a solid which was triturated with $Et_2O$ (2×) to give 3,3,6-trimethyl-1-{1-[trans-1-methyl-4-(propyloxy)cyclohexyl]-4-piperidinyl}-1,3-dihydro-2H-indol-2-one hydrochloride (E27, 7.1 mg, 13%) as a cream solid.

$^1$H NMR δ (DMSO-$d_6$, 400 MHz) 0.87 (3 H, t, J 7.5), 1.19-1.40 (11 H, m), 1.43-1.54 (2 H, m), 1.76-1.90 (4 H, m), 1.93-2.05 (4 H, m), 2.34 (3 H, s), 2.72-2.86 (2 H, m), 3.12-3.26 (3 H, m), 3.60-3.69 (2 H, m), 4.48 (1 H, m), 6.86 (1 H, d, J 7.5), 7.22 (1 H, d, J 7.5), 7.31 (1 H, s), 9.54 (1 H, m). Note: 2 H not visible in NMR spectrum as obscured by solvent or water.

LCMS: $[M+H]^+$ 413.

EXAMPLE 28

6-Methyl-1-[1-(trans-1-methyl-4-{[2-(methyloxy)ethyl]oxy}cyclohexyl)-4-piperidinyl]-1,3-dihydro-2H-indol-2-one hydrochloride. (E28)

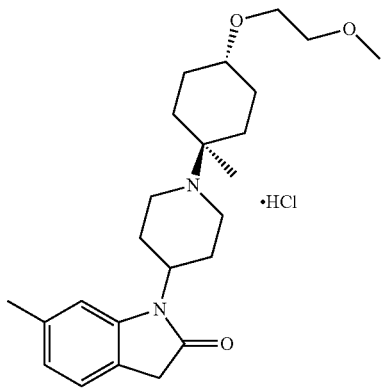

E28

EXAMPLE 29

3-{1-[trans-1-Methyl-4-(propyloxy)cyclohexyl]-4-piperidinyl}-5-[(trifluoromethyl)sulfonyl]-1,3-benzoxazol-2(3H)-one hydrochloride. (E29)

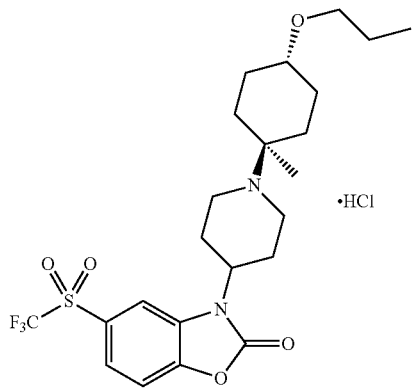

E29 p-Toluenesulfonic acid monohydrate (53 mg, 0.277 mmol) was added to a solution of bis(1,1-dimethylethyl) (4-methyl-2-{[1-(trans-1-methyl-4-{[2-(methyloxy)ethyl]oxy}cyclohexyl)-4-piperidinyl]amino}phenyl)propanedioate (D81, 106 mg, 0.11 mmol) in toluene (10 mL) and the reaction was heated to 120° C. for 2 h. The solvent was removed rotary evaporation and the crude residue was partitioned between 10% Na$_2$CO$_3$ solution and EtOAc. The aqueous layer was extracted with EtOAc (2×) and the combined organics were dried (Na$_2$SO$_4$) and concentrated by rotary evaporation to give a yellow oil. The crude residue was purified by flash column chromatography (silica, DCM to 0.5% NH$_3$/9.5% MeOH/90% DCM) to give the free base of the title compound as a colourless oil. HCl (0.15 mL, 0.15 mmol, 1 M in Et$_2$O) was added to a solution of the free base in DCM (5 mL) and the reaction stirred for 1 h. The solvent removed by rotary evaporation and the resulting solid triturated with Et$_2$O to give 6-methyl-1-[1-(trans-1-methyl-4-{[2-(methyloxy)ethyl]oxy}cyclohexyl)-4-piperidinyl]-1,3-dihydro-2H-indol-2-one hydrochloride (E28, 36 mg, 72%) as a pale yellow solid.

$^1$H NMR δ (DMSO-d$_6$, 400 MHz) 1.27-1.38 (5 H, m), 17.4-1.90 (4 H, m), 1.94-2.04 (4 H, m), 2.34 (3 H, s), 2.72-2.87 (2 H, m), 3.11-3.27 (6 H, m), 3.39-3.45 (2 H, m), 3.49 (2 H, s), 3.52-3.58 (2 H, m), 3.59-3.68 (2 H, m), 4.46 (1 H, m), 6.83 (1 H, d, J 7.4), 7.14 (1 H, d, J 7.4), 7.24 (1 H, s), 9.39 (1 H, m).

LCMS: [M+H]$^+$401.

Hunig's Base (0.02 mL, 0.12 mmol) was added to a solution of 2-({1-[trans-1-methyl-4-(propyloxy)cyclohexyl]-4-piperidinyl}amino)-4-[(trifluoromethyl)sulfonyl]phenol (D84, 22 mg, 0.05 mmol) in DCM (3 mL) at rt under Ar. The reaction was cooled to 0° C. and the triphosgene (12 mg, 0.04 mmol) was added. The mixture was stirred for 2 h at 0° C. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a yellow oil. The residue was purified via flash column chromatography (silica, DCM to 0.5% NH$_3$/9.5% MeOH/90% DCM) to give the free base of the title compound as a colourless oil. HCl (0.1 mL, 0.1 mmol, 1 M in Et$_2$O) was added to a solution of the free base in DCM (0.5 mL) and the solvent was removed by rotary evaporation. The resulting solid was triturated with Et$_2$O to give 3{1-[trans-1-methyl-4-(propyloxy)cyclohexyl]-4-piperidinyl}-5-[(trifluoromethyl)sulfonyl]-1,3-benzoxazol-2(3H)-one hydrochloride (E29, 20 mg, 76%) as a cream solid.

$^1$H NMR δ (DMSO-d$_6$, 400 MHz) 0.87 (3 H, t, J 7.4), 1.27-1.40 (5 H, m), 1.44-1.54 (2 H, m), 1.68-1.79 (2 H, m), 1.94-2.04 (4 H, m), 2.10-2.18 (2 H, m), 2.54-2.66 (2 H, m), 3.09-3.22 (3 H, m), 3.38 (2 H, t, J 6.6), 3.66-3.73 (2 H, m), 4.67 (1 H, m), 7.81 (1 H, d, J 8.5), 7.99 (1 H, dd, J 8.5 and 1.9), 8.11 (1 H, d, J 1.9), 9.25 (1 H, m).

LCMS: [M+H]$^+$505.

EXAMPLE 30

6-Methyl-3-{1-[trans-1-methyl-4-(propyloxy)cyclohexyl]-4-piperidinyl}-5-(methylsulfonyl)-1,3-benzoxazol-2(3H)-one hydrochloride. (E30)

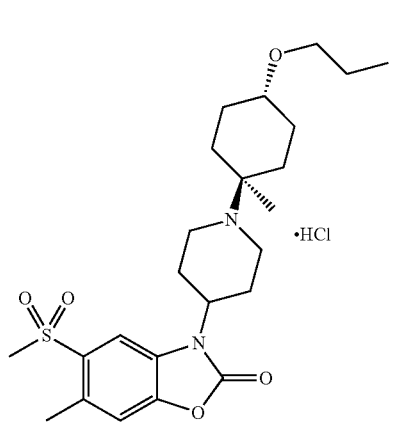

E30

Hunig's base (0.05 mL, 0.29 mmol) was added to a solution of 5-methyl-2-({1-[trans-1-methyl-4-(propyloxy)cyclohexyl]-4-piperidinyl}amino)-4-(methylsulfonyl)phenol (D88, 49 mg, 0.11 mmol) in DCM (3 mL) at rt under Ar. The reaction was cooled to 0° C. and triphosgene (22 mg, 0.07 mmol) was added. The mixture was stirred for 2 h at 0° C. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a yellow oil, which was purified via flash column chromatography (silica, DCM to 0.5% NH$_3$/9.5% MeOH/90% DCM) to give the free base of the title compound as a cream solid. HCl (0.16 mL, 0.16 mmol, 1 M in Et$_2$O) was added to a solution of the free base in DCM (0.5 mL) and the solvent was removed by rotary evaporation. The resulting solid was triturated with Et$_2$O to give 6-methyl-3-{1-[trans-1-methyl-4-(propyloxy)cyclohexyl]-4-piperidinyl}-5-(methylsulfonyl)-1,3-benzoxazol-2(3H)-one hydrochloride (E30, 43 mg, 74%) as a cream solid.

$^1$H NMR δ (DMSO-d$_6$, 400 MHz) 0.87 (3 H, t, J 7.4), 1.26-1.40 (5 H, m), 1.43-1.54 (2 H, m), 1.70-1.82 (2 H, m), 1.93-2.04 (4 H, m), 2.06-2.15 (2 H, m), 2.55-2.70 (5 H, m), 3.12-3.31 (6 H, m), 3.38 (2 H, t, J 6.6), 3.62-3.72 (2 H, m), 4.60 (1 H, m), 7.53 (1 H, s), 7.89 (1 H, s), 9.40 (1 H, m).

LCMS: [M+H]$^+$465.

EXAMPLE 31

6-Methyl-5-(methylsulfonyl)-3-{1-[trans-4-(propyloxy)cyclohexyl]-4-piperidinyl}-1,3-benzoxazol-2(3H)-one hydrochloride. (E31)

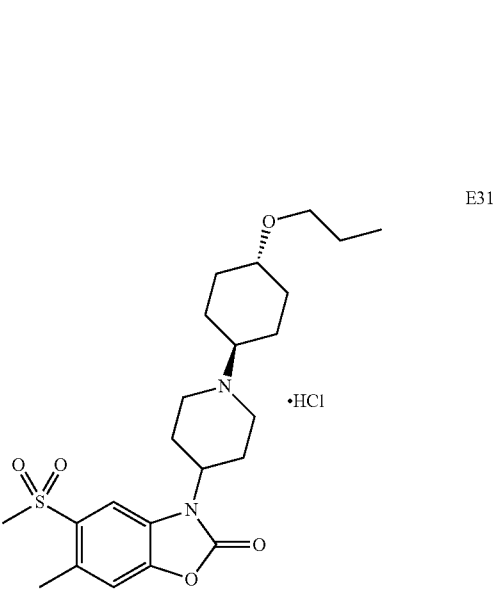 [SMILES: CCCO[C@H]1CC[C@H](N2CCC(n3c(=O)oc4cc(C)c(S(C)(=O)=O)cc43)CC2)CC1 ; Cl]

E31

Hunig's base (0.01 mL, 0.06 mmol) was added to a solution of 5-methyl-4-(methylsulfonyl)-2-({1-[trans-4-(propyloxy)cyclohexyl]-4-piperidinyl}amino)phenol (D89, 14 mg, 0.03 mmol) in DCM (3 mL) at rt under Ar. The reaction was cooled to 0° C. and the triphosgene (5 mg, 0.02 mmol) was added. The mixture was stirred for 2 h at 0° C. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a yellow oil, which was purified via flash column chromatography (silica, DCM to 0.5% NH$_3$/9.5% MeOH/90% DCM) to give the free base of the title compound as a pale yellow oil. HCl (0.1 mL, 0.1 mmol, 1 M in Et$_2$O) was added to a solution of the free base in DCM (0.5 mL) and the solvent was removed by rotary evaporation. The resulting solid was triturated with Et$_2$O to give 6-methyl-5-(methylsulfonyl)-3-{1-[trans-4-(propyloxy)cyclohexyl]-4-piperidinyl}-1,3-benzoxazol-2(3H)-one hydrochloride (E31; 11 mg, 62%) as a cream solid.

$^1$H NMR δ (DMSO-d$_6$, 400 MHz) 0.86 (3 H, t, J 7.4), 1.14-1.26 (2 H, m), 1.43-1.59 (4 H, m), 2.01-2.15 (6 H, m), 2.67 (3 H, s), 3.16-3.31 (7 H, m), 3.37 (2 H, t, J 6.6), 3.49-3.57 (2 H, m), 4.57 (1 H, m), 7.53 (1 H, s), 7.87 (1 H, s), 9.63 (1 H, m). Note: 2 H not visible in NMR spectrum as obscured by solvent.

LCMS: [M+H]$^+$451.

EXAMPLE 32

5-Methyl-3-[1-(trans-1-methyl-4-{[2-(methyloxy)ethyl]oxy}cyclohexyl)-4-piperidinyl]-2-oxo-2,3-dihydro-1,3-benzoxazole-6-carbonitrile hydrochloride. (E32)

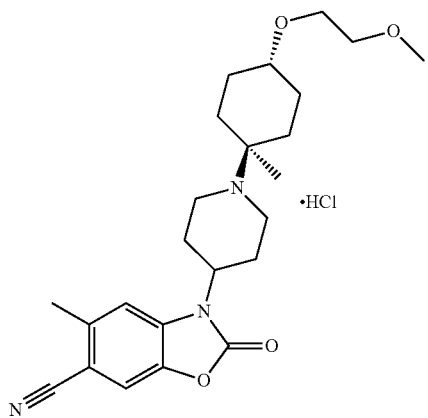

Hunig's Base (0.06 mL, 0.34 mmol) was added to a solution of 5-hydroxy-2-methyl-4-{[1-(trans-1-methyl-4-{[2-(methyloxy)ethyl]oxy}cyclohexyl)-4-piperidinyl]amino}benzonitrile (D93, 62 mg, 0.16 mmol) in DCM (3 mL) at rt under Ar. The reaction was cooled to 0° C. and the triphosgene (21 mg, 0.07 mmol) was added. The mixture was stirred for 2 h at 0° C. The reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a yellow oil. The crude residues were purified via flash column chromatography (silica, DCM to 0.5% NH$_3$/9.5% MeOH/90% DCM) to give the free base of the title compound as a colourless oil. HCl (0.2 mL, 0.2 mmol, 1 M in Et$_2$O) was added to a solution of the free base in DCM (0.5 mL) and the solvent was removed by rotary evaporation. The resulting solid was triturated with Et$_2$O to give 5-methyl-3-[1-(trans-1-methyl-4-{[2-(methyloxy)ethyl]oxy}cyclohexyl)-4-piperidinyl]-2-oxo-2,3-dihydro-1,3-benzoxazole-6-carbonitrile hydrochloride (E32, 49 mg, 64%) as a beige solid.

$^1$H NMR δ (DMSO-d$_6$, 400 MHz) 1.26-1.39 (5 H, m), 1.82-1.93 (2 H, m), 1.94-2.10 (6 H, m), 2.53 (3 H, s), 2.72-2.85 (2 H, m), 3.12-3.28 (6 H, m), 3.40-3.45 (2 H, m), 3.53-3.58 (2 H, m), 3.62-3.72 (2 H, m), 4.58 (1 H, m), 7.87 (1 H, s), 7.99 (1 H, s), 10.09 (1 H, m).

LCMS: [M+H]$^+$428.

EXAMPLE 33

5-(Difluoromethoxy)-3-{1-[trans-4-(ethyloxy)-1-methylcyclohexyl]-4-piperidinyl}-1,3-benzoxazol-2(3H)-one hydrochloride. (E33)

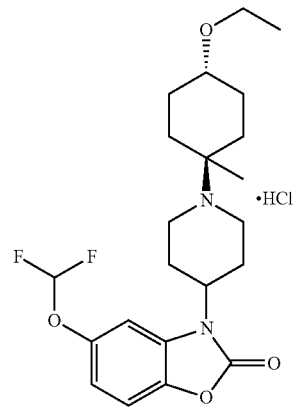

4-(Difluoromethoxy)-2-({1-[trans-4-(ethyloxy)-1-methylcyclohexyl]-4-piperidinyl}amino)-phenol (D96, 118 mg, 0.296 mmol) was dissolved in DCM (5 mL) and DIPEA (0.052 mL, 0.296 mmol) was added. The reaction mixture was cooled to 0° C. under argon and triphosgene (58.0 mg, 0.195 mmol) was added. The reaction mixture was stirred for 1 h. The reaction mixture was treated with saturated sodium bicarbonate solution (4 mL), then diluted with DCM and water (6 mL of each). The layers were separated and the organic layer dried (MgSO$_4$) and evaporated. The residue was purified by flash column chromatography, using a pre-packed silica cartridge (10 g), eluting with 0-3% 0.2 M ammonia in methanol in DCM to afford the product as a colourless oil. This was converted to an HCl salt by treating with 2 M HCl in diethyl ether, giving a white solid (E33, 45 mg).

(M+H)$^+$=425.

$^1$H NMR δ (CD$_3$OD): 1.18 (3H, t, J=6.8 Hz), 1.43-1.48 (2H, m), 1.46 (3H, s), 1.86 (2H, m), 2.12 (4H, m), 2.21 (2H, m), 2.82 (2H, m), 3.25-3.34 (3H, m), 3.57 (2H, q, J=6.8 Hz), 3.83 (2H, m), 4.55 (1H, m), 6.90 (1H, t, J=74.0 Hz), 6.96 (1H, d, J=8.4 Hz), 7.28 (1H, d, J=8.8 Hz), 7.41 (1H, s).

EXAMPLE 34

5-Methyl-3-[1-(trans-1-methyl-4-{[2-(methyloxy)ethyl]oxy}cyclohexyl)-4-piperidinyl]-1,3-benzoxazol-2(3H)-one hydrochloride. (E34)

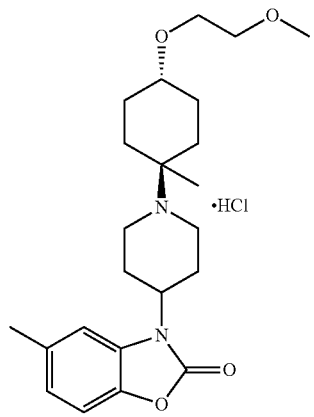

4-Methyl-2-{[1-(trans-1-methyl-4-{[2-(methyloxy)ethyl]oxy}cyclohexyl)-4-piperidinyl]-amino}phenol (D97, 56 mg, 0.149 mmol) was dissolved in DCM (3 mL) and DIPEA (0.052 mL, 0.297 mmol) was added. The reaction mixture was cooled to 0° C. and triphosgene (33 mg, 0.111 mmol) was added. The reaction mixture was stirred for 1.5 h. LC/MS analysis showed the reaction to be incomplete. An additional 0.75 eq. of triphosgene (33 mg) was added and the reaction mixture stirred for 42 h. The reaction mixture was treated with saturated sodium bicarbonate solution (2 mL) and stirred for 15 min. The reaction mixture was diluted with DCM and water (6 mL of each) and the layers separated using a phase separator cartridge. The organic layer was evaporated to dryness to give a colourless oil. The crude product was purified by flash column chromatography on a pre-packed silica cartridge (column size 10 g), eluting with 3-7% 2 M ammonia in methanol in DCM to afford the product as a colourless oil. This was treated with 2 M HCl in diethyl ether to afford the HCl salt E34 as a white solid (38 mg).

$(M+H)^+=403$.

$^1$H NMR δ (CD$_3$OD): 1.43-1.51 (1H, m), 1.47 (3H, s), 1.83 (2H, m), 2.15 (6H, m), 2.42 (3H, s), 2.80 (2H, m), 3.24-3.40 (7H, m), 3.53 (2H, m), 3.65 (2H, m), 3.83 (2H, m), 4.51 (1H, m), 6.98 (1H, d, J=8.4 Hz), 7.13 (1H, d, J=8.0 Hz), 7.33 (1H, s).

EXAMPLE 35

3-[1-(trans-1-Methyl-4-{[2-(methyloxy)ethyl]oxy}cyclohexyl)-4-piperidinyl]-5-(methyloxy)-1,3-benzoxazol-2(3H)-one hydrochloride. (E35)

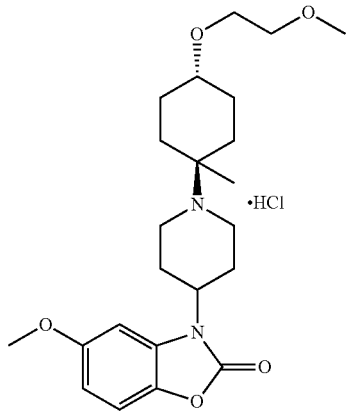

2-{[1-(trans-1-methyl-4-{[2-(methyloxy)ethyl]oxy}cyclohexyl)-4-piperidinyl]amino}-4-(methyloxy)phenol (D98, 31 mg, 0.079 mmol) was dissolved in DCM (3 mL) and DIPEA (0.043 mL, 0.246 mmol) was added. The reaction mixture was cooled to 0° C. and triphosgene (37 mg, 0.125 mmol) was added. The reaction mixture was stirred for 64 h, warming to room temperature. The reaction mixture was treated with saturated sodium bicarbonate solution. The reaction mixture was diluted with DCM and water (6 mL of each) and the layers separated with a phase separator cartridge. The organic layer was evaporated to dryness. The crude product was purified by flash column chromatography on a pre-packed silica cartridge (column size 10 g), eluting with 2-5% 0.2 M ammonia in methanol in DCM to afford the desired product as a colourless oil. This was treated with 2 M HCl in diethyl ether to afford the HCl salt E35 as a white solid (10 mg).

$(M+H)^+=419$.

$^1$H NMR δ (CD$_3$OD): 1.45-1.48 (2H, m), 1.46 (3H, s), 1.89 (2H, m), 2.15 (6H, m), 2.85 (2H, m), 3.29 (2H, m), 3.37 (4H, m), 3.52 (2H, m), 3.64 (2H, m), 3.82 (1H, s), 3.85 (3H, s), 4.55

(1H, m), 6.70 (1H, m), 7.15 (2H, m). Note: 1H not visible in NMR spectrum as obscured by solvent or water.

EXAMPLE 36

3-(1-{trans-4-[(Cyclopropylmethyl)oxy]-1-methyl-cyclohexyl}-4-piperidinyl)-5-(methylsulfonyl)-1,3-benzoxazol-2(3H)-one hydrochloride. (E36)

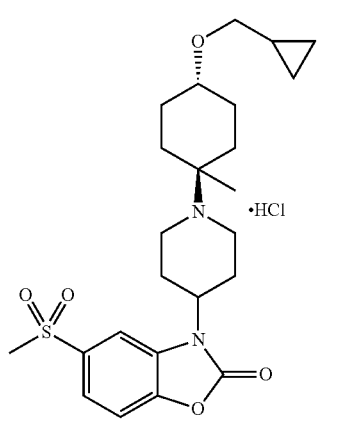

2-[(1-{trans-4-[(Cyclopropylmethyl)oxy]-1-methylcyclohexyl}-4-piperidinyl)amino]-4-(methylsulfonyl)phenol (D106, 80 mg, 0.183 mmol) was suspended in DCM (5 mL) and DIPEA (0.065 mL, 0.372 mmol) was added. The reaction mixture was cooled to 0° C. and triphosgene (35.9 mg, 0.121 mmol) was added. The reaction mixture was stirred at 0° C. for 1 h, then allowed to warm to room temperature. The reaction mixture was treated with saturated sodium bicarbonate solution (4 mL) and stirred for 10 min. The reaction mixture was diluted with DCM and water (10 mL each) and the layers separated. The aqueous layer was extracted with DCM (2×10 mL) and the combined organics were dried (MgSO$_4$) and evaporated. The crude product was purified by flash column chromatography on a pre-packed silica cartridge (column size 10 g), eluting with 3-6% 0.2 M ammonia in methanol in DCM, to afford the desired product as a colourless oil. This was treated with 2 M HCl in diethyl ether to afford the desired product E36 as an HCl salt (72 mg).

(M+H)$^+$=463.

$^1$H NMR δ (CD$_3$OD): 0.21 (2H, m), 0.50 (2H, m), 1.02 (1H, m), 1.45 (5H, m), 1.85 (2H, m), 2.12 (4H, m), 2.25 (2H, m), 2.85 (2H, m), 3.21 (3H, s), 3.32 (5H, m), 3.85 (2H, m), 4.65 (1H, m), 7.50 (1H, d, J=8.4 Hz), 7.81 (1H, m), 8.07 (1H, s).

EXAMPLE 37

3-(1-{trans-1-Methyl-4-[(1-methylethyl)oxy]cyclohexyl}-4-piperidinyl)-5-(methylsulfonyl)-1,3-benzoxazol-2(3H)-one hydrochloride. (E37)

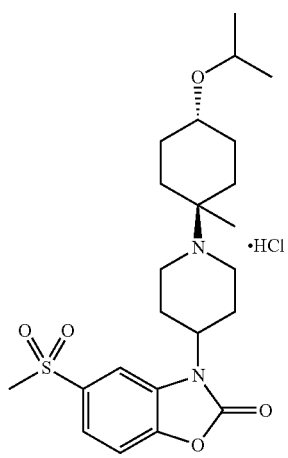

2-[(1-{trans-1-methyl-4-[(1-methylethyl)oxy]cyclohexyl}-4-piperidinyl)amino]-4-(methylsulfonyl)phenol (D113, 125 mg, 0.247 mmol) was dissolved in DCM (5 mL) and DIPEA (0.151 mL, 0.866 mmol) was added. The reaction mixture was cooled to 0° C., then triphosgene (49 mg, 0.165 mmol) was added. The reaction mixture was stirred at 0° C. for 1.5 h. The reaction mixture was treated with saturated sodium bicarbonate solution (5 mL) and stirred for 10 min. The reaction mixture was diluted with DCM and water (10 mL of each) and the layers separated. The aqueous layer was extracted with DCM (2×10 mL). The combined organics were dried (MgSO$_4$) and evaporated. The crude product was purified by flash column chromatography on a pre-packed silica cartridge (column size 10 g), eluting with 3-6% (0.2 M ammonia in methanol) in DCM to give a colourless oil. This was treated with 2 M HCl in diethyl ether to afford the desired product E37 as an HCl salt (74 mg).

(M+H)$^+$=451.

$^1$H NMR δ (CD$_3$OD): 1.15 (6H, d, J=6.0 Hz), 1.46 (5H, m), 1.84 (2H, m), 2.06 (4H, m), 2.25 (2H, m), 2.82 (2H, m), 3.20 (3H, s), 3.26 (1H, m), 3.43 (1H, m), 3.81 (3H, m), 4.63 (1H, m), 7.50 (1H, m), 7.82 (1H, m), 8.04 (1H, s). Note: 1H not visible in NMR spectrum as obscured by solvent or water.

EXAMPLE 38

3-[1-(trans-1-methyl-4-{[2-(methyloxy)ethyl]oxy}cyclohexyl)-4-piperidinyl]-5-(trifluoromethyl)-1,3-benzoxazol-2(3H)-one hydrochloride. (E38)

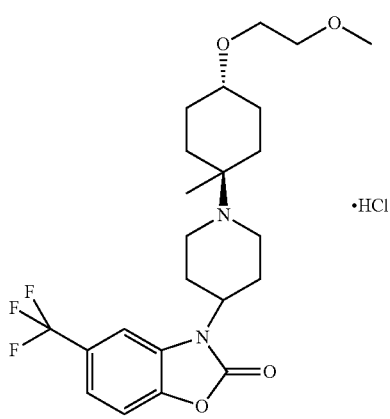

E38

2-{[1-(trans-1-Methyl-4-{[2-(methyloxy)ethyl]oxy}cyclohexyl)-4-piperidinyl]amino}-4-(trifluoromethyl)phenol (D114, 109 mg, 0.253 mmol) was dissolved in dichloromethane (DCM) (5 mL) and cooled to 0° C. in an ice bath. DIPEA (0.15 mL, 0.859 mmol) was added followed by triphosgene (50 mg, 0.168 mmol). The reaction mixture was left to stir for 30 min at 0° C. and 30 min at RT. The mixture was washed with aqueous sodium bicarbonate, passed through a phase separation cartridge and evaporated to give a clear oil. Purified by column (10 g) eluting with 0-10% 2M NH$_3$/MeOH/DCM to give a clear oil. Treated with 4M HCl in dioxan, evaporated to dryness to give a white solid 3-[1-(trans-1-methyl-4-{[2-(methyloxy)ethyl]oxy}cyclohexyl)-4-piperidinyl]-5-(trifluoromethyl)-1,3-benzoxazol-2(3H)-one hydrochloride (E38, 96.9 mg, 0.197 mmol, 78% yield).

$^1$H NMR δ (DMSO-d$_6$, 400 MHz) 1.23-1.35 (5 H, m), 1.87-2.08 (6 H, m), 2.79-2.88 (2 H, m), 3.17-3.24 (5 H, m), 3.32 (3 H, s), 3.41-3.43 (2 H, m), 3.54-3.59 (2 H, m), 3.66-3.73 (2H, m), 4.59-4.65 (1 H, m), 7.52-7.68 (2 H, m), 8.14 (1 H, s), 10.4 (1 H, m).

m/z (M+H)$^+$ 457.

EXAMPLE 39

6-Fluoro-5-methyl-3-[1-(trans-1-methyl-4-{[2-(methyloxy)ethyl]-oxy}cyclohexyl)-4-piperidinyl]-1,3-benzoxazol-2(3H)-one hydrochloride. (E39)

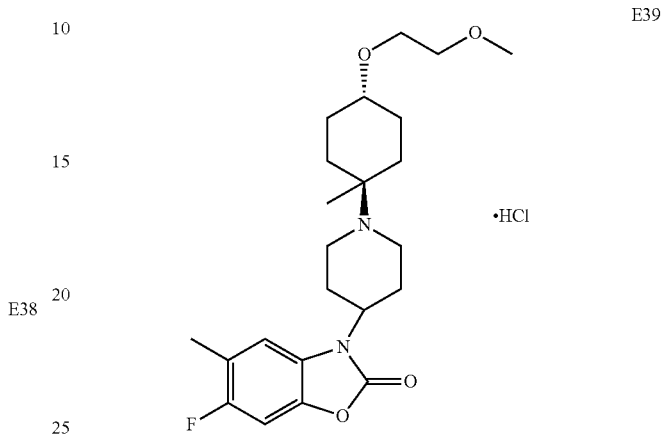

E39

The title compound was prepared from the compound of Description 73 and 2-amino-5-fluoro-4-methylphenol using the methods of Description 114 and Example 38.

$^1$H NMR δ (DMSO-d$_6$, 400 MHz) 1.23-1.32 (5 H, m), 1.82-2.02 (6 H, m), 2.27 (3 H, s) 2.81-2.90 (2 H, m), 3.15-3.24 (5 H, m), 3.32 (3 H, s), 3.40-3.43 (2 H, m), 3.53-3.59 (2 H, m), 3.64-3.71 (2H, m), 4.52-4.58 (1 H, m), 7.34-7.36 (1 H, d, J=8.0 Hz)), 7.96-7.97 (1 H, d, J=4.0 Hz)), 10.5 (1 H, m).

m/z (M+H)$^+$ 421.

EXAMPLE 40

7-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride. (E40)

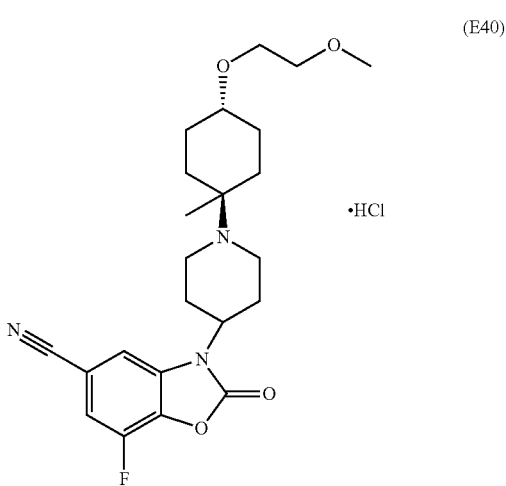 [SMILES: COCCO[C@H]1CC[C@](C)(N2CCC(n3c(=O)oc4c(F)cc(C#N)cc43)CC2)CC1 ; Cl]

(E40)

The title compound was prepared from the compound of Description 73 and 3-amino-5-fluoro-4-hydroxybenzonitrile (see WO 2005074603 for synthesis) using the methods of Description 114 and Example 38.

$^1$H NMR δ (MeOH-$d_4$, 400 MHz) 0.87-0.96 (2 H, m), 1.12-1.46 (6 H, m), 1.83-1.88 (2 H, t) 2.12-2.15 (3 H, m), 2.25-2.51 (2 H, m), 2.76-2.85 (2 H, m), 3.18-3.37 (6 H, m), 3.51-3.56 (2 H, m), 3.63-3.65 (2 H, m), 4.57-4.67 (1 H, m), 7.51-7.42 (1 H, d), 7.82 (1 H, s).

m/z (M+H)$^+$ 432.

EXAMPLE 41

7-Fluoro-5-methyl-3-[1-(trans-1-methyl-4-{[2-(methyloxy)ethyl]oxy}cyclohexyl)-4-piperidinyl]-1,3-benzoxazol-2(3H)-one hydrochloride. (E41)

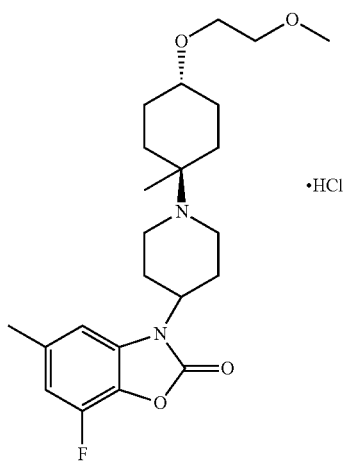

E41

The title compound was prepared from the compounds of Description 73 and Description 116 using the methods of Description 114 and Example 38.

$^1$H NMR δ (DMSO-$d_6$, 400 MHz) 1.25-1.36 (5 H, m), 1.91-2.03 (6 H, m), 2.35 (3 H, s) 2.81-2.90 (2 H, m), 3.15-3.24 (5 H, m), 3.32 (3 H, s), 3.40-3.49 (2 H, m), 3.53-3.59 (2 H, m), 3.64-3.71 (2H, m), 4.52-4.59 (1 H, m), 6.92-6.95 (1 H, d), 7.70 (1 H, s), 10.5 (1 H, m).

m/z (M+H)$^+$ 421.

EXAMPLE 42

6-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile hydrochloride. (E42)

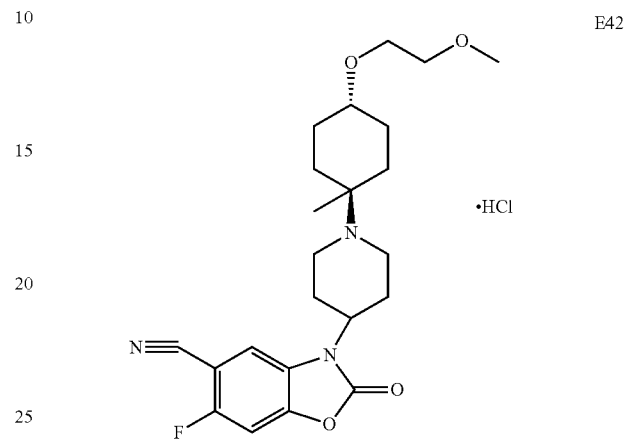

E42

The title compound was prepared from the compound of Description 73 and 5-amino-2-fluoro-4-hydroxybenzonitrile (D148) using the methods of Description 114 and Example 38.

$^1$H NMR δ (MeOH-$d_4$, 400 MHz) 1.39-1.50 (3 H, m), 1.86-1.98 (2 H, m), 2.12-2.20 (3 H, m), 2.23-2.34 (2 H, m), 2.76-2.82 (2 H, m), 3.24-3.36 (9 H, m), 3.63-3.65 (2 H, m), 3.82-3.85 (2 H, m), 4.57-4.67 (1 H, m), 7.43-7.45 (1 H, d), 7.91-7.93 (1 H, m).

m/z (M+H)$^+$ 432.

EXAMPLE 43

3-[1-(trans-1-Methyl-4-{[2-(methyloxy)ethyl]oxy}cyclohexyl)-4-piperidinyl]-5-(methylsulfonyl)-1,3-benzoxazol-2(3H)-one hydrochloride. (E43)

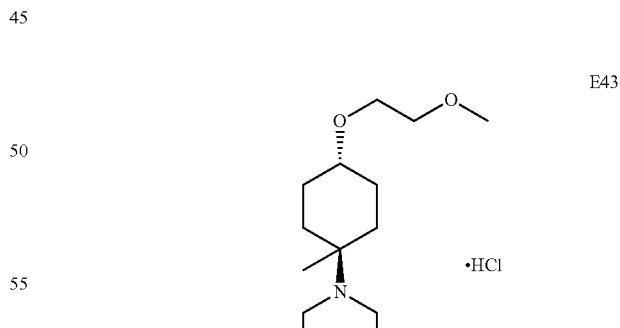

E43

The title compound was prepared from the compound of Description 73 and 2-amino-4-(methylsulfonyl)phenol using the methods of Description 114 and Example 38.

¹H NMR δ (MeOH-d₄, 400 MHz) 1.5 (2 H, m), 1.75 (2H, m), 2.2 (4H, m), 2.25 (2H, m), 2.75 (2H, m), 3.15 (3H, s), 3.3 (6 H, s and m, obscured by MeOH peak), 3.4 (3H, s), 3.55 (2H, m), 3.65 (2H, m), 3.85 (2H, m), 4.6 (1H, m), 7.5 (1H, d J=6.0 Hz), 7.8 (1H, d J=6.0 Hz), 7.95 (1H, s).

m/z (M+H)⁺ 467.

EXAMPLE 44

3-[1-(trans-1-Methyl-4-{[2-(methyloxy)ethyl]oxy}cyclohexyl)-4-piperidinyl]-5-[(methyloxy)methyl]-1,3-benzoxazol-2(3H)-one hydrochloride. (E44)

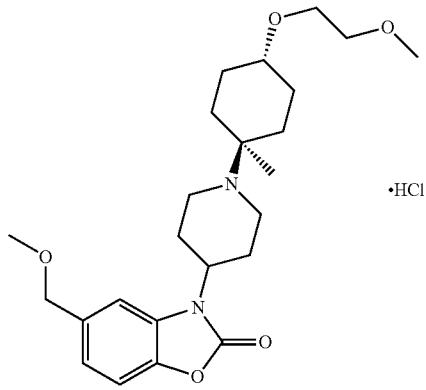

E44

To a stirred mixture of 2-{[1-(trans-1-methyl-4-{[2-(methyloxy)ethyl]oxy}cyclohexyl)-4-piperidinyl]amino}-4-[(methyloxy)methyl]phenol D121 (58 mg, 0.143 mmol), and DIPEA (0.050 mL, 0.285 mmol) in dichloromethane (DCM) (5 mL) cooled to 0° C. under argon was added, in portions, triphosgene (16.93 mg, 0.057 mmol). After stirring at 0° C. for 1 hr the reaction was quenched with dilute aq potassium bicarbonate (5 mL). The organic phase was separated, dried (MgSO₄) and concentrated to dryness in vacuo. The reside was subjected to silica gel chromatography using a Biotage Horizon with a 12+M cartridge and eluting with 0-10% MeOH/DCM over 12 CVs. The product 53 mg, was isolated as a thick colourless oil, which was dissolved in dichloromethane (DCM) (5 mL) and treated with 1M HCl (0.2 mL) after stirring for 20 mins the mixture was concentrated to dryness under vacuum and the residue triturated in diethyl ether to afford the title compound E44 as a colourless solid 44 mg, 65.8%.

¹H NMR δ (DMSO-d₆, 400 MHz) 1.33 (3H, m), 1.79-2.05 (8H, m), 2.87 (2H, q), 3.11-3.23 (5H, m), 3.25 (3H, s), 3.29 (3H, s), 3.41 (2 H, m), 3.50-3.67 (5H, m), 4.43 (1 H, s), 4.55 (1H, t), 7.10 (1 H, d), 7.31 (1 H, d), 7.86 (1 H, s), 10.28 (1 H, m).

M+H⁺ 433.

EXAMPLE 45a

1-[1-(trans-1-Methyl-4-[2-(methoxyethoxy)cyclohexyl]-4-piperidinyl]-6-(methoxymethyl)-1,3-dihydro-2H-indol-2-one. (E45a)

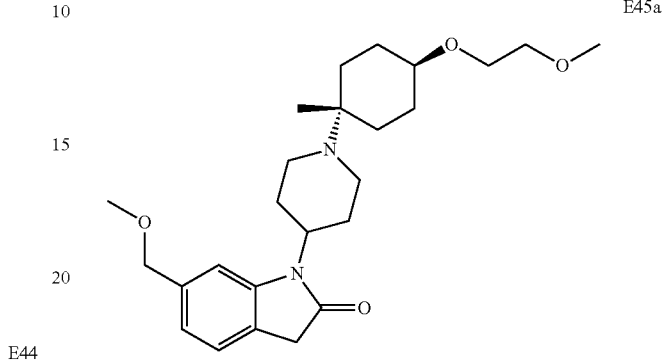

E45a

A mixture of bis(1,1-dimethylethyl) {2-amino-4-[(methyloxy)methyl]phenyl} propanedioate (D124) (100 mg, 0.285 mmol), 1-(trans-1-methyl-4-[2-(methoxyethoxy)cyclohexyl]-4-piperidinone (D73) (100 mg, 0.371 mmol), acetic acid (0.2 mL, 3.49 mmol), dichloromethane (2.5 mL), and polymer supported cyanoborohydride (100 mg, 0.410 mmol) was heated to 110° C. for 45 min in the microwave. Filtration and evaporation gave crude product which was purified by MDAP to give 1-[1-(trans-1-methyl-4-(2-(methoxyethoxy)cyclohexyl]-4-piperidinyl]-6-(methoxymethyl)-1,3-dihydro-2H-indol-2-one (E45a, 8 mg, 0.019 mmol, 6.53% yield) free base as a colourless oil.

¹H NMR δ (CDCl₃, 400 MHz, free base) 0.9 (3 H, s), 1.5 (4 H, m), 1.7 (7 H, m), 1.9 (2H, m), 2.2 (2 H, t), 2.4 (2 H, q), 3.1 (2 H, d), 3.4 (6 H, 2s), 3.5 (2 H, s), 3.6 (2 H, ABq), 4.2 (1 H, m), 4.5 (2 H, s), 6.9 (1 H, d), 7.1 (1 H, s), and 7.2 (1 H, s).

[M+H]⁺ 430.

EXAMPLE 45b

1-[1-(trans-1-Methyl-4-[2-(methoxyethoxy)cyclohexyl]-4-piperidinyl]-6-(methoxymethyl)-1,3-dihydro-2H-indol-2-one hydrochloride. (E45b)

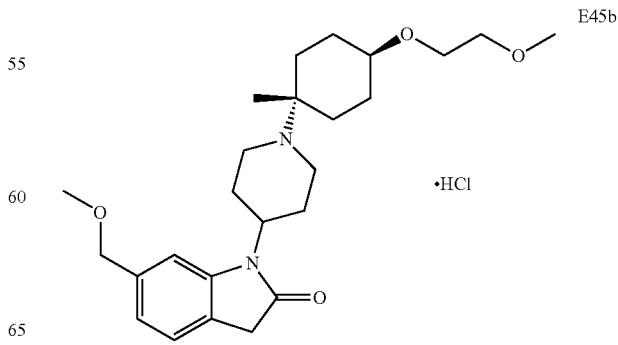

E45b

A mixture of di t-butyl {2-amino-4-(methoxymethyl)phenyl}malonate (250 mg, 0.711 mmol) (D124), 1-(trans-1-methyl-4-{[2-(methoxyethoxy}cyclohexyl)-4-piperidinone (150 mg, 0.557 mmol) (D73), acetic acid (0.2 mL, 3.49 mmol), dichloromethane (2.5 mL), and polymer supported cyanoborohydride (150 mg, 0.615 mmol) was heated to 100° C. for 1 h in the microwave. Filtration, evaporation, purification by MDAP, and conversion to the hydrochloride salt gave 1-[1-(trans-1-methyl-4-[(2-(methoxyethoxy)cyclohexyl]-4-piperidinyl)-6-(methoxymethyl)-1,3-dihydro-2H-indol-2-one hydrochloride (E45b, 19 mg, 0.039 mmol, 6.94% yield) as a beige powder from diethyl ether.

$^1$H NMR δ (DMSO-$d_6$, 400 MHz, HCl salt) 1.4 (8 H, m), 1.7 (2 H, t), 1.8 (2 H, d), 2.0 (4H, m), 2.7 (2 H, q), 3.2-3.6 (14 H, m), 4.4 (3 H, m), 6.9 (1 H, d), 7.2 (1 H, d), 7.3 (1 H, s), and 9.4 (1 H, bs).

[M+H]$^+$ 430.

EXAMPLE 46

3-{1-[trans-4-(Ethyloxy)-1-methylcyclohexyl]-4-piperidinyl}-2-oxo-2,3-dihydro-1,3-benzoxazole-5-carboxamide hydrochloride. (E46)

EXAMPLE 47

3-[1-(trans-1-Methyl-4-{[2-(methyloxy)ethyl]oxy}cyclohexyl)-4-piperidinyl]-2-oxo-2,3-dihydro-1,3-benzoxazole-5-carboxamide hydrochloride. (E47)

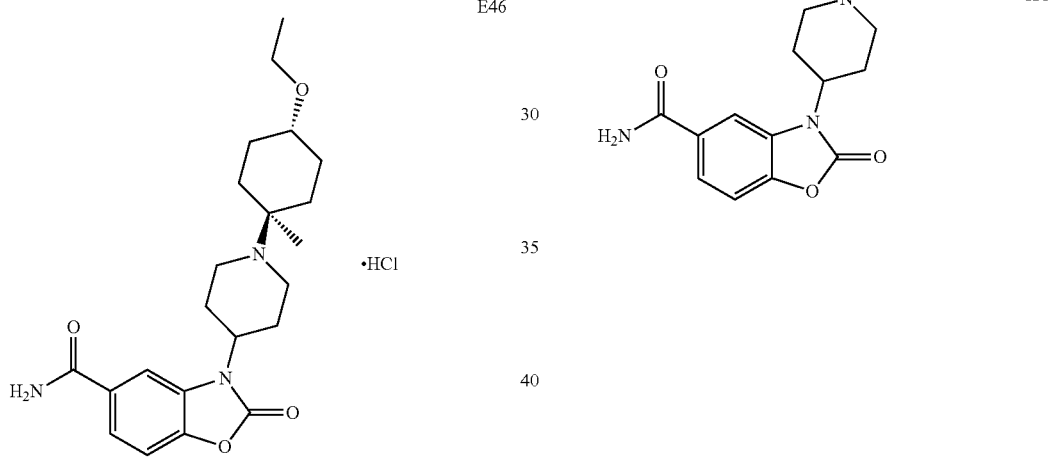

To a stirred mixture of 3-({1-[trans-4-(ethyloxy)-1-methylcyclohexyl]-4-piperidinyl}amino)-4-hydroxybenzamide D127 (48 mg, 0.128 mmol), and DIPEA (0.045 mL, 0.256 mmol) in dichloromethane (DCM) (5 mL) cooled to room temp under argon was added, in small portions, triphosgene (15.17 mg, 0.051 mmol). After stirring for 1 hr the reaction was quenched with dilute aq potassium bicarbonate (5 mL). The organic phase was separated, dried (MgSO$_4$) and concentrated to dryness in vacuo. The reside was subjected to silica gel chromatography using a Biotage Horizon with a 12+M cartridge and eluting with 0-10% MeOH/DCM over 12 CVs. The product was isolated as a thick colourless oil and was dissolved in dichloromethane (DCM) (5 mL) and treated with 1M HCl (0.2 mL) after stirring for 20 mins the mixture was concentrated to dryness under vacuum and the residue triturated in diethyl ether to give the title compound E46 as a colourless solid (34 mg, 57.7%).

$^1$H NMR δ (DMSO-$d_6$, 400 MHz) 1.09 (3H, t, J=6.8 Hz), 1.28-1.34 (6H, m), 1.89-2.09 (9H, m), 2.98 (2H, q), 3.12-3.27 (3H, m), 3.46 (2H, q), 4.64 (1H, m), 7.43 (1 H, d, J=6.8 Hz), 7.53 (1H, s), 7.79 (1H, d, J=6.8 Hz), 8.17 (1H, s), 8.49 (1H, s), 10.14 (1 H, m).

LC/MS 402 (MH+).

To a stirred mixture of 4-hydroxy-3-{[1-(trans-1-methyl-4-{[2-(methyloxy)ethyl]-oxy}cyclohexyl)-4-piperidinyl]amino}benzamide D128 (27 mg, 0.061 mmol), and DIPEA (0.021 mL, 0.122 mmol) in dichloromethane (DCM) (5 mL) at room temp under argon was added, in small portions, triphosgene (7.25 mg, 0.024 mmol). After stirring for 1 hr the reaction was quenched with dilute aq potassium bicarbonate (5 mL). The organic phase was separated, dried (MgSO$_4$) and concentrated to dryness in vacuo. The reside was subjected to silica gel chromatography using a Biotage Horizon with a 12+M cartridge and eluting with 0-10% MeOH/DCM over 12 CVs. The product was isolated as a thick colourless oil which was dissolved in dichloromethane (DCM) (5 mL) and treated with 1M HCl (0.2 mL) after stirring for 20 mins the mixture was concentrated to dryness under vacuum and the residue triturated in diethyl ether to give the title compound E47 as a colourless solid (17 mg, 56.5%).

$^1$H NMR δ (DMSO-$d_6$, 400 MHz) 1.24-1.34 (6H, m), 1.87-2.09 (9H, m), 2.87 (2H, q), 3.25 (5H, m), 3.55 (2H, m), 3.70 (3H, m), 4.64 (1H, m), 7.43 (1 H, d, J=6.8 Hz), 7.53 (1H, s), 7.79 (1H, d, J=6.8 Hz), 8.16 (1H, s), 8.46 (1H, s), 10.08 (1 H, m).

LC/MS 402 (MH$^+$).

EXAMPLE 48

5-Acetyl-3-[1-(trans-1-methyl-4-{[2-(methyloxy)ethyl]oxy}cyclohexyl)-4-piperidinyl]-1,3-benzoxazol-2(3H)-one hydrochloride. (E48)

EXAMPLE 49

3-[1-(trans-1-Methyl-4-{[2-(methyloxy)ethyl]oxy}cyclohexyl)-4-piperidinyl]-5[N-(methyloxy)ethanimidoyl]-1,3-benzoxazol-2(3H)-one hydrochloride. (E49)

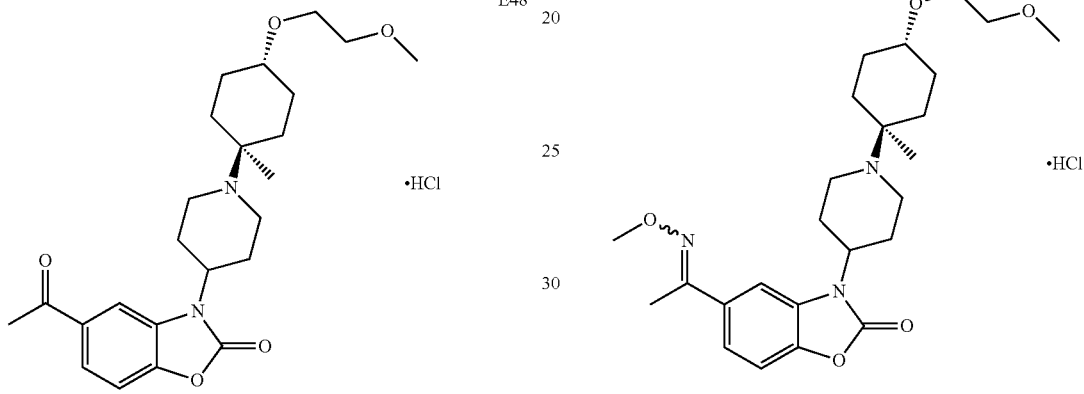

E48

E49

To a stirred solution of 1-(4-hydroxy-3-{[1-(trans-1-methyl-4-{[2-(methyloxy)ethyl]oxy}cyclohexyl)-4-piperidinyl]amino}phenyl)ethanone D131 (30 mg, 0.074 mmol) and DIPEA (0.026 mL, 0.148 mmol) in dichloromethane (DCM) (3 mL) at 0° C. under argon was slowly added triphosgene (8.80 mg, 0.030 mmol). After stirring at 0° C. for 20 mins the mixture was allowed to warm to rt. After 2 hr the mixture was washed with dilute aq. potassium carbonate solution (4 mL), dried and evaporated to dryness in vacuo. The residue was purified by MDAP which afforded the free base as a colourless gum, after a basic work up. This was dissolved in DCM (1 mL) and 1M HCl in diethyl ether (0.2 mL), after stirring for 20 mins the mixture was concentrated to dryness under vacuum to yield the title compound E48 as a cream powder (8 mg, 21.95%).

$^1$H NMR δ (CDCl$_3$, 400 MHz) (free base) 1.47-1.58 (4H, m), 1.64-1.69 (5H, m) 1.86-1.92 (4H, m), 2.21-2.38 (4H, m), 2.63 (3H, s), 3.17 (2H, d), 3.41 (3H, s), 3.46 (1H, m), 3.52-3.82 (4H, m), 4.11 (1H, s), 7.24 (1H, d), 7.74 (1H, d), 7.81 (1H, s).

LC/MS 431 (MH+).

To a stirred solution of 1-(4-hydroxy-3-{[1-(trans-1-methyl-4-{[2-(methyloxy)ethyl]oxy}-cyclohexyl)-4-piperidinyl]amino}phenyl)ethanone O-methyloxime (D133) (40 mg, 0.092 mmol) and triethylamine (0.019 mL, 0.138 mmol) in dichloromethane (DCM) (3 mL) cooled to 0° C. was slowly added triphosgene (10.95 mg, 0.037 mmol). After stirring at 0° C. for 15 mins the cooling bath was removed and the mixture allowed to reach rt and was stirred for another 2 hr. The mixture was washed with dilute aq potassium carbonate solution and brine, dried (MgSO$_4$) concentrated to dryness under vacuum. The residue was subjected to silica gel chromatography using a Biotage Horizon with a 12+M column eluting with 0-5% MeOH in DCM. A pale yellow solid was isolated, which was dissolved in DCM (3 mL) and treated with 1M HCl (0.1 mL) in diethyl ether, after stirring for 30 mins the mixture was concentrated to dryness under vacuum and the residue triturated in diethyl ether to afford the title compound E49 as a pale yellow solid (9 mg, 17.70%).

$^1$H NMR δ (DMSO-d$_6$, 400 MHz) 1.27-1.33 (5H, m), 1.88-2.07 (8H, m), 2.28 (3H, s), 2.86 (2H, m), 3.19-3.24 (6H, m), 3.41 (2H, m), 3.55 (2H, m), 3.65 (2H, d), 3.92 (3H, s), 4.59 (1H, m), 7.36 (1H, d), 7.43 (1H, d), 7.91 (1H, s), 10.31 (1H, br s).

LC/MS 460 (MH+).

EXAMPLES 50 AND 51

1-[1-(trans-4-{2-Methoxyethoxy}cyclohexyl)-4-piperidinyl]-2-oxo-2,3-dihydro-1H-indole-6-carbonitrile. (E50)

and

1-[1-(cis-4-{2-Methoxyethoxy}cyclohexyl)-4-piperidinyl]-2-oxo-2,3-dihydro-1H-indole-6-carbonitrile. (E51)

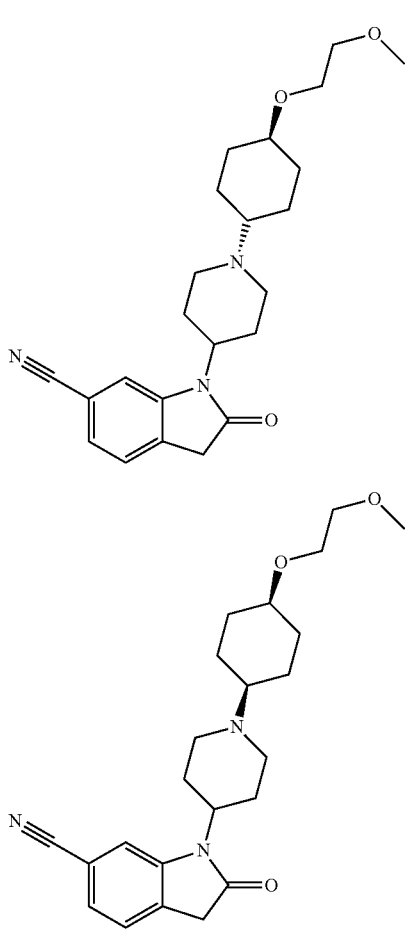

E50

E51

A mixture of 4-(6-cyano-2-oxo-2,3-dihydro-1H-indol-1-yl)piperidine hydrochloride (200 mg, 0.829 mmol) (D137), 4-(2-methoxyethoxy)cyclohexanone (200 mg, 1.161 mmol) (D61), polymer supported cyanoborohydride (300 mg, 1.230 mmol), acetic acid (0.2 mL, 3.50 mmol), and dichloromethane (5 mL) was heated in the microwave reactor at 100° C. for 15 min, then filtered and evaporated. Purification by high pH MDAP gave the faster running isomer E50, 1-[1-(trans-4-{2-methoxyethoxy}cyclohexyl)-4-piperidinyl]-2-oxo-2,3-dihydro-1H-indole-6-carbonitrile (30 mg, 0.075 mmol, 9.10% yield) free base, crystallised from diethyl ether, and then the slower running isomer E51, 1-[1-(cis-4-{2-methoxyethoxy}cyclohexyl)-4-piperidinyl]-2-oxo-2,3-dihydro-1H-indole-6-carbonitrile (45 mg, 0.113 mmol, 13.66% yield) free base, as a white foam.

trans isomer E50: [M+H]$^+$ 398; Rt 2.37

$^1$H NMR δ (MeOH-d$_4$, 250 MHz, free base) 1.3 (4 H, m), 1.7 (2 H, bs), 2.0 (2H, d), 2.2 (2 H, d), 2.5 (5 H, m), 3.1 (2 H, d), 3.3-3.6 (10 H, m), 4.3 (1 H, m), 7.4 (2 H, ABq), and 7.8 (1 H, s).

cis isomer E51: [M+H]$^+$ 398; Rt 2.45

$^1$H NMR δ (MeOH-d$_4$, 400 MHz, free base) 1.4 (2 H, m), 1.7 (6 H, m), 2.0 (2H, d), 2.5 (5 H, m), 3.2 (2 H, d), 3.4 (3 H, s), 3.6 (5 H, m), 4.3 (1 H, m), 7.4 (2 H, ABq), and 7.8 (1 H, s).

Note: 2 H not visible in NMR spectrum as obscured by solvent or water.

EXAMPLE 52

3-{1-[trans-4-(Ethyloxy)cyclohexyl]-4-piperidinyl}-5-fluoro-1,3-benzoxazol-2(3H)-one. (E52)

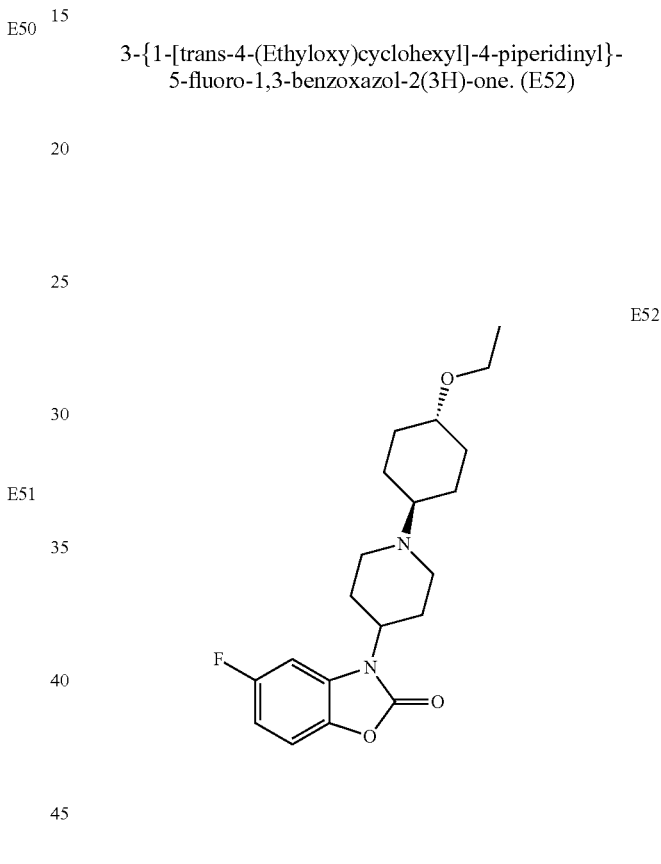

E52

A mixture of 5-fluoro-3-(4-piperidinyl)-1,3-benzoxazol-2(3H)-one hydrochloride D138 (0.2 g), 4-(ethyloxy)cyclohexanone (WO2007107566) (0.2 g), and Hunig's base (0.1 g) in N-methylpyrrolidone (5 mL) was stirred for 2 hours then treated with sodium triacetoxyborohydride (0.5 g) was added and stirring was continued for four days. The mixture was diluted with methanol, loaded onto a SCX column and the column was eluted with methanol followed by 2M ammonia in methanol. The methanolic ammonia fractions were evaporated and the residue was purified by high pH MDAP. Two peaks were collected and evaporated separately. The fast eluting isomer gave 3-{1-[trans-4-(ethyloxy)cyclohexyl]-4-piperidinyl}-5-fluoro-1,3-benzoxazol-2(3H)-one E52 as a white solid (7 mg).

$^1$H NMR (CDCl$_3$) δ: 1.20 (3H, t), 1.25-1.4 (4H, m), 1.6 (2H, m), 1.88 (4H, m), 2.12 (2H, m) 2.22-2.42 (4H, m), 3.05 (2H, m), 3.20 (1H, m), 3.51 (2H, t), 4.16 (1H, m), 6.87 (1H, m), 6.99 (1H, m), 7.17 (1H, m).

EXAMPLE 53

3-{1-[trans-4-(Ethyloxy)-1-methylcyclohexyl]-4-piperidinyl}-5-methyl[1,3]oxazolo[4,5-b]pyridin-2(3H)-one hydrochloride. (E53)

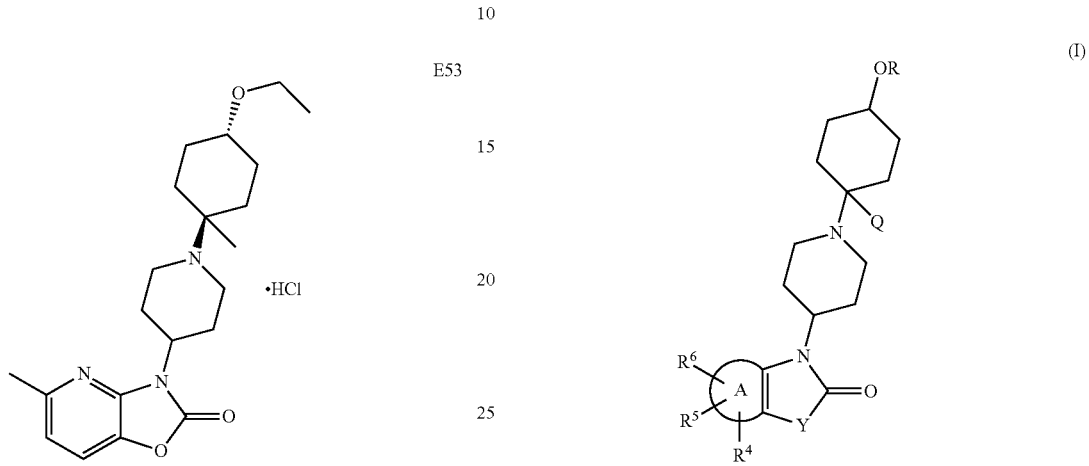

Hunig's Base (0.074 mL, 0.43 mmol) was added to a solution of 2-({1-[trans-4-(ethyloxy)-1-methylcyclohexyl]-4-piperidinyl}amino)-6-methyl-3-pyridinol D146 (82 mg, 0.21 mmol) in DCM (5 mL) at rt under Ar. The reaction was cooled to 0° C. and the triphosgene (26 mg, 0.09 mmol) was added. The mixture was stirred for 50 min at 0° C. and then the reaction was quenched with sat. NaHCO$_3$ (5 mL) and partitioned between DCM and H$_2$O. The aqueous layer was extracted with DCM (2×) and the combined organics were dried (Na$_2$SO$_4$) and concentrated by rotary evaporation to give a pale yellow solid. The crude residue was purified via Biotage (silica; DCM to 0.5% NH$_3$/9.5% MeOH/90% DCM; 12+M column) to give a residue which was further purified by high pH MDAP to give the free base of the title compound as a white solid. HCl (0.04 mL, 0.04 mmol, 1 M in Et$_2$O) was added to a solution of the free base in DCM (0.5 mL). The solvent was removed by rotary evaporation and the crude residue triturated with Et$_2$O to give 3-{1-[trans-4-(ethyloxy)-1-methylcyclohexyl]-4-piperidinyl}-5-methyl[1,3]oxazolo[4,5-b]pyridin-2(3H)-one hydrochloride (E53) (4 mg, 4%) as a white solid.

$^1$H NMR (DMSO-d$_6$) δ: 1.10 (3 H, t, J 7.0), 1.23-1.37 (5 H, m), 1.68-1.79 (2 H, m), 1.90-2.03 (4 H, m), 2.06-2.15 (2 H, m), 2.48 (s, integration obscured by solvent peak), 2.64-2.77 (2 H, m), 3.12-3.30 (3 H, m), 3.47 (2 H, q, J 7.0), 3.61-3.69 (2 H, m), 4.61 (1 H, m), 7.04 (1 H, d, J 8.1), 7.62 (1 H, d, J 8.1), 8.95 (1 H, m).

[M+H]$^+$ 374.

The compounds 3-{1-[cis-4-(Ethyloxy)cyclohexyl]-4-piperidinyl}-5-fluoro-1,3-benzoxazol-2(3H)-one and 5-methyl-3-[1-(trans-1-methyl-4-{[2-(methyloxy)ethyl]oxy}cyclohexyl)-4-piperidinyl]-2-oxo-2,3-dihydro-1,3-benzoxazole-4-carbonitrile hydrochloride can be made in a similar manner to the Examples above. 3-{1-[cis-4-(Ethyloxy)cyclohexyl]-4-piperidinyl}-5-fluoro-1,3-benzoxazol-2(3H)-one and 5-methyl-3-[1-(trans-1-methyl-4-{[2-(methyloxy)ethyl]oxy}cyclohexyl)-4-piperidinyl]-2-oxo-2,3-dihydro-1,3-benzoxazole-4-carbonitrile hydrochloride were either not tested for activity or activity was undetectable within the limits of the assays used (below the threshold of detectability).

The invention claimed is:

1. A method of treating a psychotic disorder, which method comprises administering to a mammal in need thereof an effective amount of a compound of formula (I) or a salt thereof:

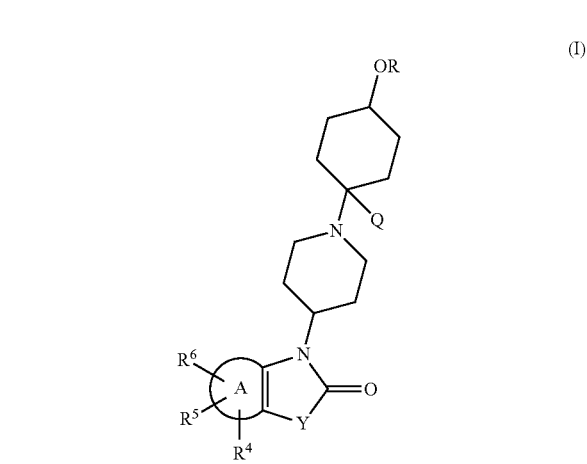

wherein
R$^4$, R$^5$ and R$^6$ are independently selected from hydrogen, halogen, C$_{1-6}$alkyl, C$_{1-6}$alkyl substituted with one or more fluorine atoms, cyano, C$_{1-6}$alkylsulfonyl, C$_{1-6}$alkylsulfonyl substituted with one or more fluorine atoms, C$_{3-6}$cycloalkyl, C$_{1-6}$alkoxy, C$_{1-6}$alkoxy substituted with one or more fluorine atoms, C$_{1-6}$alkanoyl, —C(=NOC$_{1-6}$alkyl)C$_{1-6}$alkyl, —C$_{1-6}$alkoxyC$_{1-6}$alkyl, and —C(O)NR$_a$R$_b$;
R$_a$ and R$_b$ are each independently H or C$_{1-6}$ alkyl, or together with the nitrogen atom to which they are attached form a five or six membered ring;
ring A represents a benzene ring, or a 6-membered aromatic heterocylic ring containing one or two nitrogen atoms;
R is selected from C$_{1-6}$alkyl, C$_{3-6}$cycloalkyl, C$_{3-6}$cycloalkylC$_{1-4}$alkyl, C$_{1-6}$alkyloxyC$_{1-6}$alkyl, C$_{3-6}$cycloalkyloxyC$_{1-6}$alkyl and C$_{3-6}$cycloalkylC$_{1-4}$alkyloxyC$_{1-6}$alkyl, wherein any alkyl or cycloalkyl group is optionally substituted by one or more fluorine atoms;
Q is selected from hydrogen and C$_{1-6}$alkyl; and
Y is selected from O, S, CH$_2$ optionally substituted with one or two fluorine atoms or optionally substituted with one or two methyl groups, CH$_2$CH$_2$, OCH$_2$, and CH$_2$O.

2. A method as claimed in claim 1 wherein R$^6$ is cyano.

3. A method as claimed in claim 1 wherein R is C$_{3-6}$cycloalkylC$_{1-4}$alkyl.

4. A method as claimed in claim 1 wherein Y is O.

5. A method as claimed in claim 1 wherein A is a benzene ring.

6. A method as claimed in claim 1 wherein the compound is selected from the group consisting of:
3-{1-[trans-4-(Ethyloxy)-1-methylcyclohexyl]-4-piperidinyl}-1,3-benzoxazol-2(3H)-one;
3-{1-[trans-1-Methyl-4-(propyloxy)cyclohexyl]-4-piperidinyl}-1,3-benzoxazol-2(3H)-one;
3-{1-[trans-4-(Ethyloxy)-1-methylcyclohexyl]-4-pipendinyl}-2-oxo-2,3-dihydro-1,3-benzoxazole-5-carbonitrile;

3-{1-[trans-4-(Ethyloxy)-1-methylcyclohexyl]-4-piperidlinyl}-6-fluoro-5-methyl-1,3-benzoxazol-2(3H)-one;

3-{1-[trans-4-(Ethyloxy)-1-methylcyclohexyl]-4-piperidlinyl}-5-(methylsulfonyl)-1,3-benzoxazol-2(3H)-one;

3-{1-[trans-4-(Ethyloxy)-1-methylcyclohexyl]-4-piperidinyl}-5-(ethylsulfonyl)-1,3-benzoxazol-2(3H)-one;

5-Fluoro-3-{1-[trans-1-methyl-4-(propyloxy)cyclohexyl]-4-piperidinyl}-1,3-benzoxazol-2(3H)-one;

3-{1-[trans-4-(Ethyloxy)-1-methylcyclohexyl]-4-piperidinyl}-5-fluoro-1,3-benzoxazol-2(3H)-one;

3-{1-[trans-4-(Ethyloxy)-1-methylcyclohexyl]-4-piperidinyl}-5-(methyloxy)-1,3-benzoxazol-2(3H)-one;

3-{1-[trans-4-(Ethyloxy)cyclohexyl]-4-piperidinyl}-5-methyl-1,3-benzoxazol-2(3H)-one;

4-{1-[trans-4-(Ethyloxy)-1-methylcyclohexyl]-4-piperidinyl}-6-methyl-2H-1,4-benzoxazin-3(4H)-one;

3-[1-(cis-1-Methyl-4-{[2-(methyloxy)ethyl]oxy}cyclohexyl)-4-piperidinyl]-2-oxo-2,3-dihydro-1,3-benzoxazole-5-carbonitrile;

6-Methyl-1-{1-[trans-1-methyl-4-(propyloxy)cyclohexyl]-4-piperidinyl}-1,3-dihydro-2H-indol-2-one;

3-{1-[trans-4-Ethoxy-1-methylcyclohexyl]-4-piperidlinyl}-7-fluoro-5-methyl-1,3-benzoxazol-2(3H)-one;

3-{1-[trans-4-Ethoxy-1-methylcyclohexyl]-4-piperidinyl}-6,7-difluoro-5-methyl-1,3-benzoxazol-2(3H)-one;

5-Methyl-3-{1-[trans-1-methyl-4-(methyloxy)cyclohexyl]-4-piperidinyl}-1,3-benzoxazol-2(3H)-one;

3-{1-[trans-4-(Ethyloxy)-1-methylcyclohexyl]-4-piperidinyl}-5,7-difluoro-1,3-benzoxazol-2(3H)-one;

3-{1-[trans-4-(Ethyloxy)-1-methylcyclohexyl]-4-piperidinyl}-5-[(trifluoromethyl)oxy]-1,3-benzoxazol-2(3H)-one;

3-{1-[trans-4-(Ethyloxy)-1-methylcyclohexyl]-4-piperidinyl}-5,6-difluoro-1,3-benzoxazol-2(3H)-one;

3-{1-[trans-4-(Ethyloxy)-1-methylcyclohexyl]-4-piperidinyl}-5-(trifluoromethyl)-1,3-benzoxazol-2(3H)-one;

6-Methyl-1-{1-[trans-1-methyl-4-(methyloxy)cyclohexyl]-4-piperidinyl}-1,3-dihydro-2H-indol-2-one;

3-{1-[trans-1-methyl-4-(methyloxy)cyclohexyl]-4-piperidinyl}-2-oxo-2,3-dihydro-1,3-benzoxazole-5-carbonitrile;

1-{1-[trans-4-(Ethyloxy)-1-methylcyclohexyl]-4-piperidinyl}-6-methyl-1,3-dihydro-2H-indol-2-one;

3-{1-[trans-1-Methyl-4-(propyloxy)cyclohexyl]-4-piperidinyl}-5-(methylsulfonyl)-1,3-benzoxazol-2(3H)-one;

1-{1-[trans-4-(Ethyloxy)-1-methylcyclohexyl]-4-piperidinyl}-7-methyl-3,4-dihydro-2(1H)-quinolinone;

3,3,6-Trimethyl-1-{1-[trans-1-methyl-4-(propyloxy)cyclohexyl]-4-piperidinyl}-1,3-dihydro-2H-indol-2-one;

6-Methyl-1-[1-(trans-1-methyl-4-{[2-(methyloxy)ethyl]oxy}cyclohexyl)-4-piperidinyl]-1,3-dihydro-2H-indol-2-one;

3-{1-[trans-1-Methyl-4-(propyloxy)cyclohexyl]-4-piperidinyl}-5-[(trifluoromethyl)sulfonyl]-1,3-benzoxazol-2(3H)-one;

6-Methyl-3-{1-[trans-1-methyl-4-(propyloxy)cyclohexyl]-4-piperidinyl}-5-(methylsulfonyl)-1,3-benzoxazol-2(3H)-one;

6-Methyl-5-(methylsulfonyl)-3-{1-[trans-4-(propyloxy)cyclohexyl]-4-piperidinyl}-1,3-benzoxazol-2(3H)-one;

5-Methyl-3-[1-(trans-1-methyl-4-{[2-(methyloxy)ethyl]oxy}cyclohexyl)-4-piperidinyl]-2-oxo-2,3-dihydro-1,3-benzoxazole-6-carbonitrile;

5-(Difluoromethoxy)-3-{1-[trans-4-(ethyloxy)-1-methylcyclohexyl]-4-piperidinyl}-1,3-benzoxazol-2(3H)-one;

5-Methyl-3-[1-(trans-1-methyl-4-{[2-(methyloxy)ethyl]oxy}cyclohexyl)-4-piperidinyl]-1,3-benzoxazol-2(3H)-one;

3-[1-(trans-1-Methyl-4-{[2-(methyloxy)ethyl]oxy}cyclohexyl)-4-piperidinyl]-5-(methyloxy)-1,3-benzoxazol-2(3H)-one;

3-(1-{trans-4-[(Cyclopropylmethyl)oxy]-1-methylcyclohexyl}-4-piperidinyl)-5-(methylsulfonyl)-1,3-benzoxazol-2(3H)-one;

3-(1-{trans-1-Methyl-4-[(1-methylethyl)oxy]cyclohexyl}-4-piperidinyl)-5-(methylsulfonyl)-1,3-benzoxazol-2(3H)-one;

3-[1-(trans-1-methyl-4-{[2-(methyloxy)ethyl]oxy}cyclohexyl)-4-piperidinyl]-5-(trifluoromethyl)-1,3-benzoxazol-2(3H)-one;

6-Fluoro-5-methyl-3-[1-(trans-1-methyl-4-{[2-(methyloxy)ethyl]-oxy}cyclohexyl)-4-piperidinyl]-1,3-benzoxazol-2(3H)-one;

7-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile;

7-Fluoro-5-methyl-3-[1-(trans-1-methyl-4-{[2-(methyloxy)ethyl]oxy}cyclohexyl)-4-piperidinyl]-1,3-benzoxazol-2(3H)-one;

6-Fluoro-3-[1-(trans-1-methyl-4-{[2-(methyloxy)ethyl]oxy}cyclohexyl)-4-piperidinyl]-2-oxo-2,3-dihydro-1,3-benzoxazole-5-carbonitrile;

3-[1-(trans-1-Methyl-4-{[2-(methyloxy)ethyl]oxy}cyclohexyl)-4-piperidinyl]-5-(methylsulfonyl)-1,3-benzoxazol-2(3H)-one;

3-[1-(trans-1-Methyl-4-{[2-(methyloxy)ethyl]oxy}cyclohexyl)-4-piperidinyl]-5-[(methyloxy)methyl]-1,3-benzoxazol-2(3H)-one;

1-[1-(trans-1-Methyl-4-[2-(methoxyethoxy)cyclohexyl]-4-piperidinyl]-6-(methoxymethyl)-1,3-dihydro-2H-indol-2-one;

3-{1-[trans-4-(Ethyloxy)-1-methylcyclohexyl]-4-piperidinyl}-2-oxo-2,3-dihydro-1,3-benzoxazole-5-carboxamide;

3-[1-(trans-1-Methyl-4-{[2-(methyloxy)ethyl]oxy}cyclohexyl)-4-piperidinyl]-2-oxo-2,3-dihydro-1,3-benzoxazole-5-carboxamide;

5-Acetyl-3-[1-(trans-1-methyl-4-{[2-(methyloxy)ethyl]oxy}cyclohexyl)-4-piperidinyl]-1,3-benzoxazol-2(3H)-one;

3-[1-(trans-1-Methyl-4-{[2-(methyloxy)ethyl]oxy}cyclohexyl)-4-piperidinyl]-5-[N-(methyloxy)ethanimidoyl]-1,3-benzoxazol-2(3H)-one;

1-[1-(trans-4-{2-Methoxyethoxy}cyclohexyl)-4-piperidinyl]-2-oxo-2,3-dihydro-1H-indole-6-carbonitrile;

1-[1-(cis-4-{2-Methoxyethoxy}cyclohexyl)-4-piperidinyl]-2-oxo-2,3-dihydro-1H-indole-6-carbonitrile;

3-{1-[trans-4-(Ethyloxy)cyclohexyl]-4-piperidinyl}-5-fluoro-1,3-benzoxazol-2(3H)-one;

and

3-{1-[trans-4-(Ethyloxy)-1-methylcyclohexyl]-4-piperidinyl}-5-methyl[1,3]oxazolo[4,5-b]pyridin-2(3H)-one;

and salts thereof.

7. A method as claimed in claim 1 wherein the psychotic disorder is schizophrenia, cognitive impairment or Alzheimer's disease.

8. A method as claimed in claim 1 wherein the mammal is a human.

* * * * *